US012018057B2

(12) United States Patent
Sun et al.

(10) Patent No.: US 12,018,057 B2
(45) Date of Patent: Jun. 25, 2024

(54) PEPTIDE INHIBITORS OF INTERLEUKIN-23 RECEPTOR AND THEIR USE TO TREAT INFLAMMATORY DISEASES

(71) Applicants: Janssen Biotech, Inc., Horsham, PA (US); Protagonist Therapeutics, Inc., Newark, CA (US)

(72) Inventors: Chengzao Sun, Horsham, PA (US); Brian Troy Frederick, Newark, CA (US); Sandeep Somani, Horsham, PA (US); Ashok Bhandari, Newark, CA (US); Raymond Patch, Horsham, PA (US); Stephanie Barros, Horsham, PA (US); Raffaele Ingenito, Pomezia (IT); Roberto Costante, Pomezia (IT); Danila Branca, Pomezia (IT); Elisabetta Bianchi, Pomezia (IT)

(73) Assignees: Janssen Biotech, Inc., Horsham, PA (US); Protagonist Therapeutics, Inc., Newark, CA (US)

( * ) Notice: Subject to any disclaimer, the term of this patent is extended or adjusted under 35 U.S.C. 154(b) by 0 days.

(21) Appl. No.: 17/149,544

(22) Filed: Jan. 14, 2021

(65) Prior Publication Data
US 2022/0402983 A1 Dec. 22, 2022

Related U.S. Application Data

(60) Provisional application No. 62/961,618, filed on Jan. 15, 2020.

(51) Int. Cl.
*C07K 14/47* (2006.01)
*A61K 38/00* (2006.01)
*A61K 47/60* (2017.01)

(52) U.S. Cl.
CPC .......... *C07K 14/4703* (2013.01); *A61K 47/60* (2017.08); *A61K 38/00* (2013.01)

(58) Field of Classification Search
CPC ........ A61K 38/12; A61K 47/60; A61K 38/00; A61K 38/10; C07K 7/64; C07K 14/4703
See application file for complete search history.

(56) References Cited

U.S. PATENT DOCUMENTS

| | | | |
|---|---|---|---|
| 4,684,620 A | 8/1987 | Hruby et al. | |
| 4,724,229 A | 2/1988 | Ali | |
| 5,192,746 A | 3/1993 | Lobl et al. | |
| 5,494,897 A | 2/1996 | Ishikawa et al. | |
| 5,569,741 A | 10/1996 | Coy et al. | |
| 5,990,084 A | 11/1999 | Richter et al. | |
| 6,087,334 A | 7/2000 | Beeley et al. | |
| 6,235,711 B1 | 5/2001 | Dutta | |
| 6,818,617 B1 | 11/2004 | Niewiarowski et al. | |
| 7,534,764 B2 | 5/2009 | Ganz et al. | |
| 7,589,170 B1 | 9/2009 | Smythe et al. | |
| 7,718,598 B1 | 5/2010 | Smythe et al. | |
| 8,304,382 B2 | 11/2012 | Ferreira et al. | |
| 8,313,950 B2 | 11/2012 | Rovin et al. | |
| 8,435,941 B2 | 5/2013 | Ganz et al. | |
| 8,536,140 B2 | 9/2013 | Park et al. | |
| 8,568,706 B2 | 10/2013 | Grabstein et al. | |
| 8,796,418 B2 | 8/2014 | Walensky et al. | |
| 8,946,150 B2 | 2/2015 | Gallagher et al. | |
| 8,999,935 B2 | 4/2015 | Huang | |
| 9,169,292 B2 | 10/2015 | Gallagher et al. | |
| 9,273,093 B2 | 3/2016 | Bhandari et al. | |
| 9,518,091 B2 | 12/2016 | Bhandari et al. | |
| 9,605,027 B2 | 3/2017 | Gallagher et al. | |
| 9,624,268 B2 * | 4/2017 | Bourne | A61P 5/48 |
| 9,714,270 B2 | 7/2017 | Bhandari et al. | |
| 9,809,623 B2 | 11/2017 | Bhandari et al. | |
| 9,822,157 B2 | 11/2017 | Smythe et al. | |
| 10,023,614 B2 | 7/2018 | Bhandari et al. | |
| 10,030,061 B2 | 7/2018 | Smythe et al. | |
| 10,035,824 B2 * | 7/2018 | Bhandari | A61P 19/02 |
| 10,059,744 B2 | 8/2018 | Bhandari et al. | |
| 10,196,424 B2 * | 2/2019 | Bourne | A61P 17/06 |
| 10,278,957 B2 | 5/2019 | Anandan et al. | |
| 10,301,371 B2 | 5/2019 | Bhandari et al. | |
| 10,407,468 B2 | 9/2019 | Bhandari et al. | |
| 10,442,846 B2 | 10/2019 | Smythe et al. | |
| 10,501,515 B2 | 12/2019 | Smythe et al. | |
| 10,626,146 B2 | 4/2020 | Bhandari et al. | |
| 10,729,676 B2 | 8/2020 | Anandan et al. | |
| 10,787,490 B2 | 9/2020 | Bhandari et al. | |
| 10,941,183 B2 * | 3/2021 | Bhandari | A61P 3/10 |
| 11,041,000 B2 | 6/2021 | Bhandari et al. | |

(Continued)

FOREIGN PATENT DOCUMENTS

| CA | 2015761 A1 | 11/1990 |
|---|---|---|
| CN | 101307085 A | 11/2008 |

(Continued)

OTHER PUBLICATIONS https://www.cdc.gov/diabetes/basics/what-is-type-1-diabetes.html. Accessed Dec. 22, 2022 (Year: 2022).*
https://medlineplus.gov/druginfo/meds/a682145.html. Accessed Dec. 22, 2022 (Year: 2022).*
https://www.rheumatology.org/I-Am-A/Patient-Caregiver/Diseases-Conditions/Psoriatic-Arthritis. Accessed Dec. 22, 2022 (Year: 2022).*
Crushing Guide for Oral Medication in Residential Aged Care, Waitemata District Health Board, 2011, 2 pages.
International Search Report and Written Opinion for PCT/US2016/042680, dated Jan. 13, 2017, 12 Pages.
International Search Report and Written Opinion for PCT/US2018/014257, dated May 14, 2018, 13 Pages.

(Continued)

*Primary Examiner* — Lianko G Garyu
(74) *Attorney, Agent, or Firm* — Morrison & Foerster LLP

(57) ABSTRACT

The present invention provides novel peptide inhibitors of the interleukin-23 receptor, and related compositions and methods of using these peptide inhibitors to treat or prevent a variety of diseases and disorders, including inflammatory bowel diseases.

10 Claims, No Drawings
Specification includes a Sequence Listing.

(56) References Cited

U.S. PATENT DOCUMENTS

| | | |
|---|---|---|
| 11,111,272 B2 | 9/2021 | Bhandari et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0123343 A1 | 6/2004 | La Rosa et al. |
| 2004/0176293 A1 | 9/2004 | Peterson et al. |
| 2006/0166881 A1 | 7/2006 | Hotchkiss et al. |
| 2006/0183884 A1 | 8/2006 | Blaschuk et al. |
| 2007/0032417 A1 | 2/2007 | Baell |
| 2007/0166308 A1 | 7/2007 | Pullen et al. |
| 2007/0191272 A1 | 8/2007 | Stemmer et al. |
| 2007/0197430 A1 | 8/2007 | Baell et al. |
| 2008/0019913 A1 | 1/2008 | Polt et al. |
| 2008/0213277 A1 | 9/2008 | Sasu et al. |
| 2008/0260820 A1 | 10/2008 | Borrelly et al. |
| 2008/0300180 A1 | 12/2008 | Schambye et al. |
| 2009/0053819 A1 | 2/2009 | Seymour et al. |
| 2009/0257952 A1 | 10/2009 | Cochran et al. |
| 2009/0325810 A1 | 12/2009 | Lapointe et al. |
| 2010/0151487 A1 | 6/2010 | Rovin et al. |
| 2010/0183617 A1 | 7/2010 | Herr et al. |
| 2010/0190710 A1 | 7/2010 | Chemtob et al. |
| 2010/0196441 A1 | 8/2010 | Sondermeijer et al. |
| 2010/0272731 A1 | 10/2010 | Presta et al. |
| 2010/0280098 A1 | 11/2010 | Juliano et al. |
| 2011/0059087 A1 | 3/2011 | Lewis et al. |
| 2011/0086024 A1 | 4/2011 | Arthos et al. |
| 2011/0118186 A1 | 5/2011 | Schteingart et al. |
| 2011/0142889 A1 | 6/2011 | Lee |
| 2011/0212104 A1 | 9/2011 | Beaumont et al. |
| 2011/0282029 A1 | 11/2011 | Holmes et al. |
| 2012/0021975 A1 | 1/2012 | Hoffmann et al. |
| 2012/0040894 A1 | 2/2012 | Ganz et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0137123 A1 | 5/2013 | Cucchiara et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2013/0338132 A1 | 12/2013 | Koshiba et al. |
| 2014/0005128 A1 | 1/2014 | Mo et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0118315 A1 | 4/2015 | Wilson |
| 2015/0157692 A1 | 6/2015 | Fu |
| 2015/0203555 A1 | 7/2015 | Gellman et al. |
| 2015/0284429 A1 | 10/2015 | Merutka |
| 2016/0031944 A1 | 2/2016 | Bhandari et al. |
| 2016/0039878 A1 | 2/2016 | Gallagher et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0199437 A1 | 7/2016 | Wilson |
| 2016/0222076 A1 | 8/2016 | Smythe et al. |
| 2016/0228491 A1 | 8/2016 | Wilson |
| 2016/0368966 A1 | 12/2016 | Bhandari et al. |
| 2017/0313754 A1 | 11/2017 | Bourne et al. |
| 2017/0327541 A1 | 11/2017 | Bhandari et al. |
| 2018/0022778 A1 | 1/2018 | Bourne et al. |
| 2018/0079782 A1 | 3/2018 | Bhandari et al. |
| 2018/0079783 A1 | 3/2018 | Bhandari et al. |
| 2018/0099995 A1 | 4/2018 | Bhandari et al. |
| 2018/0100004 A1 | 4/2018 | Smythe et al. |
| 2018/0105572 A1 | 4/2018 | Bhandari et al. |
| 2018/0148477 A1 | 5/2018 | Bhandari et al. |
| 2019/0002500 A1 | 1/2019 | Bhandari et al. |
| 2019/0002503 A1 | 1/2019 | Bourne et al. |
| 2019/0016756 A1 | 1/2019 | Bhandari et al. |
| 2019/0076400 A1 | 3/2019 | Anandan et al. |
| 2019/0185535 A1 | 6/2019 | Smythe et al. |
| 2019/0185536 A1 | 6/2019 | Smythe et al. |
| 2019/0231746 A1 | 8/2019 | Anandan et al. |
| 2019/0248870 A1 | 8/2019 | Bhandari et al. |
| 2019/0264197 A1 | 8/2019 | Barkan et al. |
| 2019/0270786 A1 | 9/2019 | Bhandari et al. |
| 2019/0300590 A1 | 10/2019 | Bhandari et al. |
| 2019/0337983 A1 | 11/2019 | Bhandari et al. |
| 2020/0017549 A1 | 1/2020 | Bhandari et al. |
| 2020/0017566 A1 | 1/2020 | Bourne et al. |
| 2020/0040037 A1 | 2/2020 | Bhandari et al. |
| 2020/0064357 A1 | 2/2020 | Cheng et al. |
| 2020/0207822 A1 | 7/2020 | Bhandari et al. |
| 2020/0239516 A1 | 7/2020 | Richelle et al. |
| 2020/0239523 A1 | 7/2020 | Bhandari et al. |
| 2020/0308229 A1 | 10/2020 | Bhandari et al. |
| 2020/0361992 A1 | 11/2020 | Bourne et al. |
| 2021/0009638 A1 | 1/2021 | Bhandari et al. |
| 2021/0061872 A1 | 3/2021 | Liu et al. |
| 2021/0147483 A1 | 5/2021 | Bourne et al. |
| 2021/0261622 A1 | 8/2021 | Sun et al. |
| 2021/0363185 A1 | 11/2021 | Bhandari et al. |
| 2021/0371466 A1 | 12/2021 | Bhandari et al. |
| 2022/0041658 A1 | 2/2022 | Bhandari et al. |
| 2022/0177532 A1 | 6/2022 | Di Pretoro et al. |
| 2022/0185846 A1 | 6/2022 | Manthati et al. |
| 2022/0251142 A1 | 8/2022 | Bhandari et al. |
| 2022/0348626 A1 | 11/2022 | Smythe et al. |
| 2022/0372099 A1 | 11/2022 | Liu et al. |
| 2023/0129095 A1 | 4/2023 | Bhandari et al. |

FOREIGN PATENT DOCUMENTS

| | | |
|---|---|---|
| CN | 101358201 A | 2/2009 |
| DE | 10107707 A1 | 8/2002 |
| JP | 2016-521257 A | 7/2001 |
| JP | 2011231085 A | 11/2011 |
| JP | 2017-530090 A | 10/2017 |
| WO | 9217492 A1 | 10/1992 |
| WO | 1994/011018 A1 | 5/1994 |
| WO | 1996/017617 | 6/1996 |
| WO | 9725351 A2 | 7/1997 |
| WO | 9808871 A1 | 3/1998 |
| WO | 1998/033524 A1 | 8/1998 |
| WO | 9902194 A1 | 1/1999 |
| WO | 9926615 A1 | 6/1999 |
| WO | 0006243 A2 | 2/2000 |
| WO | 0009560 A2 | 2/2000 |
| WO | 0018789 A1 | 4/2000 |
| WO | 0018790 A1 | 4/2000 |
| WO | 0023474 A1 | 4/2000 |
| WO | 0055119 A1 | 9/2000 |
| WO | 0055184 A1 | 9/2000 |
| WO | 0061580 A1 | 10/2000 |
| WO | 0168586 A2 | 9/2001 |
| WO | 03066678 A1 | 8/2003 |
| WO | 2004011650 A2 | 2/2004 |
| WO | 2004092405 A2 | 10/2004 |
| WO | 2006032104 A1 | 3/2006 |
| WO | 2007138291 A2 | 12/2007 |
| WO | 2008/101017 A2 | 8/2008 |
| WO | 2008097461 A2 | 8/2008 |
| WO | 2008134659 A2 | 11/2008 |
| WO | 2008140602 A2 | 11/2008 |
| WO | 2009002947 A2 | 12/2008 |
| WO | 2009027752 A2 | 3/2009 |
| WO | 2010065815 A2 | 6/2010 |
| WO | 2010116752 A1 | 10/2010 |
| WO | 2010124874 A1 | 11/2010 |
| WO | 2011091357 A1 | 7/2011 |
| WO | 2011149942 A2 | 12/2011 |
| WO | 2012052205 A1 | 4/2012 |
| WO | 2013086143 A1 | 6/2013 |
| WO | 2014/059213 A1 | 4/2014 |
| WO | 2014127316 A2 | 8/2014 |
| WO | 2014/145561 A2 | 9/2014 |
| WO | 2014/165448 A1 | 10/2014 |
| WO | 2014210056 A1 | 12/2014 |
| WO | 2015054500 A2 | 4/2015 |
| WO | 2015176035 A1 | 11/2015 |

(56) References Cited

FOREIGN PATENT DOCUMENTS

| WO | 2015/200916 A2 | 12/2015 |
|---|---|---|
| WO | 2015157283 A9 | 12/2015 |
| WO | 2015183963 A2 | 12/2015 |
| WO | 2016004093 A2 | 1/2016 |
| WO | 2016011208 A1 | 1/2016 |
| WO | 2016054411 A1 | 4/2016 |
| WO | 2016054445 A1 | 4/2016 |
| WO | 2016109363 A1 | 7/2016 |
| WO | 2016115168 A1 | 7/2016 |
| WO | 2016195663 A1 | 12/2016 |
| WO | 2016200364 A1 | 12/2016 |
| WO | 2017011820 A2 | 1/2017 |
| WO | 2017117411 A1 | 7/2017 |
| WO | 2017/165676 A1 | 9/2017 |
| WO | 2018/022917 A1 | 2/2018 |
| WO | 2018022937 A1 | 2/2018 |
| WO | 2018089693 A2 | 5/2018 |
| WO | 2018136646 A1 | 7/2018 |
| WO | 2019/051494 A1 | 3/2019 |
| WO | 2019157268 A1 | 8/2019 |
| WO | 2019/246349 | 12/2019 |
| WO | 2019246273 A1 | 12/2019 |
| WO | 2020014646 A1 | 1/2020 |
| WO | 2020/198682 A1 | 10/2020 |
| WO | 2021007433 A1 | 1/2021 |
| WO | 2021/046246 A1 | 3/2021 |
| WO | 2021/142373 A1 | 7/2021 |
| WO | 2021/146441 A1 | 7/2021 |
| WO | 2021/146454 A1 | 7/2021 |
| WO | 2021/146458 A1 | 7/2021 |
| WO | 2022/026629 A1 | 2/2022 |
| WO | 2022/026631 A1 | 2/2022 |
| WO | 2022/026633 A1 | 2/2022 |
| WO | 2022/212696 A1 | 3/2022 |
| WO | 2022/109328 A1 | 5/2022 |
| WO | 2022/212698 A1 | 10/2022 |
| WO | 2022/212700 A1 | 10/2022 |
| WO | 2022/266060 A1 | 12/2022 |
| WO | 2023/288017 A1 | 1/2023 |
| WO | 2023/288019 A1 | 1/2023 |
| WO | 2023/288028 A1 | 1/2023 |

OTHER PUBLICATIONS

International Search Report and Written Opinion for PCT/US2019/041665, dated Dec. 19, 2019, 11 Pages.
International Search Report and Written Opinion for PCT/US2020/041409, dated Dec. 3, 2020, 13 Pages.
International Search Report and Written Opinion for PCT/US2015/040658, dated Oct. 28, 2015, 9 Pages.
SID 24885660, National Center for Biotechnology Information, PubChem Substance Database; SID=24885660, https://pubchem.ncbi.nlm.nih.gov/substance/24885660, accessed Jul. 21, 2016, 5 Pages.
Adams et al. (2013) "Investigation of peptide thioester formation via N→Se acyl transfer." Journal of Peptide Science, 19(2):65-73.
Andreu et al. (1994) "Formation of Disulfide Bonds in Synthetic Peptides and Proteins", Peptide Synthesis Protocols, 35:91-169.
Ashby et al. (2009) "Plasma Hepcidin Levels are Elevated But Responsive to Erythropoietin Therapy in Renal Disease.", Kidney International, 75(9):976-981.
Balasubramanian et al. (Oct. 24, 2003) "RGD-Containing Peptides Activate S6k1 Through Beta3 Integrin in Adult Cardiac Muscle Cells", Journal of Biological Chemistry, 278(43):42214-42224.
Boer et al. (2011) "Design and Synthesis of Potent and Selective α4β7 Integrin Antagonists" Journal of Medicinal Chemistry, 44(16):2586-2592.
Bowie et al. (Mar. 16, 1990) "Deciphering the Message in Protein Sequences: Tolerance to Amino Acid Substitutions" Science, 247(498):1306-1310.
Brayden et al. (Dec. 2, 2011) "Oral Peptide Delivery: Prioritizing The Leading Technologies" Therapeutic Delivery, 2(12):1567-1573.

Chatterjee et al. (2008) "N-Methylation of Peptides: A New Perspective in Medicinal Chemistry" Accounts of Chemical Research, 41(10):1331-1342.
Cherry et al. (Sep. 2015) "Vedolizumab: An A4β7 Integrin Antagonist for Ulcerative Colitis and Crohn's Disease" Therapeutic Advances in Chronic Disease, 6(5):224-233.
Clark et al. (2013) "Design, Synthesis, and Characterization of Cyclic Analogues of the Iron Regulatory Peptide Hormone Hepcidin." Peptide Science, 100(5):519-526.
Clark et al. (Mar. 2011) "Understanding the Structure/Activity Relationships of the Iron Regulatory Peptide Hepcidin." Chem. Biol., 18(3):336-343.
Database EPO Proteins (Dec. 3, 2010) "Sequence from Patent WO2010124874.", XP002761649, retrieved from EBI accession No. EPOP:HI656765 Database accession No. HI656765, 1 page.
Database USPTO Proteins (Dec. 17, 2012) "Sequence from patent U.S. Pat. No. 8,313,950.", XP002761650, retrieved from EBI accession No. USPOP:AGA36544 Database accession No. AGA36544, 1 page.
Davies Johns (Aug. 2003) "The Cyclization of Peptides and Depsipeptides." J Pept. Sci., 9(8): 471-501.
De Mast et al. (2010) "Increased Serum Hepcidin and Alterations in Blood Iron Parameters Associated With Asymptomatic P. Falciparum and P. Vivax malaria" Haematologica, 95(7):1068-1074.
Definition of Isostere (Feb. 5, 2015) "Medical Definition and More from Merriam-Webster Dictionary" Available on: www.merriam-webster.com/medical/isostere, 3 pages.
Desbenoit et al. (2010) "Reversible Metalation of A Bis-Disulfide Analogue of the Cys*-X-Cys* Hepcidin Binding Site: Structural Characterisation of the Related Copper Complex", Annales Pharmaceutiques Francaises, 68(6):388-396.
Dubree et al. (2002) "Selective a4B7 Integrin Antagonists and Their Potential as Antiinflammatory Agents" Journal of Medicinal Chemistry, 45:3451-3457.
Dutta et al. (2000) "Potent Cyclic Monomeric and Dimeric Peptide Inhibitors of VLA-4 (α4β1 Integrin)-Mediated Cell Adhesion Based on the Ile-Leu-Asp-Val Tetrapeptide", Journal of Peptide Science, 6(7):321-341.
Ganz et al. (Sep. 2012) "Hepcidin and iron homeostasis" Biochimica et Biophysica Acta (BBA)—Molecular Cell Research, 1823(9):1434-1443.
Gee et al. (1998) "Cyclic Peptides as Non-carboxyl-terminal Ligands of Syntrophin PDZ Domains" The Journal of Biological Chemistry, 273(34):21980-21987.
Gentilucci et al. (2010) "Chemical Modifications Designed to Improve Peptide Stability: Incorporation of Non-Natural Amino Acids, Pseudo-Peptide Bonds, and Cyclization.", Current Pharmaceutical Design, 16(28):3185-3203.
Girelli et al. (Jun. 9, 2016) "Hepcidin in the Diagnosis of Iron Disorders" Blood, 127(23): 2809-2813.
Gormer et al. (Feb. 1, 2010) "Efficient Microwave-Assisted Synthesis of Unsymmetrical Disulfides" The Journal of Organic Chemistry, 75(5):1811-1813.
Haanstra et al. (2013) "Antagonizing the a4B1 Integrin, but no a4B7, Inhibits Leukocytic Infiltration of the Central Nervous System in Rhesus Monkey Experimental Autoimmune Encephalomyelitis" Journal of Immunology, 90(5):1961-1973.
Hruby et al. (1994) "Design of Novel Synthetic Peptides Including Cyclic Conformationally and Topographically Constrained Analogs", Methods in Molecular Biology, 35(11):201-241.
Ilyin et al. (2003) "Comparative Analysis of Mouse Hepcidin 1 and 2 Genes:Evidence for Different Patterns of Expression and Co-Inducibility During Iron Overload 1" FEBS Letters, 542(1-3): 22-26.
Jackson David Y. (2002) "Alpha 4 Integrin Antagonists", Current Pharmaceutical Design, (8)14:1229-1253.
Janssen et al. (2002) "Comparison of a Monomeric and Dimeric Radiolabeled RGD-Peptide for Tumor Targeti" Cancer Biotherapy and Radiopharmaceuticals, 17(6):641-646.
Jordan et al. (2009) "Hepcidin Revisited, Disulfide Connectivity, Dynamics, and Structure" Journal of Biological Chemistry, 284(36):24155-24167.

(56) References Cited

OTHER PUBLICATIONS

Kelleman et al. (2003) "Incorporation of Thioether Building Blocks Into An Avβ3-Specific Rgd Peptide: Synthesis and Biological Activity", Biopolymers (Peptide Science), 71(6):686-695.
Kitazume et al. (1998) "Experimental Methods in Organic Fluorine Chemistry" Gordon and Breach Science Publishers, p. 9, (3 pages).
Kluskens et al. (2009) "Angiotensin-(1-7) with Thioether Bridge: An Angiotensin-Converting Enzyme-Resistant, Potent Angiotensin-(1-7) Analog" The Journal of Pharmacology and Experimental Therapeutics, 328(3):849-855.
Knudsen et al. (May 4, 2000) "Potent Derivatives of Glucagon-Like Peptide-1 With Pharmacokinetic Properties Suitable for Once Daily Administration" Journal of Medicinal Chemistry, 43(9):1664-1669.
Krause et al. (2000) "LEAP-1, A Novel Highly Disulfide-Bonded Human Peptide, Exhibits Antimicrobial Activity" FEBS Letters, 480(2-3):147-150.
Kuchar et al. (2013) "Human Interleukin-23 Receptor Antagonists Derived From an Albumin-Binding Domain Scaffold Inhibit II-23-Dependent Ex Vivo Expansion of Il-17-Producing T-Cells" Proteins, 82(6):975-989.
Legge et al. (1964) "On The Prediction of Partition Coefficients and Rf Values of Peptides." Aust. J. Biol. Sci, 17:561-571.
Ley et al. (Mar. 2016) "Integrin-Based Therapeutics: Biological Basis, Clinical Use and New Drugs" Nature Reviews Drug Discovery, 15(3):173-183.
Li et al. (2002) "Cyclization Strategies in Peptide Derived Drug Design" Current Topics in Medical Chemistry, 2:325-341.
Liu Shuang (2006) "Radiolabeled Multimeric Cyclic Rgd Peptides as Integrin Alphavbeta3 Targeted Radiotracers for Tumor Imaging" School of Health Science, Purdue University, Molecular Pharmaceuticals, 3(5):472-487.
Madsen et al. (2007) "Structure-Activity and Protraction Relationship of Long-Acting Glucagon-Like Peptide-1 Derivatives: Importance of Fatty Acid Length, Polarity, and Bulkiness" Journal of Medicinal Chemistry, 50(24):6126-6132.
Munoz et al. (2011) "Disorders of Iron Metabolism. Part II: iron deficiency and iron overload" Journal of Clinical Pathology, 64(4):287-296.
Nemeth et al. (2006) "The N-terminus of Hepcidin is Essential for Its Interaction with Ferroportin: Structure-Function Study" Blood, 107(1):328-333.
Park et al. (2001) "Hepcidin, A Urinary Antimicrobial Peptide Synthesized in The Liver" Journal of Biological Chemistry, 276(11):7806-7810.
Parrow et al. (2011) "Prospects for A Hepcidin Mimic to Treat B-Thalassemia and Hemochromatosis" Expert Review of Haematology, 4(3):233-235.
Pattarawarapan (Aug. 2003) "Selective Formation of Homo- and Heterobivalent Peptidomimetics" J. Med. Chem., 46(17):3565-3567.
Pelton et al. (1985) "Somatostatin Analogs with Affinity for Opiate Receptors in Rat Brain Binding Assay" Peptides, 6(Suppl 1):159-163.
Preza et al. (Dec. 1, 2011) "Minihepcidins are Rationally Designed Small Peptides That Mimic Hepcidin Activity in Mice and May Be Useful for the Treatment of Iron Overload" J. Clin. Invest, 121(12):4880-4888.
Quiniou et al. (Aug. 20, 2014) "Specific Targeting of The IL-23 Receptor, Using a Novel Small Peptide Noncompetitive Antagonist, Decreases the Inflammatory Response" American Journal of Physiology-Regulatory, Integrative and Comparative Physiology, 307(10):R1216-R1230.
Ramos et al. (Nov. 1, 2012) "Minihepcidins Prevent Iron Overload in a Hepcidin-deficient Mouse Model of Severe Hemochromatosis", Blood, 120(18):3829-3836.
Rivera et al. (Sep. 15, 2005) "Synthetic Hepcidin Causes Rapid Dose-Dependent Hypoferremia and is Concentrated in Ferroportin-Containing Organs" Blood, 106(6):2196-2199.
Rostovtsev et al. (Jul. 15, 2002) "A Stepwise Huisgen Cycloaddition Process: Copper(I)-catalyzed Regioselective "ligation" of Azides and Terminal Alkynes" Angewandte Chemie International Edition, 41(14):2596-2599.
Sasaki et al. (1984) "D-Arg2-Dermorphin Tetrapeptide Analogs: A Potent and Long-Lasting Analgesic Activity After Subcutaneous Administration.", Biochemical and Biophysical Research Communications, 120(1):214-218.
Shahidi et al. (2016) "Vedolizumab for the Treatment of Ulcerative Colitis" Expert Opinion on Biological Therapy, 16(1):129-135.
Soler-Ferran et al. (2012) "Integrin α4β7 Antagonists: Activities, Mechanisms of Action and Therapeutic Prospects" Current Immunology Reviews, 8(2):118-134.
Speers et al. (Mar. 28, 2003) "Activity-Based Protein Profiling in Vivo Using a Copper(I)-Catalyzed Azide-Alkyne [3+2] Cycloaddition" Journal of the American Chemical Society, 125(16):4686-4687.
Tandara et al. (Oct. 2012) "Iron metabolism: Current Facts and Future Directions" Biochem Med, 22(3):311-328.
Temming et al. (2006) "Rational Design of RGD-Albumin Conjugates for Targeted Delivery of the Vegf-R Kinase Inhibitor Ptk787 to Angiogenic Endothelium" ChemMedChem, 1: 1200-1203.
Thermo Electron Corporation (2004) "N-terminal and C-terminal Amidation of Peptides" Technical Information, 2 pages.
Thumshirn et al. (2003) "Multimeric Cyclic RGD Peptides as Potential Tools for Tumor Targeting: Solid Phase Peptide Synthesis and Chemoselective Oxime Liqation" Chemistry—A European Journal, 9:2717-2725.
Tornoe et al. (May 3, 2002) "Peptidotriazoles on Solid Phase: [1,2,3]-Triazoles by Regiospecific Copper(I)-Catalyzed 1,3-Dipolar Cycloadditions of Terminal Alkynes to Azides" The Journal of Organic Chemistry, 67(9):3057-3064.
Tuvia et al. (Aug. 2014) "A Novel Suspension Formulation Enhances Intestinal Absorption of Macromolecules via Transient and Reversible Transport Mechanisms" Pharmaceutical Research, 31(8):2010-2021.
Wang et al. (Feb. 2003) "Bioconjugation by Copper(I)-Catalyzed Azide-Alkyne [3+2] Cycloaddition" Journal of the American Chemical Society, 125(11):3192-3193.
Xie et al. (2000) "Nerve Growth Factor (NGF) Loop 4 Dimeric Mimetics Activate ERK and AKT and Promote NGF-like Neurotrophic Effects" The Journal of Bioloqical Chemistry, 275(38):29868-29874.
Yampolsky et al. (Aug. 2005) "The Exchangeability of Amino Acids in Proteins" Genetics, 170(4):1459-1472.
Yu et al. (2010) "A Naturally Occurring, Soluble Antagonist of Human IL-23 Inhibits the Development and In Vitro Function of Human Th17 Cells", The Journal of Immunology, 185:7302-7308.
Annis, et al., "Disulfide bond formation in peptides". Methods Enzymol. (1997); 289: 198-221.
Chang, et al., "Role of disulfide bonds in the structure and activity of human insulin", Mol Cells (Dec. 2003); 16(3): 323-330.
Cheng et al., "The Biomarker Profile of PTG-200, An Oral Peptide Antagonist of IL-23 Receptor, Tracks with Efficacy in a Preclinical Model of IBD". Gastroenterology, AGA Abstracts, vol. 152, Issue 5, Supplement 1, S31, Apr. 1, 2017.
Chermahini et al., "Cyclic peptide nanocapsule as ion carrier for halides: a theoretical survey", Structural Chemistry (Oct. 2018); 29(5): 1351-1357.
Clark, et al., "The Engineering of an Orally Active Conotoxin for the Treatment of Neuropathic Pain." Angew Chem Int Ed (Sep. 2010); 49: 6545-6548.
Craik, et al., "Potential therapeutic applications of the cyclotides and related cystine knot mini-proteins." Expert Opin Investig Drugs (May 2007); 16(5): 595-604.
De Vega, et al., "Modulation of Protein-Protein Interactions by Stabilizing/Mimicking Protein Secondary Structure Elements." Curr Top Med Chem (2007); 7(1): 33-62.
Delgado et al., "The uses and properties of PEG-linked proteins". Critical Reviews in Therapeutic Drug Carrier Systems (Jan. 1, 1992); 9(3-4): 249-304.

(56) References Cited

OTHER PUBLICATIONS

Dolain, Christel, et al. "Inducing α-Helices in Short Oligopeptides through Binding by an Artificial Hydrophobic Cavity." Journal of the American Chemical Society (2010); 132.16: 5564-5565.

Dutton, et al., "A New Level of Conotoxin Diversity, a Non-native Disulfide Bond Connectivity in—Conotoxin AuIB Reduces Structural Definition but Increases Biological Activity." J Biol Chem (Oct. 2002); 277(50): 48849-48857.

Fass, D., "Disulfide bonding in protein biophysics." Annu Rev Biophys (2012); 41: 63-79. Epub Dec. 20, 2011.

Fosgerau and Hoffman, "Peptide therapeutics: current status and future directions." Drug Discovery Today (2015); 20(1): 122-128.

Foster, "Deuterium Isotope Effects in Studies of Drug Metabolism", Trends Pharmacol. Sci., 5(12):524-527 (1984).

Francis, et al., "PEGylation of cytokines and other therapeutic proteins and peptides: the importance of biological optimisation of coupling techniques". International Journal of Hematology (Jul. 1, 1998); 68(1): 1-8.

Frese et al., "Modular Combination of Enzymatic Halogenation of Tryptophan with Suzuki—Miyaura Cross-Coupling Reactions." ChemCatChem. May 20, 2016, vol. 8, No. 10, pp. 1799-1803.

Gombotz and Pettit, "Biodegradable Polymers for Protein and Peptide Drug Delivery". Bioconjugate Chem. (Jul. 1, 1995); 6(4): 332-351.

Guerler and Knapp, "Novel protein folds and their nonsequential structural analogs." Protein Sci (Aug. 2008); 17(8): 1374-1382.

Guharoy and Chakrabarti, "Secondary structure based analysis and classification of biological interfaces: identification of binding motifs in protein-protein interactions." Bioinformatics (2007); 23(15): 1909-1918. Epub May 17, 2007.

Gupta, et al., "A classification of disulfide patterns and its relationship to protein structure and function." Protein Sci (Aug. 2004); 13(8): 2045-2058.

Hartig, et al., "Intramolecular disulphide bond arrangements in nonhomologous proteins." Protein Sci Publ Protein Soc (Feb. 2005); 14(2): 474-482.

Hawe, et al., "Forced degradation of therapeutic proteins." J Pharm Sci. (Mar. 2012); 101(3): 895-913. Epub Nov. 14, 2011.

Henikoff and Henikoff, "Amino acid substitution matrices from protein blocks." Proc Natl Acad Sci U S A (Nov. 1992); 89(Nov.); 10915-10919.

Hudecz, et al., "Synthesis, conformation, biodistribution and in vitro cytotoxicity of daunomycin-branched polypeptide conjugates". Bioconjugate Chem. (Jan. 1, 1992); 3(1): 49-57.

Liu and Wang, "Endomorphins: potential roles and therapeutic indications in the development of opioid peptide analgesic drugs". Med Res Rev. (May 2012); 32(3): 536-580. Epub Feb. 1, 2011.

Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.

Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.

Maeda, et al., "Conjugates of anticancer agents and polymers: advantages of macromolecular therapeutics in vivo". Bioconjugate Chem. (Sep./Oct. 1992); 3(5): 3511-362.

Makharia, Govind K., "Current and emerging therapy for celiac disease", Frontiers in Medicine (Mar. 2014); vol. 1, Article 6, pp. 1-11.

NCBI Reference Sequence: NP_653302.2, "interleukin-23 receptor precursor [*Homo sapiens*]", Feb. 8, 2023, 4 pages.

Niederreiter, et al., "Anti-IL-12/23 in Crohn's Disease: Bench and Bedside." Curr Drug Targets (Nov. 2013); 14(12): 1379-1384.

Rubinstein and Niv, "Peptidic modulators of protein-protein interactions: Progress and challenges in computational design." Biopolymers (2009); 91(7): 505-513.

Tsukada, et al., "An Anti-α-Fetoprotein Antibody-Daunorubicin Conjugate With a Novel Poly-L-glutamic Acid Derivative as Intermediate Drug Carrier", J. Natl. Cancer Inst. (Sep. 1984); 73(3): 721-729.

White and Yudin, "Contemporary strategies for peptide macrocyclization." Nat Chem (Jun. 2011); 3(7): 509-524.

Witt, Dariusz, "Recent developments in disulfide bond formation". Synthesis (2008); 16: 2491-2509.

Zalipsky, Samuel, "Functionalized Poly(ethylene glycols) for Preparation of Biologically Relevant Conjugates". Bioconjugate Chem. (1995); 6(2): 150-165.

Garcia, Josep et al., "D-Polyarginine Lipopeptides as Intestinal Permeation Enhancers". ChemMedChem Oct. 8, 2018; 13(19): 2045-2052. Epub Aug. 20, 2018.

Gruschow, et al., "New pacidamycin antibiotics through precursor-directed biosynthesis". Chembiochem. Jan. 26, 2009; 10(2): 355-360.

Liu, Shuang, "Radiolabeled Cyclic RGD Peptides as Integrin $\alpha_v\beta_3$—Targeted Radiotracers: Maximizing Binding Affinity via Bivalency." Bioconjugate Chem. (2009); 20 (12): 2199-2213.

Maher, Sam et al., "Application of Permeation Enhancers in Oral Delivery of Macromolecules: An Update". Pharmaceutics Jan. 19, 2019; 11 (1): 41, 23 pages.

Maher, Sam et al., "Safety and efficacy of sodium caprate in promoting oral drug absorption: from in vitro to the clinic". Advanced Drug Delivery Reviews Dec. 17, 2009; 61 (15): 1427-1449. Epub Oct. 1, 2009.

Muheem, Abdul et al., "A review on the strategies for oral delivery of proteins and peptides and their clinical perspectives". Saudi Pharmaceutical Journal Jul. 2016; 24(4): 413-428. Epub Jun. 16, 2014.

PCT/US2021/013477, International Search Report and Written Opinion mailed Jun. 3, 2021, 15 pages.

PCT/US2021/013477, Invitation to Pay Additional Fees mailed Mar. 29, 2021, 3 pages.

U.S. Appl. No. 18/097,077, Bhandari et al., filed on Jan. 13, 2023. (Copy not submitted herewith pursuant to the waiver of 37 C.F.R. § 1.98(a)(2)(iii) issued by the Office on Sep. 21, 2004.).

\* cited by examiner

PEPTIDE INHIBITORS OF INTERLEUKIN-23 RECEPTOR AND THEIR USE TO TREAT INFLAMMATORY DISEASES

CROSS REFERENCES TO RELATED APPLICATIONS

This applications claims priority to U.S. Provisional Application No. 62/961,618, filed Jan. 15, 2020, which is incorporated herein in its entirety for all purposes.

SEQUENCE LISTING

This application is being filed electronically via EFS-Web and includes an electronically submitted sequence listing in .txt format. The .txt file contains a sequence listing entitled "056365_514001US_Sequence_Listing_ST25.txt" created on Jan. 14, 2021 and having a size of about 230 kilobytes. The sequence listing contained in this .txt file is part of the specification and is incorporated herein by reference in its entirety.

FIELD OF THE INVENTION

The present invention relates to novel peptide inhibitors of the interleukin-23 receptor (IL-23R), and their use to treat or prevent a variety of diseases and disorders, including inflammatory bowel disease, Crohn's disease, ulcerative colitis and psoriasis.

BACKGROUND

The interleukin-23 (IL-23) cytokine has been implicated as playing a crucial role in the pathogenesis of autoimmune inflammation and related diseases and disorders, such as multiple sclerosis, asthma, rheumatoid arthritis, psoriasis, and inflammatory bowel diseases (IBDs), e.g., ulcerative colitis and Crohn's disease. Studies in acute and chronic mouse models of IBD revealed a primary role of IL-23R and downstream effector cytokines in disease pathogenesis. IL-23R is expressed on various adaptive and innate immune cells including Th17 cells, γδ T cells, natural killer (NK) cells, dendritic cells, macrophages, and innate lymphoid cells, which are found abundantly in the intestine. At the intestine mucosal surface, the gene expression and protein levels of IL-23R are found to be elevated in IBD patients. It is believed that IL-23 mediates this effect by promoting the development of a pathogenic CD4$^+$ T cell population that produces IL-6, IL-17, and tumor necrosis factor (TNF).

Production of IL-23 is enriched in the intestine, where it is believed to play a key role in regulating the balance between tolerance and immunity through T-cell-dependent and T-cell-independent pathways of intestinal inflammation through effects on T-helper 1 (Th1) and Th17-associated cytokines, as well as restraining regulatory T-cell responses in the gut, favoring inflammation. In addition, polymorphisms in the IL-23 receptor (IL-23R) have been associated with susceptibility to inflammatory bowel diseases (IBDs), further establishing the critical role of the IL-23 pathway in intestinal homeostasis.

Psoriasis, a chronic skin disease affecting about 2%-3% of the general population has been shown to be mediated by the body's T cell inflammatory response mechanisms. Il-23 has one of several interleukins implicated as a key player in the pathogenesis of psoriasis, purportedly by maintaining chronic autoimmune inflammation via the induction of interleukin-17, regulation of T memory cells, and activation of macrophages. Expression of IL-23 and IL-23R has been shown to be increased in tissues of patients with psoriasis, and antibodies that neutralize IL-23 showed IL-23-dependent inhibition of psoriasis development in animal models of psoriasis.

IL-23 is a heterodimer composed of a unique p19 subunit and the p40 subunit shared with IL-12, which is a cytokine involved in the development of interferon-γ (IFN-γ)-producing T helper 1 (T$_H$1) cells. Although IL-23 and IL-12 both contain the p40 subunit, they have different phenotypic properties. For example, animals deficient in IL-12 are susceptible to inflammatory autoimmune diseases, whereas IL-23 deficient animals are resistant, presumably due to a reduced number of CD4$^+$ T cells producing IL-6, IL-17, and TNF in the CNS of IL-23-deficient animals. IL-23 binds to IL-23R, which is a heterodimeric receptor composed of IL-12Rβ1 and IL-23R subunits. Binding of IL-23 to IL-23R activates the Jak-stat signaling molecules, Jak2, Tyk2, and Stat1, Stat 3, Stat 4, and Stat 5, although Stat4 activation is substantially weaker and different DNA-binding Stat complexes form in response to IL-23 as compared with IL-12. IL-23R associates constitutively with Jak2 and in a ligand-dependent manner with Stat3. In contrast to IL-12, which acts mainly on naive CD4(+) T cells, IL-23 preferentially acts on memory CD4(+) T cells.

Efforts have been made to identify therapeutic moieties that inhibit the IL-23 pathway, for use in treating IL-23-related diseases and disorders. A number of antibodies that bind to IL-23 or IL-23R have been identified, including ustekinumab, an antibody that binds the p40 subunit of IL-23, which has been approved for the treatment of moderate to severe placque psoriasis, active psoriatic arthritis, moderately to severely active Crohn's disease and moderately to severly active ulcerative colitis. More recently, polypeptide inhibitors that bind to IL-23R and inhibit the binding of IL-23 to IL-23R have been identified (see, e.g., US Patent Application Publication No. US2013/0029907). Clinical trials in Crohn's Disease or psoriasis with briakinumab (which also target the common p40 subunit) and tildrakizumab, guselkumab, MEDI2070, and BI-655066 (which target the unique p19 subunit of IL-23) highlight the potential of IL-23 signaling blockade in treatment of human inflammatory diseases. While these findings are promising, challenges remain with respect to identifying stable and selective agents that preferentially target the IL-23 pathway in the intestine, which can be used for the treatment of intestinal inflammation, such as intestinal bowel diseases, including Crohn's disease, ulcerative colitis and related disorders.

Clearly, there remains a need in the art for new therapeutics targeting the IL-23 pathway, which may be used to treat and prevent IL-23-asociated diseases, including those associated with autoimmune inflammation in the intestinal tract. In addition, compounds and methods for specific targeting of IL-23R from the luminal side of the gut may provide therapeutic benefit to IBD patients suffering from local inflammation of the intestinal tissue. The present invention addresses these needs by providing novel peptide inhibitors that bind IL-23R to inhibit IL-23 binding and signaling and which are suitable for oral administration.

BRIEF SUMMARY OF THE INVENTION

The present invention provides inter alia novel peptide inhibitors of IL-23R and related methods of use.

In a first aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (I):

X3-X4-X5-X6-X7-X8-X9-X10-X11-X12-X13-X14-X15-X16     (1)

wherein

X3 is absent or any amino acid;

each X4, X5, and X6 is independently any amino acid;

X7 is unsubstituted Trp, or Trp substituted with cyano, halo, alkyl, haloalkyl, hydroxy, alkoxy, substituted or unsubstituted aryl, or substituted or unsubstituted heteroaryl;

X8 is Gln, alpha-MeLys, alpha-MeLeu, alpha-MeLys (Ac), beta-homoGln, Cit, Glu, Phe, Paf(Ac), Phe4NH2Ac Asn, Thr, Val, Aib, alpha-MeGln, alpha-MeAsn, Lys(Ac), Dab(Ac), Dap(Ac), homo-Lys(Ac), 1-Nal, 2-Nal, or Trp;

X9 is Abu, Cys, (D)Cys, alpha-MeCys, (D)Pen, Pen or Pen(sulfoxide);

X10 is unsubstituted Phe, or Phe substituted with halo, alkyl, haloalkyl, hydroxy, alkoxy, carboxy, carboxamido, 2-aminoethoxy, or 2-acetylaminoethoxy, AEF, AEF(Ac), AEF(BH), AEF(Boc), AEF(Me)2, bMeR-Phe, Phe42ae-ethyl, Phe42aeSMSB, Phe4Pip;

X11 is 6amido2Nal, 6OMe2Nal, bMe2Nal(2S,3R), rbMe2Nal, 2-Nal, aMe(2-Nal), Phe(2-Me), Phe(3-Me), Phe(4-Me), Phe(3,4-dimethoxy), 1-Nal, unsubstituted Trp, or Trp substituted with cyano, halo, alkyl, haloalkyl, hydroxy, or alkoxy;

X12 is 4diFAchx, Achx, Acpx, AmeK(Boc), 4-amino-4-carboxy-tetrahydropyran (THP), alpha-MeLys, alpha-MeLeu, alpha-MeArg, alpha-MePhe, alpha-MeLeu, alpha-MeLys, alpha-MeAsn, alpha-MeTyr, Ala, cyclohexylAla, 1-aminocyclohexylAla (Achc), Acvc, Lys, or Aib;

X13 and X14 is independently any amino acid;

i) X16 is absent; and X15 is His, Phe-tetraF, Phe_3OH, ameF, Aib, THP, Phe, substituted Phe, substituted (D)Phe, a-MePhe, substituted a-MePhe, Trp, substituted Trp, 1-Nal, aMe(1-Nal), substituted 1-Nal, 2-Nal, aMe(2-Nal), substituted 2-Nal, or N-substituted Asn; provided that the peptide inhibitor is other than:

(SEQ ID NO: 151)
Ac-[Pen]-NT-[W(7-Me)]-[Cit]-Pen]-Phe[4-(2- aminoethoxy)][2-Nal]-[a-MeLys]-[Lys(Ac)]-N-[Aib]-

NH₂;
or (SEQ ID NO: 201)
Ac-[(D)Arg]-[Abu]-Q-T-[W(7-Me)]-[Lys(Ac)]-[Cys]-

Phe[4-(2-aminoethoxy)]-[2-Nal]-[a-MeLys]-[Lys(Ac)]-

N-[a-MePhe]-NH₂;

or ii) X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn; and X15 is any amino acid;

provided that the peptide inhibitor is other than:

(SEQ ID NO: 202)
Ac-[Pen]-N-T-[W(7-Me)]-[Cit]-Pen-Phe[4-(2- aminoethoxy)]-[2-Nal]-[a-MeLys]-[Lys(Ac)]-N-[Aib]-

[(D)Tyr]-NH₂;

or iii) the peptide is (SEQ ID NO: 1)
Ac-[Pen]-N-T-[W(7-Me)]-[Lys(Ac)]-[Pen]-Phe[4-(2- aminoethoxy)]-[3-Quin]-[a-MeLys]-[Lys(Ac)]-N-

[(D)Leu]-NH₂;

(SEQ ID NO: 64)
Ac-[Abu]-Q-T-[W(7-Me)]-[Lys(Ac)]-[Cys]-Phe[4-(2- aminoethoxy)]-[2-Nal]-[a-MeLys]-[Lys(Ac)]-N-

[(D)Lys]-NH₂;

(SEQ ID NO: 65)
Ac-[Abu]-Q-T-[W(7-Me)]-[Lys(Ac)]-[Cys]-Phe[4-(2- aminoethoxy)]-[2-Nal]-[a-MeLys]-[Lys(Ac)]-N-

[(D)Leu]-NH₂;

(SEQ ID NO: 72)
Ac-[Pen]-N-[(D)Dap]-[W(7-Me)]-[Lys(Ac)]-[Pen]-

Phe[4-(2-aminoethoxy)]-[2-Nal]-[a-MeLys]-[Lys(Ac)]-

N-[(D)Leu]-NH₂;

(SEQ ID NO: 73)
Ac-[Pen]-N-[(D)Lys]-[W(7-Me)]-[Lys(Ac)]-[Pen]-

Phe[4-(2-aminoethoxy)]-[2-Nal]-[a-MeLys]-[Lys(Ac)]-

N-[(D)Leu]-NH₂;

(SEQ ID NO: 74)
Ac-[Pen]-N-[(D)Asp]-[W(7-Me)]-[Lys(Ac)]-[Pen]-

Phe[4-(2-aminoethoxy)]-[2-Nal]-[a-MeLys]-[Lys(Ac)]-

N-[(D)Leu]-NH₂;

(SEQ ID NO: 70)
Ac-[Pen]-N-T-[W(7-Me)]-[Lys(Ac)]-[Pen]-Phe[4-(2- aminoethoxy)]-[2-Nal]-[a-MeLys]-[Lys(Ac)]-N-[Aib-

Ahx]-NH₂;

(SEQ ID NO: 8)
[Propionic_acid]-[(D)Arg]-[Pen]-Q-T-W-Q-[Pen]-

Phe[4-(2-aminoethoxy)]-[2-Nal]-[THP]-E-N-[N-MebAla]-NH₂;

(SEQ ID NO: 14)
Ac-[(D)Arg]-[Pen]-Q-T-W-Q-[Pen]-Phe[4-(2- aminoethoxy)]-[2-Nal]-[THP]-E-N-[N-Me-bAla]-NH₂;

(SEQ ID NO: 44)

-continued

Ac-[(D)Arg]-[Abu]-Q-T-W-Q-[Cys]-Phe[4-(2-aminoethoxy)]-[2-Nal]-[THP]-[aMeGlu]-N-[aMeTyr]-NH$_2$;

(SEQ ID NOs: 150, 44)
Ac-[(D)Arg]-[Pen]-N-T-[W(7-Me)]-[Lys(Ac)]-[Pen]-Phe[4-(2-aminoethoxy)]-[2-Nal]-[THP]-aMeGlu]-N-[aMeTyr]-NH$_2$;
or (SEQ ID NO: 151)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[aMeTyr]-NH$_2$;

and
wherein the peptide inhibitor is cyclized via a Abu-Cys thioether bond, or Pen-Pen disulfide bond;
and
wherein X4 and X9 form a disulfide bond or a thioether bond;
and
wherein the peptide inhibitor inhibits the binding of an interleukin-23 (IL-23) to an IL-23 receptor.

In a second aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (II):

X4-X5-X6-X7-X8-X9-X10-X11-X12-X13-X14-X15-X16  (II)

wherein X7-X16 are as described for Formula (I);
X4 is Abu, Cys, (D)Cys, alpha-MeCys, (D)Pen, Pen, or Pen(sulfoxide);
X5 is Cit, Glu, Gly, Leu, Ile, beta-Ala, Ala, Lys, Asn, Pro, alpha-MeGln, alpha-MeLys, alpha-MeLeu, alpha-MeAsn, Lys(Ac), alpha-MeLys(Ac), Dab(Ac), Dap(Ac), homo-Lys(Ac), Gln, Asp, or Cys;
X6 is Thr, Aib, Asp, Dab, Gly, Pro, Ser, alpha-MeGln, alpha-MeLys, alpha-MeLeu, alpha-MeAsn, alpha-Me-Thr, alpha-MeSer, or Val;
wherein the peptide inhibitor is cyclized via a bond between X4 and X9, and
wherein the peptide inhibitor inhibits the binding of an interleukin-23 (IL-23) to an IL-23 receptor.

In certain embodiments, X15 is His, Phe_tetraF, Phe_3OH, ameF, Aib, THP, Phe, substituted Phe, substituted (D)Phe, a-MePhe, substituted a-MePhe, Trp, substituted Trp, 1-Nal, aMe(1-Nal), substituted 1-Nal, 2-Nal, aMe(2-Nal), substituted 2-Nal, or N-substituted Asn; and X16 is absent.

In certain embodiments, X15 is any amino acid; and X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiments, X15 is any amino acid; and X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, aMe(2-Nal), substituted 2-Nal, or N-substituted Asn.

In certain embodiments, N-substituted Asn is (N-Me)Asn, (N-Et)Asn, (N-n-Pr)Asn, (N-iPr)Asn, (N-iBu)Asn, (N-nBu) Asn, (N-tBu)Asn, (N-benzyl)Asn, (N-Ph)Asn, (N-2-aminophenyl)Asn, (N-3-aminophenyl)Asn, (N-4-aminophenyl) Asn, (N-pyr)Asn, (N-3-Pyz)Asn, (N-4-Pyz)Asn, (N-pip) Asn, (N-5-indolyl)Asn, (N-propylamido)Asn, or (N-imidazo-2-yl)Asn.

In certain embodiments, X5 is Cit, Glu, Gly, Lys, Asn, Pro, alpha-MeGln, alpha-MeLys, alpha-MeLeu, alpha-MeAsn, Lys(Ac), alpha-MeLys(Ac), Dab(Ac), Dap(Ac), homo-Lys(Ac), Gln, Asp, or Cys. In certain embodiments, X5 is Cit, Glu, Gly, Leu, Ile, beta-Ala, Ala, Lys, Asn, Pro, alpha-MeGln, alpha-MeLys, alpha-MeLeu, alpha-MeAsn, Lys(Ac), alpha-MeLys(Ac), Dab(Ac), Dap(Ac), homo-Lys (Ac), Gln, Asp, or Cys.

In certain embodiments, X8 is Gln, alpha-Me-Lys, alpha-MeLeu, alpha-MeLys(Ac), beta-homoGln, Cit, Glu, Phe, Paf(Ac), Phe4NH2Ac Asn, Thr, Val, Aib, alpha-MeGln, alpha-MeAsn, Lys(Ac), alpha-MeLys(Ac), Dab(Ac), Dap (Ac), homo-Lys(Ac), 1-Nal, 2-Nal, or Trp. In certain embodiments, X8 is Gln, alpha-Me-Lys, alpha-MeLeu, alpha-MeLys(Ac), beta-homoGln, Cit, Glu, Phe, Paf(Ac), Phe4NH2Ac Asn, Thr, Val, Aib, alpha-MeGln, alpha-MeAsn, Lys(Ac), Dab(Ac), Dap(Ac), homo-Lys(Ac), 1-Nal, 2-Nal, or Trp.

In one embodiment, X4 is Abu and X9 is Cys, (D)Cys, alpha-MeCys, (D)Pen, or Pen. In another embodiment, X4 is Cys, (D)Cys, alpha-MeCys, (D)Pen, or Pen; and X9 is Abu. In another embodiment, each X4 and X9 is independently Cys, (D)Cys, alpha-MeCys, (D)Pen, or Pen. In another embodiment, each X4 and X9 is Cys, (D)Cys, alpha-MeCys, (D)Pen, or Pen.

In a particular aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (XIa) or (XIb):

(XIa)
(SEQ ID NO: 323)
Pen-Asn-Thr-W'-Gln-Pen-[F(4-2ae)]-[2-Nal]-aMeLeu-

K(Ac)-Asn-X15-X16 or (XIb)
(SEQ ID NO: 324)
Pen-Asn-Thr-W-Gln-Pen-[F(4-2ae)]-W'-aMeLeu-K(Ac)-

Asn-X15-X16 wherein X15 and X16 are as described herein, and W' is Trp substituted with cyano, halo, alkyl, haloalkyl, hydroxy, or alkoxy; and the peptide inhibitor is cyclized via a Pen-Pen disulfide bond.

In another particular aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (XIc) or (XId):

(XIc)
(SEQ ID NO: 325)
Abu-Asn-Thr-W'-Gln-Cys-[F(4-2ae)]-[2-Nal-aMeLeu-

K(Ac)-Asn-X15-X16,
or (XId)
(SEQ ID NO: 326)
Abu-Asn-Thr-W-Gln-Cys-[F(4-2ae)]-W'-aMeLeu-K(Ac)-

Asn-X15-X16, wherein X15 and X16 are as described herein, and W' is Trp substituted with cyano, halo, alkyl, haloalkyl, hydroxy, or alkoxy; and the peptide inhibitor is cyclized via a Abu-Cys thioether bond.

In another particular aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (XIe) or (XIf):

(XIe)
(SEQ ID NO: 327)
Abu-Asn-Thr-W'-Gln-Pen-[F(4-2ae)]-[2-Nal]-aMeLeu-

K(Ac)-Asn-X15-X16,
or (XIf)
(SEQ ID NO: 328)
Abu-Asn-Thr-W-Gln-Pen-[F(4-2ae)]-W'-aMeLeu-K(Ac)-

Asn-X15-X16, wherein X15 and X16 are as described herein, and W' is Trp substituted with cyano, halo, alkyl, haloalkyl, hydroxy, or alkoxy; and the peptide inhibitor is cyclized via a Abu-Pen thioether bond.

In another particular aspect, the present invention provides a monocyclic peptide inhibitor of an interleukin-23 receptor, or a pharmaceutically acceptable salt or solvate thereof, wherein the peptide inhibitor comprises or consists of an amino acid sequence of Formula (Z):

$$R^1-X-R^2 \quad (Z)$$

or a pharmaceutically acceptable salt or solvate thereof, wherein $R^1$ is a bond, hydrogen, a C1-C6 alkyl, a C6-C12 aryl, a C6-C12 aryl, a C1-C6 alkyl, a C1-C20 alkanoyl, and including PEGylated versions alone or as spacers of any of the foregoing;

X is the amino acid sequence of Formula (I), Formula (II)-(XIf), or an amino acid sequence set forth in Table E1; and $R^2$ is OH or $NH_2$.

In particular embodiments of any of the peptide inhibitors disclosed herein, including peptide inhibitors comprising an amino acid sequence of Formula Formula (I)-(XIf), X4 is Pen and X9 is Pen, and the bond is a disulfide bond.

In particular embodiments, any of the peptide inhibitors described herein comprise one or more half-life extension moiety and/or one or more linker moiety conjugated to the peptide inhibitor. In particular embodiments, the half-life extension moiety is conjugated to the peptide inhibitor via one or more linker moieties.

In certain embodiments, any of the peptide inhibitors described herein further comprises a conjugated chemical substituent. In particular embodiments, the conjugated chemical substituent is a lipophilic substituent or a polymeric moiety, e.g., Ac, Palm, gamaGlu-Palm, isoGlu-Palm, PEG2-Ac, PEG4-isoGlu-Palm, (PEG)$_5$-Palm, succinic acid, glutaric acid, pyroglutaric acid, benzoic acid, IVA, octanoic acid, 1,4 diaminobutane, isobutyl, Alexa488, Alexa647, or biotin. In certain embodiments, the conjugated chemical substituent is a polyethylene glycol with a molecular mass of 400 Da to 40,000 Da. In particular embodiments, the peptide is conjugated at X8. In another particular embodiment, the peptide is conjugated at X9. In a more particular embodiment, the peptide is conjugated at X10.

In a related aspect, the present invention includes a peptide dimer inhibitor of an interleukin-23 receptor, wherein the peptide dimer inhibitor comprises two peptide monomer subunits connected via one or more linker moieties, wherein each peptide monomer subunit comprises a sequence of Formula (I), Formula (II)-(XIf), or any other sequence or structure set forth herein. In certain embodiments, one or both peptide monomer subunit is cyclized via an intramolecular bond between X4 and X9. In certain embodiments, one or both intramolecular bond is a disulfide bond or a thioether bond. In certain embodiments, the linker is any of those shown in Table 2 or described herein. In certain embodiments, the linker moiety is a diethylene glycol linker, an iminodiacetic acid (IDA) linker, a β-Ala-iminodiaceticacid (β-Ala-IDA) linker, or a PEG linker. In particular embodiments, the N-terminus of each peptide monomer subunit is connected by the linker moiety. In particular embodiments, the C-terminus of each peptide monomer subunit is connected by the linker moiety. In certain embodiments, the linker connects an internal amino acid residue of at least one of the peptide monomer subunits to the N-terminus, C-terminus, or an internal amino acid residue of the other peptide monomer subunit.

In a further related aspect, the present invention includes a polynucleotide comprising a sequence encoding a peptide inhibitor of the present invention or one or both peptide monomer subunit of a peptide dimer inhibitor of the present invention. The present invention also includes a vector comprising the polynucleotide.

In another aspect, the present invention includes a pharmaceutical composition comprising a peptide inhibitor or a peptide dimer inhibitor of the present invention, and a pharmaceutically acceptable carrier, excipient, or diluent. In particular embodiments, the pharmaceutical composition comprises an enteric coating. In certain embodiments, the enteric coating protects and releases the pharmaceutical composition within a subject's lower gastrointestinal system.

In another aspect, the present invention includes a method for treating or preventing a disease associated with IL-23 signalling, including but not limited to an Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, psoriasis, or graft versus host disease in a subject, comprising providing to the subject an effective amount of a peptide inhibitor or pharmaceutical composition of the present invention. In certain embodiments, the inflammatory bowel disease is ulcerative colitis or Crohn's disease. In particular embodimnts, the peptide inhibitor or the peptide dimer inhibitor inhibits binding of an interleukin-23 (IL-23) to the interleukin-23 receptor (IL-23R). In certain embodiments, the pharmaceutical composition is provided to the subject by an oral, intravenous, peritoneal, intradermal, subcutaneous, intramuscular, intrathecal, inhalation, vaporization, nebulization, sublingual, buccal, parenteral, rectal, intraocular, inhalation, vaginal, or topical route of administration. In particular embodiments, the pharmaceutical composition is provided orally for treating Inflammatory Bowel Disease (IBD), ulcerative colitis, Crohn's disease. In certain embodiments, the pharmaceutical composition is provided to the subject topically, parenterally, intravenously, subcutaneously, peritonealy, or intravenously for treating psoriasis.

DETAILED DESCRIPTION OF THE INVENTION

Definitions

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring. The term peptide include cyclic peptides.

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, one or more cysteines of a peptide analogue of the invention may be substituted with another residue, such as a serine. For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N  | H   | M  | F |
| S | D  | R   | L  | Y |
| T | E  | K   | I  | W |
| P | Q  |     | V  |   |
| G |    |     | C  |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|----|-----|------|----|---|
| A  | E   | H    | M  | F |
| L  | D   | R    | S  | Y |
| I  |     | K    | T  | W |
| P  |     |      | C  |   |
| G  |     |      | N  |   |
| V  |     |      | Q  |   |

The term "amino acid" or "any amino acid" as used here refers to any and all amino acids, including naturally occurring amino acids (e.g., a-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 unnatural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid. According to certain embodiments, a peptide inhibitor comprises an intramolecular bond between two amino acid residues present in the peptide inhibitor. It is understood that the amino acid residues that form the bond will be altered somewhat when bonded to each other as compared to when not bonded to each other. Reference to a particular amino acid is meant to encompass that amino acid in both its unbonded and bonded state. For example, the amino acid residue homoSerine (hSer) or homoSerine (Cl) in its unbonded form may take the form of 2-aminobutyric acid (Abu) when participating in an intramolecular bond according to the present invention. The present invention inclues both peptide inhibitors containing cross-links between X4 and X9, as well as the peptide inhibitors that do not contain cross-links between X4 and X9, e.g., before cross-link formation. As such, the names hSer and Abu are intended to indicate the same amino acids and are used interchangeably.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of Non-Natural Amino Acids and Chemical Moieties (for amino acid derivatives, all L unless stated)

| Abbreviation | Definition |
|--------------|------------|
| (1-Me)His | (1-Methyl)Histidine |
| (D)(N-Me)Tyr | NMe(D)Tyr or N-Me-(D)Tyrosine |
| (D)2-Nal | D-2-Naphthylalanine |
| (D)aMePhe | (D)-alpha-Me-Phenylalanine |

TABLE 1-continued

Abbreviations of Non-Natural Amino Acids and Chemical Moieties (for amino acid derivatives, all L unless stated)

| Abbreviation | Definition |
| --- | --- |
| (D)aMeTyr | (D)-alpha-Me-Tyrosine |
| (D)Phe[3-NH2] | (D)-(3-Amino)phenylalanine |
| (D)Ph[4-NH2], 4AmDPhe | (D)-(4-Amino)phenylalanine |
| (N-(3-Pyz))Asn | N-Pyrazol-3-yl-Asparagine |
| (N-(4-Pyz))Asn | N-Pyrazol-4-yl-Asparagine |
| (N-(5-indoyl))Asn | N-indol-5-yl-Asparagine |
| (N-(imidazol-2-yl)methyl)Asn | N-(imidazo-2-yl)methyl-Asparagine |
| (N-(propylamido))Asn | N-$CH_2CH_2CONH_2$—Asparagine |
| (N-2-aminophenyl)Asn | N-Ph(2-NH2)—Asparagine |
| (N-3-aminophenyl)Asn | N-Ph(3-NH2)—Asparagine |
| (N-4-aminophenyl)Asn | N-Ph(4-NH2)—Asparagine |
| (N-benzyl)Asn | N-benzyl-Asparagine |
| (N-Ph)Asn | N-Ph—Asparagine |
| (N-pip)Asn | N-piperidin-4-yl-Asparagine |
| (N-Pyr)Asn | N-Pyrrolidin-3-yl-Asparagine |
| 1,2,3,4-tetrahydro-norharman | L-1,2,3,4-tetrahydro-norharman |
| 1-1-Indane | 1-Aminoindane-1-carboxylic acid |
| 1-Nal (also referred to as 1-Nap) | L-1-Naphthylalanine |
| 2,5,7-tert butyl Trp | 2,5,7-Tris-tert-butyl-L-tryptophan |
| 2-2-Indane | 2-Aminoindane-2-carboxylic acid |
| 2-Nal (also referred to as 2-Nap) | L-2-Naphthylalanine |
| 2-Pal or 2Pal | L-2-Pyridylalanine |
| 3-Pal or 3Pal | L-3-Pyridylalanine |
| 4AcDPhe | (D)-(4-acyl)phenylalanine |
| 4-amino-4-carboxy-piperidine | 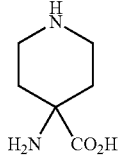<br>4-amino-4-carboxy-piperidine |
| 4-amino-4-carboxy-tetrahydropyran or THP | 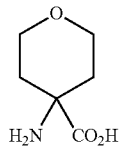<br>4-amino-4-carboxy-tetrahydropyran |
| 4diFAchx | 1-amino-4,4-difluoro-cyclohexanecarboxylic acid |
| 4-Pal or 4Pal | L-4-Pyridylalanine |
| 5-HydroxyTrp | 5-Hydroxy-L-Tryptophan |
| 5Pyal | 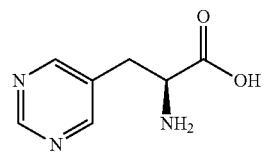<br>5-pyrimidine-alanine |
| 6amido2Nal | (6-amido-naphth-2-yl)alanine |
| 6-ChloroTrp | 6-Chloro-L-Tryptophan |
| 6OMe2Nal | L-2-(6-methoxynaphthyl)alanine |
| Abu | 2-Aminobutyric acid |
| Ac- or MeC(O)— | Acetyl |

TABLE 1-continued

Abbreviations of Non-Natural Amino Acids and Chemical Moieties (for amino acid derivatives, all L unless stated)

| Abbreviation | Definition |
|---|---|
| Acbc | 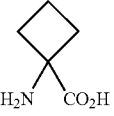<br>1-aminocyclobutane-carboxylic acid |
| Achc | 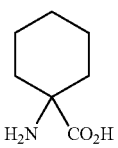<br>1-aminocyclo-hexanecarboxylic acid |
| Achc or Achx | <br>1-aminocyclo-hexanecarboxylic acid |
| Acpc | <br>1-amino-cyclopropyl-carboxylic acid |
| Acpc or Acpx | <br>1-aminocyclo-propyl-carboxylic acid |
| Acvc | 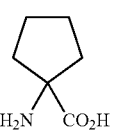<br>1-aminocyclo-pentane-carboxylic acid |
| AEA | (2-aminoethoxy)acetic acid |
| AEF(Me)$_2$ | 4(2-dimethylaminoethoxy)phenylalanine |
| AEP | 3-(2-aminoethoxy)propanoic acid |

TABLE 1-continued

Abbreviations of Non-Natural Amino Acids and Chemical Moieties (for amino acid derivatives, all L unless stated)

| Abbreviation | Definition |
| --- | --- |
| Ahx | 6-aminohexanoic acid |
| Aib | 2-aminoisobutyric acid |
| a-MeAsn, alpha-MeAsn | α-Methyl-L-Asparagine |
| a-MeGln, alpha-MeGln | α-Methyl-L-Glutamine |
| AmeK(Boc) | (N-t-butyloxycarbonyl)-alpha-Me-lysine |
| aMePhe(4-F) | α-Methyl-(4-Fluoro)phenylalanine |
| aMePhe, aMeF | alpha-Me-Phenylalanine |
| Azt | L-azetidine-2-carboxylic acid |
| Bip | L-4,4'-Biphenylalanine |
| bMe2Nal(2S,3R) | (2-naphthyl)beta-methylalanine |
| bMePhe(S,R) or bMeRPhe | (2S,3R)-beta-methylphenylalanine |
| Cav | L-Cavanine |
| Cha | Cyclohexyl-L-alanine |
| Cit | L-Citrulline |
| CONH$_2$ | Carboxamide |
| COOH | Carboxylic Acid |
| Coumarin | *(structure shown)* |
| Cpa | Cyclopentyl-L-alanine |
| Cyclobutyl | L-cyclobutylalanine |
| cyclohexylAla | (2- or beta-)-cyclohexyl-L-Alanine |
| Dab | L-Diaminobutyric acid |
| DabCOMe or Dab(Ac) | N-Acetyl-L-diaminobutyric acid |
| Dap | L-Diaminopropionic acid |
| DapCOMe or Dap(Ac) | N-Acetyl-L-Diaminopropionic acid |
| DiethylGly | *(structure shown)* |
| DMT | 2,6-DimethylTyrosine |
| dPhe42ae | (D)-4-(2-aminoethoxy)-L-phenylalanine |
| dPhe4OCF3 | 4-trifluoromethoxy-D-phenylalanine |
| DTT | Dithiothreitol |
| FPrpTriazoleMe_Acid | *(structure shown)* |
| Gla | Gamma-Carboxy-L-Glutamic acid |
| hArg | L-homoArginine |
| hCha | L-homocyclohexylalanine |

TABLE 1-continued

Abbreviations of Non-Natural Amino Acids and Chemical Moieties (for amino acid derivatives, all L unless stated)

| Abbreviation | Definition |
|---|---|
| His_3Bom | 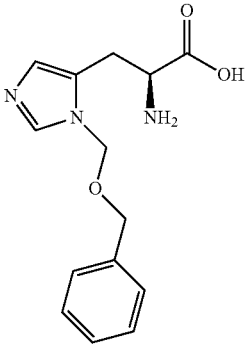 [SMILES: N[C@@H](Cc1cncn1COCc1ccccc1)C(=O)O] |
| His_3Me or 3MeHis | (3-Methyl)Histidine |
| His_Bzl | 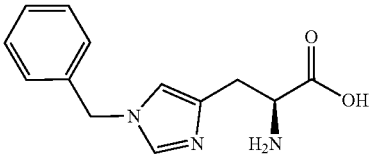 [SMILES: N[C@@H](Cc1cn(Cc2ccccc2)cn1)C(=O)O] |
| hLeu | L-homoLeucine |
| hLys(Ac) or homo-Lys(Ac) | homo-L-Lysine |
| hPhe(3,4-dimethoxy) | 3,4-dimethoxy-L-homophenylalanine |
| hSer | L-homoSerine |
| Hy | Hydrogen (Free N-terminal) |
| Hyp | 4-Hydroxy-L-Proline |
| iPr or i-Pr | Iso-Propyl |
| Lys(Ac) or K(Ac) | N-ε-acetyl-L-Lysine |
| Lys(CO2Allyl) | N-(C(O)2—Allyl)-Lysine |
| Lys(COCF$_3$) | N-ε-trifluoroacetyl-L-Lysine |
| Lys(COCF3) | N-Trifluoroacetyl-Lysine |
| Lys(COcPr) | Lys(CO—cyclopropyl) |
| Lys(COEt) | N-(C(O)—Et)-Lysine |
| Lys(COiPr) | N-(C(O)—i-Pr)-Lysine |
| Lys(COPent) | Lys(CO—pentyl) |
| Lys(COPr) | N-(C(O)—n-Pr)-Lysine |
| Lys(COtBu) | N-ε-[C(O)—t-Bu]-L-Lysine |
| Lys(R') | N-ε-[R']-L-Lysine (exemplary R'= Aib, bAla, IVA, Ala, cyclohexanoic, octanoic, —C(O)CH$_2$Ph, trifluorpropionic, Gly, acetyl, trifluoroacetyl, etc) |
| N(N2AmAnil) | N-2-aminoanilinyl-L-asparagine (L-asparagine, N-2-aminoanilinyl) |
| N(N3AmAnil) | N-3-aminoanilinyl-L-asparagine (L-asparagine, N-3-aminoanilinyl) |
| N(N4AmAnil) | N-4-aminoanilinyl-L-asparagine (L-asparagine, N-4-aminoanilinyl) |
| N(NAlkyl) | N-Alkyl-L-asparagine (L-asparagine, N-alkyl) (L) H$_2$N—C(H)(CO$_2$H)—CH$_2$—C(O)—NH(Alkyl) |
| N(NAmbu) | N-4-aminobutyl-L-asparagine (L-asparagine, N-4-aminobutyl) |
| N(NAnil) | N-anilinyl-L-asparagine (L-asparagine, N-anilinyl) |
| N(NBu) | N-butyl-L-asparagine (L-asparagine, N-butyl) |
| N(NBzl) | N-benzyl-L-asparagine (L-asparagine, N-benzyl) |
| N(Nchx) | N-cyclohexyl-L-asparagine (L-asparagine, N-cyclohexyl) |
| N(Ncpx) | N-cyclopropyl-L-asparagine (L-asparagine, N-cyclopropyl) |
| N(NEt) | N-ethyl-L-asparagine (L-asparagine, N-ethyl) |
| N(NiBu) | N-isobutyl-L-asparagine (L-asparagine, N-isobutyl) |
| N(NiPr) | N-isopropyl-L-asparagine (L-asparagine, N-isopropyl) |
| N(NMe) | N-methyl-L-asparagine (L-asparagine, N-methyl) |
| N(Npip) | N-piperidinyl-L-asparagine (L-asparagine, N-piperidinyl) |
| N(NtBu) | N-tert-butyl-L-asparagine (L-asparagine, N-tert-butyl) |
| N3_Acid | N$_3$—CH$_2$—COOH |
| Nle | L-Norleucine |
| N-MeAla | N-Methyl-L-Alanine |
| N-MeArg | N-Methyl-L-Arginine |

TABLE 1-continued

Abbreviations of Non-Natural Amino Acids and Chemical Moieties (for amino acid derivatives, all L unless stated)

| Abbreviation | Definition |
| --- | --- |
| N-MeAsn | N-Methyl-L-Asparagine |
| N-MeGln | N-Methyl-L-Glutamine |
| N-MeLys | N-Methyl-Lysine |
| N-Me-Lys(Ac) | N-ε-Acetyl-N-Methyl-L-lysine |
| N-MeTrp | N-Methyl-L-Tryptophan |
| NMeβA or NMebA | N-Methyl-beta-Alanine |
| Octgly | L-Octylglycine |
| Orn | L-Ornathine |
| Orn(COMe) or Orn(Ac) | N-Acetyl-L-ornithine (structure) |
| Paf(Ac) | 4-($CH_3C(O)NH$)—L-phenylalanine |
| Pen | L-Penicillamine |
| Pen(sulfoxide) | L-Penicillamine(sulfoxide) |
| Phe((3,4-diOMe) | 4-(3,4-dimethoxy)phenylalanine |
| Phe(2,4-$Me_2$) | 2,4-dimethyl-L-phenylalanine |
| Phe(3,4-$Cl_2$) | 3,4-dichloro-L-phenylalanine |
| Phe(3,4-dimethoxy) | 3,4-dimethoxy-L-phenylalanine |
| Phe(3,5-$F_2$) | 3,5-difluoro-L-phenylalanine |
| Phe(4_2ae_Boc) or AEF(Boc) | 4-(2-(N-t-Boc)—aminoethoxy)phenylalanine |
| Phe(4-Br) | 4-bromo-L-phenylalanine |
| Phe(4-$CF_3$) | 4-Trifluoromethyl-L-Phenylalanine |
| Phe(4-CN) | 4-cyano-L-phenylalanine |
| Phe(4-$CO_2H$) | 4-Carboxy-L-phenylalanine |
| Phe(4-$CONH_2$) or Phe(Cmd) | 4-Carbamoyl-L-phenylalanine |
| Phe(4-F) | 4-Fluoro-L-Phenylalanine |
| Phe-(4-Guanidino) | 4-Guanidine-L-Phenylalanine |
| Phe(4-Me) | 4-methyl-L-phenylalanine |
| Phe(4-$N_3$) | 4-azidophenylalanine |
| Phe(4-$NH_2$) | 4-amino-L-phenylalanine |
| Phe(4-$NH_2$), paf | 4-amino-L-phenylalanine |
| Phe(4-OAllyl) | O—Allyl-L-Tyrosine |
| Phe(4-OBzl) | O—Benzyl-L-tyrosine |
| Phe(4-OMe) | 4-Methoxy-L-phenylalanine |
| Phe(4-Phenoxy) | 4-Phenoxy-L-phenylalanine |
| Phe(penta-F) | pentafluoro-L-phenylalanine |
| Phe(t-Bu) | t-butyl-L-phenylalanine |
| Phe[(aMe)-4-(2-aminoethoxy)] | a-Methyl-4-(2-aminoethoxy)phenylalanine |
| Phe[4-(2-acetylaminoethoxy)] or Phe[4-(2-aminoethoxy)Ac] or AEF(Ac) | L-4-[(Ac—NH—$CH_2CH_2$—O)]—Ph—$CH_2$—C(H)($NH_2$)$CO_2$H or 4-(2-acetylaminoethoxy)-L-phenylalanine |
| Phe[4-(2-aminoethoxy)] or F(4-2ae) or AEF | 4-(2-aminoethoxy)-L-phenylalanine (structure) |

TABLE 1-continued

Abbreviations of Non-Natural Amino Acids and Chemical Moieties (for amino acid derivatives, all L unless stated)

| Abbreviation | Definition |
| --- | --- |
| Phe[4-aminomethyl] | (4-aminomethyl)Phenylalanine |
| Phe_4ae_BH or AEF(BH) | Phe[4-(2-(N-(4-hydroxy-3-methylphenyl)propionylamino)ethoxy) |
| Phe_4ae_Ethyl | Phe[4-(2-(N-propionylamino)ethoxy)]- |
| Phe3OH | 3-hydroxy-L-phenylalanine |
| Phe42aeSMSB | |
| Phe4NH2Ac, Paf(Ac) | 4-($CH_3C(O)NH$)—L-phenylalanine |
| Phe4Pip | 4-piperidinephenylalanine |
| Phe-tetraF | Tetrafluoro-L-phenylalanine |
| Quin or 3Quin or 3-Quin | |
| rbMe2Nal or (R)-bMe2Nal or bMe2Nal(2S,3R) | (R)-(2-naphthyl)-beta-methyl-alanine |
| Sarc or NMeGly | Sarcosine |
| Spiral_Pip | |

TABLE 1-continued

Abbreviations of Non-Natural Amino Acids and Chemical Moieties (for amino acid derivatives, all L unless stated)

| Abbreviation | Definition |
|---|---|
| SMSBC(O) | 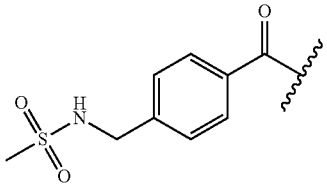 [SMILES: *C(=O)c1ccc(CNS(C)(=O)=O)cc1] |
| t-butyl-Ala | 3-(tert-butyl)-L-Alanine—OH |
| t-butyl-Gly | tert-butyl-glycine |
| Tic | (3S)-1,2,3,4-Tetrahydroisoquinoline-7-hydroxy-3-carboxylic Acid |
| Tic | 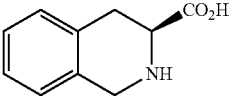<br>L-1,2,3,4-tetrahydro-isoquinoline-3-carboxylic acid |
| Trp_4Aza | 4-aza-tryptophan |
| Trp_7Aza | 7-aza-tryptophan |
| Trp5Br | 5-bromo-L-tryptophan |
| Trp5Me | 5-methyl-L-tryptophan |
| Trp7Cl | 7-chloro-L-tryptophan |
| Trp7F | 7-fluoro-L-tryptophan |
| Trp7Me | 7-methyl-L-tryptophan |
| Trp-psi | 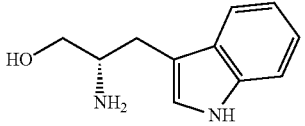 |
| Tyr(3-t-Bu) | 3-t-butyl—L-tyrosine |
| W(4-F) | 4-fluoro-L-tryptophan |
| W(5-Ca) | (5-Carboxamido)-L-Tryptophan |
| W(5-CN) | 5-cyano-L-tryptophan |
| W(5-Ph) | 5-Phenyl-Tryptophan |
| W(6-Ph) | 6-Phenyl-Tryptophan |
| W(7-(1-Nal) | 7-(naphth-1-yl)-Tryptophan |
| W(7-(2-FPh)) | 7-(2-Fluoro-phenyl)Tryptophan |
| W(7-(2-Nal) | 7-(naphth-2-yl)-Tryptophan |
| W(7-(3,5-t-Bu-Ph)) | 7-(3,5-di-tert-butylphenyl)-Tryptophan |
| W(7-(3BiPh)) | 7-(biphenyl-3-yl)-Tryptophan |
| W(7-(3-carboxamidophenyl)) | 7-(3-carboxamidophenyl)-Tryptophan |
| W(7-(3-CF3Ph)) | 7-(3-trifluoromethylphenyl)-Tryptophan |
| W(7-(3-iPrPh)) | 7-(3-isopropylphenyl)-Tryptophan |
| W(7-(3-MePh)) | 7-(3-methylphenyl)-Tryptophan |
| W(7-(3-OCF3Ph)) | 7-(3-trifluoromethoxyphenyl)-Tryptophan |
| W(7-(3-OMePh)) | 7-(3-MethoxyPhenyl)-Tryptophan |
| W(7-(3-pyrazol-1-yl)) | 7-(3-pyrazol-1-yl)-Tryptophan |
| W(7-(4-Anthracen-5-yl)) | 7-(4-Anthracen-5-yl)Tryptophan |
| W(7-(4BiPh)) | 7-(biphenyl-4-yl)-Tryptophan |
| W(7-(4-CONH2Ph)) | 7-(4-carboxamidophenyl)-Tryptophan |
| W(7-(4Quin)) | 7-(quinoline-4-yl)-Tryptophan |
| W(7-(Phenanthren-5-yl)) | 7-(Phenanthren-5-yl)Tryptophan |
| W(7-CN) | 7-cyano-L-tryptophan |
| W(7-imidazopyridinyl) | 7-(imidazopyridinyl)-Tryptophan |
| W(7-indazol-5-yl) | 7-(indazol-5-yl)-Tryptophan |
| W(7-Ph) | 7-Phenyl-Tryptophan |
| W(7-pyrimidin-5-yl) | 7-(pyrimidin-5-yl)-Tryptophan |
| W(7-thienyl) | 7-thienyl-Tryptophan |
| β-Glu | L-β-Glutamic acid |
| βhGln or b-hGln, or b-homoGln | Lβ-homoglutamine |
| βhGlu | L-β-homoglutamic acid |
| βhPhe | L-β-homophenylalanine |
| βhPro | L-β-homoproline |

TABLE 1-continued

Abbreviations of Non-Natural Amino Acids and Chemical Moieties (for amino acid derivatives, all L unless stated)

| Abbreviation | Definition |
| --- | --- |
| βhTrp | L-β-homoTryptophan |
| α-MeArg, a-MeArg, or alpha-MeArg | alpha-methyl-L-Arginine |
| α-MeCys, alpha-MeCys, or a-MeCys | alpha-methyl-L-Cysteine |
| α-MeLeu, a-MeLeu, alpha-MeLeu | alpha-methyl-L-Leucine |
| α-MeLys(Ac), a-MeLys(Ac), or alpha-MeLys(Ac) | ε-acetyl-alpha-methyl-L-Lysine |
| α-MeLys, a-MeLys, or alpha-MeLys | alpha-methyl-L-Lysine |
| α-MeOrn | alpha-methyl-L-Ornithine |
| α-MePhe or a-MePhe or a-Me-Phe | alpha-methyl-L-Phenylalanine |
| α-MeTrp | alpha-methyl-L-Tryptophan |
| α-MeTyr | alpha-methyl-L-Tyrosine |
| α-DiethylGly | α-DiethylGlycine |
| βAla, beta-Ala, or bA | beta-Alanine |
| βhAla | beta homo-L-Alanine |
| βhLeu | beta homo-L-Leucine |
| βhTrp | beta homo-L-Trptophan |
| βhTyr | beta homo-L-Tyrosine |
| βhVal | beta homo-L-Valine |

Throughout the present specification, unless naturally occurring amino acids are referred to by their full name (e.g., alanine, arginine, etc.), they are designated by their conventional three-letter or single-letter abbreviations (e.g., Ala or A for alanine, Arg or R for arginine, etc.). Unless otherwise indicated, three-letter and single-letter abbreviations of amino acids refer to the L-isomeric form of the amino acid in question. The term "L-amino acid," as used herein, refers to the "L" isomeric form of a peptide, and conversely the term "D-amino acid" refers to the "D" isomeric form of a peptide (e.g., Dasp, (D)Asp or D-Asp; Dphe, (D)Phe or D-Phe). Amino acid residues in the D isomeric form can be substituted for any L-amino acid residue, as long as the desired function is retained by the peptide. D-amino acids may be indicated as customary in lower case when referred to using single-letter abbreviations.

In the case of less common or non-naturally occurring amino acids, unless they are referred to by their full name (e.g. sarcosine, ornithine, etc.), frequently employed three- or four-character codes are employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), β-Pro (pyrrolidine-3-carboxylic acid), and 8Ado (8-amino-3,6-dioxaoctanoic acid), Abu (2-amino butyric acid), βhPro (β-homoproline), βhPhe (β-homophenylalanine) and Bip (β,β diphenylalanine), and Ida (Iminodiacetic acid).

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the invention, a C-terminal "—OH" moiety may be substituted for a C-terminal "—NH$_2$" moiety, and vice-versa.

One of skill in the art will appreciate that certain amino acids and other chemical moieties are modified when bound to another molecule. For example, an amino acid side chain may be modified when it forms an intramolecular bridge with another amino acid side chain, e.g., one or more hydrogen may be removed or replaced by the bond. Accordingly, as used herein, reference to an amino acid or modified amino acid present in a peptide dimer of the present invention (e.g., at position X4 or position X9) is meant to include the form of such amino acid or modified amino acid present in the peptide both before and after forming the intramolecular bond.

The term "dimer," as used herein, refers broadly to a peptide comprising two or more monomer subunits. Certain dimers comprise two monomer subunits comprising a sequence of Formula (I) or set forth herein. Dimers of the present invention include homodimers and heterodimers. A monomer subunit of a dimer may be linked at its C- or N-terminus, or it may be linked via internal amino acid residues. Each monomer subunit of a dimer may be linked through the same site, or each may be linked through a different site (e.g., C-terminus, N-terminus, or internal site).

The term "NH$_2$," as used herein, can refer to a free amino group present at the amino terminus of a polypeptide. The term "OH," as used herein, can refer to a free carboxy group present at the carboxy terminus of a peptide. Further, the term "Ac," as used herein, refers to Acetyl protection through acylation of the C- or N-terminus of a polypeptide. In certain peptides shown herein, the NH$_2$ locates at the C-terminus of the peptide indicates an amino group.

The term "carboxy," as used herein, refers to —CO$_2$H.

The term "isostere replacement," as used herein, refers to any amino acid or other analog moiety having chemical and/or structural properties similar to a specified amino acid. In certain embodiments, an isostere replacement is a conservative substitution or an analog of a specified amino acid.

The term "cyclized," as used herein, refers to one part of a polypeptide molecule being linked to another part of the polypeptide molecule to form a closed ring, such as by forming a disulfide bridge or thioether bond.

The term "subunit," as used herein, refers to one of a pair of polypeptide monomers that are joined to form a dimer peptide composition.

The term "linker moiety," as used herein, refers broadly to a chemical structure that is capable of linking or joining together two peptide monomer subunits to form a dimer.

The term "pharmaceutically acceptable salt," as used herein, represents salts or zwitterionic forms of the peptides or compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

The term "N(alpha)Methylation", as used herein, describes the methylation of the alpha amine of an amino acid, also generally termed as an N-methylation.

The term "sym methylation" or "Arg-Me-sym", as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds", as used herein refers to various compounds with carboxylic acid functionality that are used to acylate the N-terminus of an amino acid or a monomer or dimer, e.g., a monomer subunit prior to forming a C-terminal dimer. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, 3-Fluoromethylbutyric acid, Tetrahedro-2H-Pyran-4-carboxylic acid.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

"Halo" or "halogen" refers to bromo (Br), chloro (Cl), fluoro (F) or iodo (I) substituents.

The terms "haloalkyl" includes alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

An "alkoxy" group refers to a (alkyl)O— group, where alkyl is as defined herein.

An "aryloxy" group refers to an (aryl)O— group, where aryl is as defined herein.

"Carboxy" means a —C(O)OH radical.

"Aminocarbonyl" or "carboxamido" refers to a —CONH$_2$ radical.

"2-Aminoethoxy" refers to —OCH$_2$CH$_2$—NH$_2$ radical.

"2-Acetylaminoethoxy" refers to —OCH$_2$CH$_2$—N(H)C(O)Me radical.

The term "mammal" refers to any mammalian species such as a human, mouse, rat, dog, cat, hamster, guinea pig, rabbit, livestock, and the like.

As used herein, a "therapeutically effective amount" of the peptide inhibitor of the invention is meant to describe a sufficient amount of the peptide inhibitor to treat an IL-23/IL-23R-related disease, including but not limited to any of the diseases and disorders described herein (for example, to reduce inflammation associated with IBD). In particular embodiments, the therapeutically effective amount will achieve a desired benefit/risk ratio applicable to any medical treatment.

An "analog" of an amino acid, e.g., a "Phe analog" or a "Tyr analog" means an analog of the referenced amino acid. A variety of amino acid analogs are known and available in the art, including Phe and Tyr analogs. In certain embodiments, an amino acid analog, e.g., a Phe analog or a Tyr analog comprises one, two, three, four or five substitutions as compared to Phe or Tyr, respectively. In certain embodiments, the substitutions are present in the side chains of the amino acids. In certain embodiments, a Phe analog has the structure Phe($R^2$), wherein $R^2$ is a Hy, OH, $CH_3$, $CO_2H$, $CONH_2$, $CONH_2OCH_2CH_2NH_2$, t-Bu, $OCH_2CH_2NH_2$, phenoxy, $OCH_3$, OAllyl, Br, Cl, F, $NH_2$, N3, or guanadino. In certain embodiments, $R^2$ is $CONH_2OCH_2CH_2NH_2$, $OCH_3$, $CONH_2$, $OCH_3$ or $CO_2H$. Examples of Phe analogs include, but are not limited to: hPhe, Phe(4-OMe), α-Me-Phe, hPhe(3,4-dimethoxy), Phe(4-$CONH_2$), Phe(4-phenoxy), Phe(4-guanadino), Phe(4-tBu), Phe(4-CN), Phe(4-Br), Phe(4-OBzl), Phe(4-$NH_2$), BhPhe(4-F), Phe(4-F), Phe(3,5 DiF), Phe($CH_2CO_2H$), Phe(penta-F), Phe(3,4-$Cl_2$), Phe(3,4-F2), Phe(4-$CF_3$), ββ-diPheAla, Phe(4-$N_3$), Phe[4-(2-aminoethoxy)], 4-Phenylbenzylalanine, Phe(4-$CONH_2$), Phe(3,4-Dimethoxy), Phe(4-$CF_3$), Phe(2,3-$Cl_2$), and Phe(2,3-F2). Examples of Tyr analogs include, but are not limited to: hTyr, N-Me-Tyr, Tyr(3-tBu), Tyr(4-N3) and p3hTyr.

Peptide Inhibitors of IL-23R

Genome-wide association studies (GWAS) have demonstrated significant association of the IL-23 receptor (IL-23R) gene with inflammatory bowel disease (IBD), suggesting that perturbation of IL-23 signaling could be relevant to the pathogenesis of this disease and other inflammatory diseases and disorders. The present invention provides compositions and methods to modulate the IL-23 pathway through antagonism of IL-23R.

The present invention relates generally to peptides that have IL-23R antagonist activity, including both peptide monomers and peptide dimers. In certain embodiments, this invention demonstrates a new paradigm for treatment of IBD and other diseases and disorders by oral delivery of antagonists of IL-23. IBD represents a local inflammation of the intestinal tissue; therefore, advantageous therapeutic agents act from the luminal side of the intestine, yielding high drug concentrations in diseased tissue, minimizing systemic availability and resulting in improved efficacy and safety when compared to systemic approaches. Oral administration of the compounds of the present invention is expected to maximize drug levels in diseased intestinal tissues while limiting drug concentrations in circulation, thereby providing efficacious, safe, and durable delivery for life-long treatment of IBD and other diseases and disorders.

In certain embodiments, the present invention relates to various peptides, or peptide dimers comprising hetero- or homo-monomer subunits, that form cyclized structures through disulfide or other bonds. In certain embodiments, the disulfide or other bonds are intramolecular bonds. The cyclized structure of the peptide monomer inhibitors and the monomer subunits of the peptide dimer inhibitors has been shown to increase potency and selectivity of the peptide inhibitors. In certain embodiments, a peptide dimer inhibitor may include one or more intermolecular bonds linking the two monomer peptide subunits within the peptide dimer inhibitor, e.g., an intermolecular bridge between two Pen residues, one in each peptide monomer subunit.

The present invention provides peptide inhibitors that bind to IL-23R, which may be monomers or dimers. In particular embodiments, the peptide inhibitors inhibit the binding of IL-23 to IL-23R. In certain embodiments, the IL-23R is human IL-23R, and the IL-23 is human IL-23. In certain embodiments, a peptide inhibitor of the present invention reduces IL-23 binding to IL-23R by at least 20%, at least 30%, at least 40%, at least 50%, at least 60%, at least 70%, at least 80%, or at least 90% as compared to a negative control peptide. Methods of determining binding are known in the art and include ELISA assays, as described in the accompanying Examples.

In certain embodiments, a peptide inhibitor of the present invention has an IC50 of >1 mM, <1 mM, 500 nM to 1000 nM, <500 nM, <250 nM, <100 nM, <50 nM, <25 nM, <10 nM, <5 nM, <2 nM, <1 nM, or <5 mM, e.g., for inhibiting binding of IL-23 to IL-23R (e.g., human IL-23 and human IL-23R). Methods of determining activity are known in the art and include any of those described in the accompanying Examples.

In certain embodiments, a peptide inhibitor of the present invention has increased stability, increased gastrointestinal stability, or increased stability in stimulated intestinal fluid (SIF) or simulated gastric fluid (SGF), and/or under redox conditions (e.g., DTT) as compared to a control peptide. In certain embodiments, a control peptide is an unrelated peptide of the same or similar length. In particular embodiments, a control peptide is a peptide having the identical or a highly related amino acid sequence (e.g., >90% sequence identity) as the peptide inhibitor. In particular embodiments, a control peptide is a peptide having the identical or a highly related amino acid sequence (e.g., >90% sequence identity) as the peptide inhibitor, but which does not have a cyclized structure, e.g., through an intramolecular bond between two amino acid residues within the control peptide, or which is not dimerized, or which does not comprise a conjugate for stabilization. In particular embodiments, the only difference between the peptide inhibitor and the control peptide is that the peptide inhibitor comprises one or more amino acid substitutions that introduce one or more amino acid residues into the peptide inhibitor, wherein the introduced amino residue(s) forms an intrasulfide disulfide or thioether bond with another amino acid residue in the peptide inhibitor. One example of a control for a peptide dimer inhibitor is a monomer having the same sequence as one of the monomer subunits present in the peptide dimer inhibitor. One example of a control for a peptide inhibitor comprising a conjugate is a peptide having the same sequence but not including the conjugated moiety. In certain embodiments, a control peptide is a peptide (e.g., a naturally-occurring peptide) corresponding to a region of IL-23 that binds to IL-23R.

Methods of determining the stablity of a peptide are known in the art. In certain embodiments, the stability of a peptide inhibitor is determined using an SIF assay, e.g., as described in Example 3. In certain embodiments, the stability of a peptide inhibitor is determined using an SGF assay, e.g., as described in Example 3. In particular embodiments, a peptide inhibitor has a half-life (e.g., in SIF or SGF or DTT) under a given set of conditions (e.g., temperature) of greater than 1 minute, greater than 10 minutes, greater than 20 minutes, greater than 30 minutes, greater than 60 minutes, greater than 90 minutes, greater than 120 minutes, greater than 3 hours, or greater than four hours when exposed to SIF or SGF or DTT. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of a peptide of the present invention is determined by incubating the peptide with pre-warmed human serum (Sigma) at 37° C. Samples are taken at various time points, typically up to 24 hours, and the stability of the sample is analyzed by separating the peptide or peptide dimer from the serum proteins and then analyzing for the presence of the peptide or peptide dimer of interest using LC-MS.

In some embodiments, a peptide inhibitor of the present invention exhibits improved solubility or reduced aggregation characteristics as compared to a control peptide. Solubility may be determined via any suitable method known in the art. In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a control peptide. In some embodiments, reduced aggregation means the peptide has less aggregation in a given liquid under a given set of conditions than a control peptide.

In certain embodiments advantageous for achieving high compound concentrations in intestinal tissues when delivered orally, peptide inhibitors of the present invention are stable in the gastrointestinal (GI) environment. Proteolytic metabolism in the GI tract is driven by enzymes (including pepsins, trypsin, chymotrypsin, elastase, aminopeptidases, and carboxypeptidase A/B) that are secreted from the pancreas into the lumen or are produced as brush border enzymes. Proteases typically cleave peptides and proteins that are in an extended conformation. In the reducing environment of intestinal fluids, disulfide bonds may be broken, resulting in a linear peptide and rapid proteolysis. This luminal redox environment is largely determined by the Cys/CySS redox cycle. In enterocytes, relevant activities include numerous digestive enzymes such as CYP450 and UDP-glucuronsyl-transferase. Finally, bacteria, present in the large intestine at concentration ranging from $10^{10}$ to $10^{12}$ CFU/ml, constitute another metabolic barrier. In certain embodiments, the peptide inhibitors are stable to various pHs that range from strongly acidic in the stomach (pH 1.5-1.9), trending towards basic in the small intestine (pH 6-7.5), and then weakly acidic in the colon (pH 5-7). Such peptide inhibitors are stable during their transit through the various GI compartments, a process that has been estimated to take 3-4 h in the intestine and 6-48 h in the colon.

In some embodiments, the peptide inhibitors of the present invention have less degradation, e.g., over a period of time (i.e., more degradation stability), e.g., greater than or about 10% less, greater than or about 20% less, greater than or about 30% less, greater than or about 40 less, or greater than or about 50% less degradation than a control peptide. In some embodiments, degradation stability is determined via any suitable method known in the art. In some embodiments, the degradation is enzymatic degradation. For example, in certain embodiments, the peptide inhibitors have reduced susceptibility to degradation by trypsin, chhrmotrypsin or elastase. In some embodiments, suitable methods known in the art for determining degradation stability include the method described in Hawe et al., J Pharm Sci, VOL. 101, No. 3, 2012, p 895-913, incorporated herein in its entirety. Such methods are in some embodiments used to select potent peptide sequences with enhanced shelf lifes. In particular embodiments, peptide stability is determined using a SIF assay or SGF assay, e.g., as described in PCT Publication No. WO 2016/011208.

In certain embodiments, peptide inhibitors of the present invention inhibit or reduce IL-23-mediated inflammation. In related embodiments, peptide inhibitors of the present invention inhibit or reduce IL-23-mediated secretion of one or more cytokines, e.g., by binding to IL-23R on the cell surface, thus inhibiting IL-23 binding to the cell. In particular embodiments, peptide inhibitors of the present invention inhibit or reduce IL-23-mediated activation of Jak2, Tyk2, Stat1, Stat3, Stat4, or Stat5. Methods of determining inhibition of cytokine secretion and inhibition of signaling molecules are known in the art. For example, inhibiton of IL-23/IL-23R signaling may be determined by measuring inhibition of phospho-Stat3 levels in cell lysates, e.g., as described in PCT Publication No. WO 2016/011208.

In certain embodiments, peptide inhibitors have increased redox stability as compared to a control peptide. A variety of assays that may be used to determine redox stability are known and available in the art. Any of these may be used to determine the redox stability of peptide inhibitors of the present invention.

In certain embodiments, the present invention provides various peptide inhibitors that bind or associate with the IL-23R, in vitro or in vivo, to disrupt or block binding between IL-23 and IL-23R. In certain embodiments, the peptide inhibitors bind and/or inhibit human IL-23R. In certain embodiments, the peptide inhibitors bind and/or inhibit both human and rodent IL-23R. In certain embodiments, the peptide inhibitors bind and/or inhibit both human and rat IL-23R. In certain embodiments, the peptide inhibitors bind and/or inhibit human IL-23R, rat IL-23R, and cynomolgus monkey IL-23R. In particular embodiments, the peptide inhibitors inhibit rat IL-23R and/or cynomolgus monkey IL-23R at least 50%, at least 60%, at least 70%, at least 80%, at least 90%, or at least 95% as well as they bind or inhibit human IL-23R, e.g., as determined by an assay described herein. In certain embodiments, the peptide inhibitors preferentially bind and/or inhibit human IL-23R and/or rat IL-23R and/or cynomolgus monkey IL-23R as compared to mouse IL-23R. In particular embodiments, the peptide inhibitors preferentially bind to rat IL-23R as compared to mouse IL-23R. In particular embodiments, the peptide inhibitors preferentially bind to human IL-23R as compared to mouse IL-23R. In particular embodiments, the peptide inhibitors preferentially bind to cynomolgus monkey IL-23R as compared to mouse IL-23R. In certain embodiments, binding of a peptide inhibitor to mouse IL-23R is less than 75%, less than 50%, less than 40%, less than 30%, less than 20%, or less than 10% of binding of the same peptide inhibitor to human IL-23R and/or rat IL-23R and/or cynomolgus monkey IL-23R. In certain embodiments of peptide inhibitors that preferentially bind and/or inhibit human IL-23R and/or rat IL-23R and/or cynomolgus monkey IL-23R as compared to mouse IL-23R, the peptide inhibitor binds to a region of IL-23R that is disrupted by the presence of additional amino acids present in mouse IL-23R but not human IL-23R or rat IL-23 or cynomolgus monkey IL-23R. In certain embodiments, the additional amino acids present in the mouse IL-23R are in the region corresponding to about amino acid residue 315 to about amino acid residue 340 of the mouse IL23R protein, e.g., amino acid region NWQPWSSPFVHQTSQETGKR (SEQ ID NO:322). In particular embodiments, the peptide inhibitors bind to a region of human IL-23R from about amino acid 230 to about amino acid residue 370.

In certain embodiments, peptide inhibitors show GI-restricted localization following oral administration. In particular embodiments, greater than 50%, greater than 60%, greater than 70%, greater than 80%, or greater than 90% of orally administered peptide inhibitor is localized to gastrointestinal organs and tissues. In particular embodiments, blood plasma levels of orally administered peptide inhibitor are less than 20%, less than 10%, less than 5%, less than 2%, less than 1% or less than 0.5% the levels of peptide inhibitor found in the small intestine mucosa, colon mucosa, or proximal colon.

The various peptide inhibitors of the invention may be constructed solely of natural amino acids. Alternatively, the peptide inhibitors may include non-natural amino acids including, but not limited to, modified amino acids. In certain embodiments, modified amino acids include natural amino acids that have been chemically modified to include a group, groups, or chemical moiety not naturally present on the amino acid. The peptide inhibitors of the invention may additionally include one or more D-amino acids. Still further, the peptide inhibitors of the invention may include amino acid analogs.

In certain embodiments, peptide inhibitors of the present invention include one or more modified or unnatural amino acids. In some embodiments of the present invention, a peptide inhibitor includes one or more non-natural amino acids shown in Table 1. In certain embodiments, peptide inhibitors of the present invention include any of those described herein, including but not limited to any of those comprising an amino acid sequence or peptide inhibitor structure shown in any one of the tables herein.

The present invention also includes any of the peptide inhibitors described herein in either a free or a salt form. Thus, embodiments of any of the peptide inhibitors described herein (and related methods of use thereof) include a pharmaceutically acceptable salt of the peptide inhibitor.

The present invention also includes variants of any of the peptide inhibitors described herein, including but not limited to any of those comprising a sequence shown in any one of the tables herein, wherein one or more L-amino acid residue is substituted with the D isomeric form of the amino acid residue, e.g., an L-Ala is substituted with a D-Ala.

Peptide inhibitors described herein include isotopically-labeled peptide inhibitors. In particular embodiments, the present disclosure provides peptide inhibitors identical to any of those having or recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Furthermore, substitution with isotopes such as deuterium, i.e., $^{2}H$, can afford certain therapeutic advantages resulting from greater metabolic stability, for example increased in vivo half-life or reduced dosage requirements.

The present invention also includes any of the peptide monomer inhibitors described herein linked to a linker moiety, including any of the specific linker moieties described herein. In particular embodiments, a linker is attached to an N-terminal or C-terminal amino acid, while in other embodiments, a linker is attached to an internal amino acid. In particular embodiments, a linker is attached to two internal amino acids, e.g., an internal amino acid in each of two monomer subunits that form a dimer. In some embodiments of the present invention, a peptide inhibitor is attached to one or more linker moieties shown.

The present invention also includes peptides and peptide dimers comprising a peptide having at least 90%, at least 95%, at least 98%, or at least 99% sequence identity to the peptide sequence of a peptide inhibitor described herein. In particular embodiments, peptide inhibitors of the present invention comprise a core peptide sequence and one or more N-terminal and/or C-terminal modification (e.g., Ac and NH2) and/or one or more conjugated linker moiety and/or half-life extension moiety. As used herein, the core peptide sequence is the amino acid sequence of the peptide absent such modifications and conjugates.

In certain embodiments, a peptide inhibitor or a monomer subunit of a peptide inhibitor of the present invention comprises, consists essentially of, or consists of 7 to 35 amino acid residues, 8 to 35 amino acid residues, 9 to 35 amino acid residues, 10 to 35 amino acid residues, 7 to 25 amino acid residues, 8 to 25 amino acid residues, 9 to 25 amino acid residues, 10 to 25 amino acid residues, 7 to 20 amino acid residues, 8 to 20 amino acid residues, 9 to 20 amino acid residues, 10 to 20 amino acid residues, 7 to 18 amino acid residues, 8 to 18 amino acid residues, 9 to 18 amino acid residues, or 10 to 18 amino acid residues, and, optionally, one or more additional non-amino acid moieties, such as a conjugated chemical moiety, e.g., a PEG or linker moiety. In particular embodiments, a peptide inhibitor of the present invention (or a monomer subunit thereof), including but not limited to those of any embodiments of Formula I, is greater than 10, greater than 12, greater than 15, greater than 20, greater than 25, greater than 30 or greater than 35 amino acids, e.g., 35 to 50 amino acids. In certain embodiments, a peptide inhibitor (or a monomer subunit thereof) is less than 50, less than 35, less than 30, less than 25, less than 20, less than 15, less than 12, or less than 10 amino acids. In particular embodiments, a monomer subunit of a peptide inhibitor (or a peptide monomer inhibitor) comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues. In particular embodiments, a monomer subunit of a peptide inhibitor of the present invention comprises or consists of 10 to 23 amino acid residues and, optionally, one or more additional non-amino acid moieties, such as a conjugated chemical moiety, e.g., a PEG or linker moiety. In various embodiments, the monomer subunit comprises or consists of 7 to 35 amino acid residues, 7 to 20 amino acid residues, 8 to 20 amino acid residues, 9 to 20 amino acid residues, 10 to 20 amino acid residues, 8 to 18 amino acid residues, 8 to 19 amino acid residues, 8 to 18 amino acid residues, 9 to 18 amino acid residues, or 10 to 18 amino acid residues. In particular embodiments of any of the various Formulas described herein.

Certain illustrative peptide inhibitors described herein comprise 12 or more amino acid residues. However, the present invention also includes peptide inhibitors comprising a fragment of any of the peptide sequences described herein, including peptide inhibitors having 7, 8, 9, 10, or 11 amino acid residues. For example, peptide inhibitors of the present invention include peptides comprising or consisting of X4-X9, X4-X10, X4-X11, X4-X12, X4-X13, X4-X14, or X4-X15.

In particular embodiments of the present invention, the amino acid sequences of the peptide inhibitors are not present within an antibody, or are not present within a $V_H$ or $V_L$ region of an antibody.

Peptide Inhibitors

Peptide inhibitors of the present invention include peptides comprising or consisting of any of the amino acid sequences described herein, compounds having any of the structures described herein, including compounds comprising any of the peptide sequences described herein, and dimers of any of such peptides and compounds. Illustrative peptides of the invention comprise an amino acid sequence or structure described in any of the accompanying tables.

In certain embodiments, the present invention includes a monocyclic peptide inhibitor of an interleukin-23 receptor, or a pharmaceutically acceptable salt or solvate thereof, wherein the peptide inhibitor comprises an amino acid sequence of Formula (I):

X3-X4-X5-X6-X7-X8-X9-X10-X11-X12-X13-X14-X15-X16     (I)

wherein

X3 is absent or any amino acid;

each X4, X5, and X6 is independently any amino acid;

X7 is unsubstituted Trp, Trp-psi or Trp substituted with cyano, halo, alkyl, haloalkyl, hydroxy, alkoxy, substituted or unsubstituted aryl, or substituted or unsubstituted heteroaryl;

X8 is Gln, alpha-MeLys, alpha-MeLeu, alpha-MeLys (Ac), beta-homoGln, Cit, Glu, Phe, Paf(Ac), Phe4NH2Ac Asn, Thr, Val, Aib, alpha-MeGln, alpha-MeAsn, Lys(Ac), Dab(Ac), Dap(Ac), homo-Lys(Ac), 1-Nal, 2-Nal, or Trp;

X9 is Abu, Cys, (D)Cys, alpha-MeCys, (D)Pen, Pen or Pen(sulfoxide);

X10 is unsubstituted Phe, or Phe substituted with halo, alkyl, haloalkyl, hydroxy, alkoxy, carboxy, carboxamido, 2-aminoethoxy, or 2-acetylaminoethoxy, AEF, AEF(Ac), AEF(BH), AEF(Boc), AEF(Me)2, bMeR-Phe, Phe42ae-ethyl, Phe42aeSMSB, Phe4Pip;

X11 is 6amido2Nal, 6OMe2Nal, bMe2Nal(2S,3R), rbMe2Nal, 2-Nal, aMe(2-Nal), Phe(2-Me), Phe(3-Me), Phe(4-Me), Phe(3,4-dimethoxy), 1-Nal, unsubstituted Trp, or Trp substituted with cyano, halo, alkyl, haloalkyl, hydroxy, or alkoxy;

X12 is 4diFAchx, Achx, Acpx, AmeK(Boc), 4-amino-4-carboxy-tetrahydropyran (THP), alpha-MeLys, alpha-MeLeu, alpha-MeArg, alpha-MePhe, alpha-MeLeu, alpha-MeLys, alpha-MeAsn, alpha-MeTyr, Ala, cyclohexylAla, 1-aminocyclohexylAla (Ache), Acve, Lys, or Aib;

X13 and X14 is independently any amino acid;

i) X16 is absent; and X15 is His, Phe_tetraF, Phe_3OH, ameF, Aib, THP, Phe, substituted Phe, substituted (D)Phe, α-MePhe, substituted α-MePhe, Trp, substituted Trp, 1-Nal, aMe(1-Nal), substituted 1-Nal, 2-Nal, aMe(2-Nal), substituted 2-Nal, or N-substituted Asn; provided that the peptide inhibitor is other than:

(SEQ ID NO: 151)
Ac-[Pen]-N-T-[W(7-Me)]-[Cit]-[Pen]-Phe[4-(2-aminoethoxy)]-[2-Nal]-[a-MeLys]-[Lys(Ac)]-N-[Aib]-NH₂;
or
(SEQ ID NO: 201)
Ac-[(D)Arg]-[Abu]-Q-T-[W(7-Me)]-[Lys(Ac)]-[Cys]-Phe[4-(2-aminoethoxy)]-[2-Na]-[a-MeLys]-[Lys(Ac)]-N-[a-MePhe]-NH₂;

or ii) X16 is paf, Aib, 3Pal, Phe, substituted Phe, substituted (D)Phe, substituted or unsubstited Tyr, unsubstituted (D)Tyr, α-MePhe, substituted α-MePhe, b-hPhe, 1-Nal, aMe(1-Nal), substituted 1-Nal, 2-Nal, aMe(2-Nal), substituted 2-Nal, or N-substituted Asn; and X15 is any amino acid;

provided that the peptide inhibitor is other than:

(SEQ ID NO: 202)
Ac-[Pen]-N-T-[W(7-Me)]-[Cit]-[Pen]-Phe[4-(2-aminoethoxy)]-[2-Nal]-[a-MeLys]-[Lys(Ac)]-N-[Aib]-[(D)Tyr]-NH₂;

or iii) the peptide is:

(SEQ ID NO: 1)
Ac-[Pen]-N-T-[W(7-Me)]-[Lys(Ac)]-[Pen]-Phe[4-(2-aminoethoxy)]-[3-Quin]-[a-MeLys]-[Lys(Ac)]-N-[(D)Leu]-NH₂;

(SEQ ID NO: 64)
Ac-[Abu]-Q-T-[W(7-Me)]-[Lys(Ac)]-[Cys]-Phe[4-(2-aminoethoxy)]-[2-Nal]-[a-MeLys]-[Lys(Ac)]-N-[(D)Lys]-NH₂;

(SEQ ID NO: 65)
Ac-[Abu]-Q-T-[W(7-Me)]-[Lys(Ac)]-[Cys]-Phe[4-(2-aminoethoxy)]-[2-Nal]-[a-MeLys]-[Lys(Ac)]-N-[(D)Leu]-NH₂;

(SEQ ID NO: 72)
Ac-[Pen]-N-[(D)Dap]-[W(7-Me)]-[Lys(Ac)]-[Pen]-Phe[4-(2-aminoethoxy)]-[2-Nal]-[a-MeLys]-[Lys(Ac)]-N-[(D)Leu]-NH₂;

(SEQ ID NO: 73)
Ac-[Pen]-N-[(D)Lys]-[W(7-Me)]-[Lys(Ac)1-[Pen]-Phe[4-(2-aminoethoxy)]-[2-Nal]-[a-MeLys]-[Lys(Ac)]-N-[(D)Leu]-NH₂;

(SEQ ID NO: 74)
Ac-[Pen]-N-[(D)Asp]-[W(7-Me)]-[Lys(Ac)]-[Pen]-Phe[4-(2-aminoethoxy)]-[2-Nal]-[a-MeLys]-[Lys(Ac)]-N-[(D)Leu]-NH₂;

-continued (SEQ ID NO: 70)
Ac-[Pen]-N-T-[W(7-Me)]-[Lys(Ac)]-[Pen]-Phe[4-(2- aminoethoxy)]-[2-Nal]-[a-MeLys]-[Lys(Ac)]-N-

[Aib-Ahx]-NH₂;

(SEQ ID NO: 8)
[Propionic_acid]-[(D)Arg]-[Pen]-Q-T-W-Q-[Pen]-

Phe[4-(2-aminoethoxy)]-[2-Nal]-[THP]-E-N-[N-MebAla]-NH2;

(SEQ ID NO: 14)
Ac-[(D)Arg]-[Pen]-Q-T-W-Q-[Pen]-Phe[4-(2- aminoethoxy)]-[2-Nal]-[THP]-E-N-[N-Me-bAla]-NH2;

(SEQ ID NO: 44)
Ac-[(D)Arg]-[Abu]-Q-T-W-Q-[Cys]-Phe[4-(2- aminoethoxy)]-[2-Nal]-[THP]-[aMeGlu]-N-[aMeTyr]-

NH2;

(SEQ ID NO: 150)
Ac-[(D)Arg]-[Pen]-N-T-[W(7-Me)]-[Lys(Ac)]-[Pen]-

Phe[4-(2-aminoethoxy)]-[2-Nal]-[THP]-[aMeGlu]-N-

[aMeTyr]-NH2;
or (SEQ ID NO: 151)
Ac-[Pen]-N-T-[W(7-Me)]-[Lys(Ac)]-[Pen]-Phe[4-(2- aminoethoxy)]-[2-Nal]-[a-MeLys]-[Lys(Ac)]-N-

[aMeTyr]-NH2;

and
the peptide is cyclized via a Abu-Cys thioether bond, or Pen-Pen disulfide bond; and
wherein X4 and X9 form a disulfide bond or a thioether bond;
and
wherein the peptide inhibitor inhibits the binding of an interleukin-23 (IL-23) to an IL-23 receptor.

In certain embodiments, the present invention includes a monocyclic peptide inhibitor of an interleukin-23 receptor, or a pharmaceutically acceptable salt or solvate thereof, wherein the peptide inhibitor comprises an amino acid sequence of Formula (I):

X3-X4-X5-X6-X7-X8-X9-X10-X11-X12-X13-X14-X15-X16     (I)

wherein
X3 is absent or any amino acid;
each X4, X5, and X6 is independently any amino acid;
X7 is unsubstituted Trp, or Trp substituted with cyano, halo, alkyl, haloalkyl, hydroxy, alkoxy, substituted or unsubstituted aryl, or substituted or unsubstituted heteroaryl;
X8 is Gln, alpha-MeLys, alpha-MeLeu, alpha-MeLys(Ac), beta-homoGln, Cit, Glu, Phe, Asn, Thr, Val, Aib, alpha-MeGln, alpha-MeAsn, Lys(Ac), Dab(Ac), Dap(Ac), homo-Lys(Ac), 1-Nal, 2-Nal, or Trp;
X9 is Abu, Cys, (D)Cys, alpha-MeCys, (D)Pen, Pen or Pen(sulfoxide);
X10 is unsubstituted Phe, or Phe substituted with halo, alkyl, haloalkyl, hydroxy, alkoxy, carboxy, carboxamido, 2-aminoethoxy, or 2-acetylaminoethoxy;
X11 is 2-Nal, aMe(2-Nal), Phe(2-Me), Phe(3-Me), Phe(4-Me), Phe(3,4-dimethoxy), 1-Nal, unsubstituted Trp, or Trp substituted with cyano, halo, alkyl, haloalkyl, hydroxy, or alkoxy;
X12 is 4-amino-4-carboxy-tetrahydropyran (THP), alpha-MeLys, alpha-MeLeu, alpha-MeArg, alpha-MePhe, alpha-MeLeu, alpha-MeLys, alpha-MeAsn, alpha-MeTyr, Ala, cyclohexylAla, 1-aminocyclohexylAla (Achc), Acvc, Lys, or Aib;
X13 and X14 is independently any amino acid;
i) X16 is absent; and X15 is His, Aib, THP, Phe, substituted Phe, substituted (D)Phe, a-MePhe, substituted a-MePhe, Trp, substituted Trp, 1-Nal, aMe(1-Nal), substituted 1-Nal, 2-Nal, aMe(2-Nal), substituted 2-Nal, or N-substituted Asn;
provided that the peptide inhibitor is other than:

(SEQ ID NO: 151)
Ac-[Pen]-NT-[W(7-Me)]-[Cit]-[Pen]-Phe[4-(2- aminoethoxy)]-[2-Nal]-[a-MeLys]-[Lys(Ac)]-

N-[Aib]-NH₂;
or (SEQ ID NO: 201)
Ac-[(D)Arg]-[Abu]-Q-T-[W(7-Me)]-[Lys(Ac)]-

[Cys]-Phe[4-(2-aminoethoxy)]-[2-Na]-[a-MeLys]-

[Lys(Ac)]-N-[a-MePhe]-NH₂;

or
ii) X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn; and X15 is any amino acid;
provided that the peptide inhibitor is other than:

(SEQ ID NO: 202)
Ac-[Pen]-N-T-[W(7-Me)]-[Cit]-[Pen]-Phe[4-(2- aminoethoxy)]-[2-Nal]-[a-MeLys]-[Lys(Ac)]-N-

[Aib]-[(D)Tyr]-NH₂;

or
iii) the peptide is:

(SEQ ID NO: 1)
Ac-[Pen]-N-T-[W(7-Me)]-[Lys(Ac)]-[Pen]-Phe[4-(2- aminoethoxy)]-[3-Quin]-[a-MeLys]-[Lys(Ac)]-N-

[(D)Leu]-NH₂;

(SEQ ID NO: 64)
Ac-[Abu]-Q-T-[W(7-Me)]-[Lys(Ac)]-[Cys]-Phe[4-(2- aminoethoxy)]-[2-Nal]-[a-MeLys]-[Lys(Ac)]-N-

[(D)Lys]-NH₂;

(SEQ ID NO: 65)
Ac-[Abu]-Q-T-[W(7-Me)]-[Lys(Ac)]-[Cys]-Phe[4-(2- aminoethoxy)]-[2-Nal]-[a-MeLys]-[Lys(Ac)]-N-

[(D)Leu]-NH₂;

-continued (SEQ ID NO: 72)
Ac-[Pen]-N-[(D)Dap]-[W(7-Me)]-[Lys(Ac)]-[Pen]-
Phe[4-(2-aminoethoxy)]-[2-Nal]-[a-MeLys]-
[Lys(Ac)]-N-[(D)Leu]-NH$_2$;

(SEQ ID NO: 73)
Ac-[Pen]-N-[(D)Lys]-[W(7-Me)]-[Lys(Ac)]-[Pen]-
Phe[4-(2-aminoethoxy)]-[2-Nal]-[a-MeLys]-
[Lys(Ac)]-N-[(D)Leu]-NH$_2$;

(SEQ ID NO: 74)
Ac-[Pen]-N-[(D)Asp]-[W(7-Me)]-[Lys(Ac)]-[Pen]-
Phe[4-(2-aminoethoxy)]-[2-Nal]-[a-MeLys]-
[Lys(Ac)]-N-[(D)Leu]-NH$_2$;

(SEQ ID NO: 70)
Ac-[Pen]-N-T-[W(7-Me)]-[Lys(Ac)]-[Pen]-Phe[4-(2-
aminoethoxy)]-[2-Nal]-[a-MeLys]-[Lys(Ac)]-N-
[Aib-Ahx]-NH$_2$;

(SEQ ID NO: 8)
[Propionic_acid]-[(D)Arg]-[Pen]-Q-T-W-Q-[Pen]-
Phe[4-(2-aminoethoxy)]-[2-Nal]-[THP]-E-N-
[N-Me-bAla]-NH2;

(SEQ ID NO: 14)
Ac-[(D)Arg]-[Pen]-Q-T-W-Q-[Pen]-Phe[4-(2-
aminoethoxy)]-[2-Nal]-[THP]-E-N-[N-Me-bAla]-NH2;

(SEQ ID NO: 44)
Ac-[(D)Arg]-[Abu]-Q-T-W-Q-[Cys]-Phe[4-(2-
aminoethoxy)]-[2-Nal]-[THP]-[aMeGlu]-N-
[aMeTyr]-NH2;

(SEQ ID NO: 150)
Ac-[(D)Arg]-[Pen]-N-T-[W(7-Me)]-[Lys(Ac)]-[Pen]-
Phe[4-(2-aminoethoxy)]-[2-Nal]-[THP]-[aMeGlu]-N-
[aMeTyr]-NH2;
or (SEQ ID NO: 151)
Ac-[Pen]-N-T-[W(7-Me)]-[Lys(Ac)]-[Pen]-Phe[4-(2-
aminoethoxy)]-[2-Nal]-[a-MeLys]-[Lys(Ac)]-N-
[aMeTyr]-NH2;

and the peptide is cyclized via a Abu-Cys thioether bond, or Pen-Pen disulfide bond;

and wherein X4 and X9 form a disulfide bond or a thioether bond;

and wherein the peptide inhibitor inhibits the binding of an interleukin-23 (IL-23) to an IL-23 receptor.

In one embodiment, X3 is any amino acid. In certain embodiment, X3 is (D)Arg. In a particular embodiment, X3 is absent.

In related embodiments, the present invention includes a monocyclic peptide inhibitor of an interleukin-23 receptor, or a pharmaceutically acceptable salt or solvate thereof, wherein the peptide inhibitor comprises an amino acid sequence of Formula (II):

X4-X5-X6-X7-X8-X9-X10-X11-X12-X13-X14-X15-X16     (II)

wherein

X7-X16 are as described for Formula (I);

X4 is Abu, Cys, (D)Cys, alpha-MeCys, (D)Pen, Pen, or Pen(sulfoxide);

X5 is Cit, Glu, Gly, Leu, Ile, beta-Ala, Ala, Lys, Asn, Pro, alpha-MeGln, alpha-MeLys, alpha-MeLeu, alpha-MeAsn, Lys(Ac), alpha-MeLys(Ac), Dab(Ac), Dap(Ac), homo-Lys(Ac), Gln, Asp, or Cys;

X6 is Thr, Aib, Asp, Dab, Gly, Pro, Ser, alpha-MeGln, alpha-MeLys, alpha-MeLeu, alpha-MeAsn, alpha-MeThr, alpha-MeSer, or Val;

wherein the peptide inhibitor is cyclized via a bond between X4 and X9, and wherein the peptide inhibitor inhibits the binding of an interleukin-23 (IL-23) to an IL-23 receptor.

In certain embodiments, X15 is His, Phe_tetraF, Phe_3OH, ameF, Aib, THP, Phe, substituted Phe, substituted (D)Phe, a-MePhe, substituted a-MePhe, Trp, substituted Trp, 1-Nal, aMe(1-Nal), substituted 1-Nal, 2-Nal, aMe(2-Nal), substituted 2-Nal, or N-substituted Asn; and X16 is absent.

In certain embodiments, X15 is His, Aib, THP, Phe, substituted Phe, substituted (D)Phe, a-MePhe, substituted a-MePhe, Trp, substituted Trp, 1-Nal, aMe(1-Nal), substituted 1-Nal, 2-Nal, aMe(2-Nal), substituted 2-Nal, or N-substituted Asn; and X16 is absent.

In certain embodiments, X15 is any amino acid; and X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiments, X15 is any amino acid; and X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiments, N-substituted Asn is (N-Me)Asn, (N-Et)Asn, (N-n-Pr)Asn, (N-iPr)Asn, (N-iBu)Asn, (N-nBu)Asn, (N-tBu)Asn, (N-benzyl)Asn, (N-Ph)Asn, (N-2-aminophenyl)Asn, (N-3-aminophenyl)Asn, (N-4-aminophenyl)Asn, (N-pyr)Asn, (N-3-Pyz)Asn, (N-4-Pyz)Asn, (N-pip)Asn, (N-5-indolyl)Asn, (N-propylamido)Asn, or (N-imidazo-2-yl)Asn.

In certain embodiment, X13 is Aib, Glu, Cit, Gln, Lys(Ac), Orn(COMe), alpha-MeArg, alpha-MeGlu, alpha-MeLeu, alpha-MeLys, alpha-Me-Asn, alpha-MeLys(Ac), Dab(Ac), Dap(Ac), homo-Lys(Ac), Lys(COR3), Lys(SO2R3), or Lys; or X13 is Lys, pegylated Lys, b-homoGlu, or Lys(Y2-Ac), wherein Y2 is an amino acid, and R3 is Me, Et, n-Pr, i-Pr, CF3, n-pentyl, cyclopropyl, t-Bu, or O-allyl.

In certain embodiment, X14 is Asn, 2-Nap, Aib, Arg, Cit, Asp, Phe, Gly, Lys, Leu, Ala, (D)Ala, beta-Ala, His, Thr, n-Leu, Gln, Ser, (D)Ser, Tic, Trp, alpha-MeGln, alpha-MeAsn, alpha-MeLys(Ac), Dab(Ac), Dap(Ac), homo-Lys(Ac), or Lys(Ac).

In certain embodiments, X4 or X9 is Cys, (D)Cys, alpha-MeCys, (D)Pen, or Pen; and the bond between X4 and X9 is a disulfide bond.

In certain embodiment, X4 is Cys, (D)Cys, or alpha-MeCys.

In certain embodiment, X4 is (D)Pen, Pen, or Pen(sulfoxide).

In certain embodiment, X4 is Pen.

In certain embodiment, X9 is Cys, (D)Cys, or alpha-MeCys.

In certain embodiment, X9 is Pen or (D)Pen.

In certain embodiment, X9 is Pen.

In certain embodiment, X4 is Pen and X9 is Pen, and the bond is a disulfide bond.

In certain embodiment, X4 is Pen and X9 is Cys, and the bond is a disulfide bond.

In certain embodiment, X4 or X9 is Abu; and the bond between X4 and X9 is a thioether bond.

In certain embodiment, X4 is Abu, and X9 is Cys, (D)Cys, or alpha-MeCys. In certain embodiment, X9 is Pen or (D)Pen. In a particular embodiment, X9 is Pen. In a more particular embodiment, X9 is Cys. In a most particular embodiment, X4 is Abu, and X9 is Cys.

In certain embodiment, X4 is Abu and X9 is Cys or Pen, and the bond is a thioether bond.

In certain embodiment, X4 is Abu and X9 is Cys, and the bond is a thioether bond.

In certain embodiment, the peptide inhibitor is according to Formula (IIa) (IIb), or (IIc) or comprises a sequence of Formula (IIa) (IIb), or (IIc):

Pen-X5-X6-X7-X8-Pen-X10-X11-X12-X13-X14-
        X15-X16                                    (IIa)

Abu-X5-X6-X7-X8-Cys-X10-X11-X12-X13-X14-
        X15-X16                                    (IIb), or

Abu-X5-X6-X7-X8-Pen-X10-X11-X12-X13-X14-
        X15-X16                                    (IIc)

wherein X7-X16 are as described for Formula (I), and the peptide inhibitor is cyclized via a Pen-Pen disulfide bond, an Abu-Cys thioether bond, or an Abu-Pen thioether bond.

In certain embodiment, X5 is Asn, Gln, or Glu.

In certain embodiment, X5 is Asn, or Gln.

In certain embodiment, X5 is Asn.

In certain embodiment, the peptide inhibitor is according to Formula (IIIa), (IIIb), (IIIc), or (IIId) or comprises a sequence of Formula (IIIa), (IIIb), (IIIc), or (IIId):

Pen-Asn-X6-X7-X8-Pen-X10-X11-X12-X13-X14-
        X15-X16                                    (IIIa)

Pen-Gln-X6-X7-X8-Pen-X10—X11-X12-X13-X14-
        X15-X16                                    (IIIb)

Abu-Asn-X6-X7-X8-Cys-X10-X11-X12-X13-X14-
        X15-X16                                    (IIc) or

Abu-Gln-X6-X7-X8-Pen-X10-X11-X12-X13-X14-
        X15-X16                                    (IIId)

wherein X6 is as described for Formula (II); X7-X16 are as described for Formula (I), and the peptide inhibitor is cyclized via a Pen-Pen disulfide bond, an Abu-Cys thioether bond, or an Abu-Pen thioether bond.

In certain embodiment, X6 is Thr.

In certain embodiment, the peptide inhibitor is according to Formula (IVa), (IVb), (IVc), or (IVd) or comprises a sequence of Formula (IVa), (IVb), (IVc), or (IVd):

Pen-Asn-Thr-X7-X8-Pen-X10-X11-X12-X13-X14-
        X15-X16                                    (IVa)

Pen-Gln-Thr-X7-X8-Pen-X10-X11-X12-X13-X14-
        X15-X16                                    (IVb)

Abu-Asn-Thr-X7-X8-Cys-X10-X11-X12-X13-X14-
        X15-X16                                    (IVc) or

Abu-Gln-Thr-X7-X8-Pen-X10-X11-X12-X13-X14-
        X15-X16                                    (IVd)

wherein X7-X16 are as described for Formula (I), and the peptide inhibitor is cyclized via a Pen-Pen disulfide bond, an Abu-Cys thioether bond, or an Abu-Pen thioether bond.

In certain embodiment, X8 is Gln, alpha-Me-Lys, alpha-MeLys(Ac), Lys(Ac), Paf(Ac), Phe4NH2Ac, or Glu.

In certain embodiment, X8 is Gln. In certain embodiment, X8 is Cit. In certain embodiment, X8 is Lys(Ac).

In certain embodiment, the peptide inhibitor is according to Formula (Va), (Vb), (Vc), or (Vd) or comprises a sequence of Formula (Va), (Vb), (Vc), or (Vd):

(SEQ ID NO: 330)
    Pen-Asn-Thr-X7-Gln-Pen-X10-X11-X12-X13-X14-X15-
        X16 (Va),

Pen-Gln-Thr-X7-Gln-Pen-X10-X11-X12-X13-X14-X15-
        X16 (Vb),

Abu-Asn-Thr-X7-Gln-Cys-X10-X11-X12-X13-X14-X15-
        X16 (Vc),
    or
    Abu-Gln-Thr-X7-Gln-Pen-X10-X11-X12-X13-X14-X15-
        X16 (Vd)

wherein X7-X16 are as described for Formula (I), and the peptide inhibitor is cyclized via a Pen-Pen disulfide bond, an Abu-Cys thioether bond, or an Abu-Pen thioether bond.

In certain embodiment, X10 is Phe, Phe[4-(2-aminoethoxy)] [F(4-2ae)], Phe[4-(2-acetylaminoethoxy)], AEF, AEF (Ac), AEF(BH), AEF(Boc), AEF(Me)2, bMeRPhe, Phe42ae-ethyl, Phe42aeSMSB, Phe4Pip or Phe(4-$CONH_2$).

In certain embodiment, the peptide inhibitor is according to Formula (Va), (Vb), (Vc), or (Vd) or comprises a sequence of Formula (Va), (Vb), (Vc), or (Vd):

(SEQ ID NO: 331)
    Pen-Asn-Thr-X7-Gln-Pen-X10-X11-X12-X13-X14-X15-
        X16 (Va),

Pen-Gln-Thr-X7-Gln-Pen-X10-X11-X12-X13-X14-X15-
        X16 (Vb),

Abu-Asn-Thr-X7-Gln-Cys-X10-X11-X12-X13-X14-X15-
        X16 (Vc),
    or
    Abu-Gln-Thr-X7-Gln-Pen-X10-X11-X12-X13-X14-X15-
        X16 (Vd)

wherein X7-X16 are as described for Formula (I), and the peptide inhibitor is cyclized via a Pen-Pen disulfide bond, an Abu-Cys thioether bond, or an Abu-Pen thioether bond.

In certain embodiment, X10 is Phe, Phe[4-(2-aminoethoxy)] [F(4-2ae)], Phe[4-(2-acetylaminoethoxy)], or Phe(4-$CONH_2$).

In certain embodiment, X10 is Phe[4-(2-aminoethoxy)], or Phe[4-(2-acetylaminoethoxy)].

In certain embodiment, the peptide inhibitor is according to Formula (VIa), (VIb), (VIc), or (VId) or comprises a sequence of Formula (VIa), (VIb), (VIc), or (VId):

Pen-Asn-Thr-X7-Gln-Pen-[F(4-2ae)]-X11-X12-X13-X14-X15-X16 (VIa), (SEQ ID NO: 332)

Pen-Gln-Thr-X7-Gln-Pen-[F(4-2ae)]-X11-X12-X13-X14-X15-X16 (VIb), (SEQ ID NO: 333)

Abu-Asn-Thr-X7-Gln-Cys-[F(4-2ae)]-X11-X12-X13-X14-X15-X16 (VIc), (SEQ ID NO: 334)

or

Abu-Gln-Thr-X7-Gln-Pen-[F(4-2ae)]-X11-X12-X13-X14-X15-X16 (VId) (SEQ ID NO:335) wherein X7-X16 are as described for Formula (I), [F(4-2ae)] is Phe[4-(2-aminoethoxy)]; and the peptide inhibitor is cyclized via a Pen-Pen disulfide bond, an Abu-Cys thioether bond, or an Abu-Pen thioether bond.

In certain embodiment, the peptide inhibitor comprises an amino acid sequence of Formula (I):

X7-X8-X9-X10-X11-X12-X13-X14-X15-X16 (I)

and wherein

X15 is His, Phe_tetraF, Phe_3OH, ameF, THP, Phe, substituted Phe, (D)Phe, substituted (D)Phe, a-MePhe, bhPhe, Trp, substituted Trp, 1-Nal, aMe(1-Nal), substituted 1-Nal, 2-Nal, aMe(2-Nal), substituted 2-Nal, N(NMe), N(NEt), N(NiPr), N(NBu), N(NiBu), N(Nchx), N(Ncpx), N(NBzl), N(NtBu), N(NAnil), N(N2AmAnil), N(N3AmAnil), N(N4AmAnil), N(Npip), or N(NAmbu); and X16 is absent.

In certain embodiment, the peptide inhibitor comprises an amino acid sequence of Formula (I):

X7-X8-X9-X10-X11-X12-X13-X14-X15-X16 (I)

and wherein

X15 is His, THP, Phe, substituted Phe, (D)Phe, substituted (D)Phe, a-MePhe, bhPhe, Trp, substituted Trp, 1-Nal, aMe(1-Nal), substituted 1-Nal, 2-Nal, aMe(2-Nal), substituted 2-Nal, N(NMe), N(NEt), N(NiPr), N(NBu), N(NiBu), N(Nchx), N(Ncpx), N(NBzl), N(NtBu), N(NAnil), N(N2AmAnil), N(N3AmAnil), N(N4AmAnil), N(Npip), or N(NAmbu); and X16 is absent.

In certain embodiment, the peptide inhibitor comprises an amino acid sequence of Formula (I):

X7-X8-X9-X10-X1-X12-X13-X14-X15-X16 (I)

wherein X15 is any amino acid; and X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiment, the peptide inhibitor comprises an amino acid sequence of Formula (I):

X7-X8-X9-X10-X11-X12-X13-X14-X15-X16 (I)

wherein X15 is any amino acid; and X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiment, the peptide inhibitor is according to Formula (VIIa), (VIIb), or (VIIc) or comprises a sequence of Formula (VIIa), (VIIb), or (VIIc):

Pen-Asn-Thr-X7-Gln-Pen-[F(4-2ae)]-X11-X12-X13-X14-X15-X16 (VIIa), (SEQ ID NO: 336)

Abu-Asn-Thr-X7-Gln-Cys-[F(4-2ae)]-X11-X12-X13-X14-X15-X16 (VIIb), (SEQ ID NO: 337)

or

Abu-Asn-Thr-X7-Gln-Pen-[F(4-2ae)]-X11-X12-X13-X14-X15-X16 (VIIc) (SEQ ID NO: 338)

wherein X7 and X11 are as described for Formula (I); X12 is 4diFAchx, Achx, Acpx, AmeK(Boc), 4-amino-4-carboxy-tetrahydropyran (THP), alpha-MeLys, alpha-MeLeu, alpha-MeArg, alpha-MePhe, alpha-MeLeu, alpha-MeLys, alpha-MeAsn, alpha-MeTyr, Ala, cyclohexylAla, 1-aminocyclohexylAla (Achc), Acvc, Lys, or Aib;

X13 is Aib, Glu, Cit, Gln, Lys(Ac), Orn(COMe), alpha-MeArg, alpha-MeGlu, alpha-MeLeu, alpha-MeLys, alpha-Me-Asn, alpha-MeLys(Ac), Dab(Ac), Dap(Ac), homo-Lys(Ac), Lys(COR3), Lys(SO2R3), or Lys; or X13 is Lys, pegylated Lys, b-homoGlu, or Lys(Y2-Ac), wherein Y2 is an amino acid; R3 is Me, Et, n-Pr, i-Pr, CF3, n-pentyl, cyclopropyl, t-Bu, or O-allyl;

X14 is Asn, 2-Nap, Aib, Arg, Cit, Asp, Phe, Gly, Lys, Leu, Ala, (D)Ala, beta-Ala, His, Thr, n-Leu, Gln, Ser, (D)Ser, Tic, Trp, alpha-MeGln, alpha-MeAsn, alpha-MeLys(Ac), Dab(Ac), Dap(Ac), homo-Lys(Ac), or Lys (Ac);

X15 is His, Phe_tetraF, Phe_3OH, ameF, THP, Phe, substituted Phe, (D)Phe, substituted (D)Phe, α-MePhe, bhPhe, Trp, substituted Trp, 1-Nal, aMe(1-Nal), substituted 1-Nal, 2-Nal, aMe(2-Nal), substituted 2-Nal, N-substituted Asn is (N-Me)Asn, (N-Et)Asn, (N-n-Pr) Asn, (N-iPr)Asn, (N-iBu)Asn, (N-nBu)Asn, (N-tBu) Asn, (N-benzyl)Asn, (N-Ph)Asn, (N-2-aminophenyl) Asn, (N-3-aminophenyl)Asn, (N-4-aminophenyl)Asn, (N-pyr)Asn, (N-3-Pyz)Asn, (N-4-Pyz)Asn, (N-pip) Asn, (N-5-indolyl)Asn, (N-propylamido)Asn, or (N-imidazo-2-yl)Asn; and X16 is absent; or X15 is any amino acid; and X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn;

and the peptide inhibitor is cyclized via a Pen-Pen disulfide bond; or the peptide inhibitor is cyclized via a Abu-Cys or Abu-Pen thioether bond.

In certain embodiment, the peptide inhibitor is according to Formula (VIIa), (VIIb), or (VIIc) or comprises a sequence of Formula (VIIa), (VIIb), or (VIIc):

(SEQ ID NO: 339)
Pen-Asn-Thr-X7-Gln-Pen-[F(4-2ae)]-X11-X12-X13-X14-
X15-X16 (VIIa), (SEQ ID NO: 340)
Abu-Asn-Thr-X7-Gln-Cys-[F(4-2ae)]-X11-X12-X13-X14-
X15-X16 (VIIb),
or (SEQ ID NO: 341)
Abu-Asn-Thr-X7-Gln-Pen-[F(4-2ae)]-X11-X12-X13-X14-
X15-X16 (VIIc)

wherein X7 and X11 are as described for Formula (I); X12 is 4diFAchx, Achx, Acpx, AmeK(Boc), 4-amino-4-carboxy-tetrahydropyran (THP), alpha-MeLys, alpha-MeLeu, alpha-MeArg, alpha-MePhe, alpha-Me-Leu, alpha-MeLys, alpha-MeAsn, alpha-MeTyr, Ala, cyclohexylAla, 1-aminocyclohexylAla (Achc), Lys, or Aib;

X13 is Aib, Glu, Cit, Gln, Lys(Ac), Orn(COMe), alpha-MeArg, alpha-MeGlu, alpha-MeLeu, alpha-MeLys, alpha-Me-Asn, alpha-MeLys(Ac), Dab(Ac), Dap(Ac), homo-Lys(Ac), Lys(COR3), Lys(SO2R3), or Lys; or X13 is Lys, pegylated Lys, b-homoGlu, or Lys(Y2-Ac), wherein Y2 is an amino acid; R3 is Me, Et, n-Pr, i-Pr, CF3, n-pentyl, cyclopropyl, t-Bu, or O-allyl;

X14 is Asn, 2-Nap, Aib, Arg, Cit, Asp, Phe, Gly, Lys, Leu, Ala, (D)Ala, beta-Ala, His, Thr, n-Leu, Gln, Ser, (D)Ser, Tic, Trp, alpha-MeGln, alpha-MeAsn, alpha-MeLys(Ac), Dab(Ac), Dap(Ac), homo-Lys(Ac), or Lys (Ac);

X15 is His, THP, Phe, substituted Phe, (D)Phe, substituted (D)Phe, a-MePhe, bhPhe, Trp, substituted Trp, 1-Nal, aMe(1-Nal), substituted 1-Nal, 2-Nal, aMe(2-Nal), substituted 2-Nal, N-substituted Asn is (N-Me)Asn, (N-Et)Asn, (N-n-Pr)Asn, (N-iPr)Asn, (N-iBu)Asn, (N-nBu)Asn, (N-tBu)Asn, (N-benzyl)Asn, (N-Ph)Asn, (N-2-aminophenyl)Asn, (N-3-aminophenyl)Asn, (N-4-aminophenyl)Asn, (N-pyr)Asn, (N-3-Pyz)Asn, (N-4-Pyz)Asn, (N-pip)Asn, (N-5-indolyl)Asn, (N-propylamido)Asn, or (N-imidazo-2-yl)Asn; and X16 is absent; or X15 is any amino acid; and X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn;

and the peptide inhibitor is cyclized via a Pen-Pen disulfide bond; or the peptide inhibitor is cyclized via a Abu-Cys or Abu-Pen thioether bond.

In certain embodiments, X15 is His, Phe_tetraF, Phe_3OH, ameF, Asn, Arg, Leu, Val, Pro, (D)Pro, Ile, NMeArg, Aib, (D)Leu, beta-Ala, Cit, Gln, Asp, alpha-MeGln, alpha-MeAsn, Lys(Ac), alpha-MeLys(Ac), Dab (Ac), Dap(Ac), or homo-Lys(Ac); and X16 is paf, Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiments, X15 is His, Asn, Arg, Leu, Val, Pro, (D)Pro, Ile, NMeArg, Aib, (D)Leu, beta-Ala, Cit, Gln, Asp, alpha-MeGln, alpha-MeAsn, Lys(Ac), alpha-MeLys (Ac), Dab(Ac), Dap(Ac), or homo-Lys(Ac); and X16 is Aib, 3Pal, Phe, substituted Phe, substituted (D)Phe, substituted or unsubstited Tyr, unsubstituted (D)Tyr, a-MePhe, substituted a-MePhe, b-hPhe, 1-Nal, aMe(1-Nal), substituted 1-Nal, 2-Nal, aMe(2-Nal), substituted 2-Nal, or N-substituted Asn.

In certain embodiments, each X12, X13, or X14, is independently any amino acid. In one embodiment, the amino acid is a natural amino acid. In another embodiment, the amino acid is an unnatural amino acid.

In certain embodiments, X14 is Asn, 2-Nap, Aib, Arg, Cit, Asp, Phe, Gly, Lys, Leu, Asn, n-Leu, Gln, Ser, Tic, Trp, alpha-MeGln, alpha-MeAsn, alpha-MeLys(Ac), Dab(Ac), Dap(Ac), homo-Lys(Ac), or Lys(Ac). In certain embodiments, X14 is Asn, 2-Nap, Aib, Arg, Cit, Asp, Phe, Gly, Lys, Leu, Ala, (D)Ala, beta-Ala, His, Thr, n-Leu, Gln, Ser, (D)Ser, Tic, Trp, alpha-MeGln, alpha-MeAsn, alpha-MeLys (Ac), Dab(Ac), Dap(Ac), homo-Lys(Ac), or Lys(Ac). In certain embodiments, X14 is Asn.

In certain embodiments, X15 is THP, Phe, or α-MePhe.

In certain embodiment, X13 is Glu, Cit, Gln, Lys(Ac), alpha-MeArg, alpha-MeGlu, alpha-MeLeu, alpha-MeLys, alpha-Me-Asn, alpha-MeLys(Ac), Dab(Ac), Dap(Ac), homo-Lys(Ac), Lys(COR3), Lys(SO2R3), or Lys; or X13 is Lys, pegylated Lys, b-homoGlu, or Lys(Y2-Ac), wherein Y2 is an amino acid. In certain embodiment, X13 is Aib, Glu, Cit, Gln, Lys(Ac), Orn(COMe), alpha-MeArg, alpha-MeGlu, alpha-MeLeu, alpha-MeLys, alpha-Me-Asn, alpha-MeLys(Ac), Dab(Ac), Dap(Ac), homo-Lys(Ac), Lys(COR$^3$), Lys(SO$_2$R$^3$), or Lys; or X13 is Lys, pegylated Lys, b-homo-Glu, or Lys(Y2-Ac), wherein Y2 is an amino acid; and R$^3$ is Me, Et, n-Pr, i-Pr, CF3, n-pentyl, cyclopropyl, t-Bu, or O-allyl.

In certain embodiment, X12 is 4diFAchx, Achx, Acpx, AmeK(Boc), 4-amino-4-carboxy-tetrahydropyran (THP), alpha-MeLys, alpha-MeLeu, Ala, cyclohexylAla, Lys, Acvc, or Aib.

In certain embodiment, X12 is 4diFAchx, Achx, Acpx, AmeK(Boc), 4-amino-4-carboxy-tetrahydropyran (THP), alpha-MeLys, alpha-MeLeu, Ala, cyclohexylAla, Lys, or Aib.

In certain embodiment, X12 is 4-amino-4-carboxy-tetrahydropyran (THP), alpha-MeLys, or alpha-MeLeu.

In certain embodiment, X12 is alpha-MeLeu. In certain embodiment, X12 is alpha-MeLys. In certain embodiment, X12 is 4-amino-4-carboxy-tetrahydropyran (THP).

In certain embodiment, X13 is Glu, Gln, Lys(Ac), or Lys.

In certain embodiment, X13 is Gln, Lys(Ac), or Lys.

In certain embodiment, X13 is Lys(Ac), or Lys.

In certain embodiment, X13 is Lys(Ac).

In certain embodiment, X13 is Gln. In certain embodiment, X13 is Glu. In certain embodiment, X13 is alpha-MeGlu. In certain embodiment, X13 is Aib or OrnCOMe. In certain embodiment, X13 is Lys(COR$^3$), or Lys(SO$_2$R$^3$); and R$^3$ is Me, Et, n-Pr, i-Pr, CF3, n-pentyl, cyclopropyl, t-Bu, or O-allyl.

In certain embodiment, the peptide inhibitor is according to Formula (VIIIa), (VIIIb) or (VIIIc) or comprises a sequence of Formula (VIIIa), (VIIIb) or (VIIIc):

```
Pen-Asn-Thr-X7-Gln-Pen-[F(4-2ae)]-X11-aMeLeu-    (SEQ ID NO: 339)

K(Ac)-X14-X15-X16 (VIIIa),

Abu-Asn-Thr-X7-Gln-Cys-[F(4-2ae)]-X11-aMeLeu-    (SEQ ID NO: 340)

K(Ac)-X14-X15 (VIIIb),
or

Abu-Asn-Thr-X7-Gln-Pen-[F(4-2ae)]-X11-aMeLeu-    (SEQ ID NO: 341)

K(Ac)-X14-X15-X16 (VIIIc)
``` wherein X7, X11, X14, X15, and X16 are as described for Formula (I); and the peptide inhibitor is cyclized via a Pen-Pen disulfide bond, an Abu-Cys thioether bond, or an Abu-Pen thioether bond.

In certain embodiment, X14 is Asn.

In certain embodiment, the peptide inhibitor is according to Formula (IXa), (IXb), or (IXc) or comprises a sequence of Formula (IXa), (IXb), or (IXc):

```
Pen-Asn-Thr-X7-Gln-Pen-[F(4-2ae)]-X11-[α-MeLeu]-    (SEQ ID NO: 342)

K(Ac)-Asn-X15-X16 (IXa),

Pen-Asn-Thr-X7-Gln-Pen-[F(4-2ae)]-X11-[α-MeLeu]-    (SEQ ID NO: 343)

K(Ac)-Asn-X15-X16 (IXb),
or

Pen-Asn-Thr-X7-Gln-Pen-[F(4-2ae)]-X11-[α-MeLeu]-    (SEQ ID NO: 344)

K(Ac)-Asn-X15-X16 (IXc)
``` wherein X7, X11 and X15-X16 are as described for Formula (II), and the peptide inhibitor is cyclized via a Pen-Pen disulfide bond, an Abu-Cys thioether bond, or an Abu-Pen thioether bond.

In certain embodiment, X7 is Trp-psi-Trp substituted with cyano, halo, alkyl, haloalkyl, hydroxy, or alkoxy; and X11 is as described herein.

In certain embodiment, X7 is Trp substituted with cyano, halo, alkyl, haloalkyl, hydroxy, or alkoxy; and X11 is as described herein.

In certain embodiment, X11 is Trp substituted with cyano, halo, alkyl, haloalkyl, hydroxy, or alkoxy; and X7 is as described herein.

In certain embodiment, X7 is Trp substituted with substituted or unsubstituted aryl, or substituted or unsubstituted heteroaryl.

In certain embodiment, X7 is Trp-psi unsubstituted Trp, Trp5Br, Trp7Cl, Trp7F, Trp5Me, or Trp7Me.

In certain embodiment, X7 is unsubstituted Trp.

In certain embodiment, X7 is Trp substituted with substituted or unsubstituted phenyl. In certain embodiment, X7 is Trp substituted with substituted or unsubstituted pyridyl, or thienyl.

In certain embodiment, the peptide inhibitor is according to Formula (Xa), (Xb), (Xc), (Xd), (Xe), or (Xf) or comprises a sequence of Formula (Xa), (Xb), (Xc), (Xd), (Xe), or (Xf):

```
Pen-Asn-Thr-W'-Gln-Pen-[F(4-2ae)]-X11-aMeLeu-    (SEQ ID NO: 345)

K(Ac)-Asn-X15-X16 (Xa),

Pen-Asn-Thr-X7-Gln-Pen-[F(4-2ae)]-W'-aMeLeu-    (SEQ ID NO: 346)

K(Ac)-Asn-X15-X16 (Xb),

Abu-Asn-Thr-W'-Gln-Cys-[F(4-2ae)]-X11-aMeLeu-    (SEQ ID NO: 347)

K(Ac)-Asn-X15-X16 (Xc),

Abu-Asn-Thr-X7-Gln-Cys-[F(4-2ae)]-W'-aMeLeu-    (SEQ ID NO: 348)

K(Ac)-Asn-X15-X16 (Xd),

Abu-Asn-Thr-W'-Gln-Pen-[F(4-2ae)]-X11-aMeLeu-    (SEQ ID NO: 349)

K(Ac)-Asn-X15-X16 (Xe),
or

Abu-Asn-Thr-X7-Gln-Pen-[F(4-2ae)]-W'-aMeLeu-    (SEQ ID NO: 350)

K(Ac)-Asn-X15-X16 (Xf)
``` wherein X7, X11, X15, and X16 are as described for Formula (I); W' is Trp substituted with cyano, halo, alkyl, haloalkyl, hydroxy, phenyl, thienyl, or alkoxy; and the peptide inhibitor is cyclized via a Pen-Pen disulfide bond, an Abu-Cys thioether bond, or an Abu-Pen thioether bond.

In certain embodiments, X11 is 6amido2Nal, 6OMe2Nal, bMe2Nal(2S,3R), rbMe2Nal, 2-Nal, Phe(2-Me), Phe(3-Me), Phe(4-Me), Phe(3,4-dimethoxy), or 1-Nal.

In certain embodiments, X11 is 2-Nal, Phe(2-Me), Phe(3-Me), Phe(4-Me), Phe(3,4-dimethoxy), or 1-Nal.

In certain embodiments, X11 is 2-Nal, or 1-Nal.

In certain embodiments, X11 is 2-Nal.

In certain embodiments, X7 is unsubstituted Trp, Trp-psi, Trp5Br, Trp7Cl, Trp7F, Trp5Me, or Trp7Me.

In certain embodiments, X7 is unsubstituted Trp.

In certain embodiments, the peptide inhibitor is according to Formula (XIa), (XIb), (XIc), (XId), (XIe), or (XIf) or comprises a sequence of Formula (XIa), (XIb), (XIc), (XId), (XIe), or (XIf):

```
Pen-Asn-Thr-W'-Gln-Pen-[F(4-2ae)]-[2-Nal]-aMeLeu-    (SEQ ID NO: 323)

K(Ac)-Asn-X1-X16 5 (XIa),

Pen-Asn-Thr-W-Gln-Pen-[F(4-2ae)]-W'-aMeLeu-K(Ac)-    (SEQ ID NO: 324)

Asn-X15-X16 (XIb),

Abu-Asn-Thr-W'-Gln-Cys-[F(4-2ae)]-[2-Nal]-aMeLeu-    (SEQ ID NO: 325)

K(Ac)-Asn-X15-X16 (XIc),

Abu-Asn-Thr-W-Gln-Cys-[F(4-2ae)]-W'-aMeLeu-K(Ac)-    (SEQ ID NO: 326)

Asn-X15-X16 (XId),

Abu-Asn-Thr-W'-Gln-Pen-[F(4-2ae)]-[2-Nal]-aMeLeu-    (SEQ ID NO: 327)

K(Ac)-Asn-X15-X16 (XIe),
or
```

-continued

Abu-Asn-Thr-W-Gln-Pen-[F(4-2ae)]-W'-aMeLeu-K(Ac)-
Asn-X15-X16 (XIf), (SEQ ID NO: 328)

or

Abu-Asn-Thr-W-Gln-Pen-[F(4-2ae)]-W'-aMeLeu-K (Ac)-Asn-X15-X16 (XIf) (SEQ ID NO:328), wherein X15 and X16 are as described for Formula (I), W' is Trp substituted with cyano, halo, alkyl, haloalkyl, hydroxy, or alkoxy; and the peptide inhibitor is cyclized via a Pen-Pen disulfide bond, an Abu-Cys thioether bond, or an Abu-Pen thioether bond.

In certain embodiments, W' is Trp substituted with cyano, halo, alkyl, haloalkyl, hydroxy, or alkoxy. In one embodiment, W' is Trp substituted with alkyl. In certain embodiments, W' is Trp substituted with Me, Et, n-Pr, or i-Pr. In certain embodiments, W' is Trp substituted with Ph. In certain embodiments, W' is Trp substituted with thienyl.

In certain embodiments, W' is Trp substituted with 7-Me, or 7-Ph.

In certain embodiments, W' is Trp substituted with cyano, halo, alkyl, haloalkyl, hydroxy, or alkoxy at a 4-, 5-, 6- or 7-position.

In certain embodiments, W' is Trp substituted with cyano, F, Cl, Br, I, Me, Et, i-Pr, n-Pr, n-Bu, t-Bu, CF$_3$, hydroxy, OMe, or OEt at a 4-, 5-, 6- or 7-position. In a particular embodiment, the substitution is at 7-position.

In certain embodiments, W' is Trp substituted with 5-F, 6-F, 7-F, 5-Cl, 6-Cl, 7-Cl, 5-Me, 6-Me, 7-Me, 7-n-Pr, 7-i-Pr, 5-OH, 6-OH, 7-OH, 5-OMe, 6-OMe, or 7-OMe.

In a particular embodiment, W' is Trp substituted with 7-Me, 5-F, 7-F, 6-Cl, 6-Me, 4-OMe, 5-OMe, or 5-Br. In a more particular embodiment, W' is Trp substituted with 7-Me, 6-Me, 4-OMe, or 6-Cl. In a most particular embodiment, W' is Trp substituted with 7-Me.

In a more particular embodiment, W' is unsubstituted Trp.

In certain embodiment, X15 is THP; and X16 is absent. In certain embodiment, X15 is Phe; and X16 is absent. In certain embodiment, X15 is α-MePhe; and X16 is absent.

In certain embodiment, X15 is Trp or substituted Trp; and X16 is absent. In certain embodiment, X15 is Trp substituted with alkyl, aryl, or halo; and X16 is absent. In certain embodiment, X15 is Trp substituted with 7-Me, 5-F, or 7-Ph; and X16 is absent.

In certain embodiment, X15 is Phe or substituted Phe; and X16 is absent. In certain embodiments, X15 is Phe substituted with alkyl, alkoxy, or halo; and X16 is absent. In certain embodiments, X15 is Phe substituted with OMe, diOMe, F, or Cl; and X16 is absent.

In certain embodiments, X15 is 2-Nal or substituted 2-Nal. In certain embodiments, X15 is aMe(2-Nal); and X16 is absent.

In certain embodiment, X15 is His, Phe_tetraF, Phe3OH, or ameF; and X16 is absent.

In certain embodiment, X15 is Phe-tetraF, Phe3OH, ameF, THP, Phe, substituted Phe, (D)Phe, substituted (D)Phe, a-MePhe, Trp, substituted Trp, 1-Nal, aMe(1-Nal), substituted 1-Nal, 2-Nal, aMe(2-Nal), substituted 2-Nal, N(NMe), N(NEt), N(NiPr), N(NBu), N(NiBu), N(Nchx), N(Ncpx), N(NBzl), N(NtBu), N(NAnil), N(N2AmAnil), N(N3AmAnil), N(N4AmAnil), N(Npip), or N(NAmbu) and X16 is absent.

In certain embodiment, X15 is His, THP, Phe, substituted Phe, (D)Phe, substituted (D)Phe, a-MePhe, Trp, substituted Trp, 1-Nal, aMe(1-Nal), substituted 1-Nal, 2-Nal, aMe(2-Nal), substituted 2-Nal, N(NMe), N(NEt), N(NiPr), N(NBu), N(NiBu), N(Nchx), N(Ncpx), N(NBzl), N(NtBu), N(NAnil), N(N2AmAnil), N(N3AmAnil), N(N4AmAnil), N(Npip), or N(NAmbu) and X16 is absent.

In certain embodiments, N-substituted Asn is (N-Me)Asn, (N-Et)Asn, (N-n-Pr)Asn, (N-iPr)Asn, (N-iBu)Asn, (N-nBu)Asn, (N-tBu)Asn, (N-benzyl)Asn, (N-Ph)Asn, (N-2-aminophenyl)Asn, (N-3-aminophenyl)Asn, (N-4-aminophenyl)Asn, (N-pyr)Asn, (N-3-Pyz)Asn, (N-4-Pyz)Asn, (N-pip)Asn, (N-5-indolyl)Asn, (N-propylamido)Asn, or (N-imidazo-2-yl)Asn; and X16 is absent.

In certain embodiment, X15 or X16 is N substituted Asn; and N-substituted Asn is:

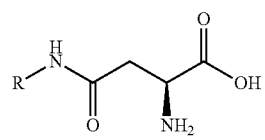

| Abbreviation | R |
| --- | --- |
| (N-benzyl)Asn | -benzyl |
| (N-Ph)Asn | -Ph |
| (N-2-aminophenyl)Asn | -Ph(2-NH2) |
| (N-3-aminophenyl)Asn | -Ph(3-NH2) |
| (N-4-aminophenyl)Asn | -Ph(4-NH2) |
| (N-Pyr)Asn | -Pyrrolidin-3-yl |
| (N-(3-Pyz))Asn | -Pyrazol-3-yl |
| (N-(4-Pyz))Asn | -Pyrazol-4-yl |
| (N-pip)Asn | -piperidin-4-yl |
| (N-(5-indoyl))Asn | -indol-5-yl |
| (N-(propylamido))Asn | —CH$_2$CH$_2$CONH$_2$ |
| (N-(imidazo-2-yl)methyl)Asn | -(imidazo-2-yl)methyl |

In certain embodiment, X15 is N(NMe), N(NEt), or N(NiPr) and X16 is absent.

In certain embodiment, X15 is Aib, Leu, Lys, His, Val, Thr, (D)Leu, (D)Lys, (D)His, (D)Val, or (D)Thr; and X16 is substituted or unsubstituted Phe or substituted or unsubstituted (D)Phe.

In certain embodiment, X15 is Asn, Phe, aMePhe, substituted Phe, or THP; and X16 is Aib, 3Pal, substituted or unsubstituted Phe or substituted or unsubstituted (D)Phe.

In certain embodiment, X15 is any amino acid and X16 is 3Pal.

In certain embodiment, X15 is any amino acid and X16 is paf, dPhe4-2ae or dPhe4OCF$_3$.

In certain embodiment, X16 is absent, (D)NMeTyr, (D)Tyr, (D)(4-amino)Phe, (D)(3-amino)Phe, (D)Phe, (D)2-Nal, aMePhe, bhPhe, or Aib.

In certain embodiments, the peptide inhibitor comprises the structure of Formula (Z):

or a pharmaceutically acceptable salt or solvate thereof, wherein

R$^1$ is a bond, hydrogen, a C1-C6 alkyl, a C6-C12 aryl, a C6-C12 aryl-C1-C6 alkyl, a C1-C20 alkanoyl, and including PEGylated versions alone or as spacers of any of the foregoing; X is the amino acid sequence of Formula (I), Formula (II)-(XIf), or an amino acid sequence set forth in any of Table E1, E2 or E3; and R$^2$ is OH or NH$_2$.

In certain embodiments, the peptide inhibitor comprises the structure of Formula (Z'):

R¹—X3-X4-X5-X6-X7-X8-X9-X10-X11-X12-X13-X14-X15-X16-R² (Z')

or a pharmaceutically acceptable salt or solvate thereof, wherein

R¹ is a bond, hydrogen, a C1-C6 alkyl, a C6-C12 aryl, a C6-C12 aryl-C1-C6 alkyl, a C1-C20 alkanoyl, and including PEGylated versions alone or as spacers of any of the foregoing; X is the amino acid sequence of Formula (I), Formula (II)-(XIf), or an amino acid sequence set forth in any of Table E1, E2 or E3; and R² is OH or NH₂.

In certain embodiments, R¹ is H or C₁-C₂₀ alkanoyl.
In certain embodiments, R¹ is H or Ac.
In certain embodiments, R¹ is Ac.
In certain embodiments of the peptide of Formula Z, X3 is absent or D(arg).
In certain embodiments of the peptide of Formula Z, X4 is Abu, Cys, (D)Cys, alpha-MeCys, (D)Pen, Pen, or Pen (sulfoxide).
In certain embodiments of the peptide of Formula Z, X4 is Cys, (D)Cys, alpha-MeCys, (D)Pen, or Pen.
In certain embodiments of the peptide of Formula Z, X5 is Asn, Gln, or Glu.
In certain embodiments of the peptide of Formula Z, X6 is Thr, Aib, Asp, Dab, Gly, Pro, Ser, alpha-MeGln, alpha-MeLys, alpha-MeLeu, alpha-MeAsn, alpha-MeThr, alpha-MeSer, or Val.
In certain embodiments of the peptide of Formula Z, X7 is unsubstituted Trp, or Trp substituted with cyano, halo, alkyl, Trp-psi, haloalkyl, hydroxy, alkoxy, substituted or unsubstituted aryl, or substituted or unsubstituted heteroaryl.
In certain embodiments of the peptide of Formula Z, X7 is unsubstituted Trp, Trp-psi, Trp5Br, Trp7Cl, Trp7F, Trp5Me, or Trp7Me.
In certain embodiments of the peptide of Formula Z, X8 is Gln, alpha-MeLys, alpha-MeLeu, alpha-MeLys(Ac), beta-homoGln, Cit, Glu, Phe, Paf(Ac), Phe4NH2Ac, Asn, Thr, Val, Aib, alpha-MeGln, alpha-MeAsn, Lys(Ac), Dab(Ac), Dap(Ac), homo-Lys(Ac), 1-Nal, 2-Nal, or Trp.
In certain embodiments of the peptide of Formula Z, X8 is Gln, alpha-Me-Lys, alpha-MeLys(Ac), Lys(Ac), Paf(Ac), Phe4NH2Ac, or Glu.
In certain embodiments of the peptide of Formula Z, X9 is Cys, (D)Cys, alpha-MeCys, (D)Pen, or Pen
In certain embodiments of the peptide of Formula Z, X10 is unsubstituted Phe, or Phe substituted with halo, alkyl, haloalkyl, hydroxy, alkoxy, carboxy, carboxamido, 2-aminoethoxy, or 2-acetylaminoethoxy.
In certain embodiments of the peptide of Formula Z, X10 is Phe, Phe[4-(2-aminoethoxy)] [F(4-2ae)], Phe[4-(2-acetylaminoethoxy)], AEF, AEF(Ac), AEF(BH), AEF(Boc), AEF(Me)2, bMeRPhe, Phe42ae-ethyl, Phe42aeSMSB, Phe4Pip or Phe(4-CONH₂).

In certain embodiments of the peptide of Formula Z, X11 is 6amido2Nal, 6OMe2Nal, bMe2Nal(2S,3R), 2-Nal, aMe(2-Nal), rbMe2Nal, Phe(2-Me), Phe(3-Me), Phe(4-Me), Phe(3,4-dimethoxy), 1-Nal, unsubstituted Trp, or Trp substituted with cyano, halo, alkyl, haloalkyl, hydroxy, or alkoxy.

In certain embodiments of the peptide of Formula Z, X11 is 6amido2Nal, 6OMe2Nal, bMe2Nal(2S,3R), rbMe2Nal, 2-Nal, Phe(2-Me), Phe(3-Me), Phe(4-Me), Phe(3,4-dimethoxy), or 1-Nal.

In certain embodiments of the peptide of Formula Z, X12 is 4diFAchx, Achx, Acpx, AmeK(Boc), 4-amino-4-carboxytetrahydropyran (THP), alpha-MeLys, alpha-MeLeu, alpha-MeArg, alpha-MePhe, alpha-MeLeu, alpha-MeLys, alpha-MeAsn, alpha-MeTyr, Ala, cyclohexylAla, 1-aminocyclohexylAla (Achc), Acvc, Lys, or Aib.

In certain embodiments of the peptide of Formula Z, X12 is 4diFAchx, Achx, Acpx, AmeK(Boc), 4-amino-4-carboxytetrahydropyran (THP), alpha-MeLys, or alpha-MeLeu.

In certain embodiments of the peptide of Formula Z, X13 is Glu, Gln, Lys(Ac), or Lys.

In certain embodiments of the peptide of Formula Z, X14 is Asn, 2-Nap, Aib, Arg, Cit, Asp, Phe, Gly, Lys, Leu, Ala, (D)Ala, beta-Ala, His, Thr, n-Leu, Gln, Ser, (D)Ser, Tic, Trp, alpha-MeGln, alpha-MeAsn, alpha-MeLys(Ac), Dab(Ac), Dap(Ac), homo-Lys(Ac), or Lys(Ac).

In certain embodiments of the peptide of Formula Z, X16 is absent; and X15 is His, Aib, THP, Phe, substituted Phe, substituted (D)Phe, a-MePhe, substituted a-MePhe, Trp, substituted Trp, I-Nal, aMe(1-Nal), substituted 1-Nal, 2-Nal, aMe(2-Nal), substituted 2-Nal, or N-substituted Asn.

In certain embodiments of the peptide of Formula Z, X15 is His, PhetetraF, Phe3OH, ameF, THP, Phe, substituted Phe, (D)Phe, substituted (D)Phe, α-MePhe, bhPhe, Trp, substituted Trp, 1-Nal, aMe(1-Nal), substituted 1-Nal, 2-Nal, aMe(2-Nal), substituted 2-Nal, N-substituted Asn is (N-Me)Asn, (N-Et)Asn, (N-n-Pr)Asn, (N-iPr)Asn, (N-iBu)Asn, (N-nBu)Asn, (N-tBu)Asn, (N-benzyl)Asn, (N-Ph)Asn, (N-2-aminophenyl)Asn, (N-3-aminophenyl)Asn, (N-4-aminophenyl)Asn, (N-pyr)Asn, (N-3-Pyz)Asn, (N-4-Pyz)Asn, (N-pip)Asn, (N-5-indolyl)Asn, (N-propylamido)Asn, or (N-imidazo-2-yl)Asn In certain embodiments of the peptide of Formula Z, X16 is Aib, Phe, 3Pal, substituted Phe, substituted (D)Phe, substituted or unsubstited Tyr, unsubstituted (D)Tyr, α-MePhe, substituted α-MePhe, b-hPhe, 1-Nal, aMe(1-Nal), substituted 1-Nal, 2-Nal, aMe(2-Nal), substituted 2-Nal, or N-substituted Asn; and X15 is any amino acid.

In certain embodiments of the peptide of Formula Z, X 16 is dPhe4-2ae or dPhe4OCF₃.

In certain embodiments, the peptide is (SEQ ID NO: 1)
Ac-[Pen]-N-T-[W(7-Me)]-[Lys(Ac)]-[Pen]-Phe[4-(2-aminoethoxy)]-[3-Quin]-[a-MeLys]-

[Lys(Ac)-N-[(D)Leu]-NH2

(SEQ ID NO: 2)
[Propionic_acid]-[(D)Arg]-[Abu]-Q-T-W-Q-[Cys]-Phe[4-(2-aminoethoxy)]-[2-Nal]-[THP]-E-

N-[THP]-NH₂;

(SEQ ID NO: 2)
[Propionic_acid]-[(D)Arg]-[Pen]-Q-T-W-Q-[Pen]-Phe[4-(2-aminoethoxy)]-[2-Nal]-[THP]-E-

N-[a-MePhe]-NH₂;

-continued (SEQ ID NO: 4)
[Propionic_acid]-[(D)Arg]-[Pen]-Q-T-W-Q-[Pen]-[Phe(4-OMe)]-[2-Nal]-[THP]-E-N-[THP]-NH$_2$;

(SEQ ID NO: 5)
[3,3,3-Trifluoropropionic acid]-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 6)
[Propionic_acid]-[(D)Arg]-[Pen]-Q-T-W-Q-[Pen]-Phe[4-(2-aminoethoxy)]-[2-Nal]-[THP]-[Lys(COCF3)]-N-[THP]-NH$_2$;

(SEQ ID NO: 7)
[Propionic_acid]-[(D)Arg]-[Pen]-Q-T-W-Q-[Pen]-Phe[4-(2-aminoethoxy)]-[2-Nal]-[THP]-[Lys(COtBu)]-N-[THP]-NH$_2$;

(SEQ ID NO: 8)
[Propionic_acid]-[(D)Arg]-[Pen]-Q-T-W-Q-[Pen]-Phe[4-(2-aminoethoxy)]-[2-Nal]-[THP]-E-N-[N-Me-bAla]-NH$_2$;

(SEQ ID NO: 9)
[Pentanoic acid]-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 10)
[Propionic_acid]-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 11)
Ac-[(D)Arg]-[Abu]-Q-T-[W(7-Ph)]-[Lys(Ac)]-[Cys]-Phe[4-(2-aminoethoxy)]-[2-Nal]-[a-MeLys]-[Lys(Ac)]-N-[a-MePhe]-NH$_2$;

(SEQ ID NO: 12)
Ac-[(D)Arg]-[Abu]-Q-T-W-Q-[Cys]-Phe[4-(2-aminoethoxy)]-[2-Nal]-[THP]-E-N-N-ac;

(SEQ ID NO: 13)
Ac-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 4)
Ac-[(D)Arg]-[Pen]-Q-T-W-Q-[Pen]-Phe[4-(2-aminoethoxy)]-[2-Nal]-[THP]-E-N-[N-Me-bAla]-NH$_2$;

(SEQ ID NO: 15)
pr-[(D)Arg]-[Pen]-Q-T-W-Q-[Pen]-Phe[4-(2-aminoethoxy)]-[2-Nal]-[THP]-Q-N-[THP]-NH$_2$;

(SEQ ID NO: 16)
Ac-[(D)Arg]-[Cys]-Q-T-W-Q-A-Phe[4-(2-aminoethoxy)]-[2-Nal]-[THP]-[Orn(COMe)]-N-[THP]-NH$_2$;

(SEQ ID NO: 17)
Ac[(D)Arg]-[Abu]-Q-T-W-Q-[Cys]-Phe[4-(2-aminoethoxy)]-[2-Nal]-[THP]-E-N-F-NH$_2$;

(SEQ ID NO: 18)
[(D)Arg]-[Pen]-Q-T-W-Q-[Pen]-[Phe(4-OMe)]-[2-Nal]-[THP]-E-N-[THP]-NH$_2$;

(SEQ ID NO: 19)
pr-[(D)Arg]-[Pen]-Q-[Hyp]-W-Q-[Pen]-Phe[4-(2-aminoethoxy)]-[2-Nal]-[THP]-E-N-[THP]-NH$_2$;

(SEQ ID NO: 20)
pr-[(D)Arg]-[Cys]-Q-T-W-Q-[Pen]-Phe[4-(2-aminoethoxy)]-[2-Nal]-[THP]-E-N-[THP]-NH$_2$;

(SEQ ID NO: 21)
pr-[(D)Arg]-[Abu]-Q-T-W-Q-[Cys]-[Phe(4-OMe)]-[2-Nal]-[THP]-E-N-[THP]-NH$_2$;

(SEQ ID NOs: 21, 22, 25)
[(D)Arg]-[Abu]-Q-T-W-Q-[Cys]-[Phe(4-OMe)]-[2-Nal]-[THP]-E-N-[THP]-NH$_2$;

```
                                                                (SEQ ID NO: 23)
pr-[(D)Arg]-[Cys]-Q-T-W-Q-[Pen]-Phe[4-(2-aminoethoxy)]-[2-Nal]-[THP]-E-N-[a-MePhe]-
NH₂;

(SEQ ID NO: 24)
N3_Acid-[(D)Arg]-[Abu]-Q-T-W-Q-[Cys]-Phe[4-(2-aminoethoxy)]-[2-Nal]-[THP]-E-N-
[THP]-NH₂;

(SEQ ID NO: 25)
FPrpTriazoleMe_Acid-[(D)Arg]-[Abu]-Q-T-W-Q-[Cys]-[Phe(4-OMe)]-[2-Nal]-[THP]-E-N-
[THP]-NH₂;

(SEQ ID NO: 26)
pr-[(D)Arg]-[Pen]-Q-T-W-Q-[Pen]-Phe[4-(2-aminoethoxy)]-[2-Nal]-[THP]-[Lys(COtBu)]-
N-F-NH₂;

(SEQ ID NO: 27)
Ac-[(D)Arg]-[Abu]-Q-T-W-Q-[Cys]-Phe[4-(2-aminoethoxy)]-[2-Nal]-[Achc]-[aMeGlu]-N-
F-NH₂;

(SEQ ID NO: 28)
Ac-[(D)Arg]-[Abu]-Q-T-W-Q-[Cys]-Phe[4-(2-aminoethoxy)]-[2-Nal]-[Achc]-[aMeGlu]-N-
F-[Aib]-NH₂;

(SEQ ID NO: 29)
Ac-[(D)Arg]-[Abu]-Q-T-W-Q-[Cys]-Phe[4-(2-aminoethoxy)]-[2-Nal]-[Achc]-[aMeGlu]-N-
[a-MePhe]-NH₂;

{SEQ ID NO: 30)
Ac-[(D)Arg]-[Abu]-Q-T-W-Q-[Cys]-Phe[4-(2-aminoethoxy)]-[2-Nal]-[THP]-Q-N-[a-
MePhe]-NH₂;

(SEQ ID NO: 31)
Ac-[(D)Arg]-[Abu]-Q-T-W-Q-[Cys]-Phe[4-(2-aminoethoxy)]-[2-Nal]-[THP]-[a-MeGlu]-N-
ameW-NH₂;

(SEQ ID NO: 32)
Ac-[(D)Arg]-[Abu]-Q-T-W-Q-[Cys]-Phe[4-(2-aminoethoxy)]-[2-Nal]-[THP]-[aMeGlu]-N-
1[2-Nal]-NH₂;

(SEQ ID NO: 33)
pr-[(D)Arg]-[Pen]-Q-T-W-Q-[Pen]-Phe[4-(2-aminoethoxy)]-[2-Nal]-[THP]-
[Lys(CO2Allyl)]-N-F-NH₂;

(SEQ ID NO: 34)
Ac-[(D)Arg]-[Abu]-Q-T-W-Q-[Cys]-Phe[4-(2-aminoethoxy)]-[2-Nal]-[THP]-[aMeGlu]-N-
[Phe(4-CONH₂)]-NH₂;

(SEQ ID NO: 35)
Ac-[(D)Arg]-[Abu]-Q-T-W-Q-[Cys]-Phe[4-(2-aminoethoxy)]-[2-Nal]-[THP]-[aMeGlu]-N-
[2-Nal]-NH₂;

(SEQ ID NO: 36)
Ac-[(D)Arg]-[Abu]-Q-T-W-Q-[Cys]-Phe[4-(2-aminoethoxy)]-[2-Nal]-[THP]-[aMeGlu]-N-
[aMe(4-F)Phe]-NH₂;

(SEQ ID NO: 37)
Ac-[(D)Arg]-[Abu]-Q-T-W-Q-[Cys]-Phe[4-(2-aminoethoxy)]-[2-Nal]-[THP]-[aMeGlu]-N-
[THP]-NH₂;

(SEQ ID NO: 38)
Ac-[(D)Arg]-[Abu]-Q-T-W-Q-[Cys]-Phe[4-(2-aminoethoxy)]-[2-Nal]-[Achc]-[aMeGlu]-N-
[THP]-NH₂;
```

-continued (SEQ ID NO: 39)
Ac-[(D)Arg]-[Abu]-Q-T-W-Q-[Pen]-Phe[4-(2-aminoethoxy)]-[2-Nal]-[Achc]-[aMeGlu]-N-[THP]-NH$_2$;

(SEQ ID NO: 40)
Ac-[(D)Arg]-[Cys]-Q-T-W-Q-[Pen]-Phe[4-(2-aminoethoxy)]-[2-Nal]-[Achc]-[aMeGlu]-N-[aMePhe]-NH$_2$;

(SEQ ID NO: 41)
Ac-[(D)Arg]-[Abu]-Q-T-W-Q-[Cys]-Phe[3,4-diOMe)]-[2-Nal]-[THP]-[aMeGlu]-N-[a-[MePhe]-NH$_2$;

(SEQ ID NO: 42)
Ac-[(D)Arg]-[Abu]-Q-T-W-Q-[Cys]-Phe[4-(2-aminoethoxy)]-[2-Nal]-[Achc]-E-N-[THP]-NH$_2$;

(SEQ ID NO: 43)
Ac-[(D)Arg]-[Abu]-Q-T-W-Q-[Cys]-Phe[4-(2-aminoethoxy)]-[2-Nal]-[THP]-[aMeGlu]-N-F-[Aib]-[a-MeLys]-NH$_2$;

(SEQ ID NO: 44)
Ac-[(D)Arg]-[Abu]-Q-T-W-Q-[Cys]-Phe[4-(2-aminoethoxy)]-[2-Nal]-[THP]-[aMeGlu]-N-[aMeTyr]-NH$_2$;

(SEQ ID NO: 45)
Ac-[(D)Arg]-[Abu]-Q-T-W-Q-[Cys]-Phe[4-(2-aminoethoxy)]-[2-Nal]-[Achc]-[aMeGlu]-N-F-[Aib]-[a-MeLys]-NH$_2$;

(SEQ ID NO: 46)
Ac-[(D)Arg]-[Abu]-Q-T-W-Q-[Cys]-Phe[4-(2-aminoethoxy)]-[2-Nal]-[THP]-[aMeGlu]-N-[Phe(3,5-diF)]-NH$_2$;

(SEQ ID NO: 47)
[(D)Arg]-[Abu]-Q-T-W-Q-[Cys]-Phe[4-(2-(Boc)aminoethoxy)]-[2-Nal]-[THP]-E-N-[THP]-NH$_2$;

(SEQ ID NO: 48)
pr-[(D)Arg]-[Abu]-Q-T-W-Q-[aMeCys]-Phe[4-(2-aminoethoxy)]-[2-Nal]-[THP]-E-N-F-NH$_2$;

(SEQ ID NO: 49)
Ac-[(D)Arg]-[Abu]-Q-T-W-Q-[Cys]-Phe[4-(2-aminoethoxy)]-[2-Nal]-[THP]-[Aib]-N-F-NH$_2$;

(SEQ ID NO: 50)
Ac-[(D)Arg]-[Abu]-Q-T-W-Q-[Cys]-Phe[4-(2-aminoethoxy)]-[2-Nal]-[THP]-[Achc]-N-[a-MePhe]-NH$_2$;

(SEQ ID NO: 51)
Ac-[(D)Arg]-[Pen]-Q-T-W-Q-[Pen]-Phe[4-(2-aminoethoxy)]-[2-Nal]-[THP]-[Lys(COcPr)]-N-[THP]-NH$_2$;

(SEQ ID NO: 52)
Ac-[(D)Arg]-[Pen]-Q-T-W-Q-[Pen]-Phe[4-(2-aminoethoxy)]-[2-Nal]-[THP]-[Lys(COPr)]-N-[THP]-NH$_2$;

(SEQ ID NO: 53)
Ac-[(D)Arg]-[Pen]-Q-T-W-Q-[Pen]-Phe[4-(2-aminoethoxy)]-[2-Nal]-[THP]-[Lys(Ac)]-N-F-NH$_2$;

(SEQ ID NO: 54)
Ac-[(D)Arg]-[Pen]-Q-T-W-Q-[Pen]-Phe[4-(2-aminoethoxy)]-[2-Nal]-[THP]-[Lys(COEt)]-N-F-NH$_2$;

(SEQ ID NO: 55)
Ac-[(D)Arg]-[Pen]-Q-T-W-Q-[Pen]-Phe[4-(2-aminoethoxy)]-[2-Nal]-[THP]-[Lys(COcPr)]-N-F-NH$_2$;

```
                                                                        (SEQ ID NO: 56)
Ac-[(D)Arg]-Pen]-Q-T-W-Q-[Pen]-Phe[4-(2-aminoethoxy)]-[2-Nal]-[THP]-[Lys(Ac)]-N-
[THP]-NH2;

(SEQ ID NO: 57)
Ac-[(D)Arg]-[Pen]-Q-T-W-Q-[Pen]-Phe[4-(2-aminoethoxy)]-[2-Nal]-[THP]-[Lys(COEt)]-N-
[THP]-NH2;

(SEQ ID NO: 58)
Ac-[(D)Arg]-[Pen]-Q-T-W-Q-[Pen]-Phe[4-(2-aminoethoxy)]-[2-Nal]-[THP]-[Lys(COPr)]-N-
F-NH2;

(SEQ ID NO: 59)
Ac-[(D)Arg]-[Pen]-Q-T-W-Q-[Pen]-Phe[4-(2-aminoethoxy)]-[2-Nal]-[THP]-[Lys(COPent)]-
N-F-NH2;

(SEQ ID NO: 60)
Ac-[(D)Arg]-[Pen]-Q-T-W-Q-[Pen]-Phe[4-(2-aminoethoxy)]-[2-Nal]-[THP]-[Lys(COCF3)]-
N-F-NH2;

(SEQ ID NO: 61)
Ac-[(D)Arg]-[Pen]-Q-T-W-Q-[Pen]-Phe[4-(2-aminoethoxy)]-[2-Nal]-[THP]-[Lys(CoiPr)]-
N-F-NH2;

(SEQ ID NO: 64)
Ac-[Abu]-Q-T-[W(7-Me)]-[Lys(Ac)]-[Cys]-Phe[4-(2-aminoethoxy)]-[2-Nal]-[a-MeLys]-
[Lys(Ac)]-N-[(D)Lys]-NH2;

(SEQ ID NO: 65)
Ac-[Abu]-Q-T-[W(7-Me)]-[Lys(Ac)]-[Cys]-Phe[4-(2-aminoethoxy)]-[2-Nal]-[a-MeLys]-
[Lys(Ac)]-N-[(D)Leu]-NH2;

(SEQ ID NO: 66)
Ac-[Abu]-Q-T-[W(7-Me)]-[Lys(Ac)]-[Cys]-Phe[4-(2-aminoethoxy)]-[2-Nal]-[a-MeLys]-
[Lys(Ac)]-N-[a-MePhe]-NH2;

(SEQ ID NO: 67)
Ac-[Abu]-Q-T-[W(7-Ph)]-[Lys(Ac)]-[Cys]-Phe[4-(2-aminoethoxy)]-[2-Nal]-[a-MeLys]-
[Lys(Ac)]-N-[a-MePhe]-NH2;

(SEQ ID NO: 68)
Ac-[Pen]-N-T-[W(7-Me)]-[Lys(Ac)]-[Pen]-Phe[4-(2-aminoethoxy)]-[2-Nal]-[a-MeLys]-
[Lys(Ac)]-N-[(D)Leu]-[a-MePhe]-NH2;

(SEQ ID NO: 69)
Ac-[Pen]-N-T-[W(7-Me)]-[Lys(Ac)]-[Pen]-Phe[4-(2-aminoethoxy)]-[2-Nal]-[a-MeLys]-
[Lys(Ac)]-N-[(D)Leu]-[(D)a-MePhe]-NH2;

(SEQ ID NO: 70)
Ac-[Pen]-N-T-[W(7-Me)]-[Lys(Ac)]-[Pen]-Phe[4-(2-aminoethoxy)]-[2-Nal]-[a-MeLys]-
[Lys(Ac)]-N-[Aib-Ahx]-NH2;

(SEQ ID NO: 71)
Ac-[Pen]-N-T-[W(7-Me)]-[Lys(Ac)]-[Pen]-Phe[4-(2-aminoethoxy)]-[2-Nal]-[a-MeLys]-
[Lys(Ac)]-N-[Aib]-[bhPhe]-NH2;

(SEQ ID NO: 72)
Ac-[Pen]-N-[(D)Dap]-[W(7-Me)]-[Lys(Ac)]-[Pen]-Phe[4-(2-aminoethoxy)]-[2-Nal]-[a-MeLys]-
[Lys(Ac)]-N-[(D)Leu]-NH2;

(SEQ ID NO: 73)
Ac-[Pen]-[(D)Lys]-[W(7-Me)]-[Lys(Ac)]-[Pen]-Phe[4-(2-aminoethoxy)]-[2-Nal]-[a-MeLys]-
[Lys(Ac)]-N-[(D)Leu]-NH2;
```

-continued (SEQ ID NO: 74)
Ac-[Pen]-N-[(D)Asp]-[W(7-Me)]-[Lys(Ac)]-[Pen]-Phe[4-(2-aminoethoxy)]-[2-Nal]-[a-MeLys]-[Lys(Ac)]-N-[(D)Leu]-NH2;

(SEQ ID NO: 75)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[THP]-NH$_2$;

(SEQ ID NO: 76)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH$_2$;

(SEQ ID NO: 77)
Ac-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH$_2$;

(SEQ ID NO: 78)
Ac-[(D)Arg]-[Abu]-Q-T-W-Q-[Cys]-Phe[4-(2-aminoethoxy)]-[2-Nal]-[THP]-[aMeGlu]-N-[Phe(3,4-diOMe)]-NH$_2$;

(SEQ ID NO: 79)
Ac-[(D)Arg]-[Abu]-Q-T-W-Q-[Cys]-Phe[4-(2-aminoethoxy)]-[2-Nal]-[THP]-[aMeGlu]-N-[(D)Phe(3,4-diOMe)]-NH$_2$;

(SEQ ID NO: 80)
Ac-[(D)Arg]-[Abu]-Q-T-W-Q-[Cys]-Phe[4-(2-aminoethoxy)]-[2-Nal]-[THP]-E-N-[aMe(2-Nal)]-NH$_2$;

(SEQ ID NO: 81)
Ac-[(D)Arg]-[Abu]-Q-T-W-Q-[Cys]-Phe[4-(2-aminoethoxy)]-[2-Nal]-[THP]-[aMeGlu]-N-[W(5-F)]-NH$_2$;

(SEQ ID NO: 82)
Ac-[Pen]-Q-T-W-[Lys(Ac)]-[Pen]-Phe[4-(2-aminoethoxy)]-[2-Nal]-[a-MeLys]-[Lys(Ac)]-N-[a-MePhe]-NH$_2$;

(SEQ ID NO: 83)
pr-[(D)Arg]-[Abu]-Q-T-W-Q-[aMeCys]-Phe[4-(2-aminoethoxy)]-[2-Nal]-[THP]-E-N-[a-MePhe]-NH$_2$;

(SEQ ID NO: 84)
Ac-[Pen]-Q-T-W-[Lys(Ac)]-[Pen]-Phe[4-(2-aminoethoxy)]-[2-Nal]-[a-MeLys]-[Lys(Ac)]-N-[THP]-NH$_2$;

(SEQ ID NO: 85)
pr-[(D)Arg]-[Abu]-Q-T-W-Q-[Cys]-Phe[4-(2-aminoethoxy)]-[2-Nal]-[THP]-E-N-[a-MePhe]-NH$_2$;

(SEQ ID NO: 86)
pr-[(D)Arg]-[Abu]-Q-T-W-Q-[Cys]-Phe[4-(2-aminoethoxy)]-[aMe(2-Nal)]-[THP]-E-N-[a-MePhe]-NH$_2$;

(SEQ ID NO: 87)
Ac-[Pen]-N-T-[W(7-Me)]-Q-[Pen]-Phe[4-(2-aminoethoxy)]-[2-Nal]-[a-MeLys]-[Lys(Ac)]-N-[THP]-NH$_2$;

(SEQ ID NO: 88)
Ac-[(D)Arg]-[Pen]-N-T-W-[Lys(Ac)]-[Pen]-Phe[4-(2-aminoethoxy)]-[2-Nal]-[Acvc]-E-N-[THP]-NH$_2$;

(SEQ ID NO: 89)
Ac-[Pen]-N-T-[W(7-Me)]-Q-[Pen]-Phe[4-(2-aminoethoxy)]-[2-Nal]-[a-MeLys]-[Lys(Ac)]-N-[a-MePhe]-NH$_2$;

-continued

```
                                                                    (SEQ ID NO: 90)
Ac-[(D)Arg]-[Pen]-N-T-[W(7-Me)]-Q-[Pen]-Phe[4-(2-aminoethoxy)]-[2-Nal]-[THP]-E-N-
[THP]-NH₂;
                                                                    (SEQ ID NO: 91)
Ac-[(D)Arg]-[Pen]-N-T-[W(7-Me)]-Q-[Pen]-Phe[4-(2-aminoethoxy)]-[2-Nal]-[THP]-E-N-
[a-MePhe]-NH₂;
                                                                    (SEQ ID NO: 92)
Ac-[(D)Arg]-[Pen]-N-T-[W(7-Me)]-[Lys(Ac)]-[Pen]-Phe[4-(2-aminoethoxy)]-[2-Nal]-
[THP]-E-N-[THP]-NH₂;
                                                                    (SEQ ID NO: 93)
Ac-[(D)Arg]-[Pen]-N-T-[W(7-Me)]-Q-[Pen]-Phe[4-(2-aminoethoxy)]-[2-Nal]-[Acvc]-E-N-
[a-MePhe]-NH₂;
                                                                    (SEQ ID NO: 94)
Ac-[(D)Arg]-[Pen]-N-T-[W(7-Me)]-[Lys(Ac)]-[Pen]-Phe[4-(2-aminoethoxy)]-[2-Nal]-
[Acvc]-E-N-[a-MePhe]-NH₂;
                                                                    (SEQ ID NO: 95)
Ac-[Pen]-N-T-W-[Lys(Ac)]-[Pen]-Phe[4-(2-aminoethoxy)]-[2-Nal]-[a-MeLys]-[Lys(Ac)]-N-
[THP]-NH₂;
                                                                 (SEQ ID NOs: 96, 109)
Ac-[(D)Arg]-[Pen]-N-T-[W(b-Me)]-[Lys(Ac)]-[Pen]-Phe[4-(2-aminoethoxy)]-[2-Nal]-
[THP]-E-N-[a-MePhe]-NH₂;
                                                                    (SEQ ID NO: 97)
Ac-[(D)Arg]-[Pen]-Q-T-W-Q-[Pen]-Phe[4-(2-aminoethoxy)]-[2-Nal]-[THP]-E-N-[a-
MePhe]-NH₂;
                                                                    (SEQ ID NO: 98)
Ac-[Pen]-N-T-W-[Lys(Ac)]-[Pen]-Phe[4-(2-aminoethoxy)]-[2-Nal]-[a-MeLys]-[Lys(Ac)]-N-
[a-MePhe]-NH₂;
                                                                    (SEQ ID NO: 99)
Ac-[(D)Arg]-[Pen]-N-T-[W(7-Me)]-Q-[Pen]-Phe[4-(2-aminoethoxy)]-[2-Nal]-[Acvc]-E-N-
[THP]-NH₂;
                                                                    (SEQ ID NO: 100)
Ac-[Pen]-N-T-[W(7-Me)]-[Lys(Ac)]-[Pen]-Phe[4-(2-aminoethoxy)]-[2-Nal]-[a-MeLys]-
[Lys(Ac)]-N-[a-MePhe]-[(D)Tyr]-NH₂;
                                                                    (SEQ ID NO: 101)
Ac-[(D)Arg]-[Pen]-N-T-[W(7-Me)]-[Lys(Ac)]-[Pen]-Phe[4-(2-aminoethoxy)]-[2-Nal]-
[Acvc]-E-N-[THP]-NH₂;
                                                                    (SEQ ID NO: 102)
Ac-[(D)Arg]-[Pen]-N-T-W-[Lys(Ac)]-[Pen]-Phe[4-(2-aminoethoxy)]-[2-Nal]-[Acvc]-E-N-
[a-MePhe]-NH₂;
                                                                    (SEQ ID NO: 103)
Ac-[Pen]-N-T-W-[Lys(COCF3)]-[Pen]-Phe[4-(2-aminoethoxy)]-[2-Nal]-[a-MeLys]-
[Lys(Ac)]-N-[THP]-NH₂;
                                                                    (SEQ ID NO: 104)
Ac-[Pen]-N-T-[W(7-Me)]-[Cit]-[Pen]-Phe[4-(2-aminoethoxy)]-[2-Nal]-[aMeLeu]-[Lys(Ac)]-
N-[a-MePhe]-NH₂;
                                                                    (SEQ ID NO: 105)
Ac-[(D)Arg]-[Pen]-N-T-W-[Lys(Ac)]-[Pen]-Phe[4-(2-aminoethoxy)]-[2-Nal]-[THP]-E-N-
[THP]-NH₂;
```

-continued (SEQ ID NO: 106)
Ac-[(D)Arg]-[Pen]-N-T-W-[Lys(Ac)]-[Pen]-Phe[4-(2-aminoethoxy)]-[2-Nal]-[THP]-E-N-[a-MePhe]-NH$_2$;

(SEQ ID NO: 107)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[THP]-[(D)Tyr]-NH$_2$;

(SEQ ID NO: 108)
Ac-[Pen]-N-T-[W(7-Me)]-[Cit]-[Pen]-Phe[4-(2-aminoethoxy)]-[2-Nal]-[aMeLeu]-[Lys(Ac)]-N-[THP]-NH$_2$;

(SEQ ID NO: 109)
Ac-[(D)Arg]-[Pen]-N-T-[W(b-Me)]-[Lys(Ac)]-[Pen]-Phe[4-(2-aminoethoxy)]-[2-Nal]-[THP]-E-N-[a-MePhe]-NH$_2$;

(SEQ ID NO: 110)
Ac-[(D)Arg]-[Pen]-Q-T-W-Q-[Pen]-Phe[4-(2-aminoethoxy)]-[2-Nal]-[THP]-E-N-[(N-benzyl)Asn]-NH$_2$;

(SEQ ID NO: 111)
Ac-[(D)Arg]-[Pen]-N-T-[W(7-Me)]-[Lys(Ac)]-[Pen]-Phe[4-(2-aminoethoxy)]-[2-Nal]-[THP]-[Lys(Ac)]-N-[a-MePhe]-NH$_2$;

(SEQ ID NO: 112)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-Phe[4-NH2]-NH$_2$;

(SEQ ID NO: 113)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[(D)Leu]-NH2;

(SEQ ID NO: 114)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-(D)Phe[4-NH2]-NH$_2$;

(SEQ ID NO: 115)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-(D)Phe[3-NH2]-NH$_2$;

(SEQ ID NO: 116)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-[3Pal]-NH$_2$;

(SEQ ID NO: 117)
Ac-[Cys]-N-T-[W(7-Me)]-[Lys(Ac)]-[aMeCys]-Phe[4-(2-aminoethoxy)]-[2-Nal]-[a-MeLys]-[Lys(Ac)]-N-[THP]-NH$_2$;

(SEQ ID NO: 118)
Ac-[Cys]-N-T-[W(7-Me)]-[Lys(Ac)]-[aMeCys]-Phe[4-(2-aminoethoxy)]-[2-Nal]-[a-MeLys]-[Lys(Ac)]-N-[a-MePhe]-NH$_2$;

(SEQ ID NO: 119)
Ac-[Cys]-N-T-[W(7-Me)]-Q-[aMeCys]-Phe[4-(2-aminoethoxy)]-[2-Nal]-[a-MeLys]-[Lys(Ac)]-N-[a-MePhe]-NH$_2$;

(SEQ ID NO: 120)
Ac-[Cys]-N-T-[W(7-Me)]-Q-[aMeCys]-Phe[4-(2-aminoethoxy)]-[2-Nal]-[a-MeLys]-[Lys(Ac)]-N-[THP]-NH$_2$;

(SEQ ID NO: 121)
Ac-[Cys]-N-T-W-[Lys(Ac)]-[aMeCys]-Phe[4-(2-aminoethoxy)]-[2-Nal]-[a-MeLys]-[Lys(Ac)]-N-[THP]-NH$_2$;

(SEQ ID NO: 122)
Ac-[Cys]-N-T-W-[Lys(Ac)]-[aMeCys]-Phe[4-(2-aminoethoxy)]-[2-Nal]-[a-MeLys]-[Lys(Ac)]-N-[a-MePhe]-NH$_2$;

(SEQ ID NO: 123)
Ac-[(D)Arg]-[Abu]-Q-T-W-Q-[Cys]-Phe[4-(2-aminoethoxy)]-[2-Nal]-[THP]-E-N-[a-MePhe]-NH$_2$;

(SEQ ID NO: 124)
Ac-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH$_2$;

(SEQ ID NO: 125)
Ac-[(D)Arg]-[Pen]-Q-T-W-Q-[Pen]-Phe[4-(2-aminoethoxy)]-[2-Nal]-[THP]-E-N-[(N-Ph)Asn]-NH$_2$;

(SEQ ID NO: 126)
Ac-[(D)Arg]-[Pen]-Q-T-W-Q-[Pen]-Phe[4-(2-aminoethoxy)]-[2-Nal]-[THP]-E-N-[(N-(2-aminophenyl))Asn]-NH$_2$;

(SEQ ID NO: 127)
Ac-[(D)Arg]-[Pen]-Q-T-W-Q-[Pen]-Phe[4-(2-aminoethoxy)]-[2-Nal]-[THP]-E-N-[(N-Pip)Asn]-NH$_2$;

(SEQ ID NO: 128)
Ac-[(D)Arg]-[Pen]-Q-T-W-Q-[Pen]-Phe[4-(2-aminoethoxy)]-[2-Nal]-[THP]-E-N-[(N-Pyr)Asn]-NH$_2$;

(SEQ ID NO: 129)
Ac-[(D)Arg]-[Pen]-Q-T-W-Q-[Pen]-Phe[4-(2-aminoethoxy)]-[2-Nal]-[THP]-E-N-[(N-(4-aminophenyl))Asn]-NH$_2$;

(SEQ ID NO: 130)
Ac-[(D)Arg]-[Pen]-Q-T-W-Q-[Pen]-Phe[4-(2-aminoethoxy)]-[2-Nal]-[THP]-E-N-[(N-(3-aminophenyl))Asn]-NH$_2$;

(SEQ ID NO: 131)
Ac-[(D)Arg]-[Pen]-Q-T-W-Q-[Pen]-Phe[4-(2-aminoethoxy)]-[2-Nal]-[THP]-E-N-[(N-(4-Pyz))Asn]-NH$_2$;

(SEQ ID NO: 132)
Ac-[(D)Arg]-[Pen]-Q-T-W-Q-[Pen]-Phe[4-(2-aminoethoxy)]-[2-Nal]-[THP]-E-N-[(N-(5-indolyl)Asn]-NH$_2$;

(SEQ ID NO: 133)
Ac-[(D)Arg]-[Pen]-Q-T-W-Q-[Pen]-Phe[4-(2-aminoethoxy)]-[2-Nal]-[THP]-E-N-[(N-(3-Pyz))Asn]-NH$_2$;

(SEQ ID NO: 358)
pr-[(D)Arg]-[Pen]-Q-T-W-Q-[Pen]-Phe[4-(2-aminoethoxy)]-[2-Nal]-THP-E-N-[THP]-NH$_2$;

(SEQ ID NO: 135)
pr-[(D)Arg]-[Pen]-Q-T-W-Q-[Pen]-Phe[(aMe)-4-(2-aminoethoxy)]-[2-Nal]-[THP]-E-N-[THP]-NH$_2$;

(SEQ ID NO: 136)
Ac-[(D)Arg]-[Pen]-Q-T-W-Q-[Pen]-Phe[4-(2-aminoethoxy)]-[2-Nal]-[THP]-E-N-[(N-propylamido)Asn]-NH$_2$;

(SEQ ID NO: 137)
Ac-[(D)Arg]-[Pen]-Q-T-W-Q-[Pen]-Phe[4-(2-aminoethoxy)]-[2-Nal]-[THP]-E-N-[(N-(imidazol-2-yl)methyl)Asn]-NH$_2$;

(SEQ ID NO: 138)
Ac-[Pen]-N-T-[W(7-Me)]-[Lys(Ac)]-[Pen]-Phe[4-(2-aminoethoxy)]-[2-Nal]-[THP]-[Lys(COCF3)]-N-[a-MePhe]-NH$_2$;

(SEQ ID NO: 139)
Ac-[Pen]-N-T-[W(7-Me)]-[Lys(Ac)]-[Pen]-Phe[4-(2-aminoethoxy)]-[2-Nal]-[THP]-[Lys(COtBu)]-N-[a-MePhe]-NH$_2$;

(SEQ ID NO: 140)
Ac-[Pen]-N-T-[W(7-Me)]-[Lys(Ac)]-[Pen]-Phe[4-(2-aminoethoxy)]-[2-Nal]-[THP]-[Lys(COCF3)]-N-[THP]-NH$_2$;

(SEQ ID NO: 141)
Ac-[Pen]-N-T-[W(7-Me)]-[Lys(Ac)]-[Pen]-Phe[4-(2-aminoethoxy)]-[2-Nal]-[THP]-[Lys(COtBu)]-N-[THP]-NH$_2$;

(SEQ ID NO: 142)
PentCO-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH$_2$;

(SEQ ID NO: 143)
Biotin-[(D)Arg]-[Pen]-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 144)
Biotin-PEG2(2:2)-[(D)Arg](x,2:1, 3:2)-Pen(1:3,3:1)-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 145)
Biotin-PEG3(2:2)-[(D)Arg](x,2:1, 3:2)-Pen(1:3,3:1)-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 146)
FlagTag-[(D)Arg]-[Pen]-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 147)
FlagTag-PEG2(2:2)-[(D)Arg](x,2:1, 3:2)-Pen(1:3,3:1)-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 148)
FlagTag-PEG3(2:2)-[(D)Arg](x,2:1, 3:2)-Pen(1:3,3:1)-N-T-[W(7-Me)]-[Lys(Ac)]-[Pen]-Phe[4-(2-aminoethoxy)]-[2-Nal]-[THP]-E-N-[THP]-NH$_2$;

(SEQ ID NO: 149)
Ac-[(D)Arg]-[Pen]-N-T-[W(7-Me)]-[Cit]-[Pen]-Phe[4-(2-aminoethoxy)]-[2-Nal]-[aMeLeu]-E-N-[a-MePhe]-NH$_2$;

(SEQ ID NO: 150)
Ac-[(D)Arg]-[Pen]-N-T-[W(7-Me)]-[Lys(Ac)]-[Pen]-Phe[4-(2-aminoethoxy)]-[2-Nal]-[THP]-[aMeGlu]-N-[aMeTyr]-NH$_2$;
or (SEQ ID NO: 151)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[aMeTyr]-NH$_2$;

and the peptide inhibitor is cyclized via a Abu-Cys thioether bond, or Pen-Pen disulfide bond.

In certain embodiments, the peptide is (SEQ ID NO: 202)
Ac-[Pen]-N-T-[W(7-Me)]-[Cit]-[Pen]-Phe[4-(2-aminoethoxy)]-[2-Nal]-[a-MeLys]-[Lys(Ac)]-N-[Aib]-[(D)Tyr]-NH2;

(SEQ ID NO: 21)
Ac-[Pen]-N-T-[W(7-F-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 223)
Ac-[Pen]-N-T-[W(7-Cl)][Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 225)
Ac-[Pen1-N-T-[W(5-Br)]-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 227)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[(D)Lys]-[(D)Phe(4-OCF3)]-am;

(SEQ ID NO: 231)
Ac-[Pen]-N-T-[W(7-Me)]-[Lys(Ac)]-[Pen]-Phe[4-(2-aminoethoxy)]-[2-Nal]-[Acvc]-E-N-[THP]-N(H)Me;

(SEQ ID NO: 232)
Ac-[Pen]-N-T-[W(7-Me)]-[Lys(Ac)]-[Pen]-Phe[4-(2-aminoethoxy)]-[2-Nal]-[THP]-E-N-[(D)Leu]-[(D)Tyr]-NH2;

(SEQ ID NO: 235)
Ac-[Pen]-N-T-[W(7-Me)]-[Lys(Ac)]-[Pen]-Phe[4-(2-aminoethoxy)]-[2-Nal]-[Acvc]-E-N-[(D)Phe(4-NH2)]-[(D)Tyr]-NH2;

(SEQ ID NO: 242)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[Phe(tetrafluoro)]-am;

(SEQ ID NO: 244)
Ac-[Pen]-N-T-[W(7-Me)]-[Lys(Ac)]-[Pen]-Phe[4-(2-aminoethoxy)]-[2-Nal]-[a-MeLys]-[Lys(Ac)]-N-[(D)Lys]-[(D)Phe[4-(2-aminoethoxy)]]-am;

(SEQ ID NO: 253)
Ac-[Pen]-N-T-[W(7-Me)]-[Lys(Ac)]-[Pen]-Phe[4-(2-acetylaminoethoxy)]-[2-Nal]-[a-MeLys]-[Lys(Ac)]-N-[THP]-NH2;

(SEQ ID NO: 254)
Ac-[Pen]-N-T-[W(7-Me)]-Phe_4NH2_Ac-[Pen]-Phe[4-(2-aminoethoxy)]_Ac-[2-Nal]-[a-MeLys]-[Lys(Ac)]-N-[THP]-NH2;

(SEQ ID NO: 255)
Ac-[Pen]-N-T-[W(7-Me)]-[Lys(Ac)]-[Pen]-[(R)bMePhe]-[2-Nal]-[a-MeLys]-[Lys(Ac)]-N-[THP]-NH2;

(SEQ ID NO: 229)
BenzHydroxylIodine_Acid-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 201)
Ac-[(D)Arg]-[Abu]-Q-T-[W(7-Me)]-[Lys(Ac)]-[Cys]-Phe[4-(2-aminoethoxy)]-[2-Nal]-[a-MeLys]-[Lys(Ac)]-N-[a-MePhe]-NH2;

-continued (SEQ ID NO: 203)
Ac-[(D)Arg]-[Pen]-Q-T-W-Q-[Pen]-Phe[4-(2-aminoethoxy)]-[2-Nal]-[THP]-E-N-[Aib]-NH2;

(SEQ ID NO: 204)
Ac-[(D)Arg]-[Abu]-Q-T-W-Q-[Cys]-Phe[4-(2-aminoethoxy)]-[2-Nal]-[THP]-E-N-[Aib]-NH2;

(SEQ ID NO: 329)
Nterm_bA(2:3)-[(D)Arg]-[Abu]-Q-T-W-Q-[Cys]-Phe[4-(2-aminoethoxy)]-[2-Nal]-[THP]-E(2:3)-N-[THP]-NH2;

(SEQ ID NO: 206)
FPrpTriazoleMe_Acid-[(D)Arg]-[Abu]-Q-T-W-Q-[Cys]-Phe[4-(2-aminoethoxy)]-[2-Nal]-[THP]-E-N-[THP]-NH2;

(SEQ ID NO: 208)
Pr-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH2;

(SEQ ID NO: 211)
N3_Acid-[(D)Arg]-[Pen]-N-T-[W(7-me)]-[Lys(Ac)]-[Pen]-Phe[4-(2-aminoethoxy)]-[2-Nal]-[THP]-E-N-[a-MePhe]-NH2;

(SEQ ID NO: 212)
MeSO2-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH2;

(SEQ ID NO: 24)
[(D)Arg]-[Abu]-Q-T-W-Q-[Cys]-Phe[4-(2-aminoethoxy)]-[2-Nal]-[THP]-E-N-[THP]-NH2;

(SEQ ID NO: 213)
Pr-[(D)Arg]-[Abu]-Q-T-W-Q-[Cys]-Phe[4-(2-aminoethoxy)]_Ethyl)]-[2-Nal]-[THP]-E-N-[THP]-NH2;

(SEQ ID NO: 215)
Ac-[(D)Arg]-[Pen]-N-T-[W(7-Me)]-[Lys(Ac)]-[Pen]-Phe[4-(2-aminoethoxy)]-[2-Nal]-[THP]-E-N-[(D)Leu]-[(D)Tyr]-NH2;

(SEQ ID NO: 216)
Ac-[(D)Arg]-[Pen]-N-T-[W(7-Me)]-[Lys(Ac)]-[Pen]-Phe[4-(2-aminoethoxy)]-[2-Nal]-[THP]-E-N-[THP]-[(D)Tyr]-NH2;

(SEQ ID NO: 217)
Ac-[(D)Arg]-[Pen]-N-T-[W(7-Me)]-[Lys(Ac)]-[Pen]-Phe[4-(2-aminoethoxy)]-[2-Nal]-[Acvc]-E-N-[THP]-[(D)Tyr]-NH2;

(SEQ ID NO: 218)
Dota-[a)]-[(D)Arg]-[Pen]-N-T-[W(7-Me)]-[Lys(Ac)]-[Pen]-Phe[4-(2-aminoethoxy)]-[2-Nal]-[THP]-E-N-[THP]-NH2;

(SEQ ID NO: 219)
Dota_PEG2_Acid-[(D)Arg]-[Pen]-N-T-[W(7-Me)]-[Lys(Ac)]-[Pen]-Phe[4-(2-aminoethoxy)]-[2-Nal]-[THP]-E-N-[THP]-NH2;

(SEQ ID NO: 220)
Dota_PEG3_Acid-[(D)Arg]-[Pen]-N-T-[W(7-Me)]-[Lys(Ac)]-[Pen]-Phe[4-(2-aminoethoxy)]-[2-Nal]-[THP]-E-N-[THP]-NH2;

(SEQ ID NO: 222)
Ac-[(D)Arg]-[Pen]-N-T-[W(7-F)]-[Lys(Ac)]-[Pen]-Phe[4-(2-aminoethoxy)]-[2-Nal]-[THP]-E-N-[a-MePhe]-NH2;

(SEQ ID NO: 224)
Ac-[(D)Arg]-[Pen]-N-T-[W(7-Cl)]-[Lys(Ac)]-[Pen]-Phe[4-(2-aminoethoxy)]-[2-Nal]-[THP]-E-N-[a-MePhe]-NH2;

-continued

```
                                                      (SEQ ID NO: 226)
Ac-[(D)Arg]-[Pen]-N-T-[W(5-Br)]-[Lys(Ac)]-[Pen]-Phe[4-(2-aminoethoxy)]-[2-Nal]-[THP]-

E-N-[a-MePhe]-NH2;

(SEQ ID NO: 228)
Ac-[(D)Arg]-[Pen]-N-T-[W(7-Me)]-[Lys(Ac)]-[Pen]-Phe[4-(2-aminoethoxy)]-[2-Nal]-

[THP]-E-N-[(D)Lys]-[(D)Phe(4-OCF3)]-am;

(SEQ ID NO: 230)
BenzHydroxylIodine_Acid-[(D)Arg]-[Pen]-N-T-[W(7-Me)]-[Lys(Ac)]-[Pen]-Phe[4-(2- aminoethoxy)-[2-Nal]-[THP]-E-N-[a-MePhe]-NH2;

(SEQ ID NO: 233)
Ac-[(D)Arg]-[Pen]-N-T-[W(7-Me)]-[Lys(Ac)]-[Pen]-Phe[4-(2-aminoethoxy)]-[2-Nal]-

[Achc]-E-N-[THP]-NH2;

(SEQ ID NO: 234)
Ac-[(D)Arg]-[Pen]-N-T-[W(7-Me)]-[Lys(Ac)]-[Pen]-Phe[4-(2-aminoethoxy)]-[2-Nal]-

[Acvc]-E-N-[THP]-N(H)Me;

(SEQ ID NO: 236)
Pr-[(D)Arg]-[Pen]-Q-T-W-Q-[Pen]-Phe[4-(2-aminoethoxy)]-[(R)(bMe)(2-Nal)]-[THP]-E-N-

[THP]-NH2;

(SEQ ID NO: 237)
Ac-[(D)Arg]-[Pen]-N-T-[W(7-Me)]-[Lys(Ac)]-[Pen]-Phe[4-(2-acetylaminoethoxy)]-[2-Nal]-

[THP]-E-N-[THP]-NH2;

(SEQ ID NO: 238)
Pr-[(D)Arg]-[Pen]-Q-T-[Trp_psi]-Q-[Pen]-Phe[4-(2-aminoethoxy)]-[2-Nal]-[THP]-E-N-

[THP]-NH2;

(SEQ ID NO: 240)
FPrpTriazoleMe_Acid-[(D)Arg]-[Pen]-N-T-[W(7-Me)]-[Lys(Ac)]-[Pen]-Phe[4-(2- aminoethoxy)]-[2-Nal]-[THP]-E-N-[a-MePhe]-NH2;

(SEQ ID NO: 241)
Ac-[(D)Arg]-[Pen]-N-T-[W(7-Me)]-[Lys(Ac)]-[Pen]-Phe_4Pip-[2-Nal]-[THP]-E-N-[a-

MePhe]-NH2;

(SEQ ID NO: 243)
Ac-[(D)Arg]-[Pen]-N-T-[W(7-Me)]-[Lys(Ac)]-[Pen]-Phe[4-(2-aminoethoxy)]-[2-Nal]-

[THP]-E-N-[Phe(tetrafluoro)]-am;

(SEQ ID NO: 245)
Ac-[(D)Arg]-[Pen]-N-T-[W(7-Me)]-[Lys(Ac)]-[Pen]-Phe[4-(2-aminoethoxy)]-[2-Nal]-

[THP]-E-N-[(D)Lys]-[(D)Phe[4-(2-aminoethoxY)]]-am;

(SEQ ID NO: 246)
Ac-[(D)Arg]-[Pen]-N-T-[W(7-Me)]-[Lys(Ac)]-[Pen]-Phe[4-(2-(SMSB)-aminoethoxy)]-[2-

Nal]-[THP]-E-N-[a-MePhe]-NH2;

(SEQ ID NO: 247)
SulfCyanine3-[(D)Arg]-[Pen]-N-T-[W(7-Me)]-[Lys(Ac)]-[Pen]-Phe[4-(2-aminoethoxy)]-[2-

Nal]-[THP]-E-N-[a-MePhe]-NH2;

(SEQ ID NO: 248)
SulfCyanine3_dPEG2-[(D)Arg]-[Pen]-N-T-[W(7-Me)]-[Lys(Ac)]-[Pen]-Phe[4-(2- aminoethoxy)]-[2-Nal]-[THP]-E-N-[a-MePhe]-NH2;

(SEQ ID NO: 249)
SulfCyanine3_dPEG3-[(D)Arg]-[Pen]-N-T-[W(7-Me)]-[Lys(Ac)]-[Pen]-Phe[4-(2- aminoethoxy)]-[2-Nal]-[THP]-E-N-[a-MePhe]-NH2;
```

-continued (SEQ ID NO: 251)
Ac-[(D)Arg]-[Pen]-N-T-[W(7-Me)]-[Lys(Ac)]-[Pen]-Phe[4-(2-aminoethoxy)]-[2-Nal]-[THP]-E-N-[Phe(3-OH)]-am;

(SEQ ID NO: 252)
SMSBCO-[(D)Arg]-[Pen]-N-T-[W(7-Me)]-[Lys(Ac)]-[Pen]-Phe[4-(2-aminoethoxy)]-[2-Nal]-[THP]-E-N-[a-MePhe]-NH2;

(SEQ ID NO: 256)
Ac-[(D)Arg]-[Pen]-N-T-[W(7-Me)]-[Lys(Ac)]-[Pen]-[(R)bMePhe]-[2-Nal]-[THP]-E-N-[THP]-NH2;

(SEQ ID NO: 257)
Ac-[(D)Arg]-[Pen]-N-T-[W(5-Me)]-[Lys(Ac)]-[Pen]-Phe[4-(2-aminoethoxy)]-[2-Nal]-[THP]-E-N-[a-MePhe]-NH2;

(SEQ ID NO: 239)
FPrpTriazoleMe_Acid-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 209)
MeSO2-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 210)
N3_Acid-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2;

(SEQ ID NO: 207)
Pr-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2;
or (SEQ ID NO: 250)
SMSBCO-[Pen]-N-T-[W(7-Me)]-[Lys(Ac)]-[Pen]-Phe[4-(2-aminoethoxy)]-[2-Nal]-[a-MeLys]-[Lys(Ac)]-N-[a-MePhe]-NH2.

In one embodiment the peptide inhibitor consists of about or less than 25 amino acids. In another embodiment the peptide inhibitor consists of about or less than 20 amino acids. In another embodiment the peptide inhibitor consists of about or less than 18 amino acids. In another embodiment the peptide inhibitor consists of about or less than 15 amino acids. In another embodiment the peptide inhibitor consists of about or less than 12 amino acids. In another embodiment the peptide inhibitor consists of about or less than 10 amino acids.

In certain embodiments, the peptide comprises:

(SEQ ID NO: 351)
EtCO-[(D)Arg]-[Pen]-N-T-W-Q-[Pen]-Phe[4(2-aminoethoxy)]-[Nal]-[THP]-E-N-[THP]-NH₂;

(SEQ ID NO: 352)
EtCO-[(D)Arg]-[Abu]-Q-T-W-Q-Cys-Phe[4(2-aminoethoxy)]-[Nal]-[THP]-E-N-[THP]-NH₂;

(SEQ ID NO: 353)
EtCO-[(D)Arg]-[Pen]-N-T-W-Q-[Pen]-Phe[4(2-aminoethoxy)]-[Nal]-[THP]-E-N-[aMePhe]-NH₂);

and wherein the peptide inhibitor is cyclized via a Pen-Pen disulfide bond or via a Abu-Cys thioether bond;
or a pharmaceutically acceptable salt or solvate thereof.

In additional embodiments, the present invention includes peptide inhibitors that comprise a peptide comprising a variant of any of the sequences of Formulas (I)-(XIf), or shown in Table E1, which comprises an isostere replacement of one or more amino acid residues of X4-X15. In particular embodiments, the isostere replacement is a conservative amino acid substitution, and in certain embodiments, the isostere replacement is a substitution with an analog of an amino acid.

In additional embodiments, the present invention includes peptide inhibitors that comprise a peptide comprising a variant of any of the sequences of Formulas (I)-(XIf), or shown in Table E1, which comprises different amino acid residues (or chemical entities) at one or both of amino acid residues X4 and X9, but wherein the amino acid residues at X4 and X9 are capable of binding each other, e.g., to form an intramolecule bond or triazole ring within the peptide. In particular embodiments, the bond is a disulfide bond, a thioether bond, a lactam bond, a triazole ring, a selenoether bond, a diselenide bond, or an olefin bond.

Additional Characteristics of Peptide Inhibitors

Any of the peptide inhibitors of the present invention may be further defined, e.g., as described below. It is understood that each of the further defining features described herein may be applied to any peptide inhibitors where the amino acids designated at particular positions allow the presence of the further defining feature. In particular embodiments, these features may be present in any of the peptides of Formula (I)-(XIf).

In various embodiments, $R^1$ is a bond, hydrogen, a C1-C6 alkyl, a C6-C12 aryl, a C6-C12 aryl C1-C6 alkyl, or a C1-C20 alkanoyl, and including PEGylated versions alone or as spacers of any of the foregoing, e.g., acetyl. It is understood that the $R^1$ may replace or be present in addition to the typical amine group located at the amino terminus of a peptide. It is further understood that $R^1$ may be absent. In certain embodiments, the peptide inhibitor comprises an N-terminus selected from hydrogen, a C1-C6 alkyl, a C6-C12 aryl, a C6-C12 aryl C1-C6 alkyl, or a C1-C20 alkanoyl, and including PEGylated versions alone or as spacers of any of the foregoing, e.g., acetyl. In particular embodiments of any of the peptide inhibitors described herein, $R^1$ or the N-terminal moiety is hydrogen. In certain embodiments, $R^1$ is a bond, e.g., a covalent bond.

In certain embodiments of any of the peptide inhibitors having any of the various Formulas set forth herein, $R^1$ or the N-terminal moiety is selected from methyl, acetyl, formyl, benzoyl, trifluoroacetyl, isovaleryl, isobutyryl, octanyl, and the conjugated amides of lauric acid, hexadecanoic acid, and γ-Glu-hexadecanoic acid. In one embodiment, $R^1$ or the N-terminal moiety is pGlu. In certain embodiments, $R^1$ is hydrogen. In particular embodiments, $R^1$ is acetyl, whereby the peptide inhibitor is acylated at its N-terminus, e.g., to cap or protect an N-terminal amino acid residue, e.g., an N-terminal Pen residue.

In certain embodiments of any of the peptide inhibitors described herein, $R^1$ or the N-terminal moiety is an acid. In certain embodiments, $R^1$ or the N-terminal moiety is an acid selected from acetic acid, formic acid, benzoic acid, trifluoroacetic acid, isovaleric acid, isobutyric acid, octanoic acid, lauric acid, hexadecanoic acid, 4-Biphenylacetic acid, 4-fluorophenylacetic acid, gallic acid, pyroglutamic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, an alkylsulfonic acid and an arylsulfonic acid.

In particular embodiments, $R^1$ or the N-terminal moiety is an alkylsulfonic acid selected from methanesulfonic acid, ethanesulfonic acid, 1,2-ethane-disulfonic acid, and 2-hydroxyethanesulfonic acid.

In particular embodiments, $R^1$ or the N-terminal moiety is an arylsulfonic acid selected from benzenesulfonic acid, 4-chlorobenzenesulfonic acid, 2-naphthalenesulfonic acid, 4-toluenesulfonic acid, and camphorsulfonic acid.

Peptide Dimers

In certain embodiments, the present invention includes dimers of the monomer peptide inhibitors described herein, including dimers of any of the monomer peptide inhibitors described herein or in the accompanying tables. These dimers fall within the scope of the general term "peptide inhibitors" as used herein. Illustrative dimers of the present invention are also shown in the accompanying tables, which indicate the dimerized monomer subnits in brackets followed by the linker. Unless otherwise indicated, the subunits are linked via their C-termini. The term "dimer," as in a peptide dimer, refers to compounds in which two peptide monomer subunits are linked. A peptide dimer inhibitor of the present invention may comprise two identical monomer subunits, resulting in a homodimer, or two non-identical monomer subunits, resulting in a heterodimer. A cysteine dimer comprises two peptide monomer subunits linked through a disulfide bond between a cysteine residue in one monomer subunit and a cysteine residue in the other monomer subunit.

In some embodiments, the peptide inhibitors of the present invention may be active in a dimer conformation, in particular when free cysteine residues are present in the peptide. In certain embodiments, this occurs either as a synthesized dimer or, in particular, when a free cysteine monomer peptide is present and under oxidizing conditions, dimerizes. In some embodiments, the dimer is a homodimer. In other embodiments, the dimer is a heterodimer.

In certain embodiments, monomer subunits of the present invention may be dimerized by a suitable linking moiety, e.g., a disulphide bridge between two cysteine residues, one in each peptide monomer subunit, or by another suitable linker moiety, including but not limited to those defined herein. Some of the monomer subunits are shown having C- and N-termini that both comprise free amine. Thus, to produce a peptide dimer inhibitor, the monomer subunit may be modified to eliminate either the C- or N-terminal free amine, thereby permitting dimerization at the remaining free amine. Further, in some instances, a terminal end of one or more monomer subunits is acylated with an acylating organic compound selected from the group consisting of: Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, monomer subunits comprise both a free carboxy terminal and a free amino terminal, whereby a user may selectively modify the subunit to achieve dimerization at a desired terminus. One having skill in the art therefore, will appreciate that the monomer subunits of the instant invention may be selectively modified to achieve a single, specific amine for a desired dimerization.

It is further understood that the C-terminal residues of the monomer subunits disclosed herein are optionally amides. Further, it is understood that, in certain embodiments, dimerization at the C-terminus is facilitated by using a suitable amino acid with a side chain having amine functionality, as is generally understood in the art. Regarding the N-terminal residues, it is generally understood that dimerization may be achieved through the free amine of the terminal residue, or may be achieved by using a suitable amino acid side chain having a free amine, as is generally understood in the art.

The linker moieties connecting monomer subunits may include any structure, length, and/or size that is compatible with the teachings herein. In at least one embodiment, a linker moiety is selected from the non-limiting group consisting of cysteine, lysine, DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. In certain embodiments, PEG2 is $HO_2CCH_2CH_2OCH_2CH_2OCH_2CH_2CO_2H$. Non-limiting examples of suitable linker moieties are provided in Table 2.

TABLE 2

| | Illustrative Linker Moieties | |
|---|---|---|
| Abbreviation | Description | Structure |
| DIG | DIGlycolic acid, | |
| PEG4 | Bifunctional PEG linker with 4 PolyEthylene Glycol units | |
| PEG13 | Bifunctional PEG linker with 13 PolyEthylene Glycol units | |
| PEG25 | Bifunctional PEG linker with 25 PolyEthylene Glycol units | |
| PEG1K | Bifunctional PEG linker with PolyEthylene Glycol Mol wt of 1000 Da | |
| PEG2K | Bifunctional PEG linker with PolyEthylene Glycol Mol wt of 2000 Da | |
| PEG3.4K | Bifunctional PEG linker with PolyEthylene Glycol Mol wt of 3400 Da | |
| PEG5K | Bifunctional PEG Linker with PolyEthylene Glycol Mol wt of 5000 Da | |
| DIG | DIGlycolic acid | |
| β-Ala-IDA | β-Ala-Iminodiacetic acid | |
| Boc-β-Ala-IDA | Boc-β-Ala-Iminodiacetic acid | |

TABLE 2-continued

Illustrative Linker Moieties

| Abbreviation | Description | Structure |
|---|---|---|
| Ac-β-Ala-IDA | Ac-β-Ala-Iminodiacetic acid | 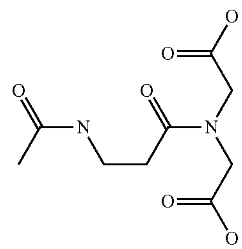 [SMILES: CC(=O)NCCC(=O)N(CC(=O)O)CC(=O)O] |
| IDA-β-Ala-Palm | Palmityl-β-Ala-Iminodiacetic acid | 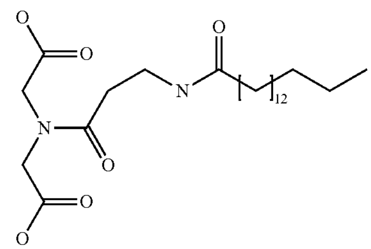 |
| GTA | Glutaric acid | 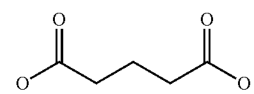 |
| PMA | Pemilic acid | 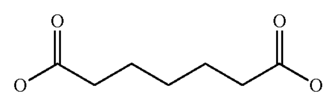 [SMILES: O=C(O)CCCCCC(=O)O] |
| AZA | Azelaic acid | 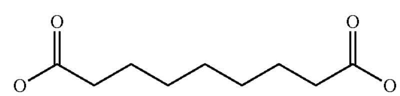 [SMILES: O=C(O)CCCCCCCC(=O)O] |
| DDA | Dodecanedioic acid | 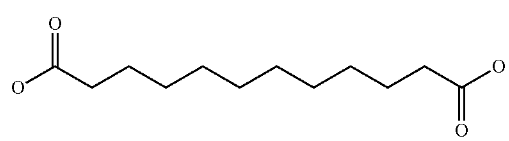 [SMILES: O=C(O)CCCCCCCCCCC(=O)O] |
| IPA | Isophalic acid | 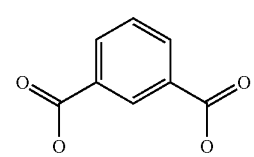 [SMILES: O=C(O)c1cccc(C(=O)O)c1] |
| 1,3-PDA | 1,3-Phenylenediacetic acid | 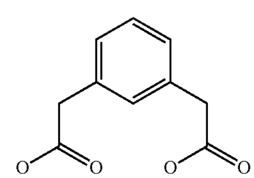 [SMILES: O=C(O)Cc1cccc(CC(=O)O)c1] |
| 1,4-PDA | 1,4-Phenylenediacetic acid | 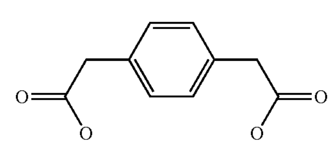 [SMILES: O=C(O)Cc1ccc(CC(=O)O)cc1] |

TABLE 2-continued

Illustrative Linker Moieties

| Abbreviation | Description | Structure |
|---|---|---|
| 1,2-PDA | 1,2-Phenylenediacetic acid | 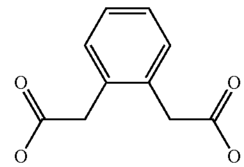 [SMILES: O=C(O)Cc1ccccc1CC(=O)O] |
| Triazine | Amino propyl Triazine di-acid | 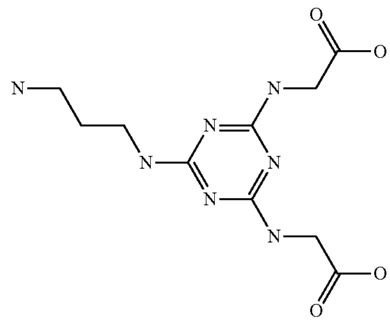 [SMILES: NCCCNc1nc(NCC(=O)O)nc(NCC(=O)O)n1] |
| Boc-Triazine | Boc-Triazine di-acid | 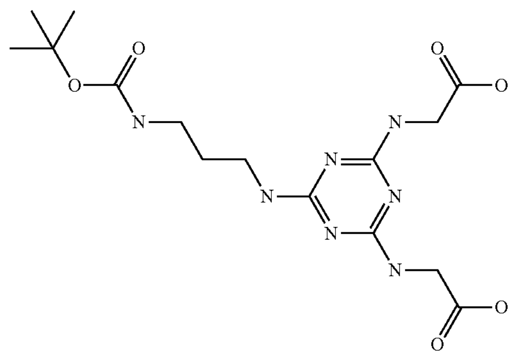 [SMILES: CC(C)(C)OC(=O)NCCCNc1nc(NCC(=O)O)nc(NCC(=O)O)n1] |
| ADA | Amino diacetic acid (which may also be referred to as Iminodiacetic acid) | 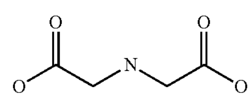 |
| AADA | n-Aceyl amino acetic acid (which may also be referred to as N-acetyl Iminodiacetic acid) | 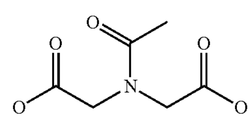 |
| PEG4-Biotin | PEG4-Biotin (Product number 10199, QuantaBioDesign) | 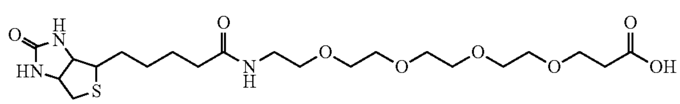 [SMILES: O=C(O)CCOCCOCCOCCOCCNC(=O)CCCCC1SCC2NC(=O)NC21] |
| IDA-Biotin | N-Biotin-β-Ala-Iminodiacetic acid | 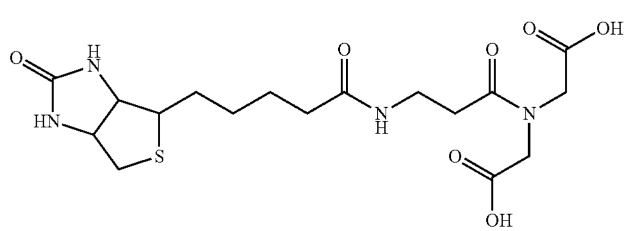 [SMILES: O=C(O)CN(CC(=O)O)C(=O)CCNC(=O)CCCCC1SCC2NC(=O)NC21] |
| Lys | Lysine | 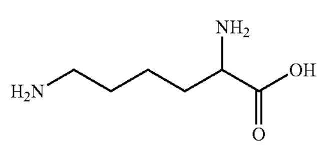 |

In some embodiments, a peptide dimer inhibitor is dimerized via a linker moiety. In some embodiments, a peptide dimer inhibitor is dimerized via an intermolecular disulfide bond formed between two cysteine residues, one in each monomer subunit. In some embodiments, a peptide dimer inhibitor is dimerized via both a linker moiety and an intermolecular disulfide bond formed between two cysteine residues. In some embodiments, the intramolecular bond is a thioether, lactam, triazole, selenoether, diselenide or olefin, instead of the disulfide bond.

One having skill in the art will appreciate that the linker (e.g., C- and N-terminal linker) moieties disclosed herein are non-limiting examples of suitable linkers, and that the present invention may include any suitable linker moiety. Thus, some embodiments of the present invention comprises a homo- or heterodimer peptide inhibitor comprised of two monomer subunits selected from the peptides shown in any of tables herein or comprising or consisting of a sequence presented in any of tables herein, wherein the C- or N-termini of the respective monomer subunits (or internal amino acid residues) are linked by any suitable linker moiety to provide a dimer peptide inhibitor having IL-23R inhibitory activity. In certain embodiments, a linker binds to the N- or C-terminus of one monomer subunit and an internal amino acid residue of the other monomer subunit making up the dimer. In certain embodiments, a linker binds to an internal amino acid residue of one monomer subunit and an internal amino acid residue of the other monomer subunit making up the dimer. In further embodiments, a linker binds to the N- or C-terminus of both subunits.

In particular embodiments, one or both of the monomer subunits comprise the sequence or structure of any one of Formula (I)-(XIf), or shown in Table E1, or any of the peptides described herein.

In certain embodiments, a peptide dimer inhibitor has the structure of Formula XII:

(R$^1$—X—R$^2$)$_2$-L  (XII)

or a pharmaceutically acceptable salt or solvate thereof,
wherein each R$^1$ is independently absent, a bond (e.g., a covalent bond), or R1 is selected from hydrogen, a C1-C6 alkyl, a C6-C12 aryl, a C6-C12 aryl C1-C6 alkyl, a C1-C20 alkanoyl, and including PEGylated versions alone or as spacers of any of the foregoing;
each R$^2$ is independently absent, a bond (e.g., a covalent bond), or selected from OH or NH$_2$;
L is a linker moiety; and
each X is an independently selected peptide monomer subunit comprising a sequence of Formula (I)-(XIf), as described herein. In certain embodiments, one or both peptide monomer subunit of a peptide dimer inhibitor is cyclized, e.g., via an intramolecular bond between X4 and X9. In certain embodiments, one or both peptide monomer subunits is linear or not cyclized.

In particular embodiments, each R$^1$ is independently a bond (e.g., a covalent bond), or selected from hydrogen, a C1-C6 alkyl, a C6-C12 aryl, a C6-C12 aryl C1-C6 alkyl, a C1-C20 alkanoyl, and including PEGylated versions alone or as spacers of any of the foregoing. In particular embodiments, the N-terminus of each subunit includes a moiety selected from hydrogen, a C1-C6 alkyl, a C6-C12 aryl, a C6-C12 aryl C1-C6 alkyl, a C1-C20 alkanoyl, and including PEGylated versions alone or as spacers of any of the foregoing.

In certain embodiments of any of the peptide inhibitors having any of the various Formulae set forth herein, each R$^1$ (or N-terminal moiety) is selected from methyl, acetyl, formyl, benzoyl, trifluoroacetyl, isovaleryl, isobutyryl, octanyl, and the conjugated amides of lauric acid, hexadecanoic acid, and γ-Glu-hexadecanoic acid.

In particular embodiments, each R$^2$ (or C-terminal moiety) is independently a bond (e.g., a covalent bond), or selected from OH or NH$_2$.

In particular embodiments of any of the peptide dimer inhibitors described herein, either or both R$^1$ is hydrogen.

In particular embodiments of peptide dimer inhibitors of the present invention, the linker moiety (L) is any of the linkers described herein or shown in Table 1 or 7. In certain embodiments, L is a lysine linker, a diethylene glycol linker, an iminodiacetic acid (IDA) linker, a β-Ala-iminodiaceticacid (β-Ala-IDA) linker, or a PEG linker.

In various embodiments of any of the peptide dimer inhibitors, each of the peptide monomer subunits is attached to a linker moiety via its N-terminus, C-terminus, or an internal amino acid residue. In certain embodiments of any of the peptide dimer inhibitors, the N-terminus of each peptide monomer subunit is connected by a linker moiety. In certain embodiments of any of the peptide dimer inhibitors, the C-terminus of each peptide monomer subunit is connected by a linker moiety. In certain embodiments of any of the peptide dimer inhibitors, each peptide monomer subunit is connected by a linker moiety attached to an internal amino acid.

Peptide Inhibitor Conjugates and Biopolymers

In certain embodiments, peptide inhibitors of the present invention, including both monomers and dimers, comprise one or more conjugated chemical substituents, such as lipophilic substituents and polymeric moieties, which may be referred to herein as half-life extension moieties. Without wishing to be bound by any particular theory, it is believed that the lipophilic substituent binds to albumin in the bloodstream, thereby shielding the peptide inhibitor from enzymatic degradation, and thus enhancing its half-life. In addition, it is believed that polymeric moieties enhance half-life and reduce clearance in the bloodstream.

In additional embodiments, any of the peptide inhibitors, e.g. peptides of Formula (I)-(XIf) further comprise a linker moiety attached to an amino acid residue present in the inhibitor, e.g., a linker moiety may be bound to a side chain of any amino acid of the peptide inhibitor, to the N-terminal amino acid of the peptide inhibitor, or to the C-terminal amino acid of the peptide inhibitor.

In additional embodiments, any of the peptide inhibitors e.g. peptides of Formulas (I)-(XIf), further comprise half-life extension moiety attached to an amino acid residue present in the inhibitor, e.g., a half-life extension moiety may be bound to a side chain of any amino acid of the peptide inhibitor, to the N-terminal amino acid of the peptide inhibitor, or to the C-terminal amino acid of the peptide inhibitor.

In additional embodiments, any of the peptide inhibitors e.g. peptides of Formulas (I)-(XIf), further comprise half-life extension moiety attached to a linker moiety that is attached to an amino acid residue present in the inhibitor, e.g., a half-life extension moiety may be bound to a linker moiety that is bound to a side chain of any amino acid of the peptide inhibitor, to the N-terminal amino acid of the peptide inhibitor, or to the C-terminal amino acid of the peptide inhibitor.

In particular embodiments, a peptide inhibitor comprises a half-life extension moiety having the structure shown below, wherein n=0 to 24 or n=14 to 24:

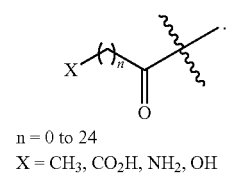
5
n = 0 to 24
X = CH$_3$, CO$_2$H, NH$_2$, OH
In certain embodiments, a peptide inhibitor of the present invention comprises a half-life extension moiety shown in Table 8.
TABLE 8
Illustrative Haf-Life Extension Moieties
| # | Half-Life Extension Moietys |
|---|---|
| C1 | C12 (Lauric acid) |
| C2 | C14 (Mysteric acid) |
| C3 | C16 (Palm or Palmitic acid) |
| C4 | C18 (Stearic acid) |
| C5 | C20 |
| C6 | C12 diacid |

TABLE 8-continued

Illustrative Half-Life Extension Moieties

| # | Half-Life Extension Moietys |
|---|---|
| C7 | 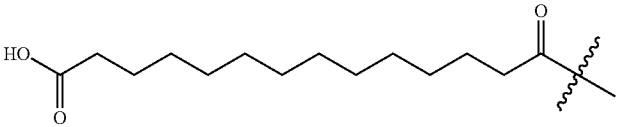<br>C14 diacid |
| C8 | 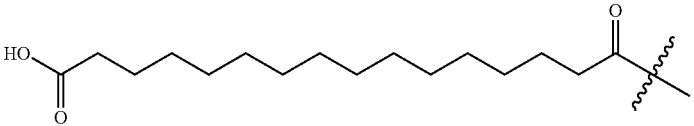<br>C16 diacid |
| C9 | 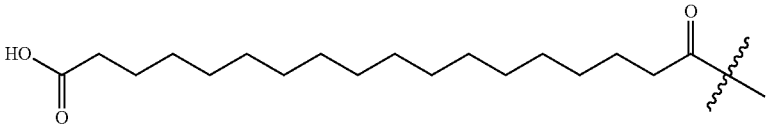<br>C18 diacid |
| C10 | 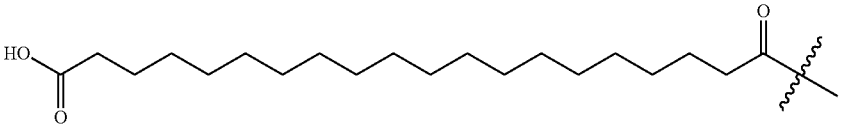<br>C20 diacid |

In certain embodiments, a half-life extension moiety is bound directly to a peptide inhibitor, while in other embodiments, a half-life extension moiety is bound to the peptide inhibitor via a linker moiety, e.g., any of those depicted in Tables 1, 2 or 4.

TABLE 4

Illustrative Linker Moieties

| # | Linker Moiety |
|---|---|
| L1 | 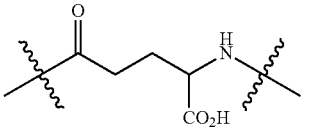<br>IsoGlu |
| L2 | 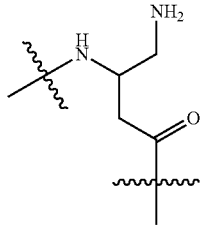<br>Dapa |

TABLE 4-continued

Illustrative Linker Moieties

| # | Linker Moiety |
|---|---|

L3

[structure: carbonyl-(CH2)5-NH-]

Ahx

L4  Lipidic based linkers:

[structure: carbonyl-(CH2)n-NH-]

n = 1 to 24

L5

[structure: -C(O)-CH2CH2-O-CH2CH2-NH-]

PEG1

L6

[structure: -C(O)-CH2CH2-O-CH2CH2-O-CH2CH2-NH-]

PEG2

L7

[structure: -C(O)-CH2CH2-(O-CH2CH2)n-O-CH2CH2-NH-]

n = 11

PEG11 (40 atoms) also known as PEG12

L8

[structure: -C(O)-CH2CH2-(O-CH2CH2)n-NH-]

n = 1 to 25

PEG based linkers

L9

[structure: -C(O)-CH2-O-CH2CH2-O-CH2CH2-NH-]

OEG

L10

[structure: isoGlu-Ahx with CO2H side chain]

IsoGlu-Ahx

TABLE 4-continued

Illustrative Linker Moieties

| # | Linker Moiety |
|---|---|
| L11 | IsoGlu-OEG-OEG |
| L12 | IsoGlu-PEG5 |
| L13 | IsoGlu-PEGn (n = 1-25) |
| L14 | βAla-PEG2 |
| L15 | βAla-PEG11 (40 atoms) |

In particular embodiments, a peptide inhibitor of the present invention comprises any of the linker moieties shown in Tables 2 or 4 and any of the half-life extension moieties shown in Table 3, including any of the following combinations shown in Table 5.

TABLE 5

Illustrative Combinations of Linkers and Half-Life Extension Moieties in Peptide Inhibitors

| Linker | Half-Life Extension Moiety |
|---|---|
| L1 | C1 |
| L2 | C1 |
| L3 | C1 |
| L4 | C1 |
| L5 | C1 |
| L6 | C1 |
| L7 | C1 |
| L8 | C1 |
| L9 | C1 |
| L10 | C1 |
| L11 | C1 |
| L12 | C1 |
| L13 | C1 |
| L14 | C1 |
| L15 | C1 |
| L1 | C2 |
| L2 | C2 |
| L3 | C2 |
| L4 | C2 |
| L5 | C2 |
| L6 | C2 |
| L7 | C2 |
| L8 | C2 |

TABLE 5-continued

Illustrative Combinations of Linkers and Half-Life Extension Moieties in Peptide Inhibitors

| Linker | Half-Life Extension Moiety |
|---|---|
| L9 | C2 |
| L10 | C2 |
| L11 | C2 |
| L12 | C2 |
| L13 | C2 |
| L14 | C2 |
| L15 | C2 |
| L1 | C3 |
| L2 | C3 |
| L3 | C3 |
| L4 | C3 |
| L5 | C3 |
| L6 | C3 |
| L7 | C3 |
| L8 | C3 |
| L9 | C3 |
| L10 | C3 |
| L11 | C3 |
| L12 | C3 |
| L13 | C3 |
| L14 | C3 |
| L15 | C3 |
| L1 | C4 |
| L2 | C4 |
| L3 | C4 |
| L4 | C4 |
| L5 | C4 |
| L6 | C4 |
| L7 | C4 |
| L8 | C4 |
| L9 | C4 |
| L10 | C4 |
| L11 | C4 |
| L12 | C4 |
| L13 | C4 |
| L14 | C4 |
| L15 | C4 |
| L1 | C5 |
| L2 | C5 |
| L3 | C5 |
| L4 | C5 |
| L5 | C5 |
| L6 | C5 |
| L7 | C5 |
| L8 | C5 |
| L9 | C5 |
| L10 | C5 |
| L11 | C5 |
| L12 | C5 |
| L13 | C5 |
| L14 | C5 |
| L15 | C5 |
| L1 | C6 |
| L2 | C6 |
| L3 | C6 |
| L4 | C6 |
| L5 | C6 |
| L6 | C6 |
| L7 | C6 |
| L8 | C6 |
| L9 | C6 |
| L10 | C6 |
| L11 | C6 |
| L12 | C6 |
| L13 | C6 |
| L14 | C6 |
| L15 | C6 |
| L1 | C7 |
| L2 | C7 |
| L3 | C7 |
| L4 | C7 |
| L5 | C7 |
| L6 | C7 |
| L7 | C7 |
| L8 | C7 |
| L9 | C7 |
| L10 | C7 |
| L11 | C7 |
| L12 | C7 |
| L13 | C7 |
| L14 | C7 |
| L15 | C7 |
| L1 | C8 |
| L2 | C8 |
| L3 | C8 |
| L4 | C8 |
| L5 | C8 |
| L6 | C8 |
| L7 | C8 |
| L8 | C8 |
| L9 | C8 |
| L10 | C8 |
| L11 | C8 |
| L12 | C8 |
| L13 | C8 |
| L14 | C8 |
| L15 | C8 |
| L2 | C9 |
| L3 | C9 |
| L4 | C9 |
| L5 | C9 |
| L6 | C9 |
| L7 | C9 |
| L8 | C9 |
| L9 | C9 |
| L10 | C9 |
| L11 | C9 |
| L12 | C9 |
| L13 | C9 |
| L14 | C9 |
| L15 | C9 |
| L1 | C10 |
| L2 | C10 |
| L3 | C10 |
| L4 | C10 |
| L5 | C10 |
| L6 | C10 |
| L7 | C10 |
| L8 | C10 |
| L9 | C10 |
| L10 | C10 |
| L11 | C10 |
| L12 | C10 |
| L13 | C10 |
| L14 | C10 |
| L15 | C10 |

In some embodiments there may be multiple linkers present between the peptide the conjugated moiety, e.g., half-life extension moiety, e.g., as depicted in Table 6.

TABLE 6

Illustrative Combinations of Linkers and Half-Life Extension Moieties in Peptide Inhibitors

| Linker | Half-Life Extension Moiety |
|---|---|
| L1-L2 | C10 |
| L2-L5-L3 | C10 |
| L3-L8 | C10 |
| L1-L2-L3 | C10 |

TABLE 6-continued

Illustrative Combinations of Linkers and Half-
Life Extension Moieties in Peptide Inhibitors

| Linker | Half-Life Extension Moiety |
|---|---|
| L5-L3-L3-L3 | C10 |
| L1-L2 | C8 |
| L2-L5-L3 | C8 |
| L3-L8 | C8 |
| L1-L2-L3 | C8 |
| L5-L3-L3-L3 | C8 |

In certain embodiments, the half-life of a peptide inhibitor of the invention that includes a conjugated chemical substituent, i.e., a half-life extension moiety, is at least 100%, at least 120%, at least 150%, at least 200%, at least 250%, at least 300%, at least 400%, or at least 500% of the half-life of the same peptide inhibitor but without the conjugated chemical substituent. In certain embodiments, the lipophilic substituents and/or polypermic moieties enhance the permeability of the peptide inhibitor through the epithelium and/or its retention in the lamina propria. In certain embodiments, the permeability through the epithelium and/or the retention in the lamina propria of a peptide inhibitor of the invention that includes a conjugated chemical substituent is at 100%, at least 120%, at least 150%, at least 200%, at least 250%, at least 300%, at least 400%, or at least 500% of the half-life of the same peptide inhibitor but without the conjugated chemical substituent.

In one embodiment, a side chain of one or more amino acid residues (e.g., Lys residues) in a peptide inhibitor of the invention is conjugated (e.g., covalently attached) to a lipophilic substituent. The lipophilic substituent may be covalently bonded to an atom in the amino acid side chain, or alternatively may be conjugated to the amino acid side chain via one or more spacers. The spacer, when present, may provide spacing between the peptide analogue and the lipophilic substituent. In particular embodiments, the peptide inhibitor comprises any of the conjugated moieties shown in peptides disclosed in Tables 2-6.

In certain embodiments, the lipophilic substituent may comprise a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a peptide inhibitor of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. In certain embodiments, the lipophilic substituent is conjugated to Lys. An amino acid shown as Lys in any of the Formula provided herein may be replaced by, e.g., Dbu, Dpr or Orn where a lipophilic substituent is added.

In certain embodiments, the peptide inhibitors of the present invention may be modified, e.g., to enhance stability, increase permeability, or enhance drug like characteristics, through conjugation of a chemical moiety to one or more amino acid side chain within the peptide. For example, the N(epsilon) of lysine N(epsilon), the β-carboxyl of aspartic, or the γ-carboxyl of glutamic acid may be appropriately functionalized. Thus, to produce the modified peptide, an amino acid within the peptide may be appropriately modified. Further, in some instances, the side chain is acylated with an acylating organic compound selected from the group consisting of: Trifluoropentyl, Acetyl, Octonyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid glutaric acid or bile acids. One having skill is the art will appreciate that a series of conjugates can be linked, e.g., for example PEG4, isoglu and combinations thereof. One having skill is the art will appreciate that an amino acid with the peptide can be isosterically replaced, for example, Lys may be replaced for Dap, Dab, α-MeLys or Orn. Examples of modified residues within a peptide are shown in Table 7.

TABLE 7

Examples of modified Lysine, Asp and Asn within the peptide

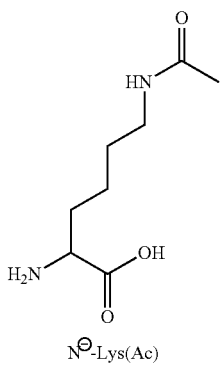

N$^{\epsilon}$-Lys(Ac)

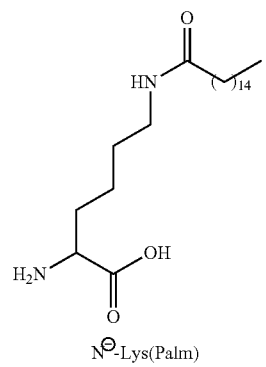

N$^{\epsilon}$-Lys(Palm)

TABLE 7-continued
Examples of modified Lysine, Asp and Asn within the peptide
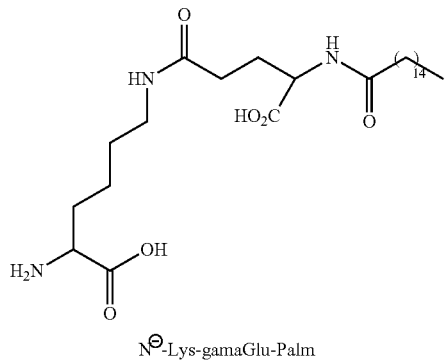
N^ε-Lys-gamaGlu-Palm
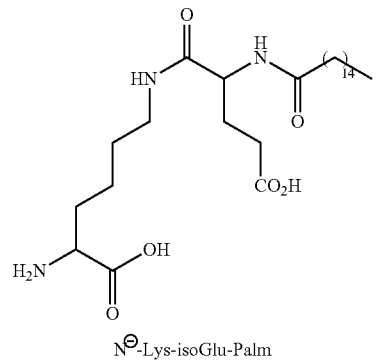
N^ε-Lys-isoGlu-Palm
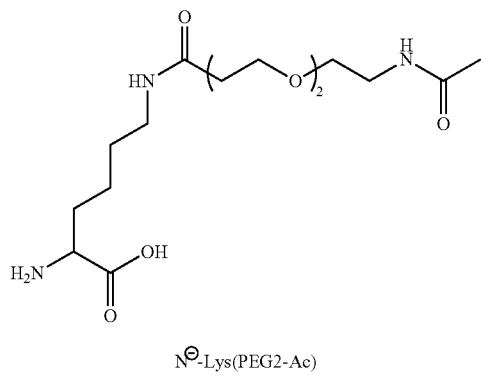
N^ε-Lys(PEG2-Ac)
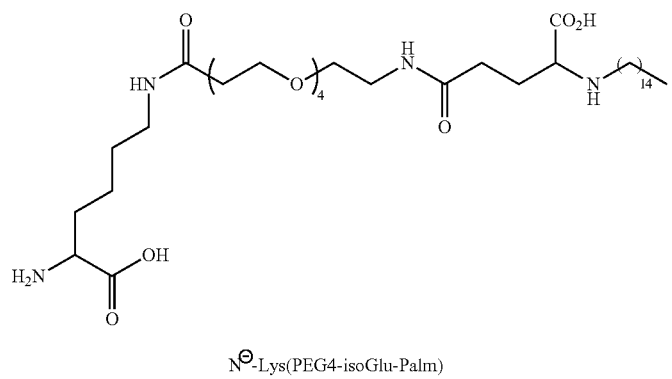
N^ε-Lys(PEG4-isoGlu-Palm)
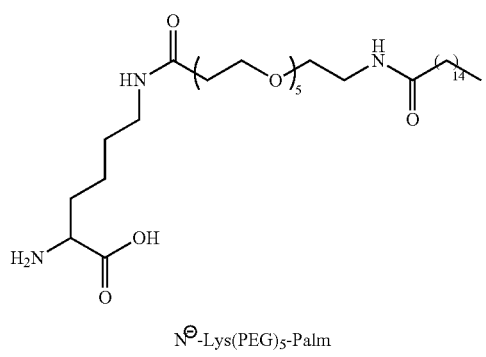
N^ε-Lys(PEG)₅-Palm
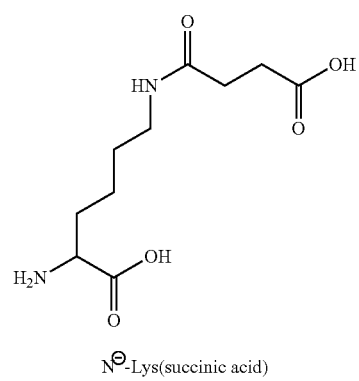
N^ε-Lys(succinic acid)
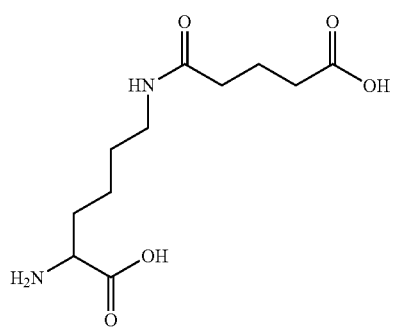
N^ε-Lys(glutaric acid)
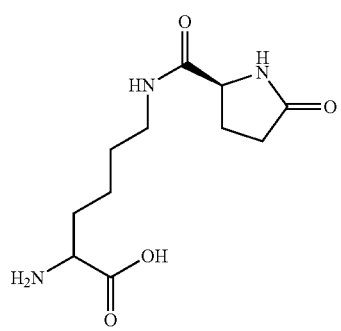
N^ε-Lys(Pyroglutaric acid)

TABLE 7-continued

Examples of modified Lysine, Asp and Asn within the peptide

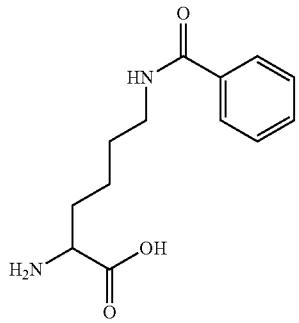

N$^{\ominus}$-Lys(Benzoic acid)

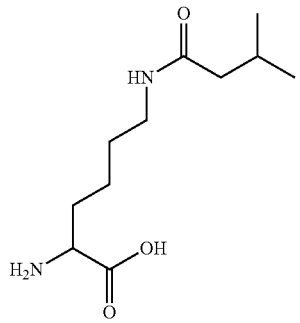

N$^{\ominus}$-Lys(IVA)

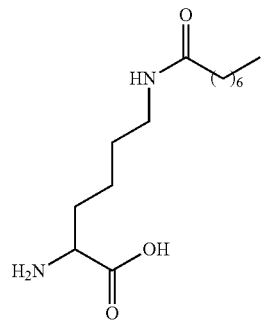

N$^{\ominus}$-Lys(octanoic acid)

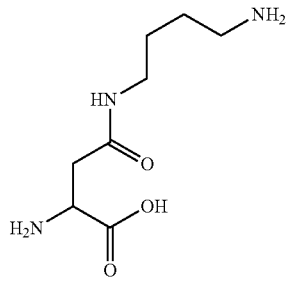

Asp(1,4 diaminobutane)

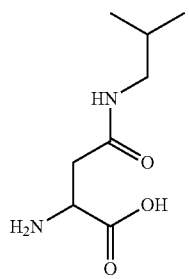

Asn(isobutyl)

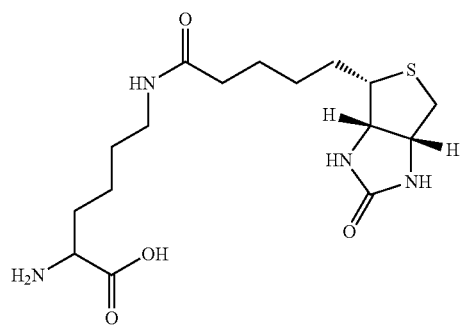

N$^{\ominus}$-Lys(Biotin)

In further embodiments of the present invention, alternatively or additionally, a side-chain of one or more amino acid residues in a peptide inhibitor of the invention is conjugated to a polymeric moiety, for example, in order to increase solubility and/or half-life in vivo (e.g. in plasma) and/or bioavailability. Such modifications are also known to reduce clearance (e.g. renal clearance) of therapeutic proteins and peptides.

As used herein, "Polyethylene glycol" or "PEG" is a polyether compound of general Formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 Da, PEO to polymers with a molecular mass above 20,000 Da, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 Da to 10,000,000 Da. While PEG and PEO with different molecular weights find use in different applications, and have different physical properties (e.g. viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are PEGs that are prepared for purpose of half life extension, for example, mono-activated, alkoxy-terminated polyalkylene oxides (POA's) such as mono-methoxy-terminated polyethyelene glycols (mPEG's); bis activated polyethylene oxides (glycols) or other PEG derivatives are also contemplated. Suitable polymers will vary substantially by weights ranging from about 200 Da to about 40,000 Da or from about 200 Da to about 60,000 Da are usually selected for the purposes of the present invention. In certain embodiments, PEGs having molecular weights from 200 to 2,000 or from 200 to 500 are used. Different forms of PEG may also be used, depending on the initiator used for the polymerization process—a common common initiator is a monofunctional methyl ether PEG, or methoxypoly(ethylene glycol), abbreviated mPEG.

Lower-molecular-weight PEGs are also available as pure oligomers, referred to as monodisperse, uniform, or discrete. These are used in certain embodiments of the present invention.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of covalently coupling a PEG structure to the peptide inhibitor of the invention, which is then referred to as a "PEGylated peptide inhibitor". In certain embodiments, the PEG of the PEGylated side chain is a PEG with a molecular weight from about 200 to about 40,000. In some embodiments, a spacer of a peptide of Formula I, Formula I', or Formula I" is PEGylated. In certain embodiments, the PEG of a PEGylated spacer is PEG3, PEG4, PEG5, PEG6, PEG7, PEG8, PEG9, PEG10, or PEG 11. In certain embodiments, the PEG of a PEGylated spacer is PEG3 or PEG8.

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a peptide inhibitor of the invention may comprise two or more such polymeric moieties, in which case the total molecular weight of all such moieties will generally fall within the ranges provided above.

In some embodiments, the polymeric moiety is coupled (by covalent linkage) to an amino, carboxyl or thiol group of an amino acid side chain. Certain examples are the thiol group of Cys residues and the epsilon amino group of Lys residues, and the carboxyl groups of Asp and Glu residues may also be involved.

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two step process. As used herein, for a single oxidation step, the trityl protecting group is often employed during assembly, allowing deprotection during cleavage, followed by solution oxidation. When a second disulfide bond is required, one has the option of native or selective oxidation. For selective oxidation requiring orthogonal protecting groups, Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation, the trityl protecting group is used for all cysteines, allowing for natural folding of the peptide. A skilled worker will be well aware of suitable techniques which can be used to perform the oxidation step.

Several chemical moieties, including poly(ethylene)glycol, react with functional groups present in the twenty naturally occurring amino acids, such as, for example, the epsilon amino group in lysine amino acid residues, the thiol present in cysteine amino acid residues, or other nucleophilic amino acid side chains. When multiple naturally occurring amino acids react in a peptide inhibitor, these non-specific chemical reactions result in a final peptide inhibitor that contains many isomers of peptides conjugated to one or more poly(ethylene)glycol strands at different locations within the peptide inhibitor.

One advantage of certain embodiments of the present invention includes the ability to add one or more chemical moiety (such as PEG) by incorporating one or more non-natural amino acid(s) that possess unique functional groups that react with an activated PEG by way of chemistry that is unreactive with the naturally occurring amino acids present in the peptide inhibitor. For example, azide and alkyne groups are unreactive with all naturally occurring functional groups in a protein. Thus, a non-natural amino acid may be incorporated in one or more specific sites in a peptide inhibitor where PEG or another modification is desired without the undesirable non-specific reactions. In certain embodiments, the particular chemistry involved in the reaction results in a stable, covalent link between the PEG strand and the peptide inhibitor. In addition, such reactions may be performed in mild aqueous conditions that are not damaging to most peptides. In certain embodiments, the non-natural amino acid residue is AHA.

Chemical moieties attached to natural amino acids are limited in number and scope. By contrast, chemical moieties attached to non-natural amino acids can utilize a significantly greater spectrum of useful chemistries by which to attach the chemical moiety to the target molecule. Essentially any target molecule, including any protein (or portion thereof) that includes a non-natural amino acid, e.g., a non-natural amino acid containing a reactive site or side chain where a chemical moiety may attach, such as an aldehyde- or keto-derivatized amino acid, can serve as a substrate for attaching a chemical moiety.

Numerous chemical moieties may be joined or linked to a particular molecule through various known methods in the art. A variety of such methods are described in U.S. Pat. No. 8,568,706. As an illustrative example, azide moieties may be useful in conjugating chemical moieties such as PEG or others described herein. The azide moiety serves as a reactive functional group, and is absent in most naturally occurring compounds (thus it is unreactive with the native amino acids of naturally occurring compounds). Azides also undergo a selective ligation with a limited number of reaction partners, and azides are small and can be introduced to biological samples without altering the molecular size of significantly. One reaction that allows incorporation or introduction of azides to molecules is the copper-mediated Huisgen [3+2] cycloaddition of an azide. This reaction can be used for the selective PEGylation of peptide inhibitors. (Tornoe et al., J. Org. Chem. 67: 3057, 2002; Rostovtsev et al., Angew. Chem., Int. Ed. 41: 596, 2002; and Wang et al., J. Am. Chem. Soc. 125: 3192, 2003, Speers et al., J. Am. Chem. Soc., 2003, 125, 4686).

Synthesis of Peptide Inhibitors

The peptide inhibitors of the present invention may be synthesized by many techniques that are known to those skilled in the art. In certain embodiments, monomer subunits are synthesized, purified, and dimerized using the techniques described in the accompanying Examples. In certain embodiments, the present invention provides a method of producing a peptide inhibitor (or monomer subunit thereof) of the present invention, comprising chemically synthesizing a peptide comprising, consisting of, or consisting essentially of a peptide having an amino acid sequence described herein, including but not limited to any of the amino acid sequences set forth in any of Formulas I, II or tables herein. In other embodiments, the peptide is recombinantly synthesized, instead of being chemically synthesized. In certain embodiments, the peptide inhibitor is a dimer, and the method comprises synthezing both monomer subunits of the peptide dimer inhibitor and then dimerizing the two monomer subunits to produce the peptide dimer inhibitor. In various embodiments, dimerization is accomplished via any of the various methods described herein. In particular embodiments, methods of producing a peptide inhibitor (or monomer subunit thereof) further comprise cyclizing the peptide inhibitor (or monomer subunit thereof) after its synthesis. In particular embodiments, cyclization is accomplished via any of the various methods described herein. In certain embodiments, the present invention provides a method of producing a peptide inhibitor (or monomer subunit thereof) of the present invention, comprising introducing an intramolecular bond, e.g., a disulfide, an amide, or a thioether bond between two amino acids residues within a peptide comprising, consisting of, or consisting essentially of a peptide having an amino acid sequence described herein, including but not limited to any of the amino acid sequences set forth in any of Formulas (I)-(IX), the accompanying Examples or Tables.

In related embodiments, the present invention includes polynucleotides that encode a polypeptide having a sequence set forth in any one of Formulas (I)-(IX), or the accompanying Examples or Table.

In addition, the present invention includes vectors, e.g., expression vectors, comprising a polynucleotide of the present invention.

Methods of Treatment

In certain embodiments, the present invention includes methods of inhibiting IL-23 binding to an IL-23R on a cell, comprising contacting the IL-23 with a peptide inhibitor of the present invention. In certain embodiments, the cell is a mammalian cell. In particular embodiments, the method is performed in vitro or in vivo. Inhibition of binding may be determined by a variety of routine experimental methods and assays known in the art.

In certain embodiments, the present invention includes methods of inhibiting IL-23 signaling by a cell, comprising contacting the IL-23 with a peptide inhibitor of the present invention. In certain embodiments, the cell is a mammalian cell. In particular embodiments, the method is performed in vitro or in vivo. In particular embodiments, the inhibition of IL-23 signalling may be determined by measuring changes in phospho-STAT3 levels in the cell.

In some embodiments, the present invention provides methods for treating a subject afflicted with a condition or indication associated with IL-21 or IL-23R (e.g., activation of the IL-23/IL-23R signaling pathway), wherein the method comprises administering to the subject a peptide inhibitor of the present invention. In one embodiment, a method is provided for treating a subject afflicted with a condition or indication characterized by inappropriate, deregulated, or increased IL-23 or IL-23R activity or signaling, comprising administering to the individual a peptide inhibitor of the present invention in an amount sufficient to inhibit (partially or fully) binding of IL-23 to IL-23R in the subject. In particular embodiments, the inhibition of IL-23 binding to IL-23R occurs in particular organs or tissues of the subject, e.g., the stomach, small intestine, large intestine/colon, intestinal mucosa, lamina propria, Peyer's Patches, mesenteric lymph nodes, or lymphatic ducts.

In some embodiments, methods of the present invention comprise providing a peptide inhibitor of the present invention to a subject in need thereof. In particular embodiments, the subject in need thereof has been diagnosed with or has been determined to be at risk of developing a disease or disorder associated with IL-23/IL-23R. In particular embodiments, the subject is a mammal.

In certain embodiments, the disease or disorder is autoimmune inflammation and related diseases and disorders, such as multiple sclerosis, asthma, rheumatoid arthritis, inflammatory bowel diseases (IBDs), juvenile IBD, adolescent IBD, Crohn's disease, ulcerative colitis, sarcoidosis, Systemic Lupus Erythematosus, ankylosing spondylitis (axial spondyloarthritis), psoriatic arthritis, or psoriasis. In particular embodiments, the disease or disorder is psoriasis (e.g., plaque psoriasis, guttate psoriasis, inverse psoriasis, pustular psoriasis, Palmo-Plantar Pustulosis, psoriasis vulgaris, or erythrodermic psoriasis), atopic dermatitis, acne ectopica, ulcerative colitis, Crohn's disease, Celiac disease (nontropical Sprue), enteropathy associated with seronegative arthropathies, microscopic colitis, collagenous colitis, eosinophilic gastroenteritis/esophagitis, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, Wiskott-Aldrich Syndrome, pouchitis, pouchitis resulting after proctocolectomy and ileoanal anastomosis, gastrointestinal cancer, pancreatitis, insulin-dependent diabetes mellitus, mastitis, cholecystitis, cholangitis, primary biliary cirrhosis, viral-associated enteropathy, pericholangitis, chronic bronchitis, chronic sinusitis, asthma, uveitis, or graft versus host disease.

In certain related embodiments, the present invention provides a method of selectively inhibiting IL-23 or IL-23R signaling (or the binding of IL-23 to IL-23R) in a subject in need thereof, comprising providing to the subject a peptide inhibitor of the present invention. In particular embodiments, the present invention includes a method of selectively inhibiting IL-23 or IL-23R signaling (or the binding of IL-23 to IL-23R) in the GI tract of a subject in need thereof, comprising providing to the subject a peptide inhibitor of the present invention by oral administration. In particular embodiments, exposure of the administered peptide inhibitor in GI tissues (e.g., small intestine or colon) is at least 10-fold, at least 20-fold, at least 50-fold, or at least 100-fold greater than the exposure in the blood. In particular embodiments, the present invention includes a method of selectively inhibiting IL23 or IL23R signaling (or the binding of IL23 to IL23R) in the GI tract of a subject in need thereof, comprising providing to the subject a peptide inhibitor, wherein the peptide inhibitor does not block the interaction between IL-6 and IL-6R or antagonize the IL-12 signaling pathway. In a further related embodiment, the present invention includes a method of inhibiting GI inflammation and/or neutrophil infiltration to the GI, comprising providing to a subject in need thereof a peptide inhibitor of the present invention. In some embodiments, methods of the present invention comprise providing a peptide inhibitor of the present invention (i.e., a first therapeutic agent) to a subject in need thereof in combination with a second therapeutic agent. In certain embodiments, the second therapeutic agent is provided to the subject before and/or simultaneously with and/or after the peptide inhibitor is administered to the subject. In particular embodiments, the second therapeutic agent is an anti-inflammatory agent. In certain embodiments, the second therapeutic agent is a non-steroidal anti-inflammatory drug, steroid, or immune modulating agent. In another embodiment, the method comprises administering to the subject a third therapeutic agent. In certain embodiments, the second therapeutic agent is an antibody that binds IL-23 or IL-23R.

Pharmaceutical Compositions

In particular embodiments, the peptide inhibitor, or the pharmaceutical composition comprising a peptide inhibitor, is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. One embodiment of a biodegradable matrix is a matrix of one of either polylactide, polyglycolide, or polylactide co-glycolide (copolymers of lactic acid and glycolic acid).

In certain embodiments, the present invention includes pharmaceutical compositions comprising one or more peptide inhibitors of the present invention and a pharmaceutically acceptable carrier, diluent or excipient. A pharmaceutically acceptable carrier, diluent or excipient refers to a non-toxic solid, semi-solid or liquid filler, diluent, encapsulating material or Formulation auxiliary of any type. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

In certain embodiments, the compositions are administered orally, parenterally, intracisternally, intravaginally, intraperitoneally, intrarectally, topically (as by powders, ointments, drops, suppository, or transdermal patch), by inhalation (such as intranasal spray), ocularly (such as intraocularly) or buccally. The term "parenteral" as used herein refers to modes of administration which include intravenous, intramuscular, intraperitoneal, intrasternal, subcutaneous, intradermal and intraarticular injection and infusion. Accordingly, in certain embodiments, the compositions are Formulated for delivery by any of these routes of administration.

In certain embodiments, pharmaceutical compositions for parenteral injection comprise pharmaceutically acceptable sterile aqueous or nonaqueous solutions, dispersions, suspensions or emulsions, or sterile powders, for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, β-cyclodextrin, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. Thes compositions may also contain adjuvants such as preservative, wetting agents, emulsifying agents, and dispersing agents. Prolonged absorption of an injectable pharmaceutical form may be brought about by the inclusion of agents which delay absorption, such as aluminum monostearate and gelatin.

Injectable depot forms include those made by forming microencapsule matrices of the peptide inhibitor in one or more biodegradable polymers such as polylactide-polyglycolide, poly(orthoesters), poly(anhydrides), and (poly)glycols, such as PEG. Depending upon the ratio of peptide to polymer and the nature of the particular polymer employed, the rate of release of the peptide inhibitor can be controlled. Depot injectable Formulations are also prepared by entrapping the peptide inhibitor in liposomes or microemulsions compatible with body tissues.

The injectable Formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical lung administration, including those for inhalation and intranasal, may involve solutions and suspensions in aqueous and non-aqueous Formulations and can be prepared as a dry powder which may be pressurized or non-pressurized. In non-pressurized powder compositions, the active ingredient may be finely divided form may be used in admixture with a larger-sized pharmaceutically acceptable inert carrier comprising particles having a size, for example, of up to 100 micrometers in diameter. Suitable inert carriers include sugars such as lactose.

Alternatively, the composition may be pressurized and contain a compressed gas, such as nitrogen or a liquefied gas propellant. The liquefied propellant medium and indeed the total composition may bey such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A peptide inhibitor of the invention may be delivered in a pharmaceutically acceptable ophthalmic vehicle, such that the peptide inhibitor is maintained in contact with the ocular surface for a sufficient time period to allow the peptide inhibitor to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the peptide inhibitors of the invention may be injected directly into the vitreous and aqueous humour.

Compositions for rectal or vaginal administration include suppositories which may be prepared by mixing the peptide inhibitorss of this invention with suitable non-irritating excipients or carriers such as cocoa butter, polyethylene glycol or a suppository wax, which are solid at room temperature but liquid at body temperature and, therefore, melt in the rectum or vaginal cavity and release the active compound.

Peptide inhibitors of the present invention may also be administered in liposomes or other lipid-based carriers. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a peptide inhibitor of the present invention, stabilizers, preservatives, excipients, and the like. In certain embodiments, the lipids comprise phospholipids, including the phosphatidyl cholines (lecithins) and serines, both natural and synthetic. Methods to form liposomes are known in the art.

Pharmaceutical compositions to be used in the invention suitable for parenteral administration may comprise sterile aqueous solutions and/or suspensions of the peptide inhibitos made isotonic with the blood of the recipient, generally using sodium chloride, glycerin, glucose, mannitol, sorbitol, and the like.

In some aspects, the invention provides a pharmaceutical composition for oral delivery. Compositions and peptide inhibitors of the instant invention may be prepared for oral administration according to any of the methods, techniques, and/or delivery vehicles described herein. Further, one having skill in the art will appreciate that the peptide inhibitors of the instant invention may be modified or integrated into a system or delivery vehicle that is not disclosed herein, yet is well known in the art and compatible for use in oral delivery of peptides.

In certain embodiments, Formulations for oral administration may comprise adjuvants (e.g. resorcinols and/or nonionic surfactants such as polyoxyethylene oleyl ether and n-hexadecylpolyethylene ether) to artificially increase the permeability of the intestinal walls, and/or enzymatic inhibitors (e.g. pancreatic trypsin inhibitors, diisopropylfluorophosphate (DFF) or trasylol) to inhibit enzymatic degradation. In certain embodiments, the peptide inhibitor of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

In particular embodiments, oral dosage forms or unit doses compatible for use with the peptide inhibitors of the present invention may include a mixture of peptide inhibitor and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of peptide inhibitor, wherein the dosage form comprises at least one of a pill, a tablet, a capsule, a gel, a paste, a drink, a syrup, ointment, and suppository. In some instances, an oral dosage form is provided that is designed and configured to achieve delayed release of the peptide inhibitor in the subject's small intestine and/or colon.

In one embodiment, an oral pharmaceutical composition comprising a peptide inhibitor of the present invention comprises an enteric coating that is designed to delay release of the peptide inhibitor in the small intestine. In at least some embodiments, a pharmaceutical composition is provided which comprises a peptide inhibitor of the present invention and a protease inhibitor, such as aprotinin, in a delayed release pharmaceutical Formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In one embodiment, a pharmaceutical composition comprising a peptide inhibitor of the present invention is provided in an enteric coating, the enteric coating being designed to protect and release the pharmaceutical composition in a controlled manner within the subject's lower gastrointestinal system, and to avoid systemic side effects. In addition to enteric coatings, the peptide inhibitors of the instant invention may be encapsulated, coated, engaged or otherwise associated within any compatible oral drug delivery system or component. For example, in some embodiments a peptide inhibitor of the present invention is provided in a lipid carrier system comprising at least one of polymeric hydrogels, nanoparticles, microspheres, micelles, and other lipid systems.

To overcome peptide degradation in the small intestine, some embodiments of the present invention comprise a hydrogel polymer carrier system in which a peptide inhibitor of the present invention is contained, whereby the hydrogel polymer protects the peptide inhibitor from proteolysis in the small intestine and/or colon. The peptide inhibitors of the present invention may further be Formulated for compatible use with a carrier system that is designed to increase the dissolution kinetics and enhance intestinal absorption of the peptide. These methods include the use of liposomes, micelles and nanoparticles to increase GI tract permeation of peptides.

Various bioresponsive systems may also be combined with one or more peptide inhibitor of the present invention to provide a pharmaceutical agent for oral delivery. In some embodiments, a peptide inhibitor of the instant invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a peptide inhibitor disclosed herein, wherein the surface of the peptide inhibitor surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the peptide inhibitor.

Other embodiments comprise a method for oral delivery of a peptide inhibitor of the present invention, wherein the peptide inhibitor is provided to a subject in combination with permeation enhancers that promote the transport of the peptides across the intestinal mucosa by increasing paracellular or transcellular permeation. Various permeation enhancers and methods for the oral delivery of therapeutic agents is described in Brayden, D. J., Mrsny, R. J., 2011. Oral peptide delivery: prioritizing the leading technologies. Ther. Delivery 2 (12), 1567-1573.

In certain embodiments, pharmaceutical compositions and Formulations of the present invention comprises a peptide inhibitor of the present invention and one or more permeation enhancer. Examples of absorption enhancers may include Bile salts, fatty acids, surfactants (anionic, cationic, and nonanionic) chelators, Zonular OT, esters, cyclodextrin, dextran sulfate, azone, crown ethers, EDTA, sucrose esters, and phosphotidyl choline, for example. Although absorption enhancers are not typically carriers by themselves, they are also widely associated with other carriers to improve oral bioavailability by transporting of peptides and proteins across the intestinal mucosa. Such substances can be added to the Formulation as excipients or incorporated to form non specific interactions with the intended peptide inhibitor.

Dietary components and/or other naturally occurring substances affirmed as enhancing tight junction permeation and as Generally Recognized As Safe (GRAS) include, e.g., asglycerides, acylcarnitines, bile salts, and medium chain fatty acids. Sodium salts of medium chain fatty acids (MCFAS) were also suggested to be permeation enhancers. The most extensively studied MCFAS is sodium caprate, a salt of capric acid, which comprises 2-3% of the fatty acids in the milk fat fraction. To date, sodium caprate is mainly used as an excipient in a suppository Formulation (Doktacillin™) for improving rectal ampicillin absorption. The permeation properties of another dietary MCFAS, sodium caprylate (8-carbon), were shown in vitro to be lower when compared to sodium caprate. Sodium caprylate and a peptidic drug were Formulated in an admixture with other excipients in oil to generate an oily suspension (OS) that enhanced permeability (Tuvia, S. et al., Pharmaceutical Research, Vol. 31, No. 8, pp. 2010-2021 (2014).

For example, in one embodiment, a permeation enhancer is combined with a peptide inhibitor, wherein the permeation enhancer comprises at least one of a medium-chain fatty acid, a long-chain fatty acid, a bile salt, an amphiphilic surfactant, and a chelating agent. In certain embodiments, medium-chain fatty acid salts promote absorption by increasing paracellular permeability of the intestinal epithelium. In one embodiment, a permeation enhancer comprising sodium N-[hydroxybenzoyl)amino] caprylate is used to form a weak noncovalent association with the peptide inhibitor of the instant invention, wherein the permeation enhancer favors membrane transport and further dissociation once reaching the blood circulation. In another embodiment, a peptide inhibitor of the present invention is conjugated to oligoarginine, thereby increasing cellular penetration of the peptide into various cell types. Further, in at least one embodiment a noncovalent bond is provided between a peptide inhibibitor of the present invention and a permeation enhancer selected from the group consisting of a cyclodextrin (CD) and a dendrimers, wherein the permeation enhancer reduces peptide aggregation and increasing stability and solubility for the peptide inhibitor molecule.

In certain embodiments, a pharmaceutical composition or Formulation comprises a peptide inhibitor of the present invention and a transient permeability enhancers (TPEs). Permeation enhancers and TPEs may be used to increase orally bioavailability or the peptide inhibitor. One example of a TPE that may be used is an oily suspension Formulation that disperses a powder containing sodioum caprylate and a therapeutic agent (Tuvia, S. et al., Pharmaceutical Research, Vol. 31, No. 8, pp. 2010-2021 (2014).

In certain embodiments, pharmaceutical composition and Formulations may include a peptide inhibitor of the present invention and one or more absorption enhancers, enzyme inhibitors, or mucoso adhesive polymers.

In particular embodiments, peptide inhibors of the present invention are Formulated in a Formulation vehicle, such as, e.g., emulsions, liposomes, microsphere or nanoparticles.

Other embodiments of the invention provide a method for treating a subject with a peptide inhibitor of the present invention having an increased half-life. In one aspect, the present invention provides a monocyclic peptide inhibitor having a half-life of at least several hours to one day in vitro or in vivo (e.g., when administered to a human subject) sufficient for daily (q.d.) or twice daily (b.i.d.) dosing of a therapeutically effective amount. In another embodiment, the peptide inhibitor has a half-life of three days or longer sufficient for weekly (q.w.) dosing of a therapeutically effective amount. Further, in another embodiment, the peptide inhibitor has a half-life of eight days or longer sufficient for bi-weekly (b.i.w.) or monthly dosing of a therapeutically effective amount. In another embodiment, the peptide inhibitor is derivatized or modified such that is has a longer half-life as compared to the underivatized or unmodified peptide inhibitor. In another embodiment, the peptide inhibitor contains one or more chemical modifications to increase serum half-life.

When used in at least one of the treatments or delivery systems described herein, a peptide inhibitor of the present invention may be employed in pure form or, where such forms exist, in pharmaceutically acceptable salt form.

The total daily usage of the peptide inhibitors and compositions of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific peptide inhibitor employed; e) the duration of the treatment; f) drugs used in combination or coincidental with the specific peptide inhibitor employed, and like factors well known in the medical arts.

In particlar embodiments, the total daily dose of the peptide inhibitors of the invention to be administered to a human or other mammal host in single or divided doses may be in amounts, for example, from 0.0001 to 300 mg/kg body weight daily or 1 to 300 mg/kg body weight daily.

Non-Invasive Detection of Intestinal Inflammation

The peptide inhibitors of the invention may be used for detection, assessment and diagnosis of intestinal inflammation by microPET imaging, wherein the peptide inhibitor is labeled with a chelating group or a detectable label, as part of a a non-invasive diagnostic procedure. In one embodiment, a peptide inhibitor is conjugated with a bifunctional chelator. In another embodiment, a peptide inhibitor is radiolabeled. The labeled peptide inhibitor is then administered to a subject orally or rectally. In one embodiment, the labeled peptide inhibitor is included in drinking water. Following uptake of the peptide inhibitor, microPET imaging may be used to visualize inflammation throughout the subject's bowels and digestive track.

EXAMPLES

Synthesis of Substituted Tryptophans

Synthesis of 7-methyl Tryptophan

7-Methyl tryptophan was purchased from a commercial source. Additionally, the compound can be synthesized following one of the methods described below.

Synthesis of 7-ethyl Tryptophan

7-Ethyl tryptophan was synthesized following the method depicted in Scheme 1:

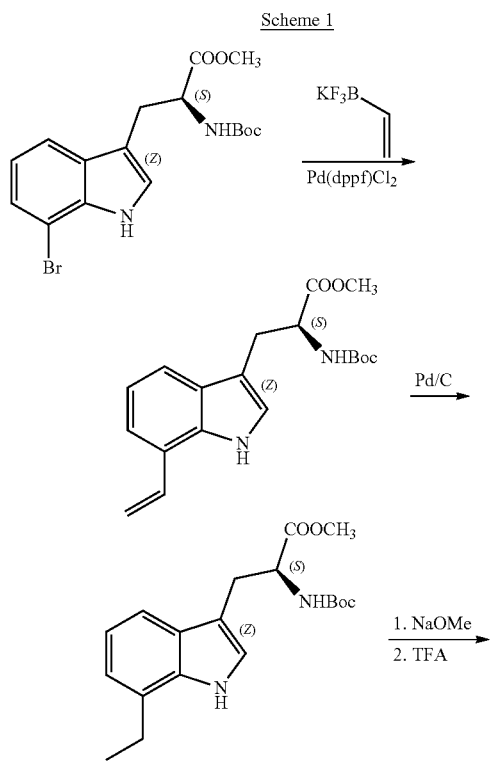

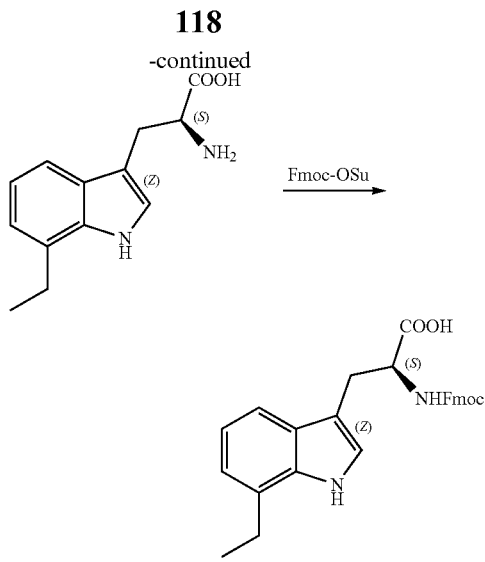

Synthesis of 7-ispropyl Tryptophan

7-Isopropyl tryptophan was synthesized following the method depicted in Scheme 2:

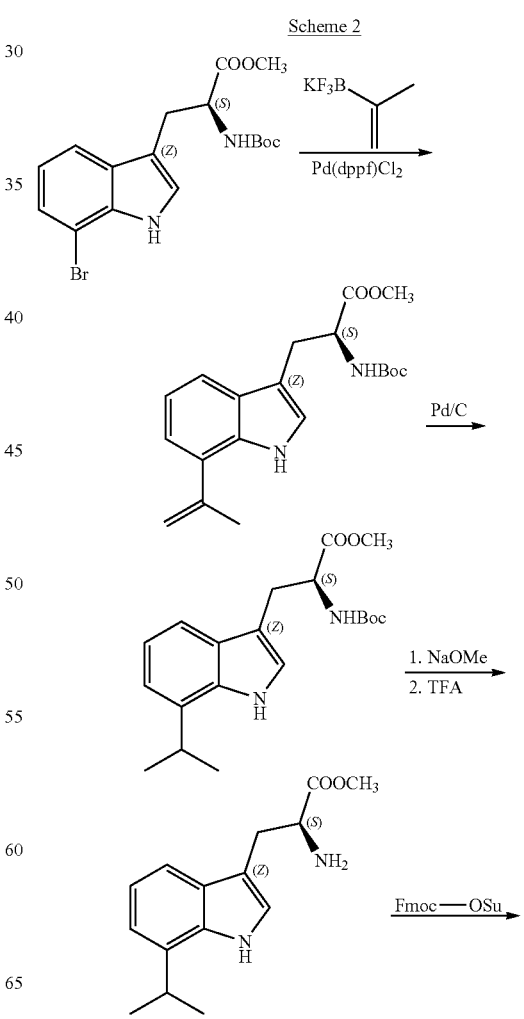

-continued

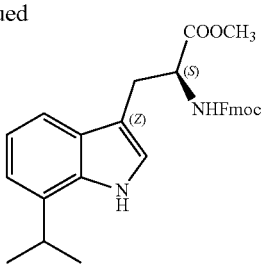

Synthesis of Additional 7-Substituted Tryptophans

Additional 7-substituted tryptophan were or can be synthesized following the method depicted in Scheme 3:

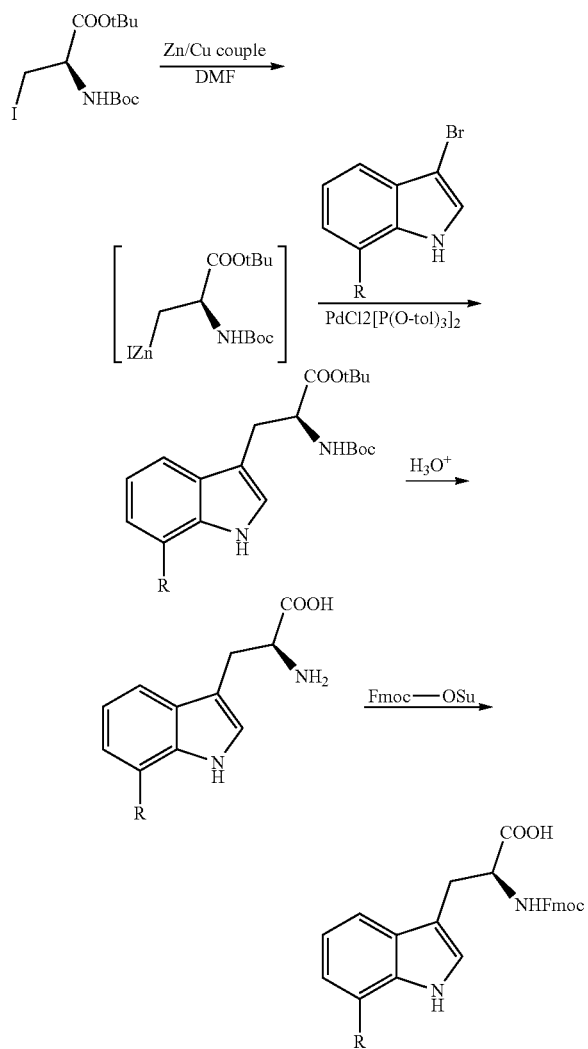

wherein R is cyano, halo, alkyl, haloalkyl, hydroxy, or alkoxy.

Example 1: Synthesis of Peptide Monomers

Peptide monomers of the present invention were synthesized using the Merrifield solid phase synthesis techniques on Protein Technology's Symphony multiple channel synthesizer. The peptides were assembled using HBTU (O-Benzotriazole-N,N,N',N'-tetramethyl-uronium-hexafluoro-phosphate), Diisopropylethylamine (DIEA) coupling conditions. For some amino acid couplings PyAOP (7-Azabenzotriazol-1-yloxy)tripyrrolidinophosponium hexafluorophosphate) and DIEA conditions were used. Rink Amide MBHA resin (100-200 mesh, 0.57 mmol/g) was used for peptide with C-terminal amides and pre-loaded Wang Resin with N-α-Fmoc protected amino acid was used for peptide with C-terminal acids. The coupling reagents (HBTU and DIEA premixed) were prepared at 100 mmol concentration. Similarly amino acids solutions were prepared at 100 mmol concentration. Peptide inhibitors of the present invention were identified based on medical chemistry optimization and/or phage display and screened to identify those having superior binding and/or inhibitory properties.

Assembly

The peptides were assembled using standard Symphony protocols. The peptide sequences were assembled as follows: Resin (250 mg, 0.14 mmol) in each reaction vial was washed twice with 4 ml of DMF followed by treatment with 2.5 ml of 20% 4-methyl piperidine (Fmoc de-protection) for 10 min. The resin was then filtered and washed two times with DMF (4 ml) and re-treated with N-methyl piperifine for additional 30 minute. The resin was again washed three times with DMF (4 ml) followed by addition 2.5 ml of amino acid and 2.5 ml of HBTU-DIEA mixture. After 45 min of frequent agitations, the resin was filtered and washed three timed with DMF (4 ml each). For a typical peptide of the present invention, double couplings were performed. After completing the coupling reaction, the resin was washed three times with DMF (4 ml each) before proceeding to the next amino acid coupling.

Ring Closing Metathesis to Form Olefins

The resin (100 μmol) was washed with 2 ml of DCM (3×1 min) and then with 2 ml of DCE (3×1 min) before being treated with a solution of 2 ml of a 6 mM solution of Grubbs' first-generation catalyst in DCE (4.94 mg ml-1; 20 mol % with regard to the resin substitution). The solution was refluxed overnight (12 h) under nitrogen before being drained. The resin was washed three times with DMF (4 ml each); DCM (4 ml) before being dried and cleavaed.

Cleavage

Following completion of the peptide assembly, the peptide was cleaved from the resin by treatment with cleavage reagent, such as reagent K (82.5% trigluoroacetic acid, 5% water, 5% thioanisole, 5% phenol, 2.5% 1,2-ethanedithiol). The cleavage reagent was able to successfully cleave the peptide from the resin, as well as all remaining side chain protecting groups.

The cleaved peptides were precipitated in cold diethyl ether followed by two washings with ethyl ether. The filtrate was poured off and a second aliquot of cold ether was added, and the procedure repeated. The crude peptide was dissolved in a solution of acetonitrile:water (7:3 with 1% TFA) and filtered. The quality of linear peptide was then verified using electrospray ionization mass spectrometry (ESI-MS) (Micromass/Waters ZQ) before being purified.

Disulfide Bond Formation Via Oxidation

The peptide containing the free thiol (for example diPen) was assembled on a Rink Amide-MBHA resin following general Fmoc-SPPS procedure. The peptide was cleaved from the resin by treatment with cleavage reagent 90% trifluoroacetic acid, 5% water, 2.5% 1,2-ethanedithiol, 2.5% tri-isopropylsilane). The cleaved peptides were precipitated in cold diethyl ether followed by two washings with ethyl ether. The filtrate was poured off and a second aliquot of cold ether was added, and the procedure repeated. The crude peptide was dissolved in a solution of acetonitrile:water (7:3 with 1% TFA) and filtered giving the wanted unoxidized peptide crude peptide The crude, cleaved peptide with X4 and X9 possessing either Cys, Pen, hCys, (D)Pen, (D)Cys or (D)hCys, was dissolved in 20 ml of water:acetonitrile. Saturated Iodine in acetic acid was then added drop wise with stirring until yellow color persisted. The solution was stirred for 15 minutes, and the reaction was monitored with analytic HPLC and LCMS. When the reaction was completed, solid ascorbic acid was added until the solution became clear. The solvent mixture was then purified by first being diluted with water and then loaded onto a reverse phase HPLC machine (Luna C18 support, 10 u, 100 A, Mobile phase A: water containing 0.1% TFA, mobile phase B: Acetonitrile (ACN) containing 0.1% TFA, gradient began with 5% B, and changed to 50% B over 60 minutes at a flow rate of 15 ml/min). Fractions containing pure product were then freeze-dried on a lyophilyzer.

Thioether Bond Formation

The peptide containing the free thiol (e.g., Cys) and hSer (OTBDMS)) was assembled on a Rink Amide-MBHA resin following general Fmoc-SPPS procedure. Chlorination was carried out by treating the resin with PPh$_3$ (10 equiv.) and Cl$_3$CCN (10 equiv.) in DCM for 2 h. The peptide was cleaved from the resin by treatment with cleavage reagent 90% trifluoroacetic acid, 5% water, 2.5% 1,2-ethanedithiol, 2.5% tri-isopropylsilane). The cleaved peptides were precipitated in cold diethyl ether followed by two washings with ethyl ether. The filtrate was poured off and a second aliquot of cold ether was added, and the procedure repeated. The crude peptide was dissolved in a solution of acetonitrile:water (7:3 with 1% TFA) and filtered giving the wanted uncyclized crude peptide The crude peptide possessing a free thiol (eg Cys, Pen, hCys, (D)Pen, (D)Cys or (D)hCys and the alkyl halide (hSer(Cl)) at either the X4 and X9 position or X9 and X4 position was dissolved in 0.1 M TRIS buffer pH 8.5. Cyclization was allowed to take place overnight at RT. The solvent mixture was then purified by first being diluted two-fold with water and then loaded onto a reverse phase HPLC machine (Luna C18 support, 10 u, 100 A, Mobile phase A: water containing 0.1% TFA, mobile phase B: Acetonitrile (ACN) containing 0.1% TFA, gradient began with 5% B, and changed to 50% B over 60 minutes at a flow rate of 15 ml/min). Fractions containing pure product were then freeze-dried on a lyophilyzer.

Purification

Analytical reverse-phase, high performance liquid chromatography (HPLC) was performed on a Gemini C18 column (4.6 mm×250 mm) (Phenomenex). Semi-Preparative reverse phase HPLC was performed on a Gemini 10 μm C18 column (22 mm×250 mm) (Phenomenex) or Jupiter 10 μm, 300 A° C18 column (21.2 mm×250 mm) (Phenomenex). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative). Separations were achieved using linear gradients of buffer B in A (Mobile phase A: water containing 0.15% TFA, mobile phase B: Acetonitrile (ACN) containing 0.1% TFA), at a flow rate of 1 mL/min (analytical) and 15 mL/min (preparative).

Example 1A: Additional Representative Synthesis of Peptide Monomers

Synthesis of Peptide

Ac-[Pen]*-N-T-[W(7-Me)]-[Lys(Ac)]-[Pen]*-Phe[4-(2-aminoethoxy)]-[Nal]-[αmeK]-[Lys(Ac)]-N-[Aib]-[Ahx]-NH$_2$ (*Pen-Pen form disulfide bond) (SEQ. ID. No. 70) (PEPTIDE #70)

The synthesis of Peptide #70 is prepared using FMOC solid phase peptide synthesis techniques.

The Peptide #70 is constructed on Rink Amide MBHA resin using standard FMOC protection synthesis conditions reported in the literature. The constructed peptide is isolated from the resin and protecting groups by cleavage with strong acid followed by precipitation. Oxidation to form the disulfide bond is performed followed by purification by RPHPLC and counterion exchange. Lyophilization of pure fractions gives the final product Peptide #70.

Swell Resin: 10 g of Rink Amide MBHA solid phase resin (0.66 mmol/g loading) is transferred to a 250 ml peptide vessel with filter frit, ground glass joint and vacuum side arm. The resin is washed 3× with DMF.

Step 1: Coupling of FMOC-Aminohexanoic acid (Ahx): Deprotection of the resin bound FMOC group is realized by adding 2 resin-bed volumes of 20% 4-methyl-piperidine in DMF to the swollen resin and shaking for 3-5 min prior to draining and adding a second, 2-resin-bed volume of the 4-methyl piperidine solution and shaking for an additional 20-30 min. After deprotection the resin is washed 3×DMF with shaking. FMOC-Aminohexanoic acid (3 eq, 7.1 g) is dissolved in 100 ml DMF along with Oxyma (4.5 eq, 4.22 g). Preactivation of the acid is accomplished by addition of DIC (3.9 eq, 4 ml) with shaking for 15 min prior to addition to the deprotected resin. An additional aliquot of DIC (2.6 eq, 2.65 ml) is then added after 15 min of coupling. The progress of the coupling reaction is monitored by the colorimetric Kaiser test. Once the reaction is judged complete the resin is washed 3×DMF with shaking prior to starting the next deprotection/coupling cycle.

Step 2: Coupling of FMOC-Aminoisobutyric acid (Aib): Deprotection of the resin bound FMOC group is realized by adding 2 resin-bed volumes of 20% 4-methyl-piperidine in DMF to the swollen resin and shaking for 3-5 min prior to draining and adding a second, 2-resin-bed volume of the 4-methyl piperidine solution and shaking for an additional 20-30 min. After deprotection the resin is washed 3×DMF with shaking. FMOC-Aminoisobutyric acid (3 eq, 6.5 g) is dissolved in 100 ml DMF along with Oxyma (4.5 eq, 4.22 g). Preactivation of the acid is accomplished by addition of DIC (3.9 eq, 4 ml) with shaking for 15 min prior to addition to the Ahx bound resin. An additional aliquot of DIC (2.6 eq, 2.65 ml) is then added after ~15 min of coupling. The progress of the coupling reaction is monitored by the colorimetric Kaiser test. Once the reaction is judged complete the resin is washed 3×DMF with shaking prior to starting the next deprotection/coupling cycle.

Step 3: Coupling of FMOC-Asn(Trt)-OH: The FMOC is removed from the N-terminus of the resin bound 3Pal and washed as previously described. FMOC-Asn(Trt)-OH (2 eq, 8 g) is dissolved in 100 ml of DMF along with Oxyma (3 eq, 2.81 g). DIC (2.6 eq, 2.65 ml) is added for preactivation of the acid for ~15 minutes prior to addition to the Aib-Ahx-Amide resin. After ~15 minutes, an additional aliquot of DIC (1.4 eq, 1.43 ml) is added to the reaction. Once the reaction is complete as determined by the Kaiser test, the resin is washed 3× with DMF prior to starting the next deprotection/coupling cycle.

Step 4: Coupling of FMOC-Lys(Ac)—OH: The FMOC is removed from the N-terminus of the resin bound peptide and the resin washed as previously described. FMOC-Lys(Ac)—OH (2 eq, 5.4 g) is dissolved in 100 ml of DMF along with Oxyma (3 eq, 2.81 g). DIC (2.6 eq, 2.65 ml) is added for preactivation of the acid ~15 minutes prior to addition to the Asn(Trt)-Aib-Ahx-Amide resin. After ~15 minutes, an additional aliquot of DIC (1.4 eq, 1.43 ml) is added to the reaction. Once the reaction was complete as determined by the Kaiser test, the resin is again washed 3× with DMF prior to starting the next deprotection/coupling cycle.

Step 5: Coupling of FMOC-aMe-Lysine(Boc)-OH: The FMOC is removed from the N-terminus of the resin bound peptide and the resin is washed as previously described. FMOC-αMe-Lysine (3 eq, 9.7 g) is dissolved in 100 ml of DMF along with Oxyma (4.5 eq, 4.22 g). DIC (3.9 eq, 4 ml) is added for preactivation of the acid ~15 minutes prior to addition to the Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test the resin is washed 3× with DMF prior to starting the next deprotection/coupling cycle.

Step 6: Coupling of FMOC-3-(2-Naphthyl)-L-alanine (Nal): The FMOC is removed from the N-terminus of the resin bound peptide and the resin washed as previously described. FMOC-3-(2-Naphthyl)-L-alanine (3 eq, 8.7 g) is dissolved in 100 ml of DMF along with Oxyma (4.5 eq, 4.22 g). DIC (3.9 eq, 4 ml) is added for preactivation of the acid ~15 minutes prior to addition to the αMeLys(Boc)-Lys(Ac)-Asn(Trt)-Aib-Ahx-Amide resin. After ~15 minutes, an additional aliquot of DIC (2.6 eq, 2.65 ml) is added. Once the reaction is complete as determined by the Kaiser test the resin was again washed 3× with DMF prior to starting the next deprotection/coupling cycle.

Step 7: Coupling of FMOC-4-[2-(Boc-amino-ethoxy)]-L-Phenylalanine (FMOC-AEF): The FMOC is removed from the N-terminus of the resin bound peptide and the resin washed as previously described. FMOC-4-[2-(Boc-amino-ethoxy)]-L-Phenylalanine (3 eq, 10.8 g) is dissolved in 100 ml of DMF along with Oxyma (4.5 eq, 4.22 g). DIC (3.9 eq, 4 ml) is added for preactivation of the acid ~15 minutes prior to addition to the Nal-αMeLys(Boc)-Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test the resin is washed 3× with DMF prior to starting the next deprotection/coupling cycle.

Step 8: Coupling of FMOC-Pen(Trt)-OH: The FMOC is removed from the N-terminus of the resin bound peptide and the resin washed as previously described. FMOC-Pen(Trt)-OH (3 eq, 12.14 g) is dissolved in 100 ml of DMF along with Oxyma (4.5 eq, 4.22 g). DIC (3.9 eq, 4 ml) is added for preactivation of the acid ~15 minutes prior to addition to the AEF-Nal-αMeLys(Boc)-Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test, the resin is again washed 3× with DMF prior to starting the next deprotection/coupling cycle.

Step 9: Coupling of FMOC-Lys(Ac)—OH: The FMOC is removed from the N-terminus of the resin bound peptide and the resin washed as previously described. FMOC-Lys(Ac)—OH (2 eq, 5.4 g) is dissolved in 100 ml of DMF along with Oxyma (3 eq, 2.81 g). DIC (2.6 eq, 2.65 ml) is added for preactivation of the acid ~15 minutes prior to addition to the Pen(Trt)-AEF-Nal-αMeLys(Boc)-Lys(Ac)-Asn(Trt)-Aib-Ahx-Amide resin. After ~15 minutes, an additional aliquot of DIC (1.4 eq, 1.43 ml) is added to the reaction. Once the reaction was complete as determined by the Kaiser test, the resin is again washed 3× with DMF prior to starting the next deprotection/coupling cycle.

Step 10: Coupling of FMOC-7-Me-Trp-OH: The FMOC is removed from the N-terminus of the resin bound peptide and the resin washed as previously described. FMOC-7-Me-Trp-OH (2 eq, 5.81 g) is dissolved in 100 ml of DMF along with Oxyma (3 eq, 2.81 g). DIC (2.6 eq, 2.65 ml) is added for preactivation of the acid ~15 minutes prior to addition to the Lys(Ac)-Pen(Trt)-AEF-Nal-αMeLys(Boc)-Lys(Ac)-Asn(Trt)-Aib-Ahx-Amide resin. After ~15 minutes, an additional aliquot of DIC (1.4 eq, 1.43 ml) is added to the reaction. Once the reaction is complete as determined by the Kaiser test, the resin is again washed 3× with DMF prior to starting the next deprotection/coupling cycle.

Step 11: Coupling of FMOC-Thr(tBu)—OH: The FMOC is removed from the N-terminus of the resin bound peptide and the resin washed as previously described. FMOC-Thr(tBu)—OH (4 eq, 10.5 g) is dissolved in 100 ml of DMF along with Oxyma (6 eq, 5.62 g). DIC (5.2 eq, 5.3 ml) is added for preactivation of the acid ~15 minutes prior to addition to the 7MeTrp-Lys(Ac)-Pen(Trt)-AEF-Nal-αMeLys(Boc)-Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test, the resin is again washed 3× with DMF prior to starting the next deprotection/coupling cycle.

Step 12: Coupling of FMOC-Asn(Trt)-OH: The FMOC is removed from the N-terminus of the resin bound peptide and the resin washed as previously described. FMOC-Asn(Trt)-OH (4 eq, 15.8 g) is dissolved in 100 ml of DMF along with Oxyma (6 eq, 5.62 g). DIC (5.2 eq, 5.3 ml) is added for preactivation of the acid ~15 minutes prior to addition to the Thr(tBu)-7MeTrp-Lys(Ac)-Pen(Trt)-AEF-Nal-αMeLys(Boc)-Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test, the resin is again washed 3× with DMF prior to starting the next deprotection/coupling cycle.

Step 13: Coupling of FMOC-Pen(Trt)-OH: The FMOC is removed from the N-terminus of the resin bound peptide and the resin washed as previously described. FMOC-Pen(Trt)-OH (2 eq, 8.1 g) is dissolved in 100 ml of DMF along with Oxyma (3 eq, 2.81 g). DIC (2.6 eq, 2.65 ml) is added for preactivation of the acid ~15 minutes prior to addition to the Asn(Trt)-Thr(tBu)-7MeTrp-Lys(Ac)-Pen(Trt)-AEF-Nal-αMeLys(Boc)-Lys(Ac)-Asn(Trt)-Aib-Ahx-Amide resin. After ~15 minutes, an additional aliquot of DIC (2.6 eq, 2.65 ml) is added to the reaction. Once the reaction is complete as determined by the Kaiser test, the resin is again washed 3× with DMF prior to the final deprotection and acetic acid capping of the constructed peptide.

Step 14: Acetyl Capping: The FMOC is removed from the N-terminus of the resin bound peptide and the resin washed as previously described. 150 ml of Capping Reagent A (THF/Acetic anhydride/Pyridine, 80:10:10) is added to the constructed Pen(Trt)-Asn(Trt)-Thr(tBu)-7MeTrp-Lys(Ac)-Pen(Trt)-AEF-Nal-αMeLys(Boc)-Lys(Ac)-Asn(Trt)-Aib-Ahx-Amide resin. The resin is washed 3× with DMF followed by 5× with DCM. The resin is divided into 5-50 ml centrifuge tubes and placed under vacuum for 1.5 hrs prior to cleavage with TFA.

Step 15: TFA Cleavage and Ether precipitation: 200 ml of the TFA cleavage cocktail (90/5/2.5/2.5 TFA/water/Tips/DODT) is prepared. 40 ml of the cleavage cocktail is added to each of the 5 tubes containing the protected resin bound peptide and shaken for two hours. The spent resin is filtered away and the filtrate divided evenly into 18-50 ml centrifuge tubes for precipitation. Cold diethyl ether is added to each forming a white precipitate that is then centrifuged. The ether is decanted to waste and 2 more ether washes of the precipitate are performed. The resulting white precipitate cake is dried overnight in the hood to give the crude reduced peptide.

Step 16: Disulfide Oxidation: The crude peptide is oxidized and purified in four 1 L batches. ~2.5 g of crude peptide is dissolved in 1 L 20% ACN/water. With stirring, a saturated solution of iodine in acetic acid/methanol is added dropwise to the 1 L peptide solution until the yellow/brown color of the $I_2$ remains and does not fade away. The light-yellow solution is allowed to sit for 5 min prior to quenching the excess $I_2$ with a pinch of ascorbic acid.

Step 17: RP-HPLC purification: The RP-HPLC purification is performed s immediately following each $I_2$ oxidation. A preparative purification column (Phenomenex, Luna, C18(2), 100 A, 250×50 mm) is equilibrated at 70 ml/min with 20% MPB in MPA (MPA=0.1% TFA/water, MPB=0.1% TFA in ACN). The 1 L of quenched oxidized peptide is loaded onto the equilibrated column at 70 ml/min. After the solvent front elutes, a gradient of 25-45% MPB at 70 ml/min is run over 60 min. The desired material is isolated in fractions and each are analyzed by analytical RPHPLC. Pure fractions are combined from all four purifications and lyophilized to give purified TFA salt ready for counterion exchange.

Step 18: Counterion Exchange to Acetate: The same preparative RP-HPLC column is equilibrated with 5% MPB in MPA at 70 ml/min (MPA=0.3% AcOH in Water, MPB=0.3% AcOH in ACN, MPC=0.5M NH4OAc in Water.) The purified peptide TFA salt is dissolved in 50/50 ACN/water and diluted to 15% ACN. The solution is loaded onto the equilibrated column at 70 ml/min and the solvent front is eluted. The captured peptide is washed with 5% MPB in MPA for 5 min. The captured peptide is then washed with 5% MPB in MPC for 40 min at 70 ml/min to exchange the counterions to Acetate. The captured peptide is washed with 5% MPB in MPA at 70 ml/min for 10 min to clear all NH4OAc from the system. Finally, the peptide is eluted with a gradient of 5-70% MPB in MPA over 60 minutes and collected in fractions.

Step 19: Final Lyophilization and Analysis: The collected fractions are analyzed by analytical RP-HPLC, and all fractions >95% purity are combined. Lyophilization of the combined fractions gives Peptide #70 as a white powder with a purity >95% as determined by RPHPLC. Peptide identity is confirmed with LC/MS.

Example 2: Peptide Inhibition of Binding of Interleukin-23 to the Interleukin-23 Receptor Peptide optimization was performed to identify peptide inhibitors of IL-23 signalling that were active at low concentrations (e.g., IC50<10 nM). Peptides were tested to identify peptides that inhibit the binding of IL-23 to human IL-23R and inhibit IL-23/IL-23R functional activity, as described below.

Assays were performed to determine peptide activity as described below, and the results of these assays are provided in Table E1-E3. Human ELISA indicates the IL23-IL23R competitive binding assay described below, Rat ELISA indicates the rat IL-23R competitive binding ELISA assay described below, and pStat3HTRF indicates the DB cells IL-23R pSTAT3 cell assay described below. The peptides depicted in Table E1 are cyclized via a disulfide bridge formed between two Pen residues in these peptides. The peptides depicted in Table E1 are cyclized via a thioether bond between the indicated amino acid residues. Table E1 provides an illustrative structure depicting thioether cyclization, which is indicated in the table by the term "cyclo," with the cyclic region bracketed immediately following the term "cyclo." For certain peptides, the residue Abu is present where indicated, whereas in other embodiments, e.g., those related to the non-cyclized form, the Abu may be referred to as a hSer(Cl) or homoSer residue.

IL23-IL23R Competitive Binding ELISA

An Immulon® 4HBX plate was coated with 50 ng/well of IL23R_huFC and incubated overnight at 4° C. The wells were washed four times with PBST, blocked with PBS containing 3% Skim Milk for 1 hour at room temperature, and washed again four times with PBST. Serial dilutions of test peptides and IL-23 at a final concentration of 2 nM diluted in Assay Buffer (PBS containing 1% Skim Milk) were added to each well, and incubated for 2 hours at room temperature. After the wells were washed, bound IL-23 was detected by incubation with 50 ng/well of goat anti-p40 polyclonal antibodies (R&D Systems #AF309) diluted in Assay Buffer for 1 hour at room temperature. The wells were again washed four times with PBST. The secondary antibodies, HRP conjugated donkey anti-goat IgG (Jackson ImmunoResearch Laboratories #705-035-147) diluted 1:5000 in Assay Buffer was then added, and incubated for 30 minutes at room temperature. The plate was finally washed as above. Signals were visualized with TMB One Component HRP Membrane Substrate, quenched with 2 M sulfuric acid and read spectrophotometrically at 450 nm. IC50 values for various test peptides determined from these data are shown in Table E1-E3.

Rat IL-23R Competitive Binding ELISA

An assay plate was coated with 300 ng/well of Rat IL-23R_huFC and incubated overnight at 4° C. The wells were washed, blocked, and washed again. Serial dilutions of test peptides and IL-23 at a final concentration of 7 nM were added to each well, and incubated for 2 hours at room temperature. After the wells were washed, bound IL-23 was detected with goat anti-p40 polyclonal antibodies, followed by an HRP conjugated donkey anti-goat IgG. Signals were visualized with TMB One Component HRP Membrane Substrate and quenched with 2 M sulfuric acid. IC50 values for various test peptides determined from these data are shown in Table E1-E3.

DB Cells IL23R pSTAT3 Cell Assay

L-23 plays a central role in supporting and maintaining Th17 differentiation in vivo. This process is thought to mediated primarily through the Signal Transducer and Activator of Transcription 3 (STAT3), with phosphorylation of STAT3 (to yield pSTAT3) leading to upregulation of RORC and pro-inflammatory IL-17. This cell assay examines the levels of pSTAT3 in IL-23R-expressing DB cells when stimulated with IL-23 in the presence of test compounds. DB cells (ATCC #CRL-2289), cultured in RPMI-1640 medium (ATCC #30-2001) supplemented with 10% FBS and 1% Glutamine, were seeded at 5×10E5 cells/well in a 96 well tissue culture plate. Serial dilutions of test peptides and IL-23 at a final concentration of 0.5 nM were added to each well, and incubated for 30 minutes at 37° C. in a 5% C02 humidified incubator. Changes in phospho-STAT3 levels in the cell lysates were detected using the Cisbio HTRF pSTAT3 Cellular Assay Kit, according to manufacturer's Two Plate Assay protocol. IC50 values determined from these data are shown in Table E1. Where not shown or is marked with "0", data was not yet determined.

PBMC pSTAT3 Assay

Cryopreserved peripheral blood mononuclear cells (PBMCs) from healthy donors were thawed and washed twice in ImmunoCult-XF T cell expansion medium (XF-TCEM) supplemented with CTL anti-aggregate wash. The cells were counted, resuspended at $2\times10^5$ cells per mL XF-TCEM supplemented with penicillin/streptomycin and 100 ng/mL IL-1β (BioLegend, 579404), and cultured in tissue culture flasks coated with anti-CD3 (eBioscience, 16-0037-85 or BD Pharmingen, 555329) at 37° C. in 5% $CO_2$. On day 4 of culture, PBMCs were collected, washed twice in RPMI-1640 supplemented with 0.1% BSA (RPMI-BSA), and incubated in RPMI-BSA in upright tissue culture flasks for 4 hours at 37° C. in 5% $CO_2$. Following this 'starvation,' a total of $6\times10^4$ cells in 30 μL RPMI-BSA was transferred into each well of a 384-well plate pre-spotted with peptide or DMSO. The cells were incubated for 30 minutes prior to the addition of IL-23 at a final concentration of 5 ng/mL. The cells were stimulated with cytokine for 30 minutes at 37° C. in 5% $CO_2$, transferred onto ice for 10 minutes, and lysed. Cell lysates were stored at −80° C. until phosphorylated STAT3 was measured using the phospho-STAT panel kit (Meso Scale Discovery, K15202D).

TABLE E1

| | | | |
|---|---|---|---|
| | $IC_{50}$s of Illustrative Peptides of present invention* | | |
| SEQ ID No./ Compound No. | Sequence | pStat3 HTRF (nM) | PBMC pSTAT3 IC50 (nM) |
| 1 | Ac—[Pen]—N—T—[W(7-Me)]-[Lys(Ac)]—[Pen]-Phe[4-(2-aminoethoxy)]-[3-Quin]-[a-MeLys]-[Lys(Ac)]—N-[(D)Leu)]-NH2 | 0.602 | |
| 2 | [Propionic_acid]-[(D)Arg]-[Abu]-Q-T-W-Q-[Cys]-Phe[4-(2-aminoethoxy)]-[2-Nal]-[THP]-E-N-[THP]-NH2 | 0.782 | 3.3 |
| 3 | [Propionic_acid]-[(D)Arg]-[Pen]-Q-T-W-Q-[Pen]-Phe[4-(2-aminoethoxy)]-[2-Nal]-[THP]-E-N-[a-MePhe]-NH2; | 2.31 | 40 |
| 4 | [Propionic_acid]-[(D)Arg]-[Pen]-Q-T-W-Q-[Pen]-[Phe(4-OMe)]-[2-Nal]-[THP]-E-N-[THP]-NH2; | 4.17 | |
| 5 | [3,3,3-Trifluoropropionic acid]-[(D)Arg]-[Pen]-Q-T-W-Q-[Pen]-Phe[4-(2-aminoethoxy)]-[2-Nal]-[THP]-E-N-[THP]-NH2; | 2.94 | 4.7 |
| 6 | [Propionic_acid]-[(D)Arg]-[Pen]-Q-T-W-Q-[Pen]-Phe[4-(2-aminoethoxy)]-[2-Nal]-[THP]-[Lys(COCF3)]—N-[THP]-NH2; | 2.46 | 8.6 |
| 7 | [Propionic_acid]-[(D)Arg]-[Pen]-Q-T-W-Q-[Pen]-Phe[4-(2-aminoethoxy)]-[2-Nal]-[THP]-[Lys(COtBu)]—N-[THP]-NH2; | 3.87 | 8.6 |
| 8 | [Propionic_acid]-[(D)Arg]-[Pen]-Q-T-W-Q-[Pen]-Phe[4-(2-aminoethoxy)]-[2-Nal]-[THP]-E-N—[N—Me-bAla]-NH2; | 24.6 | |
| 9 | [Pentanoic acid]-[(D)Arg]-[Pen]-Q-T-W-Q-[Pen]-Phe[4-(2-aminoethoxy)]-[2-Nal]-[THP]-E-N-[THP]-NH2; | 3.12 | 29 |
| 10 | [Propionic_acid]-[(D)Arg]-[Pen]-Q-T-W-Q-[Pen]-Phe[4-(2-aminoethoxy)]-[2-Nal]-[THP]-E-N-[THP]-NH2; | 4.16 | 4.6 |
| 11 | Ac-[(D)Arg]-[Abu]-Q-T-[W(7-Ph)]-[Lys(Ac)]-[Cys]-Phe[4-(2-aminoethoxy)]-[2-Nal]-[a-MeLys]-[Lys(Ac)]—N-[a-MePhe]-NH2; | 13.9 | |
| 12 | Ac-[(D)Arg]-[Abu]-Q-T-W-Q-[Cys]-Phe[4-(2-aminoethoxy)]-[2-Nal]-[THP]-E-N—N-ac; | | 20 |
| 13 | Ac-[(D)Arg]-[Pen]-Q-T-W-Q-[Pen]-Phe[4-(2-aminoethoxy)]-[2-Nal]-[THP]-E-N-[THP]-NH2; | | |
| 14 | Ac-[(D)Arg]-[Pen]-Q-T-W-Q-[Pen]-Phe[4-(2-aminoethoxy)]-[2-Nal]-[THP]-E-N—[N—Me-bAla]-NH2; | | |
| 15 | pr-[(D)Arg]-[Pen]-Q-T-W-Q-[Pen]-Phe[4-(2-aminoethoxy)]-[2-Nal]-[THP]-Q-N-[THP]-NH2; | | |
| 16 | Ac-[(D)Arg]-[Cys]-Q-T-W-Q-A-Phe[4-(2-aminoethoxy)]-[2-Nal]-[THP]-[Orn(COMe)]—N-[THP]-NH2; | | |
| 17 | Ac-[(D)Arg]-[Abu]-Q-T-W-Q-[Cys]-Phe[4-(2-aminoethoxy)]-[2-Nal]-[THP]-E-N—F—NH2; | | 3.4 |
| 18 | [(D)Arg]-[Pen]-Q-T-W-Q-[Pen]-[Phe(4-OMe)]-[2-Nal]-[THP]-E-N-[THP]-NH2; | | |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 19 | pr-[(D)Arg]-[Pen]-Q-[Hyp]-W-Q-[Pen]-Phe[4-(2-aminoethoxy)]-[2-Nal]-[THP]-E-N-[THP]-NH2; | | |
| 20 | pr-[(D)Arg]-[Cys]-Q-T-W-Q-[Pen]-Phe[4-(2-aminoethoxy)]-[2-Nal]-[THP]-E-N-[THP]-NH2; | | 3.1 |
| 21 | pr-[(D)Arg]-[Abu]-Q-T-W-Q-[Cys]-[Phe(4-OMe)]-[2-Nal]-[THP]-E-N-[THP]-NH2; | | 21 |
| 22 | [(D)Arg]-[Abu]-Q-T-W-Q-[Cys]-[Phe(4-OMe)]-[2-Nal]-[THP]-E-N-[THP]-NH2; | | 22 |
| 23 | pr-[(D)Arg]-[Cys]-Q-T-W-Q-[Pen]-Phe[4-(2-aminoethoxy)]-[2-Nal]-[THP]-E-N-[a-MePhe]-NH2; | | 17 |
| 24 | N3_Acid-[(D)Arg]-[Abu]-Q-T-W-Q-[Cys]-Phe[4-(2-aminoethoxy)]-[2-Nal]-[THP]-E-N-[THP]-NH2; | | |
| 25 | FPrpTriazoleMe_Acid-[(D)Arg]-[Abu]-Q-T-W-Q-[Cys]-[Phe(4-OMe)]-[2-Nal]-[THP]-E-N-[THP]-NH2; | | 21 |
| 26 | pr-[(D)Arg]-[Pen]-Q-T-W-Q-[Pen]-Phe[4-(2-aminoethoxy)]-[2-Nal]-[THP]-[Lys(COtBu)]—N—F—NH2; | | 8.2 |
| 27 | Ac-[(D)Arg]-[Abu]-Q-T-W-Q-[Cys]-Phe[4-(2-aminoethoxy)]-[2-Nal]-[Achc]-[aMeGlu]-N—F-NH2; | | 11 |
| 28 | Ac-[(D)Arg]-[Abu]-Q-T-W-Q-[Cys]-Phe[4-(2-aminoethoxy)]-[2-Nal]-[Achc]-[aMeGlu]-N—F-[Aib]-NH2; | | 23 |
| 29 | Ac-[(D)Arg]-[Abu]-Q-T-W-Q-[Cys]-Phe[4-(2-aminoethoxy)]-[2-Nal]-[Achc]-[aMeGlu]-N-[a-MePhe]-NH2; | | 30 |
| 30 | Ac-[(D)Arg]-[Abu]-Q-T-W-Q-[Cys]-Phe[4-(2-aminoethoxy)]-[2-Nal]-[THP]-Q-N-[a-MePhe]-NH2; | | 25 |
| 31 | Ac-[(D)Arg]-[Abu]-Q-T-W-Q-[Cys]-Phe[4-(2-aminoethoxy)]-[2-Nal]-[THP]-[aMeGlu]-N-ameW-NH2; | | 16 |
| 32 | Ac-[(D)Arg]-[Abu]-Q-T-W-Q-[Cys]-Phe[4-(2-aminoethoxy)]-[2-Nal]-[THP]-[aMeGlu]-N-1[2-Nal]-NH2; | | 19 |
| 33 | pr-[(D)Arg]-[Pen]-Q-T-W-Q-[Pen]-Phe[4-(2-aminoethoxy)]-[2-Nal]-[THP]-[Lys(CO2Allyl)]-N—F—NH2; | | 11 |
| 34 | Ac-[(D)Arg]-[Abu]-Q-T-W-Q-[Cys]-Phe[4-(2-aminoethoxy)]-[2-Nal]-[THP]-[aMeGlu]-N-[Phe(4-CONH2)]—NH2; | | 5.8 |
| 35 | Ac-[(D)Arg]-[Abu]-Q-T-W-Q-[Cys]-Phe[4-(2-aminoethoxy)]-[2-Nal]-[THP]-[aMeGlu]-N-[2-Nal]-NH2; | | 25 |
| 36 | Ac-[(D)Arg]-[Abu]-Q-T-W-Q-[Cys]-Phe[4-(2-aminoethoxy)]-[2-Nal]-[THP]-[aMeGlu]-N-[aMe(4-F)Phe]-NH2; | | 14 |
| 37 | Ac-[(D)Arg]-[Abu]-Q-T-W-Q-[Cys]-Phe[4-(2-aminoethoxy)]-[2-Nal]-[THP]-[aMeGlu]-N-[THP]-NH2; | | 11 |
| 38 | Ac-[(D)Arg]-[Abu]-Q-T-W-Q-[Cys]-Phe[4-(2-aminoethoxy)]-[2-Nal]-[Achc]-[aMeGlu]-N-[THP]-NH2; | | 4.3 |
| 39 | Ac-[(D)Arg]-[Abu]-Q-T-W-Q-[Pen]-Phe[4-(2-aminoethoxy)]-[2-Nal]-[Achc]-[aMeGlu]-N-[THP]-NH2; | | 92 |
| 40 | Ac-[(D)Arg]-[Cys]-Q-T-W-Q-[Pen]-Phe[4-(2-aminoethoxy)]-[2-Nal]-[Achc]-[aMeGlu]-N-[a-MePhe]-NH2; | | 220 |
| 41 | Ac-[(D)Arg]-[Abu]-Q-T-W-Q-[Cys]-[Phe(3,4-diOMe)]-[2-Nal]-[THP]-[aMeGlu]-N-[a-MePhe]-NH2; | | 2500 |
| 42 | Ac-[(D)Arg]-[Abu]-Q-T-W-Q-[Cys]-Phe[4-(2-aminoethoxy)]-[2-Nal]-[Achc]-E-N-[THP]-NH2; | | 6.7 |
| 43 | Ac-[(D)Arg]-[Abu]-Q-T-W-Q-[Cys]-Phe[4-(2-aminoethoxy)]-[2-Nal]-[THP]-[aMeGlu]-N—F-[Aib]-[a-MeLys]-NH2; | | 8.2 |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 44 | Ac-[(D)Arg]-[Abu]-Q-T-W-Q-[Cys]-Phe[4-(2-aminoethoxy)]-[2-Nal]-[THP]-[aMeGlu]-N-[aMeTyr]-NH2; | | 9.3 |
| 45 | Ac-[(D)Arg]-[Abu]-Q-T-W-Q-[Cys]-Phe[4-(2-aminoethoxy)]-[2-Nal]-[Achc]-[aMeGlu]-N—F-[Aib]-[a-MeLys]-NH2; | | 17 |
| 46 | Ac-[(D)Arg]-[Abu]-Q-T-W-Q-[Cys]-Phe[4-(2-aminoethoxy)]-[2-Nal]-[THP]-[aMeGlu]-N-[Phe(3,5-diF)]—NH2; | | 48 |
| 47 | [(D)Arg]-[Abu]-Q-T-W-Q-[Cys]-Phe[4-(2-(Boc)aminoethoxy)]-[2-Nal]-[THP]-E-N-[THP]-NH2; | | 5.3 |
| 48 | pr-[(D)Arg]-[Abu]-Q-T-W-Q-[aMeCys]-Phe[4-(2-aminoethoxy)]-[2-Nal]-[THP]-E-N—F—NH2; | | 7.2 |
| 49 | Ac-[(D)Arg]-[Abu]-Q-T-W-Q-[Cys]-Phe[4-(2-aminoethoxy)]-[2-Nal]-[THP]-[Aib]-N—F—NH2 | | 18 |
| 50 | Ac-[(D)Arg]-[Abu]-Q-T-W-Q-[Cys]-Phe[4-(2-aminoethoxy)]-[2-Nal]-[THP]-[Achc]-N-[a-MePhe]-NH2; | | 14 |
| 51 | Ac-[(D)Arg]-[Pen]-Q-T-W-Q-[Pen]-Phe[4-(2-aminoethoxy)]-[2-Nal]-[THP]-[Lys(COcPr)]—N-[THP]-NH2; | | 27 |
| 52 | Ac-[(D)Arg]-[Pen]-Q-T-W-Q-[Pen]-Phe[4-(2-aminoethoxy)]-[2-Nal]-[THP]-[Lys(COPr)]—N-[THP]-NH2; | | 16 |
| 53 | Ac-[(D)Arg]-[Pen]-Q-T-W-Q-[Pen]-Phe[4-(2-aminoethoxy)]-[2-Nal]-[THP]-[Lys(Ac)]—N—F-NH2; | | 29 |
| 54 | Ac-[(D)Arg]-[Pen]-Q-T-W-Q-[Pen]-Phe[4-(2-aminoethoxy)]-[2-Nal]-[THP]-[Lys(COEt)]—N—F—NH2; | | 47 |
| 55 | Ac-[(D)Arg]-[Pen]-Q-T-W-Q-[Pen]-Phe[4-(2-aminoethoxy)]-[2-Nal]-[THP]-[Lys(COcPr)]—N—F—NH2; | | 25 |
| 56 | Ac-[(D)Arg]-[Pen]-Q-T-W-Q-[Pen]-Phe[4-(2-aminoethoxy)]-[2-Nal]-[THP]-[Lys(Ac)]—N-[THP]-NH2; | | 4.9 |
| 57 | Ac-[(D)Arg]-[Pen]-Q-T-W-Q-[Pen]-Phe[4-(2-aminoethoxy)]-[2-Nal]-[THP]-[Lys(COEt)]—N-[THP]-NH2; | | 18 |
| 58 | Ac-[(D)Arg]-[Pen]-Q-T-W-Q-[Pen]-Phe[4-(2-aminoethoxy)]-[2-Nal]-[THP]-[Lys(COPr)]—N—F—NH2; | | 35 |
| 59 | Ac-[(D)Arg]-[Pen]-Q-T-W-Q-[Pen]-Phe[4-(2-aminoethoxy)]-[2-Nal]-[THP]-[Lys(COPent)]—N—F—NH2; | | 67 |
| 60 | Ac-[(D)Arg]-[Pen]-Q-T-W-Q-[Pen]-Phe[4-(2-aminoethoxy)]-[2-Nal]-[THP]-[Lys(COCF3)]—N—F—NH2; | | 44 |
| 61 | Ac-[(D)Arg]-[Pen]-Q-T-W-Q-[Pen]-Phe[4-(2-aminoethoxy)]-[2-Nal]-[THP]-[Lys(COiPr)]—N—F—NH2; | | 70 |
| 62 | Ac—[Pen]—N—T-[W(7-Ph)]-[Lys(Ac)]—[Pen]-Phe[4-(2-aminoethoxy)]-[3Quin]-[THP]-E-N-[Aib]-NH2; | 0.413 | |
| 63 | Ac—[Pen]—N—T-[W(7-Ph)]-[Lys(Ac)]—[Pen]-Phe[4-(2-aminoethoxy)]-[3Quin]-[a-MeLys]-[Lys(Ac)]—N-[Aib]-NH2; | 1.02 | |
| 64 | Ac-[Abu]-Q-T—[W(7-Me)]-[Lys(Ac)]-[Cys]-Phe[4-(2-aminoethoxy)]-[2-Nal]-[a-MeLys]-[Lys(Ac)]—N-[(D)Lys]-NH2; | 0.889 | |
| 65 | Ac-[Abu]-Q-T—[W(7-Me)]-[Lys(Ac)]-[Cys]-Phe[4-(2-aminoethoxy)]-[2-Nal]-[a-MeLys]-[Lys(Ac)]—N-[(D)Leu]-NH2; | 0.966 | |
| 66 | Ac-[Abu]-Q-T—[W(7-Me)]-[Lys(Ac)]-[Cys]-Phe[4-(2-aminoethoxy)]-[2-Nal]-[a-MeLys]-[Lys(Ac)]—N-[a-MePhe]-NH2; | 2.27 | |
| 67 | Ac-[Abu]-Q-T-[W(7-Ph)]-[Lys(Ac)]-[Cys]-Phe[4-(2-aminoethoxy)]-[2-Nal]-[a-MeLys]-[Lys(Ac)]—N-[a-MePhe]-NH2; | 5.52 | |
| 68 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[(D)Leu]-[aMePhe]-am; | 7 | |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 69 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[(D)Leu]-[(D)aMePhe]-NH2; | 2.75 | |
| 70 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[Aib-Ahx]-NH2; | 1.22 | |
| 71 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[Aib]-[bhPhe]-NH2; | 3.39 | |
| 72 | Ac—[Pen]—N-[(D)Dap]-[W(7-Me)]-[Lys(Ac)]-[Pen]-Phe[4-(2-aminoethoxy)]-[2-Nal]-[a-MeLys]-[Lys(Ac)]—N-[(D)Leu]-NH2; | 52.6 | |
| 73 | Ac—[Pen]—N-[(D)Lys]-[W(7-Me)]-[Lys(Ac)]-[Pen]-Phe[4-(2-aminoethoxy)]-[2-Nal]-[a-MeLys]-[Lys(Ac)]—N-[(D)Leu]-NH2; | 51.1 | |
| 74 | Ac—[Pen]—N-[(D)Asp]-[W(7-Me)]-[Lys(Ac)]-[Pen]-Phe[4-(2-aminoethoxy)]-[2-Nal]-[a-MeLys]-[Lys(Ac)]—N-[(D)Leu]-NH2; | 73.1 | |
| 75 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[THP]-NH2; | 0.787 | 8.9 |
| 76 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | 1.5 | 11 |
| 77 | Ac-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | 0.353 | 6.4 |
| 78 | Ac-[(D)Arg]-[Abu]-Q-T-W-Q-[Cys]-Phe[4-(2-aminoethoxy)]-[2-Nal]-[THP]-[aMeGlu]-N-[Phe(3,4-diOMe)]—NH2; | | 31 |
| 79 | Ac-[(D)Arg]-[Abu]-Q-T-W-Q-[Cys]-Phe[4-(2-aminoethoxy)]-[2-Nal]-[THP]-[aMeGlu]-N-[(D)Phe(3,4-diOMe)]—NH2; | | 25 |
| 80 | Ac-[(D)Arg]-[Abu]-Q-T-W-Q-[Cys]-Phe[4-(2-aminoethoxy)]-[2-Nal]-[THP]-E-N-[aMe(2-Nal)]-NH2; | | 46 |
| 81 | Ac-[(D)Arg]-[Abu]-Q-T-W-Q-[Cys]-Phe[4-(2-aminoethoxy)]-[2-Nal]-[THP]-[aMeGlu]-N-[W(5-F)]—NH2; | | 30 |
| 82 | Ac-[Pen]-Q-T-W-[Lys(Ac)]—[Pen]-Phe[4-(2-aminoethoxy)]-[2-Nal]-[a-MeLys]-[Lys(Ac)]—N-[a-MePhe]-NH2; | | 54 |
| 83 | pr-[(D)Arg]-[Abu]-Q-T-W-Q-[aMeCys]-Phe[4-(2-aminoethoxy)]-[2-Nal]-[THP]-E-N-[a-MePhe]-NH2; | | 33 |
| 84 | Ac-[Pen]-Q-T-W-[Lys(Ac)]—[Pen]-Phe[4-(2-aminoethoxy)]-[2-Nal]-[a-MeLys]-[Lys(Ac)]—N-[THP]-NH2; | | 54 |
| 85 | pr-[(D)Arg]-[Abu]-Q-T-W-Q-[Cys]-Phe[4-(2-aminoethoxy)]-[2-Nal]-[THP]-E-N-[a-MePhe]-NH2; | | 7.6 |
| 86 | pr-[(D)Arg]-[Abu]-Q-T-W-Q-[Cys]-Phe[4-(2-aminoethoxy)]-[aMe(2-Nal)]-[THP]-E-N-[a-MePhe]-NH2; | | |
| 87 | Ac—[Pen]—N—T—[W(7-Me)]-Q-[Pen]-Phe[4-(2-aminoethoxy)]-[2-Nal]-[a-MeLys]-[Lys(Ac)]—N-[THP]-NH2; | | 3.6 |
| 88 | Ac-[(D)Arg]-[Pen]—N—T-W-[Lys(Ac)]—[Pen]-Phe[4-(2-aminoethoxy)]-[2-Nal]-[Acvc]-E-N-[THP]-NH2; | | 3.7 |
| 89 | Ac—[Pen]—N—T—[W(7-Me)]-Q-[Pen]-Phe[4-(2-aminoethoxy)]-[2-Nal]-[a-MeLys]-[Lys(Ac)]—N-[a-MePhe]-NH2; | | 12 |
| 90 | Ac-[(D)Arg]-[Pen]—N—T—[W(7-Me)]-Q-[Pen]-Phe[4-(2-aminoethoxy)]-[2-Nal]-[THP]-E-N-[THP]-NH2; | | 3.7 |
| 91 | Ac-[(D)Arg]-[Pen]—N—T—[W(7-Me)]-Q-[Pen]-Phe[4-(2-aminoethoxy)]-[2-Nal]-[THP]-E-N-[a-MePhe]-NH2; | | 4.1 |
| 92 | Ac-[(D)Arg]-[Pen]—N—T—[W(7-Me)]-[Lys(Ac)]—[Pen]-Phe[4-(2-aminoethoxy)]-[2-Nal]-[THP]-E-N-[THP]-NH2; | 0.206 | 3.3 |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 93 | Ac-[(D)Arg]-[Pen]—N—T—[W(7-Me)]-Q-[Pen]-Phe[4-(2-aminoethoxy)]-[2-Nal]-[Acvc]-E-N-[a-MePhe]-NH2; | | 4.6 |
| 94 | Ac-[(D)Arg]-[Pen]—N—T—[W(7-Me)]-[Lys(Ac)]—[Pen]-Phe[4-(2-aminoethoxy)]-[2-Nal]-[Acvc]-E-N-[a-MePhe]-NH2; | | 12 |
| 95 | Ac—[Pen]—N—T-W-[Lys(Ac)]—[Pen]-Phe[4-(2-aminoethoxy)]-[2-Nal]-[a-MeLys]-[Lys(Ac)]—N-[THP]-NH2; | | 22 |
| 96 | Ac-[(D)Arg]-[Pen]—N—T—[W(b-Me)]-[Lys(Ac)]—[Pen]-Phe[4-(2-aminoethoxy)]-[2-Nal]-[THP]-E-N-[a-MePhe]-NH2; | | |
| 97 | Ac-[(D)Arg]-[Pen]-Q-T-W-Q-[Pen]-Phe[4-(2-aminoethoxy)]-[2-Nal]-[THP]-E-N-[a-MePhe]-NH2; | | 31 |
| 98 | Ac—[Pen]—N—T-W-[Lys(Ac)]—[Pen]-Phe[4-(2-aminoethoxy)]-[2-Nal]-[a-MeLys]-[Lys(Ac)]—N-[a-MePhe]-NH2; | | 15 |
| 99 | Ac-[(D)Arg]-[Pen]—N—T—[W(7-Me)]-Q-[Pen]-Phe[4-(2-aminoethoxy)]-[2-Nal]-[Acvc]-E-N-[THP]-NH2; | | 4.2 |
| 100 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-[(D)Tyr]-NH2; | | 21 |
| 101 | Ac-[(D)Arg]-[Pen]—N—T—[W(7-Me)]-[Lys(Ac)]—[Pen]-Phe[4-(2-aminoethoxy)]-[2-Nal]-[Acvc]-E-N-[THP]-NH2; | | 0.74 |
| 102 | Ac-[(D)Arg]-[Pen]—N—T-W-[Lys(Ac)]—[Pen]-Phe[4-(2-aminoethoxy)]-[2-Nal]-[Acvc]-E-N-[a-MePhe]-NH2; | | 8.4 |
| 103 | Ac—[Pen]—N—T-W-[Lys(COCF3)]—[Pen]-Phe[4-(2-aminoethoxy)]-[2-Nal]-[a-MeLys]-[Lys(Ac)]—N-[THP]-NH2; | | 57 |
| 104 | Ac—[Pen]—N—T—[W(7-Me)]-[Cit]-[Pen]-Phe[4-(2-aminoethoxy)]-[2-Nal]-[aMeLeu]-[Lys(Ac)]—N-[a-MePhe]-NH2; | | 8.2 |
| 105 | Ac-[(D)Arg]-[Pen]—N—T-W-[Lys(Ac)]—[Pen]-Phe[4-(2-aminoethoxy)]-[2-Nal]-[THP]-E-N-[THP]-NH2; | | 2.2 |
| 106 | Ac-[(D)Arg]-[Pen]—N—T-W-[Lys(Ac)]—[Pen]-Phe[4-(2-aminoethoxy)]-[2-Nal]-[THP]-E-N-[a-MePhe]-NH2; | | 13 |
| 107 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[THP]-[(D)Tyr]-NH2; | | 11 |
| 108 | Ac—[Pen]—N—T—[W(7-Me)]-[Cit]-[Pen]-Phe[4-(2-aminoethoxy)]-[2-Nal]-[aMeLeu]-[Lys(Ac)]—N-[THP]-NH2; | | 5.1 |
| 109 | Ac-[(D)Arg]-[Pen]—N—T—[W(b-Me)]-[Lys(Ac)]—[Pen]-Phe[4-(2-aminoethoxy)]-[2-Nal]-[THP]-E-N-[a-MePhe]-NH2; | | |
| 110 | Ac-[(D)Arg]-[Pen]-Q-T-W-Q-[Pen]-Phe[4-(2-aminoethoxy)]-[2-Nal]-[THP]-E-N-[(N-benzyl)Asn]-NH2; | | 700 |
| 111 | Ac-[(D)Arg]-[Pen]—N—T—[W(7-Me)]-[Lys(Ac)]—[Pen]-Phe[4-(2-aminoethoxy)]-[2-Nal]-[THP]-[Lys(Ac)]—N-[a-MePhe]-NH2; | 1.29 | |
| 112 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-Phe[4-NH2]—NH2; | 2.09 | |
| 113 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[(D)Leu]-NH2; | | |
| 114 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-(D)Phe[4-NH2]—NH2; | | 12 |
| 115 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-(D)Phe[3-NH2]—NH2; | | 39 |
| 116 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-[3Pal]-NH2; | | 20 |

TABLE E1-continued

IC50s of Illustrative Peptides of present invention*

| SEQ ID No./ Compound No. | Sequence | pStat3 HTRF (nM) | PBMC pSTAT3 IC50 (nM) |
|---|---|---|---|
| 117 | Ac-[Cys]-N—T—[W(7-Me)]-[Lys(Ac)]-[aMeCys]-Phe[4-(2-aminoethoxy)]-[2-Nal]-[a-MeLys]-[Lys(Ac)]—N-[THP]-NH2; | | 7.1 |
| 118 | Ac-[Cys]-N—T—[W(7-Me)]-[Lys(Ac)]-[aMeCys]-Phe[4-(2-aminoethoxy)]-[2-Nal]-[a-MeLys]-[Lys(Ac)]—N-[a-MePhe]-NH2; | | 30 |
| 119 | Ac-[Cys]-N—T—[W(7-Me)]-Q-[aMeCys]-Phe[4-(2-aminoethoxy)]-[2-Nal]-[a-MeLys]-[Lys(Ac)]—N-[a-MePhe]-NH2; | | 5.3 |
| 120 | Ac-[Cys]-N—T—[W(7-Me)]-Q-[aMeCys]-Phe[4-(2-aminoethoxy)]-[2-Nal]-[a-MeLys]-[Lys(Ac)]—N-[THP]-NH2; | | 4.9 |
| 121 | Ac-[Cys]-N—T-W-[Lys(Ac)]-[aMeCys]-Phe[4-(2-aminoethoxy)]-[2-Nal]-[a-MeLys]-[Lys(Ac)]—N-[THP]-NH2; | | 41 |
| 122 | Ac-[Cys]-N—T-W-[Lys(Ac)]-[aMeCys]-Phe[4-(2-aminoethoxy)]-[2-Nal]-[a-MeLys]-[Lys(Ac)]—N-[a-MePhe]-NH2; | | 54 |
| 123 | Ac-[(D)Arg]-[Abu]-Q-T-W-Q-[Cys]-Phe[4-(2-aminoethoxy)]-[2-Nal]-[THP]-E-N-[a-MePhe]-NH2; | | 11 |
| 124 | Ac-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | 11 |
| 125 | Ac-[(D)Arg]-[Pen]-Q-T-W-Q-[Pen]-Phe[4-(2-aminoethoxy)]-[2-Nal]-[THP]-E-N—[(N-Ph)Asn]-NH2; | | |
| 126 | Ac-[(D)Arg]-[Pen]-Q-T-W-Q-[Pen]-Phe[4-(2-aminoethoxy)]-[2-Nal]-[THP]-E-N—[(N-(2-aminophenyl))Asn]-NH2; | | |
| 127 | Ac-[(D)Arg]-[Pen]-Q-T-W-Q-[Pen]-Phe[4-(2-aminoethoxy)]-[2-Nal]-[THP]-E-N—[(N-Pip)Asn]-NH2; | | 48 |
| 128 | Ac-[(D)Arg]-[Pen]-Q-T-W-Q-[Pen]-Phe[4-(2-aminoethoxy)]-[2-Nal]-[THP]-E-N—[(N-Pyr)Asn]-NH2; | | 51 |
| 129 | Ac-[(D)Arg]-[Pen]-Q-T-W-Q-[Pen]-Phe[4-(2-aminoethoxy)]-[2-Nal]-[THP]-E-N—[(N-(4-aminophenyl))Asn]-NH2; | | |
| 130 | Ac-[(D)Arg]-[Pen]-Q-T-W-Q-[Pen]-Phe[4-(2-aminoethoxy)]-[2-Nal]-[THP]-E-N—[(N-(3-aminophenyl))Asn]-NH2; | | 9.2 |
| 131 | Ac-[(D)Arg]-[Pen]-Q-T-W-Q-[Pen]-Phe[4-(2-aminoethoxy)]-[2-Nal]-[THP]-E-N—[(N-(4-Pyz))Asn]-NH2; | | |
| 132 | Ac-[(D)Arg]-[Pen]-Q-T-W-Q-[Pen]-Phe[4-(2-aminoethoxy)]-[2-Nal]-[THP]-E-N—[(N-(5-indolyl)Asn]-NH2; | | |
| 133 | Ac-[(D)Arg]-[Pen]-Q-T-W-Q-[Pen]-Phe[4-(2-aminoethoxy)]-[2-Nal]-[THP]-E-N—[(N-(3-Pyz))Asn]-NH2; | | 21 |
| 134 | pr-[(D)Arg]-[Pen]-Q-T-W-Q-[Pen]-Phe[4-(2-aminoethoxy)]-[2-Nal]-[THP]-E-N-[THP]-NH2; | | |
| 135 | pr-[(D)Arg]-[Pen]-Q-T-W-Q-[Pen]-Phe[(aMe)-4-(2-aminoethoxy)]-[2-Nal]-[THP]-E-N-[THP]-NH2; | | |
| 136 | Ac-[(D)Arg]-[Pen]-Q-T-W-Q-[Pen]-Phe[4-(2-aminoethoxy)]-[2-Nal]-[THP]-E-N—[(N-propylamido)Asn]-NH2; | | |
| 137 | Ac-[(D)Arg]-[Pen]-Q-T-W-Q-[Pen]-Phe[4-(2-aminoethoxy)]-[2-Nal]-[THP]-E-N—[(N-(imidazol-2-yl)methyl)Asn]-NH2; | | 14 |
| 138 | Ac—[Pen]—N—T—[W(7-Me)]-[Lys(Ac)]—[Pen]-Phe[4-(2-aminoethoxy)]-[2-Nal]-[THP]-[Lys(COCF3)]—N-[a-MePhe]-NH2; | | 7.6 |
| 139 | Ac—[Pen]—N—T—[W(7-Me)]-[Lys(Ac)]—[Pen]-Phe[4-(2-aminoethoxy)]-[2-Nal]-[THP]-[Lys(COtBu)]-N-[a-MePhe]-NH2; | | 6.6 |
| 140 | Ac—[Pen]—N—T—[W(7-Me)]-[Lys(Ac)]—[Pen]-Phe[4-(2-aminoethoxy)]-[2-Nal]-[THP]-[Lys(COCF3)]—N-[THP]-NH2; | | 2.6 |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 141 | Ac—[Pen]—N—T—[W(7-Me)]-[Lys(Ac)]—[Pen]-Phe[4-(2-aminoethoxy)]-[2-Nal]-[THP]-[Lys(COtBu)]—N-[THP]-NH2; | | 3.7 |
| 142 | PentCO-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | 4.9 |
| 143 | Biotin-[(D)Arg]-[Pen]—N—T—[W(7-Me)]-[Lys(Ac)]—[Pen]-Phe[4-(2-aminoethoxy)]-[2-Nal]-[THP]-E-N-[THP]-NH2; | | |
| 144 | Biotin-PEG2(2:2)-[(D)Arg](x,2:1,3:2)-Pen(1:3,3:1)-N—T—[W(7-Me)]-[Lys(Ac)]—[Pen]-Phe[4-(2-aminoethoxy)]-[2-Nal]-[THP]-E-N-[THP]-NH2; | | |
| 145 | Biotin-PEG3(2:2)-[(D)Arg](x,2:1,3:2)-Pen(1:3,3:1)-N—T—[W(7-Me)]-[Lys(Ac)]—[Pen]-Phe[4-(2-aminoethoxy)]-[2-Nal]-[THP]-E-N-[THP]-NH2; | | |
| 146 | FlagTag-[(D)Arg]-[Pen]—N—T—[W(7-Me)]-[Lys(Ac)]—[Pen]-Phe[4-(2-aminoethoxy)]-[2-Nal]-[THP]-E-N-[THP]-NH2; | | 8.9 |
| 147 | FlagTag-PEG2(2:2)-[(D)Arg](x,2:1,3:2)-Pen(1:3,3:1)-N—T—[W(7-Me)]-[Lys(Ac)]—[Pen]-Phe[4-(2-aminoethoxy)]-[2-Nal]-[THP]-E-N-[THP]-NH2; | | |
| 148 | FlagTag-PEG3(2:2)-[(D)Arg](x,2:1,3:2)-Pen(1:3,3:1)-N—T—[W(7-Me)]-[Lys(Ac)]—[Pen]-Phe[4-(2-aminoethoxy)]-[2-Nal]-[THP]-E-N-[THP]-NH2; | | |
| 149 | Ac-[(D)Arg]-[Pen]—N—T—[W(7-Me)]-[Cit]-[Pen]-Phe[4-(2-aminoethoxy)]-[2-Nal]-[aMeLeu]-E-N-[a-MePhe]-NH2; | | 2.3 |
| 150 | Ac-[(D)Arg]-[Pen]—N—T—[W(7-Me)]-[Lys(Ac)]-[Pen]-Phe[4-(2-aminoethoxy)]-[2-Nal]-[THP]-[aMeGlu]-N-[aMeTyr]-NH2; | | 4.7 |
| 151 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[aMeTyr]-NH2; | | 5.7 |
| 201 | Ac-[(D)Arg]-[Abu]-Q-T—[W(7-Me)]-[Lys(Ac)]-[Cys]-Phe[4-(2-aminoethoxy)]-[2-Nal]-[a-MeLys]-[Lys(Ac)]—N-[a-MePhe]-NH2 | 12.7 | |
| 202 | Ac—[Pen]—N—T—[W(7-Me)]-[Cit]-[Pen]-Phe[4-(2-aminoethoxy)]-[2-Nal]-[a-MeLys]-[Lys(Ac)]—N-[Aib]-[(D)Tyr]-NH2; | 0.637 | |
| 203 | Ac-[(D)Arg]-[Pen]-Q-T-W-Q-[Pen]-Phe[4-(2-aminoethoxy)]-[2-Nal]-[THP]-E-N-[Aib]-NH2; | | |
| 204 | Ac-[(D)Arg]-[Abu]-Q-T-W-Q-[Cys]-Phe[4-(2-aminoethoxy)]-[2-Nal]-[THP]-E-N-[Aib]-NH2; | | |
| 206 | FPrpTriazoleMe_Acid-[(D)Arg]-[Abu]-Q-T-W-Q-[Cys]-Phe[4-(2-aminoethoxy)]-[2-Nal]-[THP]-E-N-[THP]-NH2; | | |
| 207 | Pr-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 208 | Pr-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 209 | MeSO2-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 210 | N3_Acid-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 211 | N3_Acid-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 212 | MeSO2-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 213 | [(D)Arg]-[Abu]-Q-T-W-Q-[Cys]-Phe[4-(2-aminoethoxy)]-[2-Nal]-[THP]-E-N-[THP]-NH2; | | |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 214 | Pr-[(D)Arg]-[Abu]-Q-T-W-Q-[Cys]-Phe[4-(2-aminoethoxy)]__Ethyl)]-[2-Nal]-[THP]-E-N-[THP]-NH2; | | |
| 215 | Ac-[(D)Arg]-[Pen]—N—T—[W(7-Me)]-[Lys(Ac)]—[Pen]-Phe[4-(2-aminoethoxy)]-[2-Nal]-[THP]-E-N-[(D)Leu]-[(D)Tyr]-NH2; | | |
| 216 | Ac-[(D)Arg]-[Pen]—N—T—[W(7-Me)]-[Lys(Ac)]—[Pen]-Phe[4-(2-aminoethoxy)]-[2-Nal]-[THP]-E-N-[THP]-[(D)Tyr]-NH2; | | |
| 217 | Ac-[(D)Arg]-[Pen]—N—T—[W(7-Me)]-[Lys(Ac)]—[Pen]-Phe[4-(2-aminoethoxy)]-[2-Nal]-[Acvc]-E-N-[THP]-[(D)Tyr]-NH2; | | |
| 218 | Dota-[a]-[(D)Arg]-[Pen]—N—T—[W(7-Me)]-[Lys(Ac)]—[Pen]-Phe[4-(2-aminoethoxy)]-[2-Nal]-[THP]-E-N-[THP]-NH2; | | |
| 219 | Dota__PEG2__Acid-[(D)Arg]-[Pen]—N—T—[W(7-Me)]-[Lys(Ac)]—[Pen]-Phe[4-(2-aminoethoxy)]-[2-Nal]-[THP]-E-N-[THP]-NH2; | | |
| 220 | Dota__PEG3__Acid-[(D)Arg]-[Pen]—N—T-[W(7-Me)]-[Lys(Ac)]—[Pen]-Phe[4-(2-aminoethoxy)]-[2-Nal]-[THP]-E-N-[THP]-NH2; | | |
| 221 | Ac—[Pen]—N—T—[W(7-F)]-[Lys(Ac)]—[Pen]-Phe[4-(2-aminoethoxy)]-[2-Nal]-[a-MeLys]-[Lys(Ac)]—N-[a-MePhe]-NH2; | | |
| 222 | Ac-[(D)Arg]-[Pen]—N—T—[W(7-F)]-[Lys(Ac)]—[Pen]-Phe[4-(2-aminoethoxy)]-[2-Nal]-[THP]-E-N-[a-MePhe]-NH2; | | |
| 223 | Ac—[Pen]—N—T—[W(7-Cl)]-[Lys(Ac)]—[Pen]-Phe[4-(2-aminoethoxy)]-[2-Nal]-[a-MeLys]-[Lys(Ac)]—N-[a-MePhe]-NH2; | | |
| 224 | Ac-[(D)Arg]-[Pen]—N—T—[W(7-Cl)]-[Lys(Ac)]—[Pen]-Phe[4-(2-aminoethoxy)]-[2-Nal]-[THP]-E-N-[a-MePhe]-NH2; | | |
| 225 | Ac—[Pen]—N—T—[W(5-Br)]-[Lys(Ac)]—[Pen]-Phe[4-(2-aminoethoxy)]-[2-Nal]-[a-MeLys]-[Lys(Ac)]—N-[a-MePhe]-NH2; | | |
| 226 | Ac-[(D)Arg]-[Pen]—N—T—[W(5-Br)]-[Lys(Ac)]—[Pen]-Phe[4-(2-aminoethoxy)]-[2-Nal]-[THP]-E-N-[a-MePhe]-NH2; | | |
| 227 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[(D)Lys]-[(D)Phe(4-OCF3)]-NH2; | | |
| 228 | Ac-[(D)Arg]-[Pen]—N—T—[W(7-Me)]-[Lys(Ac)]—[Pen]-Phe[4-(2-aminoethoxy)]-[2-Nal]-[THP]-E-N-[(D)Lys]-[(D)Phe(4-OCF3)]—NH2; | | |
| 229 | BenzHydroxylIodine__Acid-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 230 | BenzHydroxylIodine__Acid-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 231 | Ac—[Pen]—N—T—[W(7-Me)]-[Lys(Ac)]—[Pen]-Phe[4-(2-aminoethoxy)]-[2-Nal]-[Acvc]-E-N-[THP]-N(H)Me; | | |
| 232 | Ac—[Pen]—N—T—[W(7-Me)]-[Lys(Ac)]—[Pen]-Phe[4-(2-aminoethoxy)]-[2-Nal]-[THP]-E-N-[(D)Leu]-[(D)Tyr]-NH2; | | |
| 233 | Ac-[(D)Arg]-[Pen]—N—T—[W(7-Me)]-[Lys(Ac)]—[Pen]-Phe[4-(2-aminoethoxy)]-[2-Nal]-[Achc]-E-N-[THP]-NH2; | | |
| 234 | Ac-[(D)Arg]-[Pen]—N—T—[W(7-Me)]-[Lys(Ac)]—[Pen]-Phe[4-(2-aminoethoxy)]-[2-Nal]-[Acvc]-E-N-[THP]-N(H)Me; | | |
| 235 | Ac—[Pen]—N—T—[W(7-Me)]-[Lys(Ac)]—[Pen]-Phe[4-(2-aminoethoxy)]-[2-Nal]-[Acvc]-E-N-[(D)Phe(4-NH2)]-[(D)Tyr]-NH2; | | |
| 236 | Pr-[(D)Arg]-[Pen]-Q-T-W-Q-[Pen]-Phe[4-(2-aminoethoxy)]-[(R)(bMe)(2-Nal)]-[THP]-E-N-[THP]-NH2; | | |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 237 | Ac-[(D)Arg]-[Pen]—N—T—[W(7-Me)]-[Lys(Ac)]—[Pen]-Phe[4-(2-acetylaminoethoxy)]-[2-Nal]-[THP]-E-N-[THP]-NH2; | | |
| 238 | Pr-[(D)Arg]-[Pen]-Q-T-[Trp_psi]-Q-[Pen]-Phe[4-(2-aminoethoxy)]-[2-Nal]-[THP]-E-N-[THP]-NH2; | | |
| 239 | FPrpTriazoleMe_Acid-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 240 | FPrpTriazoleMe_Acid-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 241 | Ac-[(D)Arg]-[Pen]—N—T—[W(7-Me)]-[Lys(Ac)]—[Pen]-Phe_4Pip-[2-Nal]-[THP]-E-N-[a-MePhe]-NH2; | | |
| 242 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[Phe(tetrafluoro)]-NH2; | | |
| 243 | Ac-[(D)Arg]-[Pen]—N—T—[W(7-Me)]-[Lys(Ac)]—[Pen]-Phe[4-(2-aminoethoxy)]-[2-Nal]-[THP]-E-N-[Phe(tetrafluoro)]-NH2; | | |
| 244 | Ac—[Pen]—N—T—[W(7-Me)]-[Lys(Ac)]—[Pen]-Phe[4-(2-aminoethoxy)]-[2-Nal]-[a-MeLys]-[Lys(Ac)]—N-[(D)Lys]-[(D)Phe[4-(2-aminoethoxy)]]-NH2; | | |
| 245 | Ac-[(D)Arg]-[Pen]—N—T—[W(7-Me)]-[Lys(Ac)]—[Pen]-Phe[4-(2-aminoethoxy)]-[2-Nal]-[THP]-E-N-[(D)Lys]-[(D)Phe[4-(2-aminoethoxy)]]-NH2; | | |
| 246 | Ac-[(D)Arg]-[Pen]—N—T—[W(7-Me)]-[Lys(Ac)]—[Pen]-Phe[4-(2-(SMSB)-aminoethoxy)]-[2-Nal]-[THP]-E-N-[a-MePhe]-NH2; | | |
| 247 | SulfCyanine3-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 248 | SulfCyanine3_dPEG2-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 249 | SulfCyanine3_dPEG3-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 250 | SMSBCO-[Pen]—N—T—[W(7-Me)]-[Lys(Ac)]—[Pen]-Phe[4-(2-aminoethoxy)]-[2-Nal]-[a-MeLys]-[Lys(Ac)]—N-[a-MePhe]-NH2; | | |
| 251 | Ac-[(D)Arg]-[Pen]—N—T—[W(7-Me)]-[Lys(Ac)]—[Pen]-Phe[4-(2-aminoethoxy)]-[2-Nal]-[THP]-E-N-[Phe(3-OH)]—NH2; | | |
| 252 | SMSBCO-[(D)Arg]-[Pen]—N—T—[W(7-Me)]-[Lys(Ac)]—[Pen]-Phe[4-(2-aminoethoxy)]-[2-Nal]-[THP]-E-N-[a-MePhe]-NH2; | | |
| 253 | Ac—[Pen]—N—T—[W(7-Me)]-[Lys(Ac)]—[Pen]-Phe[4-(2-acetylaminoethoxy)]-[2-Nal]-[a-MeLys]-[Lys(Ac)]—N-[THP]-NH2; | | |
| 254 | Ac—[Pen]—N—T—[W(7-Me)]-Phe_4NH2_Ac-[Pen]-Phe[4-(2-aminoethoxy)]_Ac-[2-Nal]-[a-MeLys]-[Lys(Ac)]—N-[THP]-NH2; | | |
| 255 | Ac—[Pen]—N—T—[W(7-Me)]-[Lys(Ac)]—[Pen]-[(R)bMePhe]-[2-Nal]-[a-MeLys]-[Lys(Ac)]—N-[THP]-NH2; | | |
| 256 | Ac-[(D)Arg]-[Pen]—N—T—[W(7-Me)]-[Lys(Ac)]—[Pen]-[(R)bMePhe]-[2-Nal]-[THP]-E-N-[THP]-NH2; | | |
| 257 | Ac-[(D)Arg]-[Pen]—N—T—[W(5-Me)]-[Lys(Ac)]—[Pen]-Phe[4-(2-aminoethoxy)]-[2-Nal]-[THP]-E-N-[a-MePhe]-NH2; | | |
| 301 | MeCO-r-Abu-Q-T-W-Q-C-AEF-2Nal-Achx-aMeE-N—F-AIB-aMeK—CONH2 | | 24 |
| 302 | MeCO—Pen—N—T—7MeW-Cit-Pen-AEF-2Nal-aMeK—K(Ac)—N-Aib-CONH2 | | 7 |

TABLE E1-continued

IC$_{50}$s of Illustrative Peptides of present invention*

| SEQ ID No./ Compound No. | Sequence | pStat3 HTRF (nM) | PBMC pSTAT3 IC50 (nM) |
|---|---|---|---|
| 303 | MeCO-r-Pen—N—T—7MeW—K(Ac)—Pen-AEF-2Nal-4diFAchx-E-N—THP--CONH2 | | 1.3 |
| 304 | NH2--Pen—N—T—7MeW—K(Ac)—Pen-AEF(Boc)-2Nal-aMeK(Boc)—K(Ac)—N-aMePhe-CONH2 | | 28 |
| 305 | NH2-r-Pen—N—T—7MeW—K(Ac)—Pen-AEF(Boc)-2Nal-THP-E-N-aMePhe-CONH2 | | 17 |
| 306 | MeCO-r-Pen—N—T—7MeW-Paf(Ac)—Pen-AEF-2Nal-Acpx-E-N—THP---CONH2 | | 9.6 |
| 307 | EtCO-r-Pen-Q-T-W-Q-Pen-AEF-bMe2Nal(2S,3R)-THP-E-N—THP---CONH2 | | 52 |
| 308 | MeCO-r-Pen—N—T—7MeW—K(Ac)—Pen-AEF(Ac)-2Nal-Acpx-E-N—THP-CONH2 | | 8 |
| 309 | MeCO-r-Pen—N—T—7MeW—K(Ac)—Pen-AEF-2Nal-Acpx-E-N—H-paf-CONH2 | | 8 |
| 310 | MeCO-r-C—N—T—7MeW—K(Ac)- aMeC-AEF-2Nal-Acpx-E-N—THP-CONH2 | | 9.9 |
| 311 | MeCO—Pen—N—T—7MeTrp-K(Ac)—Pen-4PipPhe-2Nal-aMeK—K(Ac)—N-aMePhe---CONH2 | | 290 |
| 312 | MeCO—Pen—N—T—7MeTrp-K(Ac)—Pen-AEF-2Nal-aMeK-K(Ac)—N-bMePhe(S,R)—CONH2 | | 90 |
| 313 | MeCO-r-Pen—N—T—7MeTrp-K(Ac)—Pen-AEF-2Nal-THP-E-N-bMePhe(S,R)----CONH2 | | 21 |
| 314 | MeCO-r-Pen—N—T—7MeTrp-K(Ac)—Pen-AEF(BH)-2Nal-THP-E-N-aMePhe---CONH2 | | 75 |
| 315 | MeCO-r-Pen—N—T—7MeW—K(Ac)—Pen-AEF-2Nal-Acpx-E-N—H-4AmDPhe---CONH2 | | 2 |
| 316 | MeCO-r-Pen—N—T—7MeW—K(Ac)—Pen-AEF-2Nal-Acpx-E-N—H-4AcDPhe---CONH2 | | 2.1 |
| 317 | MeCO—Pen—N—T—7MeW—K(Ac)—Pen-AEF-2Nal-Acpx-E-N—THP---CONH2 | | 13 |
| 318 | MeCO-r-Pen—N—T—7MeW—K(Ac)—Pen-AEF-6OMe2Nal-THP-E-N-aMePhe---CONH2 | | 0 |
| 319 | MeCO—Pen—N—T—7MeW—K(Ac)—Pen-AEF(Me)2-2Nal-aMeK—K(Ac)—N—THP--CONH2 | | 0 |
| 320 | MeCO—Pen—N—T—7MeW—K(Ac)—Pen-AEF-6amido2Nal-aMeK—K(Ac)—N-aMePhe---CONH2 | | 0 |
| 321 | MeCO-r-Pen—N—T—7MeW—K(Ac)—Pen-AEF-6amido2Nal-THP-E-N-aMePhe---CONH2 | | 0 |

0—N/A
*wherein Pen/Cys and Pen/Cys form a disulfide bond or Abu and Pen/Cys form a thioether bond.

Example 3

NK Cell Based Assay

Natural killer (NK) cells, purified from human peripheral blood of healthy donors by negative selection (Miltenyi Biotech, Cat #130-092-657), were cultured in complete media (RPMI 1640 containing 10% FBS, L-glutamine and penicillin-streptomycin) in the presence of IL-2 (RnD, Cat #202-IL-010/CF) at 25 ng/mL. After 7 days, cells were centrifuged, and resuspended in complete media at 1E6 cells/mL. Recombinant IL-23 at predetermined EC$_{50}$ to EC$_{75}$ and IL-18 (RnD, Cat #B003-5) at 10 ng/mL were mixed with varying concentrations of peptides, and added to NK cells seeded at 1E5 cells per well. After 20 to 24 hours, IFNγ in the supernatant was quantified using Quantikine ELISA (RnD, Cat #DIF50). $IC_{50}$ values determined from these data are shown in Table E2. Where not shown, data was not yet determined. Where not shown (N/A), data was not yet determined.

TABLE E2

$IC_{50}$ of Illustrative Peptide Inhibitors in Primary Cell Line (NK Cell Assay)

| SEQ ID No./ Compound No. | NK Cell Assay (nM) |
| --- | --- |
| 1 | 2.89 |
| 2 | 4.45 |
| 3 | 20.1 |
| 4 | 32.1 |
| 5 | 10.3 |
| 6 | 16.8 |
| 7 | 12.6 |
| 8 | 72.3 |
| 9 | 11.6 |
| 10 | 8.29 |
| 64 | 5.44 |
| 65 | 6.03 |

TABLE E2-continued $IC_{50}$ of Illustrative Peptide Inhibitors in Primary Cell Line (NK Cell Assay)

| SEQ ID No./ Compound No. | NK Cell Assay (nM) |
| --- | --- |
| 66 | 13.1 |
| 75 | 2.69 |
| 76 | 4.01 |
| 77 | 2.33 |
| 92 | 1.46 |
| 111 | 6.51 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A peptide that is:

(SEQ ID NO: 3)
[Propionic_acid]-[(D)Arg]-[Pen]-Q-T-W-Q-[Pen]-Phe[4-(2-aminoethoxy)]-[2-Nal]-[THP]-E-N-[alpha-MePhe]-NH$_2$;

(SEQ ID NO: 4)
[Propionic_acid]-[(D)Arg]-[Pen]-Q-T-W-Q-[Pen]-[Phe(4-OMe)]-[2-Nal]-[THP]-E-N-[THP]-NH$_2$;

(SEQ ID NO: 5)
[3,3,3-Trifluoropropionic acid]-[(D)Arg]-[Pen]-Q-T-W-Q-[Pen]-Phe[4-(2-aminoethoxy)]-[2-Nal]-[THP]-E-N-[THP]-NH$_2$;

SEQ ID NO: 6)
[Propionic_acid]-[(D)Arg]-[Pen]-Q-T-W-Q-[Pen]-Phe[4-(2-aminoethoxy)]-[2-Nal]-[THP]-[Lys(COCF$_3$)]-N-[THP]-NH$_2$;

(SEQ ID NO: 7)
[Propionic_acid]-[(D)Arg]-[Pen]-Q-T-W-Q-[Pen]-Phe[4-(2-aminoethoxy)]-[2-Nal]-[THP]-[Lys(COtBu)]-N-[THP]-NH$_2$;

(SEQ ID NO: 8)
[Propionic_acid]-[(D)Arg]-[Pen]-Q-T-W-Q-[Pen]-Phe[4-(2-aminoethoxy)]-[2-Nal]-[THP]-E-N-[N-Me-beta-Ala]-NH$_2$;

(SEQ ID NO: 9)
[Pentanoic acid]-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 10)
[Propionic_acid]-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 13)
Ac-[(D)Arg]-[Pen]-Q-T-W-Q-[Pen]-Phe[4-(2-aminoethoxy)]-[2-Nal]-[THP]-E-N-[THP]-NH$_2$;

(SEQ ID NO: 14)
Ac-[(D)Arg]-[Pen]-Q-T-W-Q-[Pen]-Phe[4-(2-aminoethoxy)]-[2-Nal]-[THP]-E-N-[N-Me-beta-Ala]-NH$_2$;

(SEQ ID NO: 15)
pr-[(D)Arg]-[Pen]-Q-T-W-Q-[Pen]-Phe[4-(2-aminoethoxy)]-[2-Nal]-[THP]-Q-N-[THP]-NH$_2$;

(SEQ ID NO: 18)
[(D)Arg]-[Pen]-Q-T-W-Q-[Pen]-[Phe(4-OMe)]-[2-Nal]-[THP]-E-N-[THP]-NH$_2$;

(SEQ ID NO: 26)
pr-[(D)Arg]-[Pen]-Q-T-W-Q-[Pen]-Phe[4-(2-aminoethoxy)]-[2-Nal]-[THP]-[Lys(COtBu)]-N-F-NH$_2$;

(SEQ ID NO: 33)
pr-[(D)Arg]-[Pen]-Q-T-W-Q-[Pen]-Phe[4-(2-aminoethoxy)]-[2-Nal]-[THP]-[Lys(CO2Allyl)]-N-F-NH$_2$;

(SEQ ID NO: 51)
Ac-[(D)Arg]-[Pen]-Q-T-W-Q-[Pen]-Phe[4-(2-aminoethoxy)]-[2-Nal]-[THP]-[Lys(COcPr)]-N-[THP]-NH$_2$;

-continued

Ac-[(D)Arg]-[Pen]-Q-T-W-Q-[Pen]-Phe[4-(2-aminoethoxy)]-[2-Nal]-[THP]-[Lys(COPr)]-N-[THP]-NH$_2$; (SEQ ID NO: 52)

Ac-[(D)Arg]-[Pen]-Q-T-W-Q-[Pen]-Phe[4-(2-aminoethoxy)]-[2-Nal]-[THP]-[Lys(Ac)]-N-F-NH$_2$; (SEQ ID NO: 53)

Ac-[(D)Arg]-[Pen]-Q-T-W-Q-[Pen]-Phe[4-(2-aminoethoxy)]-[2-Nal]-[THP]-[Lys(COEt)]-N-F-NH$_2$; (SEQ ID NO: 54)

Ac-[(D)Arg]-[Pen]-Q-T-W-Q-[Pen]-Phe[4-(2-aminoethoxy)]-[2-Nal]-[THP]-[Lys(COcPr)]-N-F-NH$_2$; (SEQ ID NO: 55)

Ac-[(D)Arg]-[Pen]-Q-T-W-Q-[Pen]-Phe[4-(2-aminoethoxy)]-[2-Nal]-[THP]-[Lys(Ac)]-N-[THP]-NH$_2$; (SEQ ID NO: 56)

Ac-[(D)Arg]-[Pen]-Q-T-W-Q-[Pen]-Phe[4-(2-aminoethoxy)]-[2-Nal]-[THP]-[Lys(COEt)]-N-[THP]-NH$_2$; (SEQ ID NO: 57)

Ac-[(D)Arg]-[Pen]-Q-T-W-Q-[Pen]-Phe[4-(2-aminoethoxy)]-[2-Nal]-[THP]-[Lys(COPr)]-N-F-NH$_2$; (SEQ ID NO: 58)

Ac-[(D)Arg]-[Pen]-Q-T-W-Q-[Pen]-Phe[4-(2-aminoethoxy)]-[2-Nal]-[THP]-[Lys(COPent)]-N-F-NH$_2$; (SEQ ID NO 59)

Ac-[(D)Arg]-[Pen]-Q-T-W-Q-[Pen]-Phe[4-(2-aminoethoxy)]-[2-Nal]-[THP]-[Lys(COCF$_3$)-N-F-NH$_2$; (SEQ ID NO: 60)

Ac-[(D)Arg]-[Pen]-Q-T-W-Q-[Pen]-Phe[4-(2-aminoethoxy)]-[2-Nal]-[THP]-[Lys(COiPr)]-N-F-NH$_2$; (SEQ ID NO: 61)

Ac-[(D)Arg]-[Pen]-N-T-W-[Lys(Ac)]-[Pen]-Phe[4-(2-aminoethoxy)]-[2-Nal]-[THP]-E-N-[THP]-NH$_2$; (SEQ ID NO: 105)

Ac-[(D)Arg]-[Pen]-N-T-W-[Lys(Ac)]-[Pen]-Phe[4-(2-aminoethoxy)]-[2-Nal]-[THP]-E-N-[alpha-MePhe]-NH$_2$; (SEQ ID NO: 106)

Ac-[(D)Arg]-[Pen]-Q-T-W-Q-[Pen]-Phe[4-(2-aminoethoxy)]-[2-Nal]-[THP]-E-N-[(N-Ph)Asn]-NH$_2$; (SEQ ID NO: 125)

Ac-[(D)Arg]-[Pen]-Q-T-W-Q-[Pen]-Phe[4-(2-aminoethoxy)]-[2-Nal]-[THP]-E-N-[(N-(2-aminophenyl))Asn]-NH$_2$; (SEQ ID NO: 126)

Ac-[(D)Arg]-[Pen]-Q-T-W-Q-[Pen]-Phe[4-(2-aminoethoxy)]-[2-Nal]-[THP]-E-N-[(N-Pip)Asn]-NH$_2$; (SEQ ID NO: 127)

Ac-[(D)Arg]-[Pen]-Q-T-W-Q-[Pen]-Phe[4-(2-aminoethoxy)]-[2-Nal]-[THP]-E-N-[(N-Pyr)Asn]-NH$_2$; (SEQ ID NO: 128)

Ac-[(D)Arg]-[Pen]-Q-T-W-Q-[Pen]-Phe[4-(2-aminoethoxy)]-[2-Nal]-[THP]-E-N-[(N-(4-aminophenyl))Asn]-NH$_2$; (SEQ ID NO: 129)

Ac-[(D)Arg]-[Pen]-Q-T-W-Q-[Pen]-Phe[4-(2-aminoethoxy)]-[2-Nal]-[THP]-E-N-[(N-(3-aminophenyl))Asn]-NH$_2$; (SEQ ID NO: 130)

Ac-[(D)Arg]-[Pen]-Q-T-W-Q-[Pen]-Phe[4-(2-aminoethoxy)]-[2-Nal]-[THP]-E-N-[(N-(4-Pyz))Asn]-NH$_2$; (SEQ ID NO: 131)

Ac-[(D)Arg]-[Pen]-Q-T-W-Q-[Pen]-Phe[4-(2-aminoethoxy)]-[2-Nal]-[THP]-E-N-[(N-(5-indolyl)Asn]-NH$_2$; (SEQ ID NO: 132)

Ac-[(D)Arg]-[Pen]-Q-T-W-Q-[Pen]-Phe[4-(2-aminoethoxy)]-[2-Nal]-[THP]-E-N-[(N-(3-Pyz))Asn]-NH$_2$; (SEQ ID NO: 133)

pr-[(D)Arg]-[Pen]-Q-T-W-Q-[Pen]-Phe[4-(2-aminoethoxy)]-[2-Nal]-THP]-E-N-[THP]-NH$_2$; (SEQ ID NO: 134)

-continued (SEQ ID NO: 135)
pr-[(D)Arg]-[Pen]-Q-T-W-Q-[Pen]-Phe[(alpha-Me)-4-(2-aminoethoxy)]-[2-Nal]-[THP]-E-N-[THP]-NH₂;

(SEQ ID NO: 136)
Ac-[(D)Arg]-[Pen]-Q-T-W-Q-[Pen]-Phe[4-(2-aminoethoxy)]-[2-Nal]-[THP]-E-N-[(N-propylamido)Asn]-NH₂;
or (SEQ ID NO: 137)
Ac-[(D)Arg]-[Pen]-Q-T-W-Q-[Pen]-Phe[4-(2-aminoethoxy)]-[2-Nal]-[THP]-E-N-[(N-(imidazol-2-yl)methyl)Asn]-NH₂;

wherein the peptide is cyclized via a Pen-Pen disulfide bond;
or a pharmaceutically acceptable salt thereof.

2. The peptide of claim 1, wherein said peptide is Ac-[(D)Arg]-[Pen]-N-T-W-[Lys(Ac)]-[Pen]-Phe[4-(2-aminoethoxy)]-[2-Nal]-[THP]-E-N-[THP]—NH₂ (SEQ ID NO:105) or a pharmaceutically acceptable salt thereof.

3. A pharmaceutical composition comprising the peptide or a pharmaceutically acceptable salt thereof of claim 1 and a pharmaceutically acceptable carrier, excipient, or diluent.

4. The pharmaceutical composition of claim 3, wherein said peptide is Ac-[(D)Arg]-[Pen]-N-T-W-[Lys(Ac)]-[Pen]-Phe[4-(2-aminoethoxy)]-[2-Nal]-[THP]-E-N-[THP]—NH₂ (SEQ ID NO:105) or a pharmaceutically acceptable salt thereof.

5. A method for treating an Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, psoriasis, psoriatic arthritis, or graft versus host disease in a subject in need thereof, comprising administering an effective amount of the peptide or a pharmaceutically acceptable salt thereof of claim 1 to the subject.

6. The method of claim 5, wherein the method is for treating an Inflammatory Bowel Disease (IBD).

7. The method of claim 5, wherein the method is for treating ulcerative colitis.

8. The method of claim 5, wherein the method is for treating Crohn's disease.

9. The method of claim 5, wherein the method is for treating psoriasis.

10. The method of claim 5, wherein the method is for treating psoriatic arthritis.

* * * * *

SEQUENCE LISTING

```
<160> NUMBER OF SEQ ID NOS: 353

<210> SEQ ID NO 1
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 3-Quin
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 1
```

```
Xaa Asn Thr Xaa Lys Xaa Phe Xaa Lys Lys Asn Leu
 1               5                  10

<210> SEQ ID NO 2
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 2

Arg Xaa Gln Thr Trp Gln Xaa Phe Xaa Xaa Glu Asn Phe
 1               5                  10

<210> SEQ ID NO 3
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
```

```
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Phe is a-MePhe

<400> SEQUENCE: 3

Xaa Arg Xaa Gln Thr Trp Gln Xaa Phe Xaa Xaa Glu Asn Phe
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe(4-OMe)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 4

Arg Xaa Gln Thr Trp Gln Xaa Phe Xaa Xaa Glu Asn Xaa
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is
      3,3,3-Trifluoropropionic acid
<220> FEATURE:
<221> NAME/KEY: MISC_FEATURE
<222> LOCATION: (1)..(1)
<223> OTHER INFORMATION: Arg is (D)Arg
```

```
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 5

Arg Xaa Gln Thr Trp Gln Xaa Phe Xaa Xaa Glu Asn Xaa
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-Trifluoroacetyl-Lysine
<220> FEATURE:
<221> NAME/KEY: MISC_FEATURE
<222> LOCATION: (13)..(13)
<223> OTHER INFORMATION: Xaa is THP

<400> SEQUENCE: 6

Arg Xaa Gln Thr Trp Gln Xaa Phe Xaa Xaa Lys Asn Xaa
1               5                   10
```

```
<210> SEQ ID NO 7
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-Epsilon-[C(O)-t-Bu]-L-Lysine (Lys
<220> FEATURE:
<221> NAME/KEY: MISC_FEATURE
<222> LOCATION: (13)..(13)
<223> OTHER INFORMATION: Xaa is THP

<400> SEQUENCE: 7

Arg Xaa Gln Thr Trp Gln Xaa Phe Xaa Xaa Lys Asn Xaa
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
```

```
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Ala is N-Me-bAla

<400> SEQUENCE: 8

Arg Xaa Gln Thr Trp Gln Xaa Phe Xaa Xaa Glu Asn Ala
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 9

Arg Xaa Gln Thr Trp Gln Xaa Phe Xaa Xaa Glu Asn Xaa
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Propionic acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
```

```
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 10

Arg Xaa Gln Thr Trp Gln Xaa Phe Xaa Xaa Glu Asn Xaa
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is acetyl acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (5)..(5)
<223> OTHER INFORMATION: Xaa is W(7-Ph)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Lys is a-MeLys
<220> FEATURE:
<221> NAME/KEY: MISC_FEATURE
<222> LOCATION: (11)..(11)
<223> OTHER INFORMATION: Lys is Lys(Ac)
<220> FEATURE:
<221> NAME/KEY: MISC_FEATURE
<222> LOCATION: (13)..(13)
<223> OTHER INFORMATION: Phe is a-MePhe

<400> SEQUENCE: 11

Arg Xaa Gln Thr Xaa Lys Cys Phe Xaa Lys Lys Asn Phe
1               5                   10

<210> SEQ ID NO 12
<211> LENGTH: 13
<212> TYPE: PRT
<213> ORGANISM: Artificial sequence
<220> FEATURE:
```

```
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

<400> SEQUENCE: 12

Arg Xaa Gln Thr Trp Gln Cys Phe Xaa Xaa Glu Asn Asn
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 13

Arg Xaa Gln Thr Trp Gln Xaa Phe Xaa Xaa Glu Asn Xaa
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
```

```
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

<400> SEQUENCE: 14

Arg Xaa Gln Thr Trp Gln Xaa Phe Xaa Xaa Glu Asn Ala
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 15

Arg Xaa Gln Thr Trp Gln Xaa Phe Xaa Xaa Gln Asn Xaa
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Arg is (D)Arg
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa isTHP
<220> FEATURE:
<221> NAME/KEY: MISC_FEATURE
<222> LOCATION: (11)..(11)
<223> OTHER INFORMATION: Xaa is Orn(COMe)
<220> FEATURE:
<221> NAME/KEY: MISC_FEATURE
<222> LOCATION: (13)..(13)
<223> OTHER INFORMATION: Xaa is THP

<400> SEQUENCE: 16

Arg Cys Gln Thr Trp Gln Ala Phe Xaa Xaa Xaa Asn Xaa
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

<400> SEQUENCE: 17

Arg Xaa Gln Thr Trp Gln Cys Phe Xaa Xaa Glu Asn Phe
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
```

```
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe(4-OMe)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 18

Arg Xaa Gln Thr Trp Gln Xaa Phe Xaa Xaa Glu Asn Xaa
 1               5                  10

<210> SEQ ID NO 19
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 4-Hydroxy-L-Proline
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 19

Arg Xaa Gln Xaa Trp Gln Xaa Phe Xaa Xaa Glu Asn Xaa
 1               5                  10

<210> SEQ ID NO 20
<211> LENGTH: 13
<212> TYPE: PRT
<213> ORGANISM: Artificial sequence
<220> FEATURE:
<223> OTHER INFORMATION: Synthetic construct
<220> FEATURE:
```

```
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 20

Arg Cys Gln Thr Trp Gln Xaa Phe Xaa Xaa Glu Asn Xaa
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe(4-OMe)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 21

Arg Xaa Gln Thr Trp Gln Cys Phe Xaa Xaa Glu Asn Xaa
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic construct
```

```
-continued

<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe(4-OMe)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 22

Arg Xaa Gln Thr Trp Gln Cys Phe Xaa Xaa Glu Asn Xaa
1               5                   10

<210> SEQ ID NO 23
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 23

Arg Cys Gln Thr Trp Gln Xaa Phe Xaa Xaa Glu Asn Phe
1               5                   10

<210> SEQ ID NO 24
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

```
<223> OTHER INFORMATION: N terminal modification is N3_Acid
      (N3-CH2-COOH)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 24

Arg Xaa Gln Thr Trp Gln Cys Phe Xaa Xaa Glu Asn Xaa
1               5                   10

<210> SEQ ID NO 25
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FPrpTriazoleMe Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe(4-OMe)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 25

Arg Xaa Gln Thr Trp Gln Cys Phe Xaa Xaa Glu Asn Xaa
1               5                   10

<210> SEQ ID NO 26
<211> LENGTH: 13
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-Epsilon-[C(O)-t-Bu]-L-Lysine

<400> SEQUENCE: 26

Arg Xaa Gln Thr Trp Gln Xaa Phe Xaa Xaa Lys Asn Phe
1               5                  10

<210> SEQ ID NO 27
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu

<400> SEQUENCE: 27

Arg Xaa Gln Thr Trp Gln Cys Phe Xaa Xaa Glu Asn Phe
1               5                  10

<210> SEQ ID NO 28
<211> LENGTH: 14
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (14)..(14)
<223> OTHER INFORMATION: Xaa is Aib

<400> SEQUENCE: 28

Arg Xaa Gln Thr Trp Gln Cys Phe Xaa Xaa Glu Asn Phe Xaa
1               5                   10

<210> SEQ ID NO 29
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is a-MePhe

<400> SEQUENCE: 29

Arg Xaa Gln Thr Trp Gln Cys Phe Xaa Xaa Glu Asn Phe
1               5                   10

<210> SEQ ID NO 30
```

```
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 30

Arg Xaa Gln Thr Trp Gln Cys Phe Xaa Xaa Gln Asn Phe
1               5                   10

<210> SEQ ID NO 31
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Trp is ameTryptophan

<400> SEQUENCE: 31

Arg Xaa Gln Thr Trp Gln Cys Phe Xaa Xaa Glu Asn Trp
1               5                   10

<210> SEQ ID NO 32
<211> LENGTH: 13
```

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MePhe
<220> FEATURE:
<221> NAME/KEY: MISC_FEATURE
<222> LOCATION: (13)..(13)
<223> OTHER INFORMATION: Xaa is 1[2-Nal]

<400> SEQUENCE: 32

Arg Xaa Gln Thr Trp Gln Cys Phe Xaa Xaa Glu Asn Xaa
1               5                   10

<210> SEQ ID NO 33
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-(C(O)2-Allyl)-Lysine

<400> SEQUENCE: 33
```

-continued

```
Arg Xaa Gln Thr Trp Gln Xaa Phe Xaa Xaa Lys Asn Phe
1               5                   10

<210> SEQ ID NO 34
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlue
<220> FEATURE:
<221> NAME/KEY: MISC_FEATURE
<222> LOCATION: (13)..(13)
<223> OTHER INFORMATION: Phe is Phe(4-CONH2)

<400> SEQUENCE: 34

Arg Xaa Gln Thr Trp Gln Cys Phe Xaa Xaa Glu Asn Phe
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Xaa is 2-Nal
```

<400> SEQUENCE: 35

Arg Xaa Gln Thr Trp Gln Cys Phe Xaa Xaa Glu Asn Xaa
1               5                   10

<210> SEQ ID NO 36
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is aMe(4-F)Phe

<400> SEQUENCE: 36

Arg Xaa Gln Thr Trp Gln Cys Phe Xaa Xaa Glu Asn Phe
1               5                   10

<210> SEQ ID NO 37
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:

```
<221> NAME/KEY: MISC_FEATURE
<222> LOCATION: (13)..(13)
<223> OTHER INFORMATION: Xaa is THP

<400> SEQUENCE: 37

Arg Xaa Gln Thr Trp Gln Cys Phe Xaa Xaa Glu Asn Xaa
1               5                   10

<210> SEQ ID NO 38
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Xaa is THP

<400> SEQUENCE: 38

Arg Xaa Gln Thr Trp Gln Cys Phe Xaa Xaa Glu Asn Xaa
1               5                   10

<210> SEQ ID NO 39
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
```

```
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is a-MePhe

<400> SEQUENCE: 39

Arg Xaa Gln Thr Trp Gln Xaa Phe Xaa Xaa Glu Asn Xaa
1               5                   10

<210> SEQ ID NO 40
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (7)..(7)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is a-MePhe

<400> SEQUENCE: 40

Arg Cys Gln Thr Trp Gln Xaa Phe Xaa Xaa Glu Asn Phe
1               5                   10

<210> SEQ ID NO 41
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe(3,4-diOMe)
<220> FEATURE:
<221> NAME/KEY: MISC_FEATURE
<222> LOCATION: (9)..(9)
```

```
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is a-MePhe

<400> SEQUENCE: 41

Arg Xaa Gln Thr Trp Gln Cys Phe Xaa Xaa Glu Asn Phe
1               5                   10

<210> SEQ ID NO 42
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 42

Arg Xaa Gln Thr Trp Gln Cys Phe Xaa Xaa Glu Asn Xaa
1               5                   10

<210> SEQ ID NO 43
<211> LENGTH: 15
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
```

```
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (14)..(14)
<223> OTHER INFORMATION: Xaa is Aib
<220> FEATURE:
<221> NAME/KEY: MISC_FEATURE
<222> LOCATION: (15)..(15)
<223> OTHER INFORMATION: Lys is a-MeLys

<400> SEQUENCE: 43

Arg Xaa Gln Thr Trp Gln Cys Phe Xaa Xaa Glu Asn Phe Xaa Lys
1               5                   10                  15

<210> SEQ ID NO 44
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Tyr is aMeTyr

<400> SEQUENCE: 44

Arg Xaa Gln Thr Trp Gln Cys Phe Xaa Xaa Glu Asn Tyr
1               5                   10

<210> SEQ ID NO 45
<211> LENGTH: 15
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
```

```
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclohexanecarboxylic acid
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (14)..(14)
<223> OTHER INFORMATION: Xaa is Aib
<220> FEATURE:
<221> NAME/KEY: MISC_FEATURE
<222> LOCATION: (15)..(15)
<223> OTHER INFORMATION: Lys is a-MeLys

<400> SEQUENCE: 45

Arg Xaa Gln Thr Trp Gln Cys Phe Xaa Xaa Glu Asn Phe Xaa Lys
1               5                   10                  15

<210> SEQ ID NO 46
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is Phe(3,5-diF)

<400> SEQUENCE: 46

Arg Xaa Gln Thr Trp Gln Cys Phe Xaa Xaa Glu Asn Phe
1               5                   10

<210> SEQ ID NO 47
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-(Boc)aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 47

Arg Xaa Gln Thr Trp Gln Cys Phe Xaa Xaa Glu Asn Xaa
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (7)..(7)
<223> OTHER INFORMATION: Cys is a-MeCys
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

<400> SEQUENCE: 48

Arg Xaa Gln Thr Trp Gln Cys Phe Xaa Xaa Glu Asn Phe
1               5                   10

<210> SEQ ID NO 49
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
```

```
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Xaa is Aib

<400> SEQUENCE: 49

Arg Xaa Gln Thr Trp Gln Cys Phe Xaa Xaa Xaa Asn Phe
1               5                   10

<210> SEQ ID NO 50
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Xaa is 1-aminocyclohexanecarboxylic acid
<220> FEATURE:
<221> NAME/KEY: MISC_FEATURE
<222> LOCATION: (13)..(13)
<223> OTHER INFORMATION: Phe is a-MePhe

<400> SEQUENCE: 50

Arg Xaa Gln Thr Trp Gln Cys Phe Xaa Xaa Xaa Asn Phe
1               5                   10

<210> SEQ ID NO 51
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
```

```
<221> NAME/KEY: MISC_FEATURE
<222> LOCATION: (2)..(2)
<223> OTHER INFORMATION: Xaa is Abu
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(CO-cyclopropyl)
<220> FEATURE:
<221> NAME/KEY: MISC_FEATURE
<222> LOCATION: (13)..(13)
<223> OTHER INFORMATION: Xaa is THP

<400> SEQUENCE: 51

Arg Xaa Gln Thr Trp Gln Xaa Phe Xaa Xaa Lys Asn Xaa
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(CO-cyclopropyl)
<220> FEATURE:
<221> NAME/KEY: MISC_FEATURE
<222> LOCATION: (13)..(13)
<223> OTHER INFORMATION: Xaa is THP

<400> SEQUENCE: 52

Arg Xaa Gln Thr Trp Gln Xaa Phe Xaa Xaa Lys Asn Xaa
1               5                   10
```

```
<210> SEQ ID NO 53
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(Ac)

<400> SEQUENCE: 53

Arg Xaa Gln Thr Trp Gln Xaa Phe Xaa Xaa Lys Asn Phe
1               5                   10

<210> SEQ ID NO 54
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-(C(O)-Et)-Lysine

<400> SEQUENCE: 54

Arg Xaa Gln Thr Trp Gln Xaa Phe Xaa Xaa Lys Asn Phe
```

```
1               5                   10
```

<210> SEQ ID NO 55
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(CO-cyclopropyl)

<400> SEQUENCE: 55

```
Arg Xaa Gln Thr Trp Gln Xaa Phe Xaa Xaa Lys Asn Phe
1               5                   10
```

<210> SEQ ID NO 56
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(Ac)
<220> FEATURE:

```
<221> NAME/KEY: MISC_FEATURE
<222> LOCATION: (13)..(13)
<223> OTHER INFORMATION: Xaa is THP

<400> SEQUENCE: 56

Arg Xaa Gln Thr Trp Gln Xaa Phe Xaa Xaa Lys Asn Xaa
1               5                   10

<210> SEQ ID NO 57
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-(C(O)-Et)-Lysine
<220> FEATURE:
<221> NAME/KEY: MISC_FEATURE
<222> LOCATION: (13)..(13)
<223> OTHER INFORMATION: Xaa is THP

<400> SEQUENCE: 57

Arg Xaa Gln Thr Trp Gln Xaa Phe Xaa Xaa Lys Asn Xaa
1               5                   10

<210> SEQ ID NO 58
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is he[4-(2-aminoethoxy)]
<220> FEATURE:
<221> NAME/KEY: MISC_FEATURE
```

-continued

```
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-(C(O)-n-Pr)-Lysine

<400> SEQUENCE: 58

Arg Xaa Gln Thr Trp Gln Xaa Phe Xaa Xaa Lys Asn Phe
 1               5                  10

<210> SEQ ID NO 59
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(CO-pentyl)

<400> SEQUENCE: 59

Arg Xaa Gln Thr Trp Gln Xaa Phe Xaa Xaa Lys Asn Phe
 1               5                  10

<210> SEQ ID NO 60
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
```

```
<223> OTHER INFORMATION: Xaa is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

<400> SEQUENCE: 60

Arg Xaa Gln Thr Trp Gln Xaa Phe Xaa Xaa Lys Asn Phe
1               5                   10

<210> SEQ ID NO 61
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is N-(C(O)-i-Pr)-Lysine

<400> SEQUENCE: 61

Arg Xaa Gln Thr Trp Gln Xaa Phe Xaa Xaa Lys Asn Phe
1               5                   10

<210> SEQ ID NO 62
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is [W(7-Ph)]
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
```

```
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 3-Quin
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (12)..(12)
<223> OTHER INFORMATION: Xaa is Aib

<400> SEQUENCE: 62

Xaa Asn Thr Xaa Lys Xaa Phe Xaa Xaa Glu Asn Xaa
1               5                   10

<210> SEQ ID NO 63
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Ph)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 3-Quin
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is Aib

<400> SEQUENCE: 63

Xaa Asn Thr Xaa Lys Xaa Phe Xaa Lys Lys Asn Xaa
1               5                   10

<210> SEQ ID NO 64
<211> LENGTH: 12
<212> TYPE: PRT
<213> ORGANISM: Artificial sequence
<220> FEATURE:
<223> OTHER INFORMATION: Synthetic construct
<220> FEATURE:
```

```
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Lys is (D)Lys

<400> SEQUENCE: 64

Xaa Gln Thr Xaa Lys Cys Phe Xaa Lys Lys Asn Lys
1               5                   10

<210> SEQ ID NO 65
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 65
```

Xaa Gln Thr Xaa Lys Cys Phe Xaa Lys Lys Asn Leu
1               5                   10

<210> SEQ ID NO 66
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 66

Xaa Gln Thr Xaa Lys Cys Phe Xaa Lys Lys Asn Phe
1               5                   10

<210> SEQ ID NO 67
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys

```
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 67

Xaa Gln Thr Xaa Lys Cys Phe Xaa Lys Lys Asn Phe
1               5                   10

<210> SEQ ID NO 68
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu
<220> FEATURE:
<221> NAME/KEY: MISC_FEATURE
<222> LOCATION: (13)..(13)
<223> OTHER INFORMATION: Phe is a-MePhe

<400> SEQUENCE: 68

Xaa Asn Thr Xaa Lys Xaa Phe Xaa Lys Lys Asn Leu Phe
1               5                   10

<210> SEQ ID NO 69
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
```

```
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu
<220> FEATURE:
<221> NAME/KEY: MISC_FEATURE
<222> LOCATION: (13)..(13)
<223> OTHER INFORMATION: Phe is (D)a-MePhe

<400> SEQUENCE: 69

Xaa Asn Thr Xaa Lys Xaa Phe Xaa Lys Lys Asn Leu Phe
1               5                   10

<210> SEQ ID NO 70
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
```

```
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is 2-aminoisobutyric acid
<220> FEATURE:
<221> NAME/KEY: MISC_FEATURE
<222> LOCATION: (13)..(13)
<223> OTHER INFORMATION: Xaa is 6-aminohexanoic acid

<400> SEQUENCE: 70

Xaa Asn Thr Xaa Lys Xaa Phe Xaa Lys Lys Asn Xaa Xaa
1               5                   10

<210> SEQ ID NO 71
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is 2-aminoisobutyric acid
<220> FEATURE:
<221> NAME/KEY: MISC_FEATURE
<222> LOCATION: (13)..(13)
<223> OTHER INFORMATION: Phe is bhPhe

<400> SEQUENCE: 71

Xaa Asn Thr Xaa Lys Xaa Phe Xaa Lys Lys Asn Xaa Phe
1               5                   10

<210> SEQ ID NO 72
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
```

```
<220> FEATURE:
<221> NAME/KEY: MISC_FEATURE
<222> LOCATION: (3)..(3)
<223> OTHER INFORMATION: Xaa is (D)Dap
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 72

Xaa Asn Xaa Xaa Lys Xaa Phe Xaa Lys Lys Asn Leu
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (3)..(3)
<223> OTHER INFORMATION: Lys is (D)Lys
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
```

-continued

```
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 73

Xaa Asn Lys Xaa Lys Xaa Phe Xaa Lys Lys Asn Leu
1               5                   10

<210> SEQ ID NO 74
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (3)..(3)
<223> OTHER INFORMATION: Asp is (D)Asp
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 74

Xaa Asn Asp Xaa Lys Xaa Phe Xaa Lys Lys Asn Leu
1               5                   10

<210> SEQ ID NO 75
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
```

```
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 75

Xaa Asn Thr Xaa Lys Xaa Phe Xaa Lys Lys Asn Xaa
1               5                   10

<210> SEQ ID NO 76
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
```

```
<221> NAME/KEY: MISC_FEATURE
<222> LOCATION: (12)..(12)
<223> OTHER INFORMATION: Phe is a-MePhe

<400> SEQUENCE: 76

Xaa Asn Thr Xaa Lys Xaa Phe Xaa Lys Lys Asn Phe
1               5                   10

<210> SEQ ID NO 77
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)]
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 77

Arg Xaa Asn Thr Xaa Lys Xaa Phe Xaa Xaa Glu Asn Phe
1               5                   10

<210> SEQ ID NO 78
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
```

```
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is Phe(3,4-diOMe)

<400> SEQUENCE: 78

Arg Xaa Gln Thr Trp Gln Cys Phe Xaa Xaa Glu Asn Phe
1               5                   10

<210> SEQ ID NO 79
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Phe is (D)Phe(3,4-diOMe

<400> SEQUENCE: 79

Arg Xaa Gln Thr Trp Gln Cys Phe Xaa Xaa Glu Asn Phe
1               5                   10

<210> SEQ ID NO 80
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
```

```
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is aMe(2-Nal)

<400> SEQUENCE: 80

Arg Xaa Gln Thr Trp Gln Cys Phe Xaa Xaa Glu Asn Xaa
1               5                   10

<210> SEQ ID NO 81
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Xaa is W(5-F)]

<400> SEQUENCE: 81

Arg Xaa Gln Thr Trp Gln Cys Phe Xaa Xaa Glu Asn Xaa
1               5                   10

<210> SEQ ID NO 82
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
```

```
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 82

Xaa Gln Thr Trp Lys Xaa Phe Xaa Lys Lys Asn Phe
1               5                   10

<210> SEQ ID NO 83
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (7)..(7)
<223> OTHER INFORMATION: Cys is a-MeCys
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 83

Arg Xaa Gln Thr Trp Gln Cys Phe Xaa Xaa Glu Asn Phe
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Xaa is Pen
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 84

Xaa Gln Thr Trp Lys Xaa Phe Xaa Lys Lys Asn Xaa
1               5                   10

<210> SEQ ID NO 85
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 85

Arg Xaa Gln Thr Trp Gln Cys Phe Xaa Xaa Glu Asn Phe
1               5                   10

<210> SEQ ID NO 86
<211> LENGTH: 13
```

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is aMe(2-Nal)
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 86

Arg Xaa Gln Thr Trp Gln Cys Phe Xaa Xaa Glu Asn Phe
1               5                   10

<210> SEQ ID NO 87
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 87
```

Xaa Asn Thr Xaa Gln Xaa Phe Xaa Lys Lys Asn Xaa
1               5                   10

<210> SEQ ID NO 88
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 88

Arg Xaa Asn Thr Trp Lys Xaa Phe Xaa Xaa Glu Asn Xaa
1               5                   10

<210> SEQ ID NO 89
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys

```
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 89

Xaa Asn Thr Xaa Gln Xaa Phe Xaa Lys Lys Asn Phe
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 90

Arg Xaa Asn Thr Xaa Gln Xaa Phe Xaa Xaa Glu Asn Xaa
1               5                   10

<210> SEQ ID NO 91
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
```

```
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 91

Arg Xaa Asn Thr Xaa Gln Xaa Phe Xaa Xaa Glu Asn Phe
1               5                   10

<210> SEQ ID NO 92
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 92

Arg Xaa Asn Thr Xaa Lys Xaa Phe Xaa Xaa Glu Asn Xaa
1               5                   10

<210> SEQ ID NO 93
<211> LENGTH: 13
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Phe is a-MePhe

<400> SEQUENCE: 93

Arg Xaa Asn Thr Xaa Gln Xaa Phe Xaa Xaa Glu Asn Phe
1               5                   10

<210> SEQ ID NO 94
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
```

```
<220> FEATURE:
<221> NAME/KEY: MISC_FEATURE
<222> LOCATION: (13)..(13)
<223> OTHER INFORMATION: Phe is a-MePhe

<400> SEQUENCE: 94

Arg Xaa Asn Thr Xaa Lys Xaa Phe Xaa Xaa Glu Asn Phe
1               5                   10

<210> SEQ ID NO 95
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Lys is THP

<400> SEQUENCE: 95

Xaa Asn Thr Trp Lys Xaa Phe Xaa Lys Lys Asn Xaa
1               5                   10

<210> SEQ ID NO 96
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(b-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
```

```
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 96

Arg Xaa Asn Thr Xaa Lys Xaa Phe Xaa Xaa Glu Asn Phe
1               5                   10

<210> SEQ ID NO 97
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 97

Arg Xaa Gln Thr Trp Gln Xaa Phe Xaa Xaa Glu Asn Phe
1               5                   10

<210> SEQ ID NO 98
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
```

```
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 98

Xaa Asn Thr Trp Lys Xaa Phe Xaa Lys Lys Asn Phe
1               5                   10

<210> SEQ ID NO 99
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 99

Arg Xaa Asn Thr Xaa Gln Xaa Phe Xaa Xaa Glu Asn Xaa
1               5                   10

<210> SEQ ID NO 100
```

```
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe
<220> FEATURE:
<221> NAME/KEY: MISC_FEATURE
<222> LOCATION: (13)..(13)
<223> OTHER INFORMATION: Tyr is (D)Tyr

<400> SEQUENCE: 100

Xaa Asn Thr Xaa Lys Xaa Phe Xaa Lys Lys Asn Phe Tyr
1               5                   10

<210> SEQ ID NO 101
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
```

```
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 101

Arg Xaa Asn Thr Xaa Lys Xaa Phe Xaa Xaa Glu Asn Xaa
1               5                   10

<210> SEQ ID NO 102
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Phe is a-MePhe

<400> SEQUENCE: 102

Arg Xaa Asn Thr Trp Lys Xaa Phe Xaa Xaa Glu Asn Phe
1               5                   10

<210> SEQ ID NO 103
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
```

```
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 103

Xaa Asn Thr Trp Lys Xaa Phe Xaa Lys Lys Asn Xaa
1               5                   10

<210> SEQ ID NO 104
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)]
<220> FEATURE:
<221> NAME/KEY: MISC_FEATURE
<222> LOCATION: (5)..(5)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 104

Xaa Asn Thr Xaa Xaa Xaa Phe Xaa Leu Lys Asn Phe
1               5                   10

<210> SEQ ID NO 105
```

```
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 105

Arg Xaa Asn Thr Trp Lys Xaa Phe Xaa Xaa Glu Asn Xaa
1               5                   10

<210> SEQ ID NO 106
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
```

```
<221> NAME/KEY: MISC_FEATURE
<222> LOCATION: (13)..(13)
<223> OTHER INFORMATION: Phe is a-MePhe

<400> SEQUENCE: 106

Arg Xaa Asn Thr Trp Lys Xaa Phe Xaa Xaa Glu Asn Phe
1               5                   10

<210> SEQ ID NO 107
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is a-Lys(Ac)
<220> FEATURE:
<221> NAME/KEY: MISC_FEATURE
<222> LOCATION: (12)..(12)
<223> OTHER INFORMATION: Xaa is THP
<220> FEATURE:
<221> NAME/KEY: MISC_FEATURE
<222> LOCATION: (13)..(13)
<223> OTHER INFORMATION: Tyr is (D)Tyr

<400> SEQUENCE: 107

Xaa Asn Thr Xaa Lys Xaa Phe Xaa Lys Lys Asn Xaa Tyr
1               5                   10

<210> SEQ ID NO 108
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
```

```
<222> LOCATION: (5)..(5)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 108

Xaa Asn Thr Xaa Xaa Xaa Phe Xaa Leu Lys Asn Xaa
1               5                   10

<210> SEQ ID NO 109
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(b-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 109

Arg Xaa Asn Thr Xaa Lys Xaa Phe Xaa Xaa Glu Asn Phe
```

```
1               5                    10
```

<210> SEQ ID NO 110
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-benzyl)Asn]

<400> SEQUENCE: 110

```
Arg Xaa Gln Thr Trp Gln Xaa Phe Xaa Xaa Glu Asn Asn
1               5                    10
```

<210> SEQ ID NO 111
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:

```
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Lys is Lys(Ac)
<220> FEATURE:
<221> NAME/KEY: MISC_FEATURE
<222> LOCATION: (13)..(13)
<223> OTHER INFORMATION: Phe is a-MePhe

<400> SEQUENCE: 111

Arg Xaa Asn Thr Xaa Lys Xaa Phe Xaa Xaa Lys Asn Phe
1               5                   10

<210> SEQ ID NO 112
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is Phe[4-NH2]

<400> SEQUENCE: 112

Xaa Asn Thr Xaa Lys Xaa Phe Xaa Lys Lys Asn Phe
1               5                   10

<210> SEQ ID NO 113
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
```

```
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Leu is (D)Leu

<400> SEQUENCE: 113

Xaa Asn Thr Xaa Lys Xaa Phe Xaa Lys Lys Asn Leu
1               5                   10

<210> SEQ ID NO 114
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe
```

```
<220> FEATURE:
<221> NAME/KEY: MISC_FEATURE
<222> LOCATION: (13)..(13)
<223> OTHER INFORMATION: Phe is (D)Phe[4-NH2]

<400> SEQUENCE: 114

Xaa Asn Thr Xaa Lys Xaa Phe Xaa Lys Lys Asn Phe Phe
1               5                   10

<210> SEQ ID NO 115
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe
<220> FEATURE:
<221> NAME/KEY: MISC_FEATURE
<222> LOCATION: (13)..(13)
<223> OTHER INFORMATION: Phe is (D)Phe[3-NH2]

<400> SEQUENCE: 115

Xaa Asn Thr Xaa Lys Xaa Phe Xaa Lys Lys Asn Phe Phe
1               5                   10

<210> SEQ ID NO 116
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
```

<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe
<220> FEATURE:
<221> NAME/KEY: MISC_FEATURE
<222> LOCATION: (13)..(13)
<223> OTHER INFORMATION: Xaa is 3-Pal

<400> SEQUENCE: 116

Xaa Asn Thr Xaa Lys Xaa Phe Xaa Lys Lys Asn Phe Xaa
1               5                   10

<210> SEQ ID NO 117
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 117

```
Cys Asn Thr Xaa Lys Cys Phe Xaa Lys Lys Asn Xaa
1               5                   10
```

<210> SEQ ID NO 118
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 118

```
Cys Asn Thr Xaa Lys Cys Phe Xaa Lys Lys Asn Phe
1               5                   10
```

<210> SEQ ID NO 119
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is W(7-Me)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 119

Cys Asn Thr Xaa Gln Cys Phe Xaa Lys Lys Asn Phe
1               5                   10

<210> SEQ ID NO 120
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 120

Cys Asn Thr Xaa Gln Cys Phe Xaa Lys Lys Asn Xaa
1               5                   10

<210> SEQ ID NO 121
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:

```
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 121

Cys Asn Thr Trp Lys Cys Phe Xaa Lys Lys Asn Xaa
1               5                   10

<210> SEQ ID NO 122
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Cys is a-MeCys
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 122

Cys Asn Thr Trp Lys Cys Phe Xaa Lys Lys Asn Phe
1               5                   10

<210> SEQ ID NO 123
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
```

```
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 123

Arg Xaa Gln Thr Trp Gln Cys Phe Xaa Xaa Glu Asn Phe
1               5                   10

<210> SEQ ID NO 124
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 124

Arg Xaa Asn Thr Xaa Lys Xaa Phe Xaa Xaa Glu Asn Phe
1               5                   10

<210> SEQ ID NO 125
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
```

```
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-Ph)Asn

<400> SEQUENCE: 125

Arg Xaa Gln Thr Trp Gln Xaa Phe Xaa Xaa Glu Asn Asn
1               5                   10

<210> SEQ ID NO 126
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(2-aminophenyl))Asn]

<400> SEQUENCE: 126

Arg Xaa Gln Thr Trp Gln Xaa Phe Xaa Xaa Glu Asn Asn
1               5                   10

<210> SEQ ID NO 127
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
```

```
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-Pip)Asn

<400> SEQUENCE: 127

Arg Xaa Gln Thr Trp Gln Xaa Phe Xaa Xaa Glu Asn Asn
1               5                   10

<210> SEQ ID NO 128
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-Pyr)Asn

<400> SEQUENCE: 128

Arg Xaa Gln Thr Trp Gln Xaa Phe Xaa Xaa Glu Asn Asn
1               5                   10

<210> SEQ ID NO 129
<211> LENGTH: 13
<212> TYPE: PRT
<213> ORGANISM: Artificial sequence
<220> FEATURE:
<223> OTHER INFORMATION: Synthetic construct
<220> FEATURE:
```

<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(4-aminophenyl))Asn

<400> SEQUENCE: 129

Arg Xaa Gln Thr Trp Gln Xaa Phe Xaa Xaa Glu Asn Asn
1               5                   10

<210> SEQ ID NO 130
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(3-aminophenyl))Asn

<400> SEQUENCE: 130

Arg Xaa Gln Thr Trp Gln Xaa Phe Xaa Xaa Glu Asn Asn
1               5                   10

<210> SEQ ID NO 131
<211> LENGTH: 13
<212> TYPE: PRT
<213> ORGANISM: Artificial sequence

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(4-Pyz))Asn

<400> SEQUENCE: 131

Arg Xaa Gln Thr Trp Gln Xaa Phe Xaa Xaa Glu Asn Asn
1               5                   10

<210> SEQ ID NO 132
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is N-(5-indolyl)Asn

<400> SEQUENCE: 132

Arg Xaa Gln Thr Trp Gln Xaa Phe Xaa Xaa Glu Asn Asn
1               5                   10

<210> SEQ ID NO 133
```

```
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is -Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(3-Pyz))Asn

<400> SEQUENCE: 133

Arg Xaa Gln Thr Trp Gln Xaa Phe Xaa Xaa Glu Asn Asn
1               5                   10

<210> SEQ ID NO 134
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 134
```

Arg Xaa Gln Thr Trp Gln Xaa Phe Xaa Xaa Glu Asn Xaa
1               5                   10

<210> SEQ ID NO 135
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[(aMe)-4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 135

Arg Xaa Gln Thr Trp Gln Xaa Phe Xaa Xaa Glu Asn Xaa
1               5                   10

<210> SEQ ID NO 136
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP

```
<220> FEATURE:
<221> NAME/KEY: MISC_FEATURE
<222> LOCATION: (13)..(13)
<223> OTHER INFORMATION: Asn is (N-propylamido)Asn

<400> SEQUENCE: 136

Arg Xaa Gln Thr Trp Gln Xaa Phe Xaa Xaa Glu Asn Asn
1               5                   10

<210> SEQ ID NO 137
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Asn is (N-(imidazol-2-yl)methyl)Asn

<400> SEQUENCE: 137

Arg Xaa Gln Thr Trp Gln Xaa Phe Xaa Xaa Glu Asn Asn
1               5                   10

<210> SEQ ID NO 138
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]-
<220> FEATURE:
```

```
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (12)..(12)
<223> OTHER INFORMATION: Phe is a-MePhe

<400> SEQUENCE: 138

Xaa Asn Thr Xaa Lys Xaa Phe Xaa Xaa Lys Asn Phe
1               5                   10

<210> SEQ ID NO 139
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]-
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (10)..(10)
<223> OTHER INFORMATION: Lys is N-Epsilon-[C(O)-t-Bu]-L-Lysine
<220> FEATURE:
<221> NAME/KEY: MISC_FEATURE
<222> LOCATION: (12)..(12)
<223> OTHER INFORMATION: Phe is a-MePhe

<400> SEQUENCE: 139

Xaa Asn Thr Xaa Lys Xaa Phe Xaa Xaa Lys Asn Phe
1               5                   10

<210> SEQ ID NO 140
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
```

```
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (12)..(12)
<223> OTHER INFORMATION: Xaa is THP

<400> SEQUENCE: 140

Xaa Asn Thr Xaa Lys Xaa Phe Xaa Xaa Lys Asn Xaa
1               5                   10

<210> SEQ ID NO 141
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (10)..(10)
<223> OTHER INFORMATION: Lys is N-Epsilon-[C(O)-t-Bu]-L-Lysine
<220> FEATURE:
<221> NAME/KEY: MISC_FEATURE
<222> LOCATION: (12)..(12)
<223> OTHER INFORMATION: Xaa is THP

<400> SEQUENCE: 141

Xaa Asn Thr Xaa Lys Xaa Phe Xaa Xaa Lys Asn Xaa
```

```
1               5                   10
```

<210> SEQ ID NO 142
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N Terminal Modification is Pentco
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 142

```
Arg Xaa Asn Thr Xaa Lys Xaa Phe Xaa Xaa Glu Asn Phe
1               5                   10
```

<210> SEQ ID NO 143
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Biotin
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)

```
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 143

Arg Xaa Asn Thr Xaa Lys Xaa Phe Xaa Xaa Glu Asn Xaa
 1               5                  10

<210> SEQ ID NO 144
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Biotin-PEG2(2:2)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)]
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 144

Arg Xaa Asn Thr Xaa Lys Xaa Phe Xaa Xaa Glu Asn Xaa
 1               5                  10
```

```
<210> SEQ ID NO 145
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Biotin-PEG3(2:2)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)]
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 145

Arg Xaa Asn Thr Xaa Lys Xaa Phe Xaa Xaa Glu Asn Xaa
1               5                   10

<210> SEQ ID NO 146
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FlagTag
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
```

<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 146

Arg Xaa Asn Thr Xaa Lys Xaa Phe Xaa Xaa Glu Asn Xaa
1               5                   10

<210> SEQ ID NO 147
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FlagTag-PEG2(2:2)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)]
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 147

Arg Xaa Asn Thr Xaa Lys Xaa Phe Xaa Xaa Glu Asn Xaa
1               5                   10

<210> SEQ ID NO 148

```
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FlagTag-PEG3(2:2)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 148

Arg Xaa Asn Thr Xaa Lys Xaa Phe Xaa Xaa Glu Asn Xaa
1               5                   10

<210> SEQ ID NO 149
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
```

```
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Leu is a-MeLeu
<220> FEATURE:
<221> NAME/KEY: MISC_FEATURE
<222> LOCATION: (13)..(13)
<223> OTHER INFORMATION: Phe is a-MePhe

<400> SEQUENCE: 149

Arg Xaa Asn Thr Xaa Xaa Xaa Phe Xaa Leu Glu Asn Phe
1               5                   10

<210> SEQ ID NO 150
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is a-MeGlu
<220> FEATURE:
<221> NAME/KEY: MISC_FEATURE
<222> LOCATION: (13)..(13)
<223> OTHER INFORMATION: Tyr is a-MeTyr

<400> SEQUENCE: 150

Arg Xaa Asn Thr Xaa Lys Xaa Phe Xaa Xaa Glu Asn Tyr
1               5                   10

<210> SEQ ID NO 151
<211> LENGTH: 12
<212> TYPE: PRT
<213> ORGANISM: Artificial sequence
<220> FEATURE:
```

```
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Tyr is a-MeTyr

<400> SEQUENCE: 151

Xaa Asn Thr Xaa Lys Xaa Phe Xaa Lys Lys Asn Tyr
1               5                   10

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000
```

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

```
<400> SEQUENCE: 168

000

<210> SEQ ID NO 169
<400> SEQUENCE: 169

000

<210> SEQ ID NO 170
<400> SEQUENCE: 170

000

<210> SEQ ID NO 171
<400> SEQUENCE: 171

000

<210> SEQ ID NO 172
<400> SEQUENCE: 172

000

<210> SEQ ID NO 173
<400> SEQUENCE: 173

000

<210> SEQ ID NO 174
<400> SEQUENCE: 174

000

<210> SEQ ID NO 175
<400> SEQUENCE: 175

000

<210> SEQ ID NO 176
<400> SEQUENCE: 176

000

<210> SEQ ID NO 177
<400> SEQUENCE: 177

000

<210> SEQ ID NO 178
<400> SEQUENCE: 178

000

<210> SEQ ID NO 179
<400> SEQUENCE: 179
```

000

<210> SEQ ID NO 180
<400> SEQUENCE: 180
000

<210> SEQ ID NO 181
<400> SEQUENCE: 181
000

<210> SEQ ID NO 182
<400> SEQUENCE: 182
000

<210> SEQ ID NO 183
<400> SEQUENCE: 183
000

<210> SEQ ID NO 184
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE

```
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Lys is a-MeLys
<220> FEATURE:
<221> NAME/KEY: MISC_FEATURE
<222> LOCATION: (11)..(11)
<223> OTHER INFORMATION: Lys is Lys(Ac)
<220> FEATURE:
<221> NAME/KEY: MISC_FEATURE
<222> LOCATION: (13)..(13)
<223> OTHER INFORMATION: Phe is a-MePhe

<400> SEQUENCE: 201

Arg Xaa Gln Thr Xaa Lys Cys Phe Xaa Lys Lys Asn Phe
1               5                   10

<210> SEQ ID NO 202
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
```

```
<220> FEATURE:
<221> NAME/KEY: MISC_FEATURE
<222> LOCATION: (12)..(12)
<223> OTHER INFORMATION: Xaa is Aib
<220> FEATURE:
<221> NAME/KEY: MISC_FEATURE
<222> LOCATION: (13)..(13)
<223> OTHER INFORMATION: Tyr is (D)Tyr

<400> SEQUENCE: 202

Xaa Asn Thr Xaa Xaa Xaa Phe Xaa Lys Lys Asn Xaa Tyr
1               5                   10

<210> SEQ ID NO 203
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is Aib

<400> SEQUENCE: 203

Arg Xaa Gln Thr Trp Gln Xaa Phe Xaa Xaa Glu Asn Xaa
1               5                   10

<210> SEQ ID NO 204
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
```

```
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is Aib

<400> SEQUENCE: 204

Arg Xaa Gln Thr Trp Gln Cys Phe Xaa Xaa Glu Asn Xaa
1               5                   10

<210> SEQ ID NO 205

<400> SEQUENCE: 205

000

<210> SEQ ID NO 206
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FPrpTriazoleMe Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 206

Arg Xaa Gln Thr Trp Gln Cys Phe Xaa Xaa Glu Asn Xaa
1               5                   10

<210> SEQ ID NO 207
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
```

```
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 207

Xaa Asn Thr Xaa Lys Xaa Phe Xaa Lys Lys Asn Phe
1               5                   10

<210> SEQ ID NO 208
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Pheis a-MePhe
```

-continued

<400> SEQUENCE: 208

Arg Xaa Asn Thr Xaa Lys Xaa Phe Xaa Xaa Glu Asn Phe
1               5                   10

<210> SEQ ID NO 209
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeSo2
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 209

Xaa Asn Thr Xaa Lys Xaa Phe Xaa Lys Lys Asn Phe
1               5                   10

<210> SEQ ID NO 210
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: C terminal modification is N3_Acid
      (N3-CH2-COOH)
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE

```
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 210

Xaa Asn Thr Xaa Lys Xaa Phe Xaa Lys Lys Asn Phe
1               5                   10

<210> SEQ ID NO 211
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is N3_Acid
      (N3-CH2-COOH)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe
```

```
<400> SEQUENCE: 211

Arg Xaa Asn Thr Xaa Lys Xaa Phe Xaa Xaa Glu Asn Phe
1               5                   10

<210> SEQ ID NO 212
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeSO2
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 212

Arg Xaa Asn Thr Xaa Lys Xaa Phe Xaa Xaa Glu Asn Phe
1               5                   10

<210> SEQ ID NO 213
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
```

```
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 213

Arg Xaa Gln Thr Trp Gln Cys Phe Xaa Xaa Glu Asn Xaa
 1               5                  10

<210> SEQ ID NO 214
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]_Ethyl]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 214

Arg Xaa Gln Thr Trp Gln Cys Phe Xaa Xaa Glu Asn Xaa
 1               5                  10

<210> SEQ ID NO 215
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
```

```
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Leu is (D)Leu
<220> FEATURE:
<221> NAME/KEY: MISC_FEATURE
<222> LOCATION: (14)..(14)
<223> OTHER INFORMATION: Tyr is (D)Tyr

<400> SEQUENCE: 215

Arg Xaa Asn Thr Xaa Lys Xaa Phe Xaa Xaa Glu Asn Leu Tyr
1               5                   10

<210> SEQ ID NO 216
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP
<220> FEATURE:
<221> NAME/KEY: MISC_FEATURE
```

<222> LOCATION: (14)..(14)
<223> OTHER INFORMATION: Tyr is (D)Tyr

<400> SEQUENCE: 216

Arg Xaa Asn Thr Xaa Lys Xaa Phe Xaa Xaa Glu Asn Xaa Tyr
1               5                   10

<210> SEQ ID NO 217
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP
<220> FEATURE:
<221> NAME/KEY: MISC_FEATURE
<222> LOCATION: (14)..(14)
<223> OTHER INFORMATION: Tyr is (D)Tyr

<400> SEQUENCE: 217

Arg Xaa Asn Thr Xaa Lys Xaa Phe Xaa Xaa Glu Asn Xaa Tyr
1               5                   10

<210> SEQ ID NO 218
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Dota-[a])
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen

```
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa is THP

<400> SEQUENCE: 218

Arg Xaa Asn Thr Xaa Lys Xaa Phe Xaa Xaa Glu Asn Xaa
1               5                   10

<210> SEQ ID NO 219
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Dota_PEG2_Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
```

<223> OTHER INFORMATION: Xaa is THP

<400> SEQUENCE: 219

Arg Xaa Asn Thr Xaa Lys Xaa Phe Xaa Xaa Glu Asn Xaa
1               5                   10

<210> SEQ ID NO 220
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Dota_PEG3_Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 220

Arg Xaa Asn Thr Xaa Lys Xaa Phe Xaa Xaa Glu Asn Xaa
1               5                   10

<210> SEQ ID NO 221
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-F)
<220> FEATURE:
<221> NAME/KEY: MISC_FEATURE
<222> LOCATION: (5)..(5)
<223> OTHER INFORMATION: Lys is Lys(Ac)
<220> FEATURE:

```
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 221

Xaa Asn Thr Xaa Lys Xaa Phe Xaa Lys Lys Asn Phe
1               5                   10

<210> SEQ ID NO 222
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-F)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 222

Arg Xaa Asn Thr Xaa Lys Xaa Phe Xaa Xaa Glu Asn Phe
1               5                   10
```

```
<210> SEQ ID NO 223
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Cl)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 223

Xaa Asn Thr Xaa Lys Xaa Phe Xaa Lys Lys Asn Phe
1               5                   10

<210> SEQ ID NO 224
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Cl)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
```

```
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 224

Arg Xaa Asn Thr Xaa Lys Xaa Phe Xaa Xaa Glu Asn Phe
1               5                   10

<210> SEQ ID NO 225
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(5-Br)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 225

Xaa Asn Thr Xaa Lys Xaa Phe Xaa Lys Lys Asn Phe
1               5                   10

<210> SEQ ID NO 226
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
```

```
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(5-Br)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 226

Arg Xaa Asn Thr Xaa Lys Xaa Phe Xaa Xaa Glu Asn Phe
1               5                   10

<210> SEQ ID NO 227
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
```

```
<223> OTHER INFORMATION: Lys is (D)Lys
<220> FEATURE:
<221> NAME/KEY: MISC_FEATURE
<222> LOCATION: (13)..(13)
<223> OTHER INFORMATION: Phe is (D)Phe(4-OCF3)

<400> SEQUENCE: 227

Xaa Asn Thr Xaa Lys Xaa Phe Xaa Lys Lys Asn Lys Phe
1               5                   10

<210> SEQ ID NO 228
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Lys is (D)Lys
<220> FEATURE:
<221> NAME/KEY: MISC_FEATURE
<222> LOCATION: (14)..(14)
<223> OTHER INFORMATION: Phe is (D)Phe(4-OCF3)

<400> SEQUENCE: 228

Arg Xaa Asn Thr Xaa Lys Xaa Phe Xaa Xaa Glu Asn Lys Phe
1               5                   10

<210> SEQ ID NO 229
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is
      BenzHydroxylIodine_Acid
<220> FEATURE:
<221> NAME/KEY: MISC_FEATURE
<222> LOCATION: (1)..(1)
<223> OTHER INFORMATION: Xaa is Pen
```

```
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 229

Xaa Asn Thr Xaa Lys Xaa Phe Xaa Lys Lys Asn Phe
1               5                   10

<210> SEQ ID NO 230
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is
      BenzHydroxylIodine_Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
```

```
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is a-MePhe

<400> SEQUENCE: 230

Arg Xaa Asn Thr Xaa Lys Xaa Phe Xaa Xaa Glu Asn Phe
1               5                   10

<210> SEQ ID NO 231
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: C terminal modification is a methylamine
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is 1-aminocyclopentanecarboxylic acid
<220> FEATURE:
<221> NAME/KEY: MISC_FEATURE
<222> LOCATION: (12)..(12)
<223> OTHER INFORMATION: Xaa is THP

<400> SEQUENCE: 231

Xaa Asn Thr Xaa Lys Xaa Phe Xaa Xaa Glu Asn Xaa
1               5                   10

<210> SEQ ID NO 232
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
```

```
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (12)..(12)
<223> OTHER INFORMATION: Leu is (D)Leu
<220> FEATURE:
<221> NAME/KEY: MISC_FEATURE
<222> LOCATION: (13)..(13)
<223> OTHER INFORMATION: Tyr is (D)Tyr

<400> SEQUENCE: 232

Xaa Asn Thr Xaa Lys Xaa Phe Xaa Xaa Glu Asn Leu Tyr
1               5                   10

<210> SEQ ID NO 233
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 233

Arg Xaa Asn Thr Xaa Lys Xaa Phe Xaa Xaa Glu Asn Xaa
1               5                   10
```

```
<210> SEQ ID NO 234
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: C terminal modification is methylamine
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopentanecarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 234

Arg Xaa Asn Thr Xaa Lys Xaa Phe Xaa Xaa Glu Asn Xaa
1               5                   10

<210> SEQ ID NO 235
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
```

```
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is 1-aminocyclopentanecarboxylic acid
<220> FEATURE:
<221> NAME/KEY: MISC_FEATURE
<222> LOCATION: (12)..(12)
<223> OTHER INFORMATION: Phe is (D)Phe(4-NH2)
<220> FEATURE:
<221> NAME/KEY: MISC_FEATURE
<222> LOCATION: (13)..(13)
<223> OTHER INFORMATION: Tyr is (D)Tyr

<400> SEQUENCE: 235

Xaa Asn Thr Xaa Lys Xaa Phe Xaa Xaa Glu Asn Phe Tyr
1               5                   10

<210> SEQ ID NO 236
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is (R)(bMe)(2-Nal)
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa is THP

<400> SEQUENCE: 236

Arg Xaa Gln Thr Trp Gln Xaa Phe Xaa Xaa Glu Asn Xaa
1               5                   10

<210> SEQ ID NO 237
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
```

```
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-acetylaminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 237

Arg Xaa Asn Thr Xaa Lys Xaa Phe Xaa Xaa Glu Asn Xaa
1               5                   10

<210> SEQ ID NO 238
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: C terminal modification is Propyl
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Trp is Trp_psi
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa is THP
<220> FEATURE:
```

<221> NAME/KEY: misc_feature
<222> LOCATION: (14)..(14)
<223> OTHER INFORMATION: Xaa can be any naturally occurring amino acid

<400> SEQUENCE: 238

Xaa Arg Xaa Gln Thr Trp Gln Xaa Phe Xaa Xaa Glu Asn Xaa
1               5                   10

<210> SEQ ID NO 239
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FPrpTriazoleMe_Acid
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 239

Xaa Asn Thr Xaa Lys Xaa Phe Xaa Lys Lys Asn Phe
1               5                   10

<210> SEQ ID NO 240
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is FPrpTriazoleMe_Acid
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen

```
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 240

Arg Xaa Asn Thr Xaa Lys Xaa Phe Xaa Xaa Glu Asn Phe
1               5                   10

<210> SEQ ID NO 241
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe_4Pip
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 241
```

Arg Xaa Asn Thr Xaa Leu Xaa Phe Xaa Xaa Glu Asn Phe
1               5                   10

<210> SEQ ID NO 242
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is Phe(tetrafluoro)

<400> SEQUENCE: 242

Xaa Asn Thr Xaa Lys Xaa Phe Xaa Lys Lys Asn Phe
1               5                   10

<210> SEQ ID NO 243
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)

```
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (12)..(12)
<223> OTHER INFORMATION: Phe is Phe(tetrafluoro)

<400> SEQUENCE: 243

Arg Xaa Asn Thr Xaa Lys Xaa Phe Xaa Xaa Glu Asn Phe
1               5                   10

<210> SEQ ID NO 244
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Lys is (D)Lys
<220> FEATURE:
<221> NAME/KEY: MISC_FEATURE
<222> LOCATION: (13)..(13)
<223> OTHER INFORMATION: Phe is (D)Phe[4-(2-aminoethoxy)]

<400> SEQUENCE: 244

Xaa Asn Thr Xaa Lys Xaa Phe Xaa Lys Lys Asn Lys Phe
1               5                   10

<210> SEQ ID NO 245
<211> LENGTH: 14
```

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Lys is (D)Lys
<220> FEATURE:
<221> NAME/KEY: MISC_FEATURE
<222> LOCATION: (14)..(14)
<223> OTHER INFORMATION: Phe is (D)Phe[4-(2-aminoethoxy)]

<400> SEQUENCE: 245

Arg Xaa Asn Thr Xaa Lys Xaa Phe Xaa Xaa Glu Asn Lys Phe
1               5                   10

<210> SEQ ID NO 246
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
```

<222> LOCATION: (8)..(8)
<223> OTHER INFORMATION: Phe is Phe[4-(2-(SMSB)-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 246

Arg Xaa Asn Thr Xaa Lys Xaa Phe Xaa Xaa Glu Asn Phe
1               5                   10

<210> SEQ ID NO 247
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: C terminal modification is SulfCyanine3
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 247

Arg Xaa Asn Thr Xaa Lys Xaa Phe Xaa Xaa Glu Asn Phe
1               5                   10

<210> SEQ ID NO 248
<211> LENGTH: 13
<212> TYPE: PRT
<213> ORGANISM: Artificial sequence
<220> FEATURE:
<223> OTHER INFORMATION: Synthetic construct

```
<220> FEATURE:
<221> NAME/KEY: MISC_FEATURE
<223> OTHER INFORMATION: N terminal modification is SulfCyanine3_dPEG2
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 248

Arg Xaa Asn Thr Xaa Lys Xaa Phe Xaa Xaa Glu Asn Phe
1               5                   10

<210> SEQ ID NO 249
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is SulfCyanine3_dPEG2
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
```

```
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 249

Arg Xaa Asn Thr Xaa Lys Xaa Phe Xaa Xaa Glu Asn Phe
 1               5                  10

<210> SEQ ID NO 250
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is SMSBCO
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]-
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 250

Xaa Asn Thr Xaa Lys Xaa Phe Xaa Lys Lys Asn Phe
 1               5                  10

<210> SEQ ID NO 251
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]-
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is Phe(3-OH)

<400> SEQUENCE: 251

Arg Xaa Asn Thr Xaa Lys Xaa Phe Xaa Xaa Glu Asn Phe
1               5                   10

<210> SEQ ID NO 252
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is SMSBCO
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
```

```
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 252

Arg Xaa Asn Thr Xaa Lys Xaa Phe Xaa Xaa Glu Asn Phe
1               5                   10

<210> SEQ ID NO 253
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-acetylaminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 253

Xaa Asn Thr Xaa Lys Xaa Phe Xaa Lys Lys Asn Xaa
1               5                   10

<210> SEQ ID NO 254
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
```

```
<222> LOCATION: (5)..(5)
<223> OTHER INFORMATION: Phe is Phe_4NH2_Ac
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 254

Xaa Asn Thr Xaa Phe Xaa Phe Xaa Lys Lys Asn Xaa
1               5                   10

<210> SEQ ID NO 255
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is (R)bMePhe
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 255

Xaa Asn Thr Xaa Lys Xaa Phe Xaa Lys Lys Asn Xaa
```

<210> SEQ ID NO 256
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(7-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is (R)bMePhe
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 256

Arg Xaa Asn Thr Xaa Lys Xaa Phe Xaa Xaa Glu Asn Xaa
1               5                   10

<210> SEQ ID NO 257
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is W(5-Me)
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:

<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 257

Arg Xaa Asn Thr Xaa Lys Xaa Phe Xaa Xaa Glu Asn Phe
1               5                   10

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (7)..(7)
<223> OTHER INFORMATION: Xaa is AEF (4-(2-aminoethoxy)-L-phenylalanine)
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is 1-aminocyclohexanecarboxylic acid
<220> FEATURE:
<221> NAME/KEY: MISC_FEATURE
<222> LOCATION: (10)..(10)
<223> OTHER INFORMATION: Xaa is alpha-methyl glutamic acid
<220> FEATURE:
<221> NAME/KEY: MISC_FEATURE
<222> LOCATION: (13)..(13)
<223> OTHER INFORMATION: Xaa is 2-aminoisobutyric acid
<220> FEATURE:
<221> NAME/KEY: MISC_FEATURE
<222> LOCATION: (14)..(14)
<223> OTHER INFORMATION: Lys is a-MeLys

<400> SEQUENCE: 301

Xaa Gln Thr Trp Gln Cys Xaa Xaa Xaa Xaa Asn Phe Xaa Lys
1               5                   10

<210> SEQ ID NO 302
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeW
<220> FEATURE:
<221> NAME/KEY: MISC_FEATURE
<222> LOCATION: (5)..(5)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is AEF (4-(2-aminoethoxy)-L-phenylalanine)
<220> FEATURE:
<221> NAME/KEY: MISC_FEATURE
<222> LOCATION: (8)..(8)
<223> OTHER INFORMATION: Xaa is 2-Nal
<220> FEATURE:

```
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is 2-aminoisobutyric acid

<400> SEQUENCE: 302

Xaa Asn Thr Xaa Xaa Xaa Xaa Xaa Lys Lys Asn Xaa
1               5                   10

<210> SEQ ID NO 303
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7 MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF (4-(2-aminoethoxy)-L-phenylalanine)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa is 1-amino-4,4-difluoro-
      cyclohexanecarboxylic acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa is THP

<400> SEQUENCE: 303

Arg Xaa Asn Thr Xaa Lys Xaa Xaa Xaa Xaa Glu Asn Xaa
1               5                   10

<210> SEQ ID NO 304
<211> LENGTH: 11
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeW
<220> FEATURE:
<221> NAME/KEY: MISC_FEATURE
<222> LOCATION: (5)..(5)
<223> OTHER INFORMATION: Lys Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is 4-(2-(N-t-Boc)-aminoethoxy)phenylalanine
<220> FEATURE:
<221> NAME/KEY: MISC_FEATURE
<222> LOCATION: (8)..(8)
<223> OTHER INFORMATION: Xaa is2-Nal
<220> FEATURE:
<221> NAME/KEY: MISC_FEATURE
<222> LOCATION: (9)..(9)
<223> OTHER INFORMATION: Lys is a-MeLys(Boc)
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 304

Xaa Asn Thr Xaa Lys Xaa Xaa Lys Lys Asn Phe
1               5                   10

<210> SEQ ID NO 305
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is 4-(2-(N-t-Boc)-aminoethoxy)phenylalanine
<220> FEATURE:
<221> NAME/KEY: MISC_FEATURE
<222> LOCATION: (9)..(9)
<223> OTHER INFORMATION: Xaa is 2-Nal
```

```
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhed

<400> SEQUENCE: 305

Arg Xaa Asn Thr Xaa Lys Xaa Xaa Xaa Xaa Glu Asn Phe
1               5                   10

<210> SEQ ID NO 306
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Xaa is 4-amino-L-phenylalanine
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 306

Arg Xaa Asn Thr Xaa Xaa Xaa Xaa Xaa Xaa Glu Asn Xaa
1               5                   10

<210> SEQ ID NO 307
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is EtCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
```

```
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is bMe2Nal(2S,3R)
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 307

Arg Xaa Gln Thr Trp Gln Xaa Xaa Xaa Xaa Glu Asn Xaa
1               5                   10

<210> SEQ ID NO 308
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF(Ac)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (13)..(3)
<223> OTHER INFORMATION: Xaa is THP
<220> FEATURE:
<221> NAME/KEY: misc_feature
<222> LOCATION: (13)..(13)
<223> OTHER INFORMATION: Xaa can be any naturally occurring amino acid

<400> SEQUENCE: 308

Arg Xaa Asn Thr Xaa Lys Xaa Xaa Xaa Xaa Glu Asn Xaa
1               5                   10

<210> SEQ ID NO 309
<211> LENGTH: 14
<212> TYPE: PRT
```

<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (14)..(14)
<223> OTHER INFORMATION: Xaa is 4-amino-L-phenylalanine

<400> SEQUENCE: 309

Arg Xaa Asn Thr Xaa Lys Xaa Xaa Xaa Xaa Glu Asn His Xaa
1               5                   10

<210> SEQ ID NO 310
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is aMeC
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:

```
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (13)..(13)
<223> OTHER INFORMATION: Xaa is THP

<400> SEQUENCE: 310

Arg Cys Asn Thr Xaa Lys Xaa Xaa Xaa Xaa Glu Asn Xaa
 1               5                  10

<210> SEQ ID NO 311
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeTrp
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is 4PipPhe
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 311

Xaa Asn Thr Xaa Lys Xaa Phe Xaa Xaa Xaa Asn Phe
 1               5                  10

<210> SEQ ID NO 312
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
```

```
<223> OTHER INFORMATION: Xaa is 7MeTrp
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is AEF
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MePhe
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is bMePhe(S,R)-

<400> SEQUENCE: 312

Xaa Asn Thr Xaa Lys Xaa Xaa Xaa Lys Lys Asn Phe
1               5                   10

<210> SEQ ID NO 313
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeTrp
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is bMePhe(S,R)

<400> SEQUENCE: 313
```

```
Arg Xaa Asn Thr Xaa Lys Xaa Xaa Xaa Glu Asn Phe
1               5               10
```

<210> SEQ ID NO 314
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeTrp
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF(BH)
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 314

```
Arg Xaa Asn Thr Xaa Lys Xaa Xaa Xaa Glu Asn Phe
1               5               10
```

<210> SEQ ID NO 315
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:

```
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (14)..(14)
<223> OTHER INFORMATION: Phe is 4AmDPhe

<400> SEQUENCE: 315

Arg Xaa Asn Thr Xaa Lys Xaa Xaa Xaa Xaa Glu Asn His Phe
1               5                   10

<210> SEQ ID NO 316
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is 1-aminocyclopropylcarboxylic acid
<220> FEATURE:
<221> NAME/KEY: MISC_FEATURE
<222> LOCATION: (14)..(14)
<223> OTHER INFORMATION: Phe is 4acDPhe

<400> SEQUENCE: 316

Arg Xaa Asn Thr Xaa Lys Xaa Xaa Xaa Xaa Glu Asn His Phe
1               5                   10

<210> SEQ ID NO 317
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
```

```
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeW
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is AEF
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is 1-aminocyclopropylcarboxylic acid
<220> FEATURE:
<221> NAME/KEY: MISC_FEATURE
<222> LOCATION: (12)..(12)
<223> OTHER INFORMATION: Xaa is THP

<400> SEQUENCE: 317

Xaa Asn Thr Xaa Lys Xaa Xaa Xaa Xaa Glu Asn Xaa
1               5                   10

<210> SEQ ID NO 318
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is Meco
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 6OMe2Nal
<220> FEATURE:
<221> NAME/KEY: MISC_FEATURE
<222> LOCATION: (10)..(10)
<223> OTHER INFORMATION: Xaa isTHP
<220> FEATURE:
<221> NAME/KEY: MISC_FEATURE
<222> LOCATION: (13)..(13)
```

<223> OTHER INFORMATION: Phe is a-MePhe

<400> SEQUENCE: 318

Arg Xaa Asn Thr Xaa Lys Xaa Xaa Xaa Xaa Glu Asn Phe
1               5                   10

<210> SEQ ID NO 319
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeW
<220> FEATURE:
<221> NAME/KEY: MISC_FEATURE
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is AEF(Me)2
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is THP

<400> SEQUENCE: 319

Xaa Asn Thr Xaa Lys Xaa Xaa Xaa Lys Lys Asn Xaa
1               5                   10

<210> SEQ ID NO 320
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is 7MeW
<220> FEATURE:
<221> NAME/KEY: MISC_FEATURE -continued

```
<222> LOCATION: (5)..(5)
<223> OTHER INFORMATION: Lys is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is AEF
<220> FEATURE:
<221> NAME/KEY: MISC_FEATURE
<222> LOCATION: (8)..(8)
<223> OTHER INFORMATION: Xaa is 6amido2Nal
<220> FEATURE:
<221> NAME/KEY: MISC_FEATURE
<222> LOCATION: (9)..(9)
<223> OTHER INFORMATION: Lys is a-MeLys
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Phe is a-MePhe

<400> SEQUENCE: 320

Xaa Asn Thr Xaa Lys Xaa Xaa Xaa Lys Lys Asn Phe
1               5                   10

<210> SEQ ID NO 321
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is MeCo
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (5)..(5)
<223> OTHER INFORMATION: Xaa is 7MeW
<220> FEATURE:
<221> NAME/KEY: MISC_FEATURE
<222> LOCATION: (6)..(6)
<223> OTHER INFORMATION: Lys is Lys(Ac)
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Xaa is AEF
<220> FEATURE:
<221> NAME/KEY: MISC_FEATURE
<222> LOCATION: (9)..(9)
<223> OTHER INFORMATION: Xaa is 6amido2Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 321

Arg Xaa Asn Thr Xaa Lys Xaa Xaa Xaa Xaa Glu Asn Phe
1               5                   10
```

<210> SEQ ID NO 322
<211> LENGTH: 20
<212> TYPE: PRT
<213> ORGANISM: Artificial sequence
<220> FEATURE:
<223> OTHER INFORMATION: Synthetic constuct

<400> SEQUENCE: 322

Asn Trp Gln Pro Trp Ser Ser Pro Phe Val His Gln Thr Ser Gln Glu
1               5                   10                  15

Thr Gly Lys Arg
            20

<210> SEQ ID NO 323
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Trp is Trp substituted with cyano, halo, alkyl,
      haloalkyl, hydroxy, or alkoxy
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 323

Xaa Asn Thr Trp Gln Xaa Phe Xaa Leu Lys Asn Xaa Xaa
1               5                   10

<210> SEQ ID NO 324
<211> LENGTH: 13
<212> TYPE: PRT
<213> ORGANISM: Artificial sequence
<220> FEATURE:
<223> OTHER INFORMATION: Synthetic construct
<220> FEATURE:

```
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is [F(4-2ae)]
<220> FEATURE:
<221> NAME/KEY: MISC_FEATURE
<222> LOCATION: (8)..(8)
<223> OTHER INFORMATION: Trp is Trp substituted with cyano, halo, alkyl,
      haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 324

Xaa Asn Thr Trp Gln Xaa Phe Trp Leu Lys Asn Xaa Xaa
1               5                   10

<210> SEQ ID NO 325
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Trp is Trp substituted with cyano, halo, alkyl,
      haloalkyl, hydroxy, or alkoxy
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
```

```
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 325

Xaa Asn Thr Trp Gln Cys Phe Xaa Leu Lys Asn Xaa Xaa
1               5                   10

<210> SEQ ID NO 326
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: W is Trp substituted with cyano, halo, alkyl,
      haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 326

Xaa Asn Thr Trp Gln Cys Phe Trp Leu Lys Asn Xaa Xaa
1               5                   10

<210> SEQ ID NO 327
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: W is Trp substituted with cyano, halo, alkyl,
      haloalkyl, hydroxy, or alkoxy
<220> FEATURE:
<221> NAME/KEY: MISC_FEATURE
<222> LOCATION: (6)..(6)
<223> OTHER INFORMATION: Xaa is Pen
```

```
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstituted Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 327

Xaa Asn Thr Trp Gln Xaa Phe Xaa Leu Lys Asn Xaa Xaa
1               5                   10

<210> SEQ ID NO 328
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: W is Trp substituted with cyano, halo, alkyl,
      haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is is paf, Aib, 3Pal, Phe, substituted Phe,
      substituted (D)Phe, substituted or unsubstituted Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or

<400> SEQUENCE: 328
```

```
Xaa Asn Thr Trp Gln Xaa Phe Trp Leu Lys Asn Xaa Xaa
1               5                   10
```

<210> SEQ ID NO 329
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is NTerm_bA(2:3)
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4-(2-aminoethoxy)]
<220> FEATURE:
<221> NAME/KEY: MISC_FEATURE
<222> LOCATION: (9)..(9)
<223> OTHER INFORMATION: Xaa is 2-Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (11)..(11)
<223> OTHER INFORMATION: Glu is Glu(2:3)
<220> FEATURE:
<221> NAME/KEY: MISC_FEATURE
<222> LOCATION: (13)..(13)
<223> OTHER INFORMATION: Xaa is THP

<400> SEQUENCE: 329

```
Arg Xaa Gln Thr Trp Gln Cys Phe Xaa Xaa Glu Asn Xaa
1               5                   10
```

<210> SEQ ID NO 330
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Xaa is unsubstituted Phe, or Phe substituted
      with halo, alkyl, haloalkyl, hydroxy, alkoxy, carboxy,
      carboxamido, 2-aminoethoxy, or 2-acetylaminoethoxy, AEF, AEF(Ac),
      AEF(BH), AEF(Boc), AEF(Me)2, bMeRPhe, Phe42ae-ethyl, Phe42aeSMSB,
      Phe4Pip
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted

```
           with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is apaf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 330

Xaa Asn Thr Xaa Gln Cys Xaa Xaa Xaa Xaa Xaa Xaa Xaa
1               5                   10

<210> SEQ ID NO 331
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Xaa is unsubstituted Phe, or Phe substituted
      with halo, alkyl, haloalkyl, hydroxy, alkoxy, carboxy,
      carboxamido, 2-aminoethoxy, or 2-acetylaminoethoxy, AEF, AEF(Ac),
      AEF(BH), AEF(Boc), AEF(Me)2, bMeRPhe, Phe42ae-ethyl, Phe42aeSMSB,
      Phe4Pip
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 331
```

```
Xaa Asn Thr Xaa Gln Cys Xaa Xaa Xaa Xaa Xaa Xaa Xaa
 1               5                   10
```

<210> SEQ ID NO 332
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 332

```
Xaa Asn Thr Xaa Gln Xaa Phe Xaa Xaa Xaa Xaa Xaa Xaa
 1               5                   10
```

<210> SEQ ID NO 333
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted

```
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 333

Xaa Gln Thr Xaa Gln Xaa Phe Xaa Xaa Xaa Xaa Xaa Xaa
1               5                   10

<210> SEQ ID NO 334
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
```

```
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 334

Xaa Asn Thr Xaa Gln Cys Phe Xaa Xaa Xaa Xaa Xaa Xaa
1               5                   10

<210> SEQ ID NO 335
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 335

Xaa Gln Thr Xaa Gln Xaa Phe Xaa Xaa Xaa Xaa Xaa Xaa
1               5                   10

<210> SEQ ID NO 336
<211> LENGTH: 13
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
     with cyano, halo, alkyl, haloalkyl, hydroxy, alkoxy, substituted
     or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
     rbMe2Nal, 2-Nal, aMe(2-Nal), Phe(2-Me), Phe(3-Me), Phe(4-Me),
     Phe(3,4-dimethoxy), 1-Nal, unsubstituted Trp, or Trp substituted
     with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
     4-amino-4-carboxy-tetrahydropyran (THP), alpha-MeLys,
     alpha-MeLeu, alpha-MeArg, alpha-MePhe, alpha-MeLeu, alpha-MeLys,
     alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
     substituted (D)Phe, substituted or unsubstited Tyr, unsubstituted
     (D)Tyr, a-MePhe, substituted a-MePhe, b-hPhe, 1-Nal, aMe(1-Nal),
     substituted 1-Nal, 2-Nal, aMe(2-Nal), substituted 2-Nal, or
     N-substituted Asn

<400> SEQUENCE: 336

Xaa Asn Thr Xaa Gln Xaa Phe Xaa Xaa Xaa Xaa Xaa Xaa
1               5                   10

<210> SEQ ID NO 337
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
     with cyano, halo, alkyl, haloalkyl, hydroxy, alkoxy, substituted
     or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
     rbMe2Nal, 2-Nal, aMe(2-Nal), Phe(2-Me), Phe(3-Me), Phe(4-Me),
     Phe(3,4-dimethoxy), 1-Nal, unsubstituted Trp, or Trp substituted
     with cyano, halo, alkyl, haloalkyl, hydroxy, or alkoxy
<220> FEATURE:
```

```
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 337

Xaa Asn Thr Xaa Gln Cys Phe Xaa Xaa Xaa Xaa Xaa Xaa
1               5                   10

<210> SEQ ID NO 338
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Xaa is 4diFAchx, Achx, Acpx, AmeK(Boc),
      4-amino-4-carboxy-tetrahydropyran (THP), alpha-MeLys,
      alpha-MeLeu, alpha-MeArg, alpha-MePhe, alpha-MeLeu, alpha-MeLys,
      alpha-MeAsn, alpha-MeTyr, Ala, cyclohexylAla,
<220> FEATURE:
<221> NAME/KEY: MISC_FEATURE
<222> LOCATION: (10)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 338

Xaa Asn Thr Xaa Gln Xaa Phe Xaa Xaa Xaa Xaa Xaa Xaa
```

<210> SEQ ID NO 339
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (11)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstituted Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 339

Xaa Asn Thr Xaa Gln Xaa Phe Xaa Leu Lys Xaa Xaa Xaa
1               5                   10

<210> SEQ ID NO 340
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE

```
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (11)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 340

Xaa Asn Thr Xaa Gln Cys Phe Xaa Leu Lys Xaa Xaa
1               5                   10

<210> SEQ ID NO 341
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (11)..(12)
<223> OTHER INFORMATION: Xaa is any amino acid
```

```
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 341

Xaa Asn Thr Xaa Gln Xaa Phe Xaa Leu Lys Xaa Xaa Xaa
1               5                   10

<210> SEQ ID NO 342
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 342

Xaa Asn Thr Xaa Gln Xaa Phe Xaa Leu Lys Asn Xaa Xaa
1               5                   10

<210> SEQ ID NO 343
<211> LENGTH: 13
<212> TYPE: PRT
<213> ORGANISM: Artificial sequence
<220> FEATURE:
<223> OTHER INFORMATION: Synthetic construct
```

```
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 343

Xaa Asn Thr Xaa Gln Xaa Phe Xaa Leu Lys Asn Xaa Xaa
1               5                   10

<210> SEQ ID NO 344
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
```

```
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 344

Xaa Asn Thr Xaa Gln Xaa Phe Xaa Leu Lys Asn Xaa Xaa
1               5                   10

<210> SEQ ID NO 345
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
```

```
           (D)Tyr, a-MePhe, substituted a-MePhe, b-hPhe, 1-Nal, aMe(1-Nal),
           substituted 1-Nal, 2-Nal, aMe(2-Nal), substituted 2-Nal, or
           N-substituted Asn

<400> SEQUENCE: 345

Xaa Asn Thr Trp Gln Xaa Phe Xaa Leu Lys Asn Xaa Xaa
1               5                   10

<210> SEQ ID NO 346
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
           with cyano, halo, alkyl, haloalkyl, hydroxy, alkoxy, substituted
           or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: W is Trp substituted with cyano, halo, alkyl,
           haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
           substituted (D)Phe, substituted or unsubstited Tyr, unsubstituted
           (D)Tyr, a-MePhe, substituted a-MePhe, b-hPhe, 1-Nal, aMe(1-Nal),
           substituted 1-Nal, 2-Nal, aMe(2-Nal), substituted 2-Nal, or
           N-substituted Asn

<400> SEQUENCE: 346

Xaa Asn Thr Xaa Gln Xaa Phe Trp Leu Lys Asn Xaa Xaa
1               5                   10

<210> SEQ ID NO 347
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
```

```
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 347

Xaa Asn Thr Trp Gln Cys Phe Xaa Leu Lys Asn Xaa Xaa
1               5                   10

<210> SEQ ID NO 348
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: W is Trp substituted with cyano, halo, alkyl,
      haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (12)..(12)
<223> OTHER INFORMATION: Xaa is any amino acid
<220> FEATURE:
```

<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 348

Xaa Asn Thr Xaa Gln Cys Phe Trp Leu Lys Asn Xaa Xaa
1               5                   10

<210> SEQ ID NO 349
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: Xaa is 6amido2Nal, 6OMe2Nal, bMe2Nal(2S,3R),
      rbMe2Nal, 2-Nal, aMe(2-Nal), Phe(2-Me), Phe(3-Me), Phe(4-Me),
      Phe(3,4-dimethoxy), 1-Nal, unsubstituted Trp, or Trp substituted
      with cyano, halo, alkyl, haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys Ac
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 349

Xaa Asn Thr Trp Gln Xaa Phe Xaa Leu Lys Asn Xaa Xaa
1               5                   10

<210> SEQ ID NO 350
<211> LENGTH: 13
<212> TYPE: PRT

```
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Abu
<220> FEATURE:
<221> NAME/KEY: MISC_FEATURE
<222> LOCATION: (4)..(4)
<223> OTHER INFORMATION: Xaa is unsubstituted Trp, or Trp substituted
      with cyano, halo, alkyl, haloalkyl, hydroxy, alkoxy, substituted
      or unsubstituted aryl, or substituted or unsubstituted heteroaryl
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is F(4-2ae)
<220> FEATURE:
<221> NAME/KEY: MISC_FEATURE
<222> LOCATION: (8)..(8)
<223> OTHER INFORMATION: W is Trp substituted with cyano, halo, alkyl,
      haloalkyl, hydroxy, or alkoxy
<220> FEATURE:
<221> NAME/KEY: MISC_FEATURE
<222> LOCATION: (9)..(9)
<223> OTHER INFORMATION: Leu is a-MeLeu
<220> FEATURE:
<221> NAME/KEY: MISC_FEATURE
<222> LOCATION: (10)..(10)
<223> OTHER INFORMATION: Lys is Lys(Ac)
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is paf, Aib, 3Pal, Phe, substituted Phe,
      substituted (D)Phe, substituted or unsubstited Tyr, unsubstituted
      (D)Tyr, a-MePhe, substituted a-MePhe, b-hPhe, 1-Nal, aMe(1-Nal),
      substituted 1-Nal, 2-Nal, aMe(2-Nal), substituted 2-Nal, or
      N-substituted Asn

<400> SEQUENCE: 350

Xaa Asn Thr Xaa Gln Xaa Phe Trp Leu Lys Asn Xaa Xaa
1               5                   10

<210> SEQ ID NO 351
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is EtCo
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
<220> FEATURE:
<221> NAME/KEY: MISC_FEATURE
<222> LOCATION: (8)..(8)
<223> OTHER INFORMATION: Phe is Phe[4(2-aminoethoxy)]
<220> FEATURE:
```

```
<221> NAME/KEY: MISC_FEATURE
<222> LOCATION: (9)..(9)
<223> OTHER INFORMATION: Xaa is Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 351

Arg Xaa Asn Thr Trp Gln Xaa Phe Xaa Xaa Glu Asn Xaa
1               5                   10

<210> SEQ ID NO 352
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is EtCo
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Abu
<220> FEATURE:
<221> NAME/KEY: MISC_FEATURE
<222> LOCATION: (8)..(8)
<223> OTHER INFORMATION: Phe is Phe[4(2-aminoethoxy)]
<220> FEATURE:
<221> NAME/KEY: MISC_FEATURE
<222> LOCATION: (9)..(9)
<223> OTHER INFORMATION: Xaa is Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Xaa is THP

<400> SEQUENCE: 352

Arg Xaa Gln Thr Trp Gln Cys Phe Xaa Xaa Glu Asn Xaa
1               5                   10

<210> SEQ ID NO 353
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N terminal modification is EtCo
<220> FEATURE:
<221> NAME/KEY: MISC_FEATURE
<222> LOCATION: (1)..(1)
<223> OTHER INFORMATION: Arg is (D)Arg
<220> FEATURE:
<221> NAME/KEY: MISC_FEATURE
<222> LOCATION: (2)..(2)
<223> OTHER INFORMATION: Xaa is Pen
<220> FEATURE:
<221> NAME/KEY: MISC_FEATURE
<222> LOCATION: (7)..(7)
<223> OTHER INFORMATION: Xaa is Pen
```

```
<220> FEATURE:
<221> NAME/KEY: MISC_FEATURE
<222> LOCATION: (8)..(8)
<223> OTHER INFORMATION: Phe is Phe[4(2-aminoethoxy)]
<220> FEATURE:
<221> NAME/KEY: MISC_FEATURE
<222> LOCATION: (9)..(9)
<223> OTHER INFORMATION: Xaa is Nal
<220> FEATURE:
<221> NAME/KEY: MISC_FEATURE
<222> LOCATION: (10)..(10)
<223> OTHER INFORMATION: Xaa is THP
<220> FEATURE:
<221> NAME/KEY: MISC_FEATURE
<222> LOCATION: (13)..(13)
<223> OTHER INFORMATION: Phe is a-MePhe

<400> SEQUENCE: 353

Arg Xaa Asn Thr Trp Gln Xaa Phe Xaa Xaa Glu Asn Phe
 1               5                  10
```

UNITED STATES PATENT AND TRADEMARK OFFICE
CERTIFICATE OF CORRECTION

PATENT NO. : 12,018,057 B2
APPLICATION NO. : 17/149544
DATED : June 25, 2024
INVENTOR(S) : Chengzao Sun et al.

It is certified that error appears in the above-identified patent and that said Letters Patent is hereby corrected as shown below:

In the Claims

At Column 473, Line number 42, Claim 1, please replace:
"SEQ ID NO: 6)"
With:
-- (SEQ ID NO: 6) --.

At Column 475, Line number 43, Claim 1, please replace:
"(SEQ ID NO 59)"
With:
-- (SEQ ID NO: 59) --.

At Column 475, Line 51, Claim 1, please replace:
"[Lys(COCF$_3$)-"
With:
-- [Lys(COCF$_3$)]- --.

At Column 476, Line 66, Claim 1, please replace:
"THP]"
With:
-- [THP] --.

At Column 477, in Line 26, Claim 2, please replace:
"—NH2"
With:
-- -NH$_2$ --.

At Column, 478, in Line 1, Claim 4, please replace:
"—NH2"

Signed and Sealed this
Third Day of June, 2025

Coke Morgan Stewart
*Acting Director of the United States Patent and Trademark Office*

With:

-- -NH$_2$ --.